(12) United States Patent
Siegel et al.

(10) Patent No.: US 6,495,347 B1
(45) Date of Patent: Dec. 17, 2002

(54) INDUCTION OF A TH1-LIKE RESPONSE IN VITRO

(75) Inventors: Marvin Siegel, Blue Bell, PA (US); N. Randall Chu, Victoria (CA); Lee A. Mizzen, Victoria (CA)

(73) Assignee: Stressgen Biotechnologies Corporation, Victoria (CA)

( * ) Notice: Subject to any disclaimer, the term of this patent is extended or adjusted under 35 U.S.C. 154(b) by 0 days.

(21) Appl. No.: 09/613,303

(22) Filed: Jul. 10, 2000

Related U.S. Application Data
(60) Provisional application No. 60/143,757, filed on Jul. 8, 1999.

(51) Int. Cl.[7] .......................... C12P 21/04; A61K 39/00
(52) U.S. Cl. .................................... 435/69.7; 424/192.1
(58) Field of Search ....................... 435/69.7; 424/192.1

(56) References Cited

U.S. PATENT DOCUMENTS

| | | | |
|---|---|---|---|
| 4,716,038 A | 12/1987 | Stanford et al. | 424/92 |
| 4,724,144 A | 2/1988 | Rook et al. | 424/93 |
| 4,918,166 A | 4/1990 | Kingsman et al. | 530/350 |
| 5,114,844 A | 5/1992 | Cohen et al. | 435/7 |
| 5,348,945 A | 9/1994 | Berberian et al. | 514/21 |
| 5,504,005 A | 4/1996 | Bloom et al. | 435/253 |
| 5,578,300 A | 11/1996 | Schmidt et al. | 424/78.08 |
| 5,580,563 A | 12/1996 | Tam | 424/197 |
| 5,599,545 A | 2/1997 | Stanford et al. | 424/282.1 |
| 5,736,146 A | 4/1998 | Cohen et al. | 424/197.11 |

(List continued on next page.)

FOREIGN PATENT DOCUMENTS

| | | |
|---|---|---|
| EP | 0 262 710 | 4/1988 |
| EP | 0 322 990 | 7/1989 |
| GB | 2 251 186 | 7/1992 |
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO 90/15873 | 12/1990 |
| WO | WO 91/02542 | 3/1991 |

(List continued on next page.)

OTHER PUBLICATIONS

Anthony et al "Priming of CD8+ CTL Effector Cells In Mice By Immunization With a Stress Protein–Influenza Virus Nucleoprotein Fusion Molecule", Vaccine, 17:373–383 (1999).

Barrios et al. "Heat Shock Proteins As Carrier Molecules: In Vivo Helper Effect Mediated By *Escherichia coli* GroEL and DnaK Proteins Requires Cross–Linking With Antigen", Clin. Exp. Immunol., 98:229–233 (1994).

Chu et al "Cancer Immunotherapy Using Adjuvant–free, Fusion Protein Encoding M. bovis BCG HSP65 and HPV16 E7", Faseb Journal, 12(5):A909 (Mar. 20, 1998).

Chu et al. "Immunotherapy of a Human Papillomavirus (HPV) Type 16 E7–Expressing Tumour By Administration of Fusion Protein Comprising *Mycobacterium bovis* Bacille Calmette–Guérin (BCG) hsp65 and HPV16 E7", Clin. Exp. Immunol., 121:216–225 (2000).

(List continued on next page.)

*Primary Examiner*—Hankyel T. Park
(74) *Attorney, Agent, or Firm*—Fish & Richardson P.C.

(57) ABSTRACT

The invention provides compositions and methods for stimulating a Th1-like response in vitro. Compositions include fusion proteins and conjugates that contain at least a portion of a heat shock protein. A Th1-like response can be elicited by contacting in vitro a cell sample containing naive lymphocytes with a fusion protein or conjugate of the invention. The Th1-like response can be detected by measuring IFN-gamma produced by the cell sample.

64 Claims, 37 Drawing Sheets

U.S. PATENT DOCUMENTS

| | | | |
|---|---|---|---|
| 5,750,119 A | 5/1998 | Srivastava | 424/277.1 |
| 5,830,464 A | 11/1998 | Srivastava | 424/93.71 |
| 5,837,251 A | 11/1998 | Srivastava | 424/193.1 |
| 5,858,368 A | 1/1999 | Smith et al. | 424/192.1 |
| 5,935,576 A | 8/1999 | Srivastava | 424/184.1 |
| 5,948,646 A | 9/1999 | Srivastava | 435/69.3 |
| 5,961,979 A | 10/1999 | Srivastava | 424/193.1 |
| 5,985,270 A | 11/1999 | Srivastava | 424/93.71 |
| 5,997,873 A | 12/1999 | Srivastava | 424/193.1 |
| 6,007,806 A | 12/1999 | Lathe et al. | 424/93.2 |
| 6,007,821 A | 12/1999 | Srivastava et al. | 424/193.1 |
| 6,017,540 A | 1/2000 | Srivastava et al. | 424/193.1 |
| 6,017,544 A | 1/2000 | Srivastava | 424/277.1 |
| 6,030,618 A | 2/2000 | Srivastava | 424/184.1 |
| 6,048,530 A | 4/2000 | Srivastava | 424/193.1 |
| 6,130,087 A | 10/2000 | Srivastava et al. | 435/372.3 |
| 6,136,315 A | 10/2000 | Srivastava | 424/193.1 |
| 6,139,841 A | 10/2000 | Srivastava | 424/193.1 |
| 6,143,299 A | 11/2000 | Srivastava | 424/193.1 |
| 6,156,302 A | 12/2000 | Srivastava | 424/93.1 |
| 6,162,436 A | 12/2000 | Srivastava | 424/193.1 |
| 6,168,793 B1 | 1/2001 | Srivastava | 424/193.1 |
| 6,187,312 B1 | 2/2001 | Srivastava | 424/193.1 |
| 6,322,790 B1 | 11/2001 | Srivastava | 424/193.1 |
| 6,335,183 B1 | 1/2002 | Young et al. | 435/69.7 |
| 6,338,952 B1 | 1/2002 | Young et al. | 435/69.7 |

FOREIGN PATENT DOCUMENTS

| | | |
|---|---|---|
| WO | WO 91/15572 | 10/1991 |
| WO | WO 92/08484 | 5/1992 |
| WO | WO 92/08488 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 96/10421 | 4/1996 |
| WO | WO 96/19496 | 6/1996 |
| WO | WO 96/26277 | 8/1996 |
| WO | WO 97/06821 | 2/1997 |
| WO | WO 97/26910 | 7/1997 |
| WO | WO 98/23735 | 6/1998 |
| WO | WO 98/35705 | 8/1998 |
| WO | WO 99/07860 | 2/1999 |
| WO | WO 00/19828 | 4/2000 |
| WO | WO 00/23093 | 4/2000 |
| WO | WO 01/17554 | 3/2001 |
| WO | WO 01/52791 | 7/2001 |
| WO | WO 01/52877 | 7/2001 |
| WO | WO 01/52890 | 7/2001 |
| WO | WO 01/53457 | 7/2001 |
| WO | WO 02/00242 | 1/2002 |

OTHER PUBLICATIONS

Suzue et al. "Adjuvant–Free hsp70 Fusion Protein System Elicits Humoral and Cellular Immune Responses to HIV–1 p24", The Journal Of Immunology, 156:873–879 (1996).

Zhou, G., "New Fusion Protein for Immunotherapy of Venereal Disease and Cancer—Is a Heat Shock Protein of Mycobacterium Bovis", Database WPI, Derwent Publications Ltd., XP002154481, (Mar. 29, 2000), Abstract.

Agranovsky et al., "Putative 65 kDa Protein of Beet Yellows Closterovirus Is a Homologue of HSP70 Heat Shock Proteins," J. Mol. Biol., 217:603–610 (1991).

Ardeshir et al., "A 75 Kd Merozoite Surface Protein of Plasmodium Falciparum which is Related to the 70 kd Heat–Shcok Proteins," EMBO J., 6(2):493–499 (1987).

Arnosti et al., "Characterization of heat shock in *Bacillus subtilis*," J. Bact., 168(3):1243–1249 (Dec. 1986).

Arrigo and Welch, "Characterization and Purification of the Small 28,000–Dalton Mammalian Heat Shock Protein", J. Biol. Chem., 262(32):15359–15369 (1987).

Barrios et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming," Eur. J. Immunol., 22:1365–1372 (1992).

Beech et al., "CD4+ Th2 cells specific for mycobacterial 65–kilodalton heat shock protein protect against pristane–induced arthritis," J. Immunol. 159:3692–3697 (1997).

Bennett et al., "Help for Cytotoxic–T–cell Responses is Mediated by CD40 Signalling," Nature 393:478–480 (Jun. 4, 1998).

Bertelli et al., "BCG–Induced Resistance in *Trypanosoma cruzi* Experimental Infections," Tropenmed Parasitol, 32:93–96 (1981).

Birk et al., "T–cell autoimmunity in type 1 diabetes mellitus," Curr. Opin. Immunol., 5:903–909 (1993).

Blachere et al., "Heat Shock Protein–Peptide Complexes, Reconstituted in Vitro, Elicit Peptide–specific Cytotoxic T Lymphocyte Response and Tumor Immunity," J. Exp. Med. 186(8):1315–1322 (Oct. 20, 1997).

Blander and Horwitz, "Major Cytoplasmic Membrane Protein of Legionella Pneumophila, a Genus Common Antigen and Member of the hsp 60 Family of Heat Shock Proteins, Induces Protective Immunity in a Guinea Pig Model of Legionnaires' Disease," J. Clin. Invest., 91:717–723 (1993).

Borysiewicz et al, "A recombinant vaccinia virus encoding human papillomavirus types 16 and 18, E6 and E7 proteins as immunotherapy for cervical cancer," Lancet, 347:1523–27 (1996).

Breloer et al., "In Vivo and In Vitro Activation of T Cells After Administration of Ag–Negative Heat Shock Proteins," J. Of Immun. 162:3141–3147 (1999).

Butini et al., "Comparative Analysis of HIV–specific CTL Activity in Lymphoid Tissue and Peripheral Blood," J. Cell Biochem. Suppl. 18B Abstract J306 (1994).

Cain and Howett, "Preventing cervical cancer," Science, 288:1753–54 (2000).

Cassell et al., "A Phase II Study on the Postsurgical Management of Stage Malignant Melanoma With a Newcastle Disease Virus Oncolysate," Cancer, 52:856–860 (Sep. 1983).

Cassell et al., "Viral Oncolysate in the Management of Malignant Melanoma, I. Preparation of the Oncolysate and Measurement of Immunologic Responses" Cancer, 40:672–679 (Aug. 1977).

Catelli et al., "The common 90–kd protein component of non–transformed '8S' steroid receptors is a heat–shock protein", EMBO J., 4(12):3131–3135 (1985).

Chandrasekhar et al., "Purification and Properties of the groES Morphogenetic Protein of *Escherichia coli*", J. Biol. Chem., 261(26):12414–12419 (1986).

Chen et al., "Human 60–kDa Heat–Shock Protein: A Danger Signal to the Innate Immune System," J. Of Immunol. 162:3212–3219 (1999).

Cohen et al., "Immunity to 60 kDa heat shock protein in autoimmune diabetes," Diab. Nutr. Metab., 9(4):229–232 (1996).

Cohen, "Jitters jeopardize AIDS vaccine trials ," Science, 262: 980–981 (1993).

Dahlseid et al., "PBP74, a new member of the mammalian 70–kDa heat shock protein family, is a mitochondrial protein," Mol Biol Cell. 5(11):1265–1275 (1994).

de Gruijl et al., "T cell proliferative responses against human papillomavirus type 16 E7 oncoprotein are most prominent in cervial intraepithelial neoplasia patients with a persistent viral infection," Journal Of General Virology, 77:2183–2191 (1996).

De Velasco et al., "Synthetic Peptides Representing T–Cell Epitopes Act as Carriers in Pneumococcal Polysaccharide Conjugate Vaccines," Infect. & Immun., 63:961–968 (1995).

Del Guidice, "Hsp70: a carrier molecule with built–in adjuvanticity," Experientia, 50:1061–1066 (1994).

Del Guidice et al., "Heat shock proteins as "super"–carriers for sporozoite peptide vaccines?", Research In Immunol., 162:703–707 (1991).

Del Guidice et al., "Priming to Heat Shock Proteins in Infants Vaccinated against Pertussis," J. Immunol., 150(5):2025–2032 (1993).

DeNagel et al., "Heat shock proteins in Immune Responses," Crit. Rev. Immunol., 13(1):71–81 (1993).

Doherty et al, Evasion of host immune responses by tumours and viruses, "Vaccines against virally induced cancers," Wiley, Chicester (Ciba Foundation Symposium 187), pp. 245–260. See page 245, Abstract.

DuBois et al., "Isolation of a Tumor–Associated Transplantation Antigen (TATA) From an SV40–Induced Sarcoma. Resemblance to the TATA of Chemically Induced Neoplasms," Int. J. Cancer, 34:561–566 (1984).

Dubois et al., "Protective immunization of the squirrel monkey againt asexual blood stages of *Plasmodium falciparum* by use of parasite protein fractions," Proc. Natl. Acad. Sci., 81:229–232 (1984).

Elias et al., "Induction and therapy of autoimmune diabetes in the non–obese diabetic (NOD/Lt) mouse by a 65–kDa heat shock protein," Proc. Natl. Acad. Sci. USA, 87:1576–1580 (1990).

Falk et al., "Cell Mediated Immunity to Human Tumors," Arch. Surg., 107:261–265 (Aug. 1973).

Ferrero et al., "The GroES homolog of *Helicobacter pylori* confers protective immunity against mucosal infection in mice," Proc. Natl. Acad. Sci. USA, 92:6499–6503 (1995).

Flaherty et al., "Three–dimensional Structure of the ATPase Fragment of a 70K Heat–Shock Cognate Protein," Nature 346:623–628 (1990).

Fox, "No Winners Against AIDS", Biotechnology, 12:128 (1994).

Friedland et al., "Mycobacterial 65–kD heat shock protein induces release of proinflammatory cytokines from human monocytic cells," Clin. Exp. Immunol., 91:58–62 (1993).

Galloway, "Papillomarivus oncoproteins as vaccine candidates," Lancet, 347:1498–99 (1996).

Gomes et al., "Heat shock protein synthesis during development in *Caulobacter crescentus*," J. Bact., 168(2):923–930 (Nov. 1986).

Gomez et al., "Vaccination with Recombinant Heat Shock Protein 60 from *Histoplasma capsulatum* Protects Mice against Pulmonary Histoplasmosis," Infect. & Immun., 63:2587–2595 (1995).

Haanen et al., "Selection of a human T helper type 1–like T cell subset by mycobacteria," J. Exp. Med., 174:583–592 (1991).

Haghbin et al., "Immunotherapy with Oral BCG and Serial Immune Evaluation in Childhood Lymphoblastic Leukemia Following Three Years of Chemotherapy," Cancer, 46:2577–2586 (Dec. 1980).

Hastie et al., "HSP27 Elevated in Mild Allergic Inflammation Protects Airway Epithelium from H2SO4 Effects," Am J. Physiol., 273 (Lung Cell. Mol. Physiol. 17):L401–L409 (1997).

Haynes, "Scientific and Social Issues of Human Immunodeficiency Virus Vaccine Development", Science, 260:1279–1286 (1993).

Huang et al., "In Vivo Cytotoxic T Lymphocyte Elicitation by Mycobacterial Heat Shock Protein 70 Fusion Proteins Maps to a Discrete Domain and Is CD4 T Cell Independent," J. Exp. Med. 191(2):403–408 (Jan. 17, 2000).

Hudson et al., "Active Specific Immunotherapy for Ovarian Cancer," The Lancet, 2:877–879 (Oct. 23, 1976).

Hughes et al., "A Study in Clinical Cancer Immunotherapy," Cancer, 26:269–278 (Aug. 1970).

Humphrey et al., "Adjuvant Immunotherapy for Melanoma," J. Of Sur. Oncol., 25:303–305 (1984).

Hunt and Calderwood, "Characterization and Sequence of a Mouse hsp70 Gene and Its Expression in Mouse Cell Lines," Gene 87:199–204 (1990).

Husson and Young, "Genes for the major protein antigens of *Mycobacterium tuberculosis*: The etiologic agents of tuberculosis and leprosy share an immunodominant antigen," Proc. Natl. Acad. Sci. USA, 84:1679–1683 (1987).

Huygen et al., "Spleen cell cytokine secretion in *Mycobacterium bovis* BCG–infected mice," Infection And Immunity, 60(7):2880–2886 (1992).

Jacquier–Sarlin, "Protective effects of hsp70 in inflammation," Experientia, 50(11–12):1031–1038 (1994).

Jarecki–Black et al., "The Effect of BCG–Vaccine Upon Experimental Visceral Leishmaniasis in Hampsters," Ann. Clin. Lab. Sci., 14:464–466 (1984).

Jindal, "Heat Shock Proteins: Applications in health and disease," Trends In Biotech, 14(1):17–20, 1996.

Jondal et al., "MHC Class I–Restricted CTL Responses to Exogenous Antigens," Immunity 5:295–203 (Oct. 1996).

Kaufmann et al., "Enumeration of T cells reactive with Mycobacterium tuberculosis organisms and specific for the recombinant mycobacterial 64–kDa protein", Eur. J. Immunol., 17:351–357 (1987).

Kaufmann et al., "Heat–shock protein 60: implications for pathogenesis of an protection against bacterial infections," Immunological Reviews, 121:67–90 (1991).

Kiessling et al., "Role of hsp60 during autoimmune and bacterial inflammation," Immunological Reviews, 121:91–111 (1991).

Kimmig and Wenk, "Suppression of Parasitaemia from *Litomosoides carinii* by Immunisation with BCG and Microfilariae," Z. Parasitenkd, 67:317–327 (1982).

Kol et al., "Chlamydial and Human Heat Shock Protein 60s Activate Human Vascular Endothelium, Smooth Muscle Cells, and Macrophages," J. Clin. Invest. 103:571–577 (1999).

Konen–Waisman et al., "Self and Foreign 60–Kilodalton Heath Shock Protein T Cell Epitope Peptides Serve As Immunogenic Carriers for a T Cell–Independent Sugar Antigen," Journ. Immunol., 154:5977–5985 (1995).

Konen–Waisman et al., "Self Heat–Shock Protein (hsp60) Peptide Serves in a Conuugate Vaccine against a Lethal Pneumococcal Infection," J. Infect. Diseases 179:403–413 (1999).

La Thangue and Latchman, "A Cellular Protein Related to Heat–Shocked Protein 90 Accumulates during Herpes Simplex Virus Infection and Is Overexpressed in Transformed Cells," Experimental Cell Research, 178:169–179 (1988).

Lamb et al., "Stress Proteins may Provide a Link Between the Immune Response to Infection and Autoimmunity", Int'l. Immun., 1(2):191–196 (1989).

Layton et al., Induction of HIV–Specific Cytotoxic T lymphocytes In Vivo with Hybrid HIV–1 V3:Ty–Virus–Like–Particles, J. Immunology, 151(2):1097–1107 (Jul. 1993).

Leung et al., "The immunobiology of heat shock proteins," J. Investig. Allergol. Clin. Immunol., 1(1):23–30, (1991).

Levi et al., "Synthetic recombinant influenza vaccine induces efficient long–term immunity and cross–strain protection," Vaccine, 14:85–92 (1996).

Li and Srivastava, "Tumor Rejection Antigen gp96/grp94 is an ATPase: Implications for Protein Folding and Antigen Presentation," The EMBO Journal, 12(8):3143–3151 (1993).

Lindquist and Craig, "The Heat–Shock Proteins," Annu. Rev. Genet., 22:631–677 (1988).

Lussow et al., "Mycobacterial heat–shocked proteins as carrier molecules," Eur. J. Immunol, 21:2297–2302 (1991).

Maytin, "Heat shock proteins and molecular chaperones: implications for adaptive responses in the skin," J. Invest. Dermatol., 104:448–455 (1995).

McCulloch et al., "Recurrent Malignant Melanoma: Effect of Adjuvant Immunotherapy on Survival," Can. Med. Assoc. J., 117:33–36 (Jul. 1977).

Miller et al., "Immunotherapy in autoimmune diseases," Curr. Opinion In Immun., 3:936–940 (1991).

Minowada et al., "Clinical implications of the stress response," J. Clin. Invest., 95:3–12 (1995).

Moré et al., Activation of cytotoxic T cells in vitro by recombinant gp96 fusion proteins irrespective of the 'fused' antigenic peptide sequence, Immunology Letters, 69:275–282 (1999).

Motal, "Glocosylphosphatidylinositol–linked Db does not induce an influenza–specific cytotoxic T lymphocyte response or recycle membrane–bound peptides," Eur. J. Immunol., 25:1121–1124 (1995).

Murphy and Lefford, "Host Defenses in Murine Malaria: Induction of a Protracted State of Immunity with a Formalin–Killed *Plasmodium berghei* Blood Parasite Vaccine," Infec. Immun., 22:798–803 (1978).

Murray et al., "Viral Oncolysate in the Management of Malignant Melanoma, II. Clinical Studies" Cancer, 40:680–686 (Aug. 1977).

Nadler et al., "Interaction of the Immunosupressant Deoxyspergualin with a Member of the Hsp70 Family of Heat Shock Proteins," Science, 258:484–486 (1992).

Nair et al., "Calreticulin Displays in Vivo Peptide–Binding Activity and Can Elicit CTL Responses Against Bound Peptides," J. Immun. 162:6426–6432 (1999).

Noll and Autenrieti, "Immunity against *Yersinia enterocolitica* by Vaccination with Yersinia HSP60 Immunostimulating Complexes or Yersinia HSP60 plus Interleukin–12", Infect. & Immun., 64:2955–2961 (1996).

Oettgen and Old, "Chapter 6: The History of Cancer Immunotherapy." In Biologic Therapy Of Cancer, De Vita, V.T., Hellman, S. and Rosenberg, S.A., eds., (London: J.B. Lippincott) pp. 98–103 (1991).

Orme et al., "Cytokine secretion by CD4 T lymphocytes acquired in responses to Mycobacterium tuberculosis infection," J. Immunol., 151(1):518–525 (1993).

Palladino et al., "Expression of a Shared Tumor–Specific Antigen by Two Chemically Induced BALB/c Sarcomas," Cancer Research, 47:5074–5079 (Oct. 1987).

Peetermans et al., "Mycobacterial heat–shock protein 65 induces proinflammatory cytokines but does not activate human mononuclear phagocytes," Scan. J. Immunol., 39:613–617 (1994).

Pinskey et al., "Intravesical Administration of Bacillus Calmette–Guerin in Patients with Recurrent Superficial Carcinoma of the Urinary Bladder: Report of a Prospective, Randomized Trail," Cancer Treat. Rep., 69:47–53 (Jan. 1985).

Polla et al., "Heat shock proteins and inflammation," Current Topics In Microbiology And Immunology, 167:93–105 (1991).

Polla et al., "Regulation and functions of stress proteins in allergy and inflammation," Clinical And Experimental Allergy, 23:548–556 (1993).

Polla et al., "Spontaneous heat shock protein synthesis by alveolar macrophages in interstitial lung disease associated with phagocytosis of eosinophils," Eur. Respir. J., 6:483–488 (1993).

Rico et al., "Characterization of the Immunostimulatory Properties of Leishmania infantum HSP70 by Fusion to the *Escherichia coli* Maltose–Binding Protein in Normal nu/nu BALB/c Mice," Infection and Immunity 66:347–352 (Jan. 1998).

Roman et al., "Synthetic peptides non–covalently bound to bacterial hsp 70 elicit peptide–specific T–cell responses in vivo," Immunology, 88(4):487–492 (1992).

Schild et al., "Stress Proteins and Immunity Mediated by Cytotoxic T Lymphocytes," Current Opinion In Immun. 11:109–113 (1999).

Schoenberger et al., "T–cell Help for Cytotoxic T Lymphocytes is Mediated by CD40–CD40L Interactions," Nature 393:480–483 (Jun. 4, 1998).

Shinnick et al., "The Etiologic Agents of Leprosy and Tuberculosis Share an Immunoreactive protein Antigen with the Vaccine Strain *Mycobacterium bovis* BCG", Infect. And Immun., 55(8):1932–1935 (1987).

Silverstein, "The History of Immunology," In Fundamental Immunology, 2.sup.nd Edition, Paul, W.E., ed., (NY:Raven Press), pp. 21, 23–24 (1989).

Sparks et al., "Immunology and Adjuvant Chemoimmunotherapy of Breast Cancer," Arch Surg, 111:1057–1062 (Oct. 1976).

Spencer et al., "Nonspecific Protection of Mice against Influenza Virus Infection by Local or Systemic Immunization with Bacille Calmette–Guerin," J. Infect, 171–175 (Aug. 1977).

Srivastava and Udono, "Heat Shock Protein–Peptide Complexes in Cancer Immunotherapy," Current Opinion In Immun., 6:728–732 (1994).

Srivastava and Old, "Individually Distinct Transplantation Antigens of Chemically Induced Mouse Tumors," Immunology Today, 9:78–83 (Mar. 1988).

Srivastava and Das, "The Serologically Unique Cell Surface Antigen of Zajdela Ascitic Hepatoma is Also Its Tumor–Associated Transplantation Antigen," Int. J. Cancer, 33:417–422 (1984).

Srivastava and Maki, "Stress–Induced Proteins in Immune Response to Cancer," Curr. Top. Of Microbiol. Immunol., 167:109–123 (1991).

Srivastava et al., "Tumor Rejection Antigens of Chemically Induced Sarcomas of Inbred Mice," Proc. Natl. Acad. Sci., USA, 83:3407–3411 (May 1986).

Sturrock et al., "Attempts to Induce Resistance to *Schistosoma mansoni* and *S. haematobium* in Kenyan Baboons (*Papio anubis*) Using Non–Specific Immunostimulants," Parasitology, 90:101–110 (1985).

Suto and Srivastava, "A Mechanism for the Specific Immunogenicity of Heat Shock Protein–Chaperoned Peptides," Science 269:1585–1588 (Sep. 15, 1995).

Suzue et al., "Heat Shock Fusion Proteins as Vehicles for Antigen Delivery Into the Major Histocompatibility Complex Class I Presentation Pathway," Proc. Natl. Acad. Sci. USA, 94:13146–13151 (Nov. 1997).

Tamura et al., "Immunotherapy of Tumors with Autologous Tumor–Derived Heat Shock Protein Preparations," Science 278:117–120 (Oct. 3, 1997).

Thole et al., "Antigenic relatedness of a strongly immunogenic 65 kDA mycobacterial protein antigen with a similarly sized ubiquitous bacterial common antigen", Microbial Pathogenesis, 4:71–83 (1988).

Thole et al., "Characterization, Sequence Determination, and Immunogenicity of a 64–Kilodalton Protein of Mycobacterium bovis BCG Expressed in *Escherichia coli* K–12," Infection & Immunol., 55(6):1466–1475 (1987).

Udono et al., "Cellular Requirements for Tumor–Specific Immunity Elicited by Heat Shock Proteins: Tumor Rejection Antigen gp96 Primes CD8 T Cells in vivo," Proc. Natl. Acad. Sci. USA 91:3077–3081 (Apr. 1994).

Udono and Srivastava, "Heat Shock Protein 70–associated Peptides Elicit Specific Cancer Immunity," J. Exp. Med., 178:1391–1396 (Oct. 1993).

Ullrich et al., "A Mouse Tumor–Specific Transplantation Antigens is a Heat Shock–Related Protein," Proc. Natl. Acad, Sci., USA, 83:3121–3125 (May 1986).

Van Eden et al., "Cloning of the mycobacterial epitope recognized by T lymphocytes in adjuvant arthritis", Nature, 331(14):171–173 (1988).

Verdegaal et al., "Heat Shcok Protein 65 Induces CD62e, CD106, and CD54 on Cultured Human Endothelial Cells and Increases Their Adhesiveness for Monocytes and Granulocytes," Jour. Immunol., 157:369–376 (1996).

Vignola et al., "Increased expression of heat shock protein 70 on airway cells in asthma and chronic bronchitis," Am. J. Respir. Cell Mol. Biol., 13:683–691 (1995).

Vodkin and Williams, "A Heat Shock Operon in *Coxiella burnetii* Produces a Major Antigen Homologous to a Protein in Both Mycobacteria and *Escherichia coli*", J. Of Bacteriology, 170(3):1227–1234 (1988).

Voellmy et al. "Isolation and functional analysis of a human 70,000–dalton heat shock protein gene segment," Proc Natl Acad Sci U S A. 82(15):4949–53 (1985).

Welch et al., "Biochemical characterization of the mammalian stress proteins and identification of two stress proteins as glucose– and Ca2+–ionophore–regulated proteins," J. Biol. Chem., 258(11):7102–7111 (1983).

Welch and Feramisco, "Purification of the Major Mammalian Heat Shock Proteins" J. Biol. Chem., 257(24):14949–14959 (1982).

Welch and Feramisco, "Rapid Purification of Mammalian 70,000–Dalton Stress Proteins: Affinity of the Proteins for Nucleotides", Mol. Cell. Biol., 5(6):1229–1237 (1985).

Young et al., "The 65kDa antigen of mycobacteria—a common bacterial protein?", Immunol. Today, 8(7–8):215–219 (1987).

Young et al., "Genes for the major protein antigens of the leprosy parasite mycobacterium leprae," Nature, 316:450–452 (1985).

Young et al., "Stress proteins are immune targets in leprosy and tuberculosis," Proc. Natl. Acad. Sci. USA, 85:4267–4270 (1988).

Young, "Stress Proteins and Immunology," Annu. Rev. Immunol., 8:401–420 (1990).

Zhu et al., "Structural Analysis of Substrate Binding by the Molecular Chaperone DnaK," Science 272:1606–1614 (Jun. 14, 1996).

Zylicz et al., "The grpE Protein of *Escherichia coli*", J. Biol. Chem., 262(36):17437–17442 (1987).

Zylicz and Georgopoulos, "Purification and Properties of the *Escherichia coli* dnaK Replication Protein", J. Biol. Chem., 259(14):8820–8825 (1984).

```
3/1                                    33/11
atg gCC AAG ACA ATT GCG TAC GAC GAA GAG GCC CGT CGC GGC CTC GAG CGG GGC TTG AAC
 M   A   K   T   I   A   Y   D   E   E   A   R   R   G   L   E   R   G   L   N
63/21                                  93/31
GCC CTC GCC GAT GCG GTA AAG GTG ACA TTG GGC CCC AAG GGC CGC AAC GTC GTC CTG GAA
 A   L   A   D   A   V   K   V   T   L   G   P   K   G   R   N   V   V   L   E
123/41                                 153/51
AAG AAG TGG GGT GCC CCC ACG ATC ACC AAC GAT GGT GTG TCC ATC GCC AAG GAG ATC GAG
 K   K   W   G   A   P   T   I   T   N   D   G   V   S   I   A   K   E   I   E
183/61                                 213/71
CTG GAG GAT CCG TAC GAG aag atc ggc GCC GAG CTG GTC AAA GAG GTA GCC AAG AAG ACC
 L   E   D   P   Y   E   K   I   G   A   E   L   V   K   E   V   A   K   K   T
243/81                                 273/91
GAT GAC GTC GCC GGT GAC GGC ACC ACG ACG GCC ACC GTG CTG GCC CAG GCG TTG GTT CGC
 D   D   V   A   G   D   G   T   T   T   A   T   V   L   A   Q   A   L   V   R
303/101                                333/111
gAg GGC CTG CGC AAC GTC GCG GCC GGC GCC AAC CCG CTC GGT CTC AAA CGC GGC ATC GAA
 E   G   L   R   N   V   A   A   G   A   N   P   L   G   L   K   R   G   I   E
363/121                                393/131
AAG GCC GTG GAG AAG GTC ACC GAG ACC CTG CTC AAG GGC GCC AAG GAG GTC GAG ACC AAG
 K   A   V   E   K   V   T   E   T   L   L   K   G   A   K   E   V   E   T   K
423/141                                453/151
GAG CAG ATT GCG GCC ACC GCA GCG ATT TCG GCG GGT GAC CAG TCC ATC GGT GAC CTG ATC
 E   Q   I   A   A   T   A   A   I   S   A   G   D   Q   S   I   G   D   L   I
483/161                                513/171
GCC GAG GCG ATG GAC AAG GTG GGC AAC GAG GGC GTC ATC ACC GTC GAG GAG TCC AAC ACC
 A   E   A   M   D   K   V   G   N   E   G   V   I   T   V   E   E   S   N   T
543/181                                573/191
TTT GGG CTG CAG CTC GAG CTC ACC GAG GGT ATG CGG TTC GAC AAG GGC TAC ATC TCG GGG
 F   G   L   Q   L   E   L   T   E   G   M   R   F   D   K   G   Y   I   S   G
603/201                                633/211
TAC TTC GTG ACC GAC CCG GAG CGT CAG GAG GCG GTC CTG GAG GAC CCC TAC ATC CTG CTG
 Y   F   V   T   D   P   E   R   Q   E   A   V   L   E   D   P   Y   I   L   L
663/221                                693/231
GTC AGC TCC AAG GTG TCC ACT GTC AAG GAT CTG CTG CCG CTC CTC GAG AAG GTC ATC GGA
 V   S   S   K   V   S   T   V   K   D   L   L   P   L   L   E   K   V   I   G
723/241                                753/251
GCC GGT AAG CCG CTG CTG ATC ATC GCC GAG GAC GTC GAG GGC GAG GCG CTG TCC ACC CTG
 A   G   K   P   L   L   I   I   A   E   D   V   E   G   E   A   L   S   T   L
783/261                                813/271
GTC GTC AAC AAG ATC CGC GGC ACC TTC AAG TCG GTG GCG GTC AAG GCT CCC GGC TTC GGC
 V   V   N   K   I   R   G   T   F   K   S   V   A   V   K   A   P   G   F   G
843/281                                873/291
GAC CGC CGC AAG GCG ATG CTG CAG GAT ATG GCC ATT CTC ACC GGT GGT CAG GTG ATC AGC
 D   R   R   K   A   M   L   Q   D   M   A   I   L   T   G   G   Q   V   I   S
903/301                                933/311
GAA GAG GTC GGC CTG ACG CTG GAG AAC GCC GAC CTG TCG CTG CTA GGC AAG GCC CGC AAG
 E   E   V   G   L   T   L   E   N   A   D   L   S   L   L   G   K   A   R   K
963/321                                993/331
GTC GTG GTC ACC AAG GAC GAG ACC ACC ATC GTC GAG GGC GCC GGT GAC ACC GAC GCC ATC
 V   V   V   T   K   D   E   T   T   I   V   E   G   A   G   D   T   D   A   I
1023/341                               1053/351
GCC GGA CGA GTG GCC CAG ATC CGC CAG GAG ATC GAG AAC AGC GAC TCC GAC TAC GAC CGT
 A   G   R   V   A   Q   I   R   Q   E   I   E   N   S   D   S   D   Y   D   R
1083/361                               1113/371
GAG AAG CTG CAG GAG CGG CTG GCC AAG CTG GCC GGT GGT GTC GCG GTG ATC AAG GCC GGT
 E   K   L   Q   E   R   L   A   K   L   A   G   G   V   A   V   I   K   A   G
1143/381                               1173/391
GCC GCC ACC GAG GTC GAA CTC AAG GAG CGC AAG CAC CGC ATC GAG GAT GCG GTT CGC AAT
 A   A   T   E   V   E   L   K   E   R   K   H   R   I   E   D   A   V   R   N
1203/401                               1233/411
GCC AAG GCC GCC GTC GAG GAG GGC ATC GTC GCC GGT GGG GGT GTG ACG CTG TTG CAA GCG
 A   K   A   A   V   E   E   G   I   V   A   G   G   G   V   T   L   L   Q   A
```

FIG. 1A

```
1263/421                                1293/431
GCC CCG ACC CTG GAC GAG CTG AAG CTC GAA GGC GAC GAG GCG ACC GGC GCC AAC ATC GTG
 A   P   T   L   D   E   L   K   L   E   G   D   E   A   T   G   A   N   I   V
1323/441                                1353/451
AAG GTC GCG CTG GAG GCC CCG CTG AAG CAG ATC GCC TTC AAC TCC GGG CTG GAG CCG GGC
 K   V   A   L   E   A   P   L   K   Q   I   A   F   N   S   G   L   E   P   G
1383/461                                1413/471
GTG GTG GCC GAG AAG GTG CGC AAC CTG CCG GCT GGC CAC GGA CTG AAC GCT CAG ACC GGT
 V   V   A   E   K   V   R   N   L   P   A   G   H   G   L   N   A   Q   T   G
1443/481                                1473/491
GTC TAC GAG GAT CTG CTC GCT GCC GGC GTT GCT GAC CCG GTC AAG GTG ACC CGT TCG GCG
 V   Y   E   D   L   L   A   A   G   V   A   D   P   V   K   V   T   R   S   A
1503/501                                1533/511
CTG CAG AAT GCG GCG TCC ATC GCG GGG CTG TTC CTG ACC ACC GAG GCC GTC GTT GCC GAC
 L   Q   N   A   A   S   I   A   G   L   F   L   T   T   E   A   V   V   A   D
1563/521                                1593/531
AAG CCG GAA AAG GAG AAG GCT TCC GTT CCC GGT GGC GGC GAC ATG GGT GGC ATG GAT TTC
 K   P   E   K   E   K   A   S   V   P   G   G   G   D   M   G   G   M   D   F
1623/541
TGA
 *
```

FIG. 1B

```
3/1                                              33/11
ATG gAT GGA GAT ACA CCT ACA TTG CAT GAA TAT ATG TTA GAT TTG CAA CCA GAG ACA ACT
 M   D   G   D   T   P   T   L   H   E   Y   M   L   D   L   Q   P   E   T   T
63/21                                            93/31
GAT CTC TAC TGT TAT GAG CAA TTA AAT GAC AGC TCA GAG GAG GAG GAT GAA ATA GAT GGT
 D   L   Y   C   Y   E   Q   L   N   D   S   S   E   E   E   D   E   I   D   G
123/41                                           153/51
CCA GCT GGA CAA GCA GAA CCG GAC AGA GCC CAT TAC AAT ATT GTA ACC TTT TGT TGC AAG
 P   A   G   Q   A   E   P   D   R   A   H   Y   N   I   V   T   F   C   C   K
183/61                                           213/71
TGT GAC TCT ACG CTT CGG TTG TGC GTA CAA AGC ACA CAC GTA GAC ATT CGT ACT TTG GAA
 C   D   S   T   L   R   L   C   V   Q   S   T   H   V   D   I   R   T   L   E
243/81                                           273/91
GAC CTG TTA ATG GGC ACA CTA GGA ATT GTG TGC CCC ATC TGT TCT CAG AAA CCA TAA
 D   L   L   M   G   T   L   G   I   V   C   P   I   C   S   Q   K   P   *
```

FIG. 2

```
3/1                                                          33/11
ATG GGC AGC AGC CAT CAT CAT CAT CAT CAC AGC AGC GGC CTG GTG CCG CGC GGC AGC CAT
 M   G   S   S   H   H   H   H   H   H   S   S   G   L   V   P   R   G   S   H
63/21                                                        93/31
ATG gct agc ATG CAT GGA GAT ACA CCT ACA TTG CAT GAA TAT ATG TTA GAT TTG CAA CCA
 M   A   S   M   H   G   D   T   P   T   L   H   E   Y   M   L   D   L   Q   P
123/41                                                       153/51
GAG ACA ACT GAT CTC TAC TGT TAT GAG CAA TTA AAT GAC AGC TCA GAG GAG GAG GAT GAA
 E   T   T   D   L   Y   C   Y   E   Q   L   N   D   S   S   E   E   E   D   E
183/61                                                       213/71
ATA GAT GGT CCA GCT GGA CAA GCA GAA CCG GAC AGA GCC CAT TAC AAT ATT GTA ACC TTT
 I   D   G   P   A   G   Q   A   E   P   D   R   A   H   Y   N   I   V   T   F
243/81                                                       273/91
TGT TGC AAG TGT GAC TCT ACG CTT CGG TTG TGC GTA CAA AGC ACA CAC GTA GAC ATT CGT
 C   C   K   C   D   S   T   L   R   L   C   V   Q   S   T   H   V   D   I   R
303/101                                                      333/111
ACT TTG GAA GAC CTG TTA ATG GGC ACA CTA GGA ATT GTG TGC CCC ATC TGT TCT CAG AAA
 T   L   E   D   L   L   M   G   T   L   G   I   V   C   P   I   C   S   Q   K
363/121
CCA TAA
 P   *
```

FIG. 3

```
3/1                                             33/11
atg gCC AAG ACA ATT GCG TAC GAC GAA GAG GCC CGT CGC GGC CTC GAG CGG GGC TTG AAC
 M   A   K   T   I   A   Y   D   E   E   A   R   R   G   L   E   R   G   L   N
63/21                                           93/31
GCC CTC GCC GAT GCG GTA AAG GTG ACA TTG GGC CCC AAG GGC CGC AAC GTC GTC CTG GAA
 A   L   A   D   A   V   K   V   T   L   G   P   K   G   R   N   V   V   L   E
123/41                                          153/51
AAG AAG TGG GGT GCC CCC ACG ATC ACC AAC GAT GGT GTG TCC ATC GCC AAG GAG ATC GAG
 K   K   W   G   A   P   T   I   T   N   D   G   V   S   I   A   K   E   I   E
183/61                                          213/71
CTG GAG GAT CCG TAC GAG aag atc ggc GCC GAG CTG GTC AAA GAG GTA GCC AAG AAG ACC
 L   E   D   P   Y   E   K   I   G   A   E   L   V   K   E   V   A   K   K   T
243/81                                          273/91
GAT GAC GTC GCC GGT GAC GGC ACC ACG ACG GCC ACC GTG CTG GCC CAG GCG TTG GTT CGC
 D   D   V   A   G   D   G   T   T   T   A   T   V   L   A   Q   A   L   V   R
303/101                                         333/111
gAg GGC CTG CGC AAC GTC GCG GCC GGC GCC AAC CCG CTC GGT CTC AAA CGC GGC ATC GAA
 E   G   L   R   N   V   A   A   G   A   N   P   L   G   L   K   R   G   I   E
363/121                                         393/131
AAG GCC GTG GAG AAG GTC ACC GAG ACC CTG CTC AAG GGC GCC AAG GAG GTC GAG ACC AAG
 K   A   V   E   K   V   T   E   T   L   L   K   G   A   K   E   V   E   T   K
423/141                                         453/151
GAG CAG ATT GCG GCC ACC GCA GCG ATT TCG GCG GGT GAC CAG TCC ATC GGT GAC CTG ATC
 E   Q   I   A   A   T   A   A   I   S   A   G   D   Q   S   I   G   D   L   I
483/161                                         513/171
GCC GAG GCG ATG GAC AAG GTG GGC AAC GAG GGC GTC ATC ACC GTC GAG GAG TCC AAC ACC
 A   E   A   M   D   K   V   G   N   E   G   V   I   T   V   E   E   S   N   T
543/181                                         573/191
TTT GGG CTG CAG CTC GAG CTC ACC GAG GGT ATG CGG TTC GAC AAG GGC TAC ATC TCG GGG
 F   G   L   Q   L   E   L   T   E   G   M   R   F   D   K   G   Y   I   S   G
603/201                                         633/211
TAC TTC GTG ACC GAC CCG GAG CGT CAG GAG GCG GTC CTG GAG GAC CCC TAC ATC CTG CTG
 Y   F   V   T   D   P   E   R   Q   E   A   V   L   E   D   P   Y   I   L   L
663/221                                         693/231
GTC AGC TCC AAG GTG TCC ACT GTC AAG GAT CTG CTG CCG CTC CTC GAG AAG GTC ATC GGA
 V   S   S   K   V   S   T   V   K   D   L   L   P   L   L   E   K   V   I   G
723/241                                         753/251
GCC GGT AAG CCG CTG CTG ATC ATC GCC GAG GAC GTC GAG GGC GAG GCG CTG TCC ACC CTG
 A   G   K   P   L   L   I   I   A   E   D   V   E   G   E   A   L   S   T   L
783/261                                         813/271
GTC GTC AAC AAG ATC CGC GGC ACC TTC AAG TCG GTG GCG GTC AAG GCT CCC GGC TTC GGC
 V   V   N   K   I   R   G   T   F   K   S   V   A   V   K   A   P   G   F   G
843/281                                         873/291
GAC CGC CGC AAG GCG ATG CTG CAG GAT ATG GCC ATT CTC ACC GGT GGT CAG GTG ATC AGC
 D   R   R   K   A   M   L   Q   D   M   A   I   L   T   G   G   Q   V   I   S
903/301                                         933/311
GAA GAG GTC GGC CTG ACG CTG GAG AAC GCC GAC CTG TCG CTG CTA GGC AAG GCC CGC AAG
 E   E   V   G   L   T   L   E   N   A   D   L   S   L   L   G   K   A   R   K
963/321                                         993/331
GTC GTG GTC ACC AAG GAC GAG ACC ACC ATC GTC GAG GGC GCC GGT GAC ACC GAC GCC ATC
 V   V   V   T   K   D   E   T   T   I   V   E   G   A   G   D   T   D   A   I
1023/341                                        1053/351
GCC GGA CGA GTG GCC CAG ATC CGC CAG GAG ATC GAG AAC AGC GAC TCC GAC TAC GAC CGT
 A   G   R   V   A   Q   I   R   Q   E   I   E   N   S   D   S   D   Y   D   R
1083/361                                        1113/371
GAG AAG CTG CAG GAG CGG CTG GCC AAG CTG GCC GGT GGT GTC GCG GTG ATC AAG GCC GGT
 E   K   L   Q   E   R   L   A   K   L   A   G   G   V   A   V   I   K   A   G
1143/381                                        1173/391
GCC GCC ACC GAG GTC GAA CTC AAG GAG CGC AAG CAC CGC ATC GAG GAT GCG GTT CGC AAT
 A   A   T   E   V   E   L   K   E   R   K   H   R   I   E   D   A   V   R   N
1203/401                                        1233/411
GCC AAG GCC GCC GTC GAG GAG GGC ATC GTC GCC GGT GGG GGT GTG ACG CTG TTG CAA GCG
 A   K   A   A   V   E   E   G   I   V   A   G   G   G   V   T   L   L   Q   A
```

FIG. 4A

```
1263/421                                1293/431
GCC CCG ACC CTG GAC GAG CTG AAG CTC GAA GGC GAC GAG GCG ACC GGC GCC AAC ATC GTG
 A   P   T   L   D   E   L   K   L   E   G   D   E   A   T   G   A   N   I   V
1323/441                                1353/451
AAG GTG GCG CTG GAG GCC CCG CTG AAG CAG ATC GCC TTC AAC TCC GGG CTG GAG CCG GGC
 K   V   A   L   E   A   P   L   K   Q   I   A   F   N   S   G   L   E   P   G
1383/461                                1413/471
GTG GTG GCC GAG AAG GTG CGC AAC CTG CCG GCT GGC CAC GGA CTG AAC GCT CAG ACC GGT
 V   V   A   E   K   V   R   N   L   P   A   G   H   G   L   N   A   Q   T   G
1443/481                                1473/491
GTC TAC GAG GAT CTG CTC GCT GCC GGC GTT GCT GAC CCG GTC AAG GTG ACC CGT TCG GCG
 V   Y   E   D   L   L   A   A   G   V   A   D   P   V   K   V   T   R   S   A
1503/501                                1533/511
CTG CAG AAT GCG GCG TCC ATC GCG GGG CTG TTC CTG ACC ACC GAG GCC GTC GTT GCC GAC
 L   Q   N   A   A   S   I   A   G   L   F   L   T   T   E   A   V   V   A   D
1563/521                                1593/531
AAG CCG GAA AAG GAG AAG GCT TCC GTT CCC GGT GGC GGC GAC ATG GGT GGC ATG GAT TTC
 K   P   E   K   E   K   A   S   V   P   G   G   G   D   M   G   G   M   D   F
1623/541                                1653/551
cat atg cat gga gat aca cct aca ttg cat gaa tat atg tta gat ttg caa cca gag aca
 H   M   H   G   D   T   P   T   L   H   E   Y   M   L   D   L   Q   P   E   T
1683/561                                1713/571
act gat ctc tac tgt tat gag caa tta aat gac agc tca gag gag gag gat gaa ata gat
 T   D   L   Y   C   Y   E   Q   L   N   D   S   S   E   E   E   D   E   I   D
1743/581                                1773/591
ggt cca gct gga caa gca gaa ccg gac aga gcc cat tac aat att gta acc ttt tgt tgc
 G   P   A   G   Q   A   E   P   D   R   A   H   Y   N   I   V   T   F   C   C
1803/601                                1833/611
aag tgt gac tct acg ctt cgg ttg tgc gta caa agc aca cac gta gac att cgt act ttg
 K   C   D   S   T   L   R   L   C   V   Q   S   T   H   V   D   I   R   T   L
1863/621                                1893/631
gaa gac ctg tta atg ggc aca cta gga att gtg tgc ccc atc tgt tct cag aaa cca TAA
 E   D   L   L   M   G   T   L   G   I   V   C   P   I   C   S   Q   K   P   *
```

FIG. 4B

```
1303/421                                1333/431
GAG CAA TTA AAT GAC AGC TCA GAG GAG GAG GAT GAA ATA GAT GGT CCA GCT GGA CAA GCA
 E   Q   L   N   D   S   S   E   E   E   D   E   I   D   G   P   A   G   Q   A
1363/441                                1393/451
GAA CCG GAC AGA GCC CAT TAC AAT ATT GTA ACC TTT TGT TGC AAG TGT GAC TCT ACG CTT
 E   P   D   R   A   H   Y   N   I   V   T   F   C   C   K   C   D   S   T   L
1423/461                                1453/471
CGG TTG TGC GTA CAA AGC ACA CAC GTA GAC ATT CGT ACT TTG GAA GAC CTG TTA ATG GGC
 R   L   C   V   Q   S   T   H   V   D   I   R   T   L   E   D   L   L   M   G
1483/481                                1513/491
ACA CTA GGA ATT GTG TGC CCC ATC TGT TCT CAG AAA CCA TAG
 T   L   G   I   V   C   P   I   C   S   Q   K   P   *
```

FIG. 5B

```
43/1                                          73/11
ATG GCC CAA AGG GAA TGG GTC GAA AAA GAC  TTC TAC CAG GAG CTG GGC GTC TCC TCT GAT
 M   A   Q   R   E   W   V   E   K   D    F   Y   Q   E   L   G   V   S   S   D
103/21                                        133/31
GCC AGT CCT GAA GAG ATC AAA CGT GCC TAT  CGG AAG TTG GCG CGC GAC CTG CAT CCG GAC
 A   S   P   E   E   I   K   R   A   Y    R   K   L   A   R   D   L   H   P   D
163/41                                        193/51
GCG AAC CCG GGC AAC CCG GCC GCC GGC GAA  CGG TTC AAG GCG GTT TCG GAG GCG CAT AAC
 A   N   P   G   N   P   A   A   G   E    R   F   K   A   V   S   E   A   H   N
223/61                                        253/71
GTG CTG TCG GAT CCG GCC AAG CGC AAG GAG  TAC GAC GAA ACC CGC CGC CTG TTC GCC GGC
 V   L   S   D   P   A   K   R   K   E    Y   D   E   T   R   R   L   F   A   G
283/81                                        313/91
GGC GGG TTC GGC GGC CGT CGG TTC GAC AGC  GGC TTT GGG GGC GGG TTC GGC GGT TTC GGG
 G   G   F   G   G   R   R   F   D   S    G   F   G   G   G   F   G   G   F   G
343/101                                       373/111
GTC GGT GGA GAC GGC GCC GAG TTC AAC CTC  AAC GAC TTG TTC GAC GCC GCC AGC CGA ACC
 V   G   G   D   G   A   E   F   N   L    N   D   L   F   D   A   A   S   R   T
403/121                                       433/131
GGC GGT ACC ACC ATC GGT GAC TTG TTC GGT  GGC TTG TTC GGA CGC GGT GGC AGC GCC CGT
 G   G   T   T   I   G   D   L   F   G    G   L   F   G   R   G   G   S   A   R
463/141                                       493/151
CCC AGC CGC CCG CGA CGC GGC AAC GAC CTG  GAG ACC GAG ACC GAG TTG GAT TTC GTG GAG
 P   S   R   P   R   R   G   N   D   L    E   T   E   T   E   L   D   F   V   E
523/161                                       553/171
GCC GCC AAG GGC GTG GCG ATG CCG CTG CGA  TTA ACC AGC CCG GCG CCG TGC ACC AAC TGC
 A   A   K   G   V   A   M   P   L   R    L   T   S   P   A   P   C   T   N   C
583/181                                       613/191
CAT GGC AGC GGG GCC CGG CCA GGC ACC AGC  CCA AAG GTG TGT CCC ACT TGC AAC GGG TCG
 H   G   S   G   A   R   P   G   T   S    P   K   V   C   P   T   C   N   G   S
643/201                                       673/211
GGC GTG ATC AAC CGC AAT CAG GGC GCG TTC  GGC TTC TCC GAG CCG TGC ACC GAC TGC CGA
 G   V   I   N   R   N   Q   G   A   F    G   F   S   E   P   C   T   D   C   R
703/221                                       733/231
GGT AGC GGC TCG ATC ATC GAG CAC CCC TGC  GAG GAG TGC AAA GGC ACC GGC GTG ACC ACC
 G   S   G   S   I   I   E   H   P   C    E   E   C   K   G   T   G   V   T   T
763/241                                       793/251
CGC ACC CGA ACC ATC AAC GTG CGG ATC CCG  CCC GGT GTC GAG GAT GGG CAG CGC ATC CGG
 R   T   R   T   I   N   V   R   I   P    P   G   V   E   D   G   Q   R   I   R
823/261                                       853/271
CTA GCC GGT CAG GGC GAG GCC GGG TTG CGC  GGC GCT CCC TCG GGG GAT CTC TAC GTG ACG
 L   A   G   Q   G   E   A   G   L   R    G   A   P   S   G   D   L   Y   V   T
883/281                                       913/291
GTG CAT GTG CGG CCC GAC AAG ATC TTC GGC  CGC GAC GGC GAC GAC CTC ACC GTC ACC GTT
 V   H   V   R   P   D   K   I   F   G    R   D   G   D   D   L   T   V   T   V
943/301                                       973/311
CCG GTC AGC TTC ACC GAA TTG GCT TTG GGC  TCG ACG CTG TCG GTG CCT ACC CTG GAC GGC
 P   V   S   F   T   E   L   A   L   G    S   T   L   S   V   P   T   L   D   G
1003/321                                      1033/331
ACG GTC GGG GTC CGG GTG CCC AAA GGC ACC  GCT GAC GGC CGC ATT CTG CGT GTG CGC GGA
 T   V   G   V   R   V   P   K   G   T    A   D   G   R   I   L   R   V   R   G
1063/341                                      1093/351
CGC GGT GTG CCC AAG CGC AGT GGG GGT AGC  GGC GAC CTA CTT GTC ACC GTG AAG GTG GCC
 R   G   V   P   K   R   S   G   G   S    G   D   L   L   V   T   V   K   V   A
1123/361                                      1153/371
GTG CCG CCC AAT TTG GCA GGC GCC GCT CAG  GAA GCT CTG GAA GCC TAT GCG GCG GCG GAG
 V   P   P   N   L   A   G   A   A   Q    E   A   L   E   A   Y   A   A   A   E
1183/381                                      1213/391
CGG TCC AGT GGT TTC AAC CCG CGG GCC GGA  TGG GCA GGT AAT CGC ATG CAT GGA GAT ACA
 R   S   S   G   F   N   P   R   A   G    W   A   G   N   R   M   H   G   D   T
1243/401                                      1273/411
CCT ACA TTG CAT GAA TAT ATG TTA GAT TTG  CAA CCA GAG ACA ACT GAT CTC TAC TGT TAT
 P   T   L   H   E   Y   M   L   D   L    Q   P   E   T   T   D   L   Y   C   Y
```

FIG. 5A

```
3/1                                         33/11
ATG GGC AGC AGC CAT CAT CAT CAT CAT CAC AGC AGC GGC CTG GTG CCG CGC GGC AGC CAT
 M   G   S   S   H   H   H   H   H   H   S   S   G   L   V   P   R   G   S   H
63/21                                       93/31
ATG gct agc atg ggc tcc atc ggc gca gca agc atg gaa ttt tgt ttt gat gta ttc aag
 M   A   S   M   G   S   I   G   A   A   S   M   E   F   C   F   D   V   F   K
123/41                                      153/51
gag ctc aaa gtc cac cat gcc aat gag aac atc ttc tac tgc ccc att gcc atc atg tca
 E   L   K   V   H   H   A   N   E   N   I   F   Y   C   P   I   A   I   M   S
183/61                                      213/71
gct cta gcc atg gta tac ctg ggt gca aaa gac agc acc agg aca cag ata aat aag gtt
 A   L   A   M   V   Y   L   G   A   K   D   S   T   R   T   Q   I   N   K   V
243/81                                      273/91
gtt cgc ttt gat aaa ctt cca gga ttc gga gac agt att gaa gct cag tgt ggc aca tct
 V   R   F   D   K   L   P   G   F   G   D   S   I   E   A   Q   C   G   T   S
303/101                                     333/111
gta aac gtt cac tct tca ctt aga gac atc ctc aac caa atc acc aaa cca aat gat gtt
 V   N   V   H   S   S   L   R   D   I   L   N   Q   I   T   K   P   N   D   V
363/121                                     393/131
tat tcg ttc agc ctt gcc agt aga ctt tat gct gaa gag aga tac cca atc ctg cca gaa
 Y   S   F   S   L   A   S   R   L   Y   A   E   E   R   Y   P   I   L   P   E
423/141                                     453/151
tac ttg cag tgt gtg aag gaa ctg tat aga gga ggc ttg gaa cct atc aac ttt caa aca
 Y   L   Q   C   V   K   E   L   Y   R   G   G   L   E   P   I   N   F   Q   T
483/161                                     513/171
gct gca gat caa gcc aga gag ctc atc aat tcc tgg gta gaa agt cag aca aat gga att
 A   A   D   Q   A   R   E   L   I   N   S   W   V   E   S   Q   T   N   G   I
543/181                                     573/191
atc aga aat gtc ctt cag cca agc tcc gtg gat tct caa act gca atg gtt ctg gtt aat
 I   R   N   V   L   Q   P   S   S   V   D   S   Q   T   A   M   V   L   V   N
603/201                                     633/211
gcc att gtc ttc aaa gga ctg tgg gag aaa aca ttt aag gat gaa gac aca caa gca atg
 A   I   V   F   K   G   L   W   E   K   T   F   K   D   E   D   T   Q   A   M
663/221                                     693/231
cct ttc aga gtg act gag caa gaa agc aaa cct gtg cag atg atg tac cag att ggt tta
 P   F   R   V   T   E   Q   E   S   K   P   V   Q   M   M   Y   Q   I   G   L
723/241                                     753/251
ttt aga gtg gca tca atg gct tct gag aaa atg aag atc ctg gag ctt cca ttt gcc agt
 F   R   V   A   S   M   A   S   E   K   M   K   I   L   E   L   P   F   A   S
783/261                                     813/271
ggg aca atg agc atg ttg gtg ctg ttg cct gat gaa gtc tca ggc ctt gag cag ctt gag
 G   T   M   S   M   L   V   L   L   P   D   E   V   S   G   L   E   Q   L   E
843/281                                     873/291
agt ata atc aac ttt gaa aaa ctg act gaa tgg acc agt tct aat gtt atg gaa gag agg
 S   I   I   N   F   E   K   L   T   E   W   T   S   S   N   V   M   E   E   R
903/301                                     933/311
aag atc aaa gtg tac tta cct cgc atg aag atg gag gaa aaa tac aac ctc aca tct gtc
 K   I   K   V   Y   L   P   R   M   K   M   E   E   K   Y   N   L   T   S   V
963/321                                     993/331
tta atg gct atg ggc att act gac gtg ttt agc tct tca gcc aat ctg tct ggc atc tcc
 L   M   A   M   G   I   T   D   V   F   S   S   S   A   N   L   S   G   I   S
1023/341                                    1053/351
tca gca gag agc ctg aag ata tct caa gct gtc cat gca gca cat gca gaa atc aat gaa
 S   A   E   S   L   K   I   S   Q   A   V   H   A   A   H   A   E   I   N   E
1083/361                                    1113/371
gca ggc aga gag gtg gta ggg tca gca gag gct gga gtg gat gct gca agc gtc tct gaa
 A   G   R   E   V   V   G   S   A   E   A   G   V   D   A   A   S   V   S   E
1143/381                                    1173/391
gaa ttt agg gct gac cat cca ttc ctc ttc tgt atc aag cac atc gca acc aac gcc gtt
 E   F   R   A   D   H   P   F   L   F   C   I   K   H   I   A   T   N   A   V
1203/401
ctc ttc ttt ggc aga tgt gtt gga tcc taa
 L   F   F   G   R   C   V   G   S   *
```

FIG. 6

```
3/1                                          33/11
atg gGC AGC AGC CAT CAT CAT CAT CAT CAC AGC AGC GGC CTG GTG CCG CGC GGC AGC cat
 M   G   S   S   H   H   H   H   H   H   S   S   G   L   V   P   R   G   S   H
63/21                                        93/31
atg GCC AAG ACA ATT GCG TAC GAC GAA GAG GCC CGT CGC GGC CTC GAG CGG GGC TTG AAC
 M   A   K   T   I   A   Y   D   E   E   A   R   R   G   L   E   R   G   L   N
123/41                                       153/51
GCC CTC GCC GAT GCG GTA AAG GTG ACA TTG GGC CCC AAG GGC CGC AAC GTC GTC CTG GAA
 A   L   A   D   A   V   K   V   T   L   G   P   K   G   R   N   V   V   L   E
183/61                                       213/71
AAG AAG TGG GGT GCC CCC ACG ATC ACC AAC GAT GGT GTG TCC ATC GCC AAG GAG ATC GAG
 K   K   W   G   A   P   T   I   T   N   D   G   V   S   I   A   K   E   I   E
243/81                                       273/91
CTG GAG GAT CCG TAC GAG aag atc ggc GCC GAG CTG GTC AAA GAG GTA GCC AAG AAG ACC
 L   E   D   P   Y   E   K   I   G   A   E   L   V   K   E   V   A   K   K   T
303/101                                      333/111
GAT GAC GTC GCC GGT GAC GGC ACC ACG ACG GCC ACC GTG CTG GCC CAG GCG TTG GTT CGC
 D   D   V   A   G   D   G   T   T   T   A   T   V   L   A   Q   A   L   V   R
363/121                                      393/131
gAg GGC CTG CGC AAC GTC GCG GCC GGC GCC AAC CCG CTC GGT CTC AAA CGC GGC ATC GAA
 E   G   L   R   N   V   A   A   G   A   N   P   L   G   L   K   R   G   I   E
423/141                                      453/151
AAG GCC GTG GAG AAG GTC ACC GAG ACC CTG CTC AAG GGC GCC AAG GAG GTC GAG ACC AAG
 K   A   V   E   K   V   T   E   T   L   L   K   G   A   K   E   V   E   T   K
483/161                                      513/171
GAG CAG ATT GCG GCC ACC GCA GCG ATT TCG GCG GGT GAC CAG TCC ATC GGT GAC CTG ATC
 E   Q   I   A   A   T   A   A   I   S   A   G   D   Q   S   I   G   D   L   I
543/181                                      573/191
GCC GAG GCG ATG GAC AAG GTG GGC AAC GAG GGC GTC ATC ACC GTC GAG GAG TCC AAC ACC
 A   E   A   M   D   K   V   G   N   E   G   V   I   T   V   E   E   S   N   T
603/201                                      633/211
TTT GGG CTG CAG CTC GAG CTC ACC GAG GGT ATG CGG TTC GAC AAG GGC TAC ATC TCG GGG
 F   G   L   Q   L   E   L   T   E   G   M   R   F   D   K   G   Y   I   S   G
663/221                                      693/231
TAC TTC GTG ACC GAC CCG GAG CGT CAG GAG GCG GTC CTG GAG GAC CCC TAC ATC CTG CTG
 Y   F   V   T   D   P   E   R   Q   E   A   V   L   E   D   P   Y   I   L   L
723/241                                      753/251
GTC AGC TCC AAG GTG TCC ACT GTC AAG GAT CTG CTG CCG CTC CTC GAG AAG GTC ATC GGA
 V   S   S   K   V   S   T   V   K   D   L   L   P   L   L   E   K   V   I   G
783/261                                      813/271
GCC GGT AAG CCG CTG CTG ATC ATC GCC GAG GAC GTC GAG GGC GAG GCG CTG TCC ACC CTG
 A   G   K   P   L   L   I   I   A   E   D   V   E   G   E   A   L   S   T   L
843/281                                      873/291
GTC GTC AAC AAG ATC CGC GGC ACC TTC AAG TCG GTG GCG GTC AAG GCT CCC GGC TTC GGC
 V   V   N   K   I   R   G   T   F   K   S   V   A   V   K   A   P   G   F   G
903/301                                      933/311
GAC CGC CGC AAG GCG ATG CTG CAG GAT ATG GCC ATT CTC ACC GGT GGT CAG GTG ATC AGC
 D   R   R   K   A   M   L   Q   D   M   A   I   L   T   G   G   Q   V   I   S
963/321                                      993/331
GAA GAG GTC GGC CTG ACG CTG GAG AAC GCC GAC CTG TCG CTG CTA GGC AAG GCC CGC AAG
 E   E   V   G   L   T   L   E   N   A   D   L   S   L   L   G   K   A   R   K
1023/341                                     1053/351
GTC GTG GTC ACC AAG GAC GAG ACC ACC ATC GTC GAG GGC GCC GGT GAC ACC GAC GCC ATC
 V   V   V   T   K   D   E   T   T   I   V   E   A   G   D   T   D   A   I
1083/361                                     1113/371
GCC GGA CGA GTG GCC CAG ATC CGC CAG GAG ATC GAG AAC AGC GAC TCC GAC TAC GAC CGT
 A   G   R   V   A   Q   I   R   Q   E   I   E   N   S   D   S   D   Y   D   R
1143/381                                     1173/391
GAG AAG CTG CAG GAG CGG CTG GCC AAG CTG GCC GGT GGT GTC GCG GTG ATC AAG GCC GGT
 E   K   L   Q   E   R   L   A   K   L   A   G   G   V   A   V   I   K   A   G
1203/401                                     1233/411
GCC GCC ACC GAG GTC GAA CTC AAG GAG CGC AAG CAC CGC ATC GAG GAT GCG GTT CGC AAT
 A   A   T   E   V   E   L   K   E   R   K   H   R   I   E   D   A   V   R   N
```

FIG. 7A

```
1263/421
GCC AAG GCC GCC GTC GAG GAG GGC ATC GTC
 A   K   A   A   V   E   E   G   I   V
1323/441
GCC CCG ACC CTG GAC GAG CTG AAG CTC GAA
 A   P   T   L   D   E   L   K   L   E
1383/461
AAG GTG GCG CTG GAG GCC CCG CTG AAG CAG
 K   V   A   L   E   A   P   L   K   Q
1443/481
GTG GTG GCC GAG AAG GTG CGC AAC CTG CCG
 V   V   A   E   K   V   R   N   L   P
1503/501
GTC TAC GAG GAT CTG CTC GCT GCC GGC GTT
 V   Y   E   D   L   L   A   A   G   V
1563/521
CTG CAG AAT GCG GCG TCC ATC GCG GGG CTG
 L   Q   N   A   A   S   I   A   G   L
1623/541
AAG CCG GAA AAG GAG AAG GCT TCC GTT CCC
 K   P   E   K   E   K   A   S   V   P
1683/561
gct agc ATG ggc tcc atc ggc gca gca agc
 A   S   M   G   S   I   G   A   A   S
1743/581
ctc aaa gtc cac cat gcc aat gag aac atc
 L   K   V   H   H   A   N   E   N   I
1803/601
cta gcc atg gta tac ctg ggt gca aaa gac
 L   A   M   V   Y   L   G   A   K   D
1863/621
cgc ttt gat aaa ctt cca gga ttc gga gac
 R   F   D   K   L   P   G   F   G   D
1923/641
aac gtt cac tct tca ctt aga gac atc ctc
 N   V   H   S   S   L   R   D   I   L
1983/661
tcg ttc agc ctt gcc agt aga ctt tat gct
 S   F   S   L   A   S   R   L   Y   A
2043/681
ttg cag tgt gtg aag gaa ctg tat aga gga
 L   Q   C   V   K   E   L   Y   R   G
2103/701
gca gat caa gcc aga gag ctc atc aat tcc
 A   D   Q   A   R   E   L   I   N   S
2163/721
aga aat gtc ctt cag cca agc tcc gtg gat
 R   N   V   L   Q   P   S   S   V   D
2223/741
att gtc ttc aaa gga ctg tgg gag aaa aca
 I   V   F   K   G   L   W   E   K   T
2283/761
ttc aga gtg act gag caa gaa agc aaa cct
 F   R   V   T   E   Q   E   S   K   P
2343/781
aga gtg gca tca atg gct tct gag aaa atg
 R   V   A   S   M   A   S   E   K   M
2403/801
aca atg agc atg ttg gtg ctg ttg cct gat
 T   M   S   M   L   V   L   L   P   D
2463/821
ata atc aac ttt gaa aaa ctg act gaa tgg
 I   I   N   F   E   K   L   T   E   W
2523/841
atc aaa gtg tac tta cct cgc atg aag atg
 I   K   V   Y   L   P   R   M   K   M
2583/861
atg gct atg ggc att act gac gtg ttt agc
 M   A   M   G   I   T   D   V   F   S 1293/431
GCC GGT GGG GGT GTG ACG CTG TTG CAA GCG
 A   G   G   V   T   L   L   Q   A
1353/451
GGC GAC GAG GCG ACC GGC GCC AAC ATC GTG
 G   D   E   A   T   G   A   N   I   V
1413/471
ATC GCC TTC AAC TCC GGG CTG GAG CCG GGC
 I   A   F   N   S   G   L   E   P   G
1473/491
GCT GGC CAC GGA CTG AAC GCT CAG ACC GGT
 A   G   H   G   L   N   A   Q   T   G
1533/511
GCT GAC CCG GTC AAG GTG ACC CGT TCG GCG
 A   D   P   V   K   V   T   R   S   A
1593/531
TTC CTG ACC ACC GAG GCC GTC GTT GCC GAC
 F   L   T   T   E   A   V   V   A   D
1653/551
GGT GGC GGC GAC ATG GGT GGC ATG GAT TTC
 G   G   G   D   M   G   G   M   D   F
1713/571
atg gaa ttt tgt ttt gat gta ttc aag gag
 M   E   F   C   F   D   V   F   K   E
1773/591
ttc tac tgc ccc att gcc atc atg tca gct
 F   Y   C   P   I   A   I   M   S   A
1833/611
agc acc agg aca cag ata aat aag gtt gtt
 S   T   R   T   Q   I   N   K   V   V
1893/631
agt att gaa gct cag tgt ggc aca tct gta
 S   I   E   A   Q   C   G   T   S   V
1953/651
aac caa atc acc aaa cca aat gat gtt tat
 N   Q   I   T   K   P   N   D   V   Y
2013/671
gaa gag aga tac cca atc ctg cca gaa tac
 E   E   R   Y   P   I   L   P   E   Y
2073/691
ggc ttg gaa cct atc aac ttt caa aca gct
 G   L   E   P   I   N   F   Q   T   A
2133/711
tgg gta gaa agt cag aca aat gga att atc
 W   V   E   S   Q   T   N   G   I   I
2193/731
tct caa act gca atg gtt ctg gtt aat gcc
 S   Q   T   A   M   V   L   V   N   A
2253/751
ttt aag gat gaa gac aca caa gca atg cct
 F   K   D   E   D   T   Q   A   M   P
2313/771
gtg cag atg atg tac cag att ggt tta ttt
 V   Q   M   M   Y   Q   I   G   L   F
2373/791
aag atc ctg gag ctt cca ttt gcc agt ggg
 K   I   L   E   L   P   F   A   S   G
2433/811
gaa gtc tca ggc ctt gag cag ctt gag agt
 E   V   S   G   L   E   Q   L   E   S
2493/831
acc agt tca aat gtt atg gaa gag agg aag
 T   S   S   N   V   M   E   E   R   K
2553/851
gag gaa aaa tac aac ctc aca tct gtc tta
 E   E   K   Y   N   L   T   S   V   L
2613/871
tct tca gcc aat ctg tct ggc atc tcc tca
 S   S   A   N   L   S   G   I   S   S
```

FIG. 7B

```
2643/881                              2673/891
gca gag agc ctg aag ata tct caa gct gtc cat gca gca cat gca gaa atc aat gaa gca
 A   E   S   L   K   I   S   Q   A   V   H   A   A   H   A   E   I   N   E   A
2703/901                              2733/911
ggc aga gag gtg gta ggg tca gca gag gct gga gtg gat gct gca agc gtc tct gaa gaa
 G   R   E   V   V   G   S   A   E   A   G   V   D   A   A   S   V   S   E   E
2763/921                              2793/931
ttt agg gct gac cat cca ttc ctc ttc tgt atc aag cac atc gca acc aac gcc gtt ctc
 F   R   A   D   H   P   F   L   F   C   I   K   H   I   A   T   N   A   V   L
2823/941
ttc ttt ggc aga tgt gtt gga tcc TAA
 F   F   G   R   C   V   G   S   *
```

FIG. 7C

```
1/1                                    31/11
atg tcc cct ata cta ggt tat tgg aaa att aag ggc ctt gtg caa ccc act cga ctt ctt
 M   S   P   I   L   G   Y   W   K   I   K   G   L   V   Q   P   T   R   L   L
61/21                                  91/31
ttg gaa tat ctt gaa gaa aaa tat gaa gag cat ttg tat gag cgc gat gaa ggt gat aaa
 L   E   Y   L   E   E   K   Y   E   E   H   L   Y   E   R   D   E   G   D   K
121/41                                 151/51
tgg cga aac aaa aag ttt gaa ttg ggt ttg gag ttt ccc aat ctt cct tat tat att gat
 W   R   N   K   K   F   E   L   G   L   E   F   P   N   L   P   Y   Y   I   D
181/61                                 211/71
ggt gat gtt aaa tta aca cag tct atg gcc atc ata cgt tat ata gct gac aag cac aac
 G   D   V   K   L   T   Q   S   M   A   I   I   R   Y   I   A   D   K   H   N
241/81                                 271/91
atg ttg ggt ggt tgt cca aaa gag cgt gca gag att tca atg ctt gaa gga gcg gtt ttg
 M   L   G   G   C   P   K   E   R   A   E   I   S   M   L   E   G   A   V   L
301/101                                331/111
gat att aga tac ggt gtt tcg aga att gca tat agt aaa gac ttt gaa act ctc aaa gtt
 D   I   R   Y   G   V   S   R   I   A   Y   S   K   D   F   E   T   L   K   V
361/121                                391/131
gat ttt ctt agc aag cta cct gaa atg ctg aaa atg ttc gaa gat cgt tta tgt cat aaa
 D   F   L   S   K   L   P   E   M   L   K   M   F   E   D   R   L   C   H   K
421/141                                451/151
aca tat tta aat ggt gat cat gta acc cat cct gac ttc atg ttg tat gac gct ctt gat
 T   Y   L   N   G   D   H   V   T   H   P   D   F   M   L   Y   D   A   L   D
481/161                                511/171
gtt gtt tta tac atg gac cca atg tgc ctg gat gcg ttc cca aaa tta gtt tgt ttt aaa
 V   V   L   Y   M   D   P   M   C   L   D   A   F   P   K   L   V   C   F   K
541/181                                571/191
aaa cgt att gaa gct atc cca caa att gat aag tac ttg aaa tcc agc aag tat ata gca
 K   R   I   E   A   I   P   Q   I   D   K   Y   L   K   S   S   K   Y   I   A
601/201                                631/211
tgg cct ttg cag ggc tgg caa gcc acg ttt ggt ggt ggc gac cat cct cca aaa tcg gat
 W   P   L   Q   G   W   Q   A   T   F   G   G   G   D   H   P   P   K   S   D
661/221                                691/231
ctg gtt ccg cgt gga tcc cca gga att ccc ggg tcg aCT CGA GCA CCA CCA CCA CCA CCA
 L   V   P   R   G   S   P   G   I   P   G   S   T   R   A   P   P   P   P   P
721/241
CTG AGA TCC GGC TGC TAA
 L   R   S   G   C   *
```

FIG. 8

```
1/1                                      31/11
atg tcc cct ata cta ggt tat tgg aaa att  aag ggc ctt gtg caa ccc act cga ctt ctt
 M   S   P   I   L   G   Y   W   K   I    K   G   L   V   Q   P   T   R   L   L
61/21                                    91/31
ttg gaa tat ctc gaa gaa aaa tat gaa gag  cat ttg tat gag cgc gat gaa ggt gat aaa
 L   E   Y   L   E   E   K   Y   E   E    H   L   Y   E   R   D   E   G   D   K
121/41                                   151/51
tgg cga aac aaa aag ttt gaa ttg ggt ttg  gag ttt ccc aat ctt cct tat tat att gat
 W   R   N   K   K   F   E   L   G   L    E   F   P   N   L   P   Y   Y   I   D
181/61                                   211/71
ggt gat gtt aaa tta aca cag tct atg gcc  atc ata cgt tat ata gct gac aag cac aac
 G   D   V   K   L   T   Q   S   M   A    I   I   R   Y   I   A   D   K   H   N
241/81                                   271/91
atg ttg ggt ggt tgt cca aaa gag cgt gca  gag att tca atg ctt gaa gga gcg gtt ttg
 M   L   G   G   C   P   K   E   R   A    E   I   S   M   L   E   G   A   V   L
301/101                                  331/111
gat att aga tac ggt gtt tcg aga att gca  tat agt aaa gac ttt gaa act ctc aaa gtt
 D   I   R   Y   G   V   S   R   I   A    Y   S   K   D   F   E   T   L   K   V
361/121                                  391/131
gat ttt ctt agc aag cta cct gaa atg ctg  aaa atg ttc gaa gat cgt tta tgt cat aaa
 D   F   L   S   K   L   P   E   M   L    K   M   F   E   D   R   L   C   H   K
421/141                                  451/151
aca tat tta aat ggt gat cat gta acc cat  cct gac ttc atg ttg tat gac gct ctt gat
 T   Y   L   N   G   D   H   V   T   H    P   D   F   M   L   Y   D   A   L   D
481/161                                  511/171
gtt gtt tta tac atg gac cca atg tgc ctg  gat gcg ttc cca aaa tta gtt tgt ttt aaa
 V   V   L   Y   M   D   P   M   C   L    D   A   F   P   K   L   V   C   F   K
541/181                                  571/191
aaa cgt att gaa gct atc cca caa att gat  aag tac ttg aaa tcc agc aag tat ata gca
 K   R   I   E   A   I   P   Q   I   D    K   Y   L   K   S   S   K   Y   I   A
601/201                                  631/211
tgg cct ttg cag ggc tgg caa gcc acg ttt  ggt ggt ggc gac cat cct cca aaa tcg gat
 W   P   L   Q   G   W   Q   A   T   F    G   G   G   D   H   P   P   K   S   D
661/221                                  691/231
ctg gtt ccg cgt gga tcc ATG CAT GGA GAT  ACA CCT ACA TTG CAT GAA TAT ATG TTA GAT
 L   V   P   R   G   S   M   H   G   D    T   P   T   L   H   E   Y   M   L   D
721/241                                  751/251
TTG CAA CCA GAG ACA ACT GAT CTC TAC TGT  TAT GAG CAA TTA AAT GAC AGC TCA GAG GAG
 L   Q   P   E   T   T   D   L   Y   C    Y   E   Q   L   N   D   S   S   E   E
781/261                                  811/271
GAG GAT GAA ATA GAT GGT CCA GCT GGA CAA  GCA GAA CCG GAC AGA GCC CAT TAC AAT ATT
 E   D   E   I   D   G   P   A   G   Q    A   E   P   D   R   A   H   Y   N   I
841/281                                  871/291
GTA ACC TTT TGT TGC AAG TGT GAC TCT ACG  CTT CGG TTG TGC GTA CAA AGC ACA CAC GTA
 V   T   F   C   C   K   C   D   S   T    L   R   L   C   V   Q   S   T   H   V
901/301                                  931/311
GAC ATT CGT ACT TTG GAA GAC CTG TTA ATG  GGC ACA CTA GGA ATT GTG TGC CCC ATC TGT
 D   I   R   T   L   E   D   L   L   M    G   T   L   G   I   V   C   P   I   C
961/321
TCT CAG AAA CCA TAA
 S   Q   K   P   *
```

FIG. 9

```
3/1                                             33/11
ATG GAT GGA GAT ACA CCT ACA TTG CAT GAA         TAT ATG TTA GAT TTG CAA CCA GAG ACA ACT
 M   D   G   D   T   P   T   L   H   E           Y   M   L   D   L   Q   P   E   T   T
63/21                                           93/31
GAT CTC TAC TGT TAT GAG CAA TTA AAT GAC         AGC TCA GAG GAG GAG GAT GAA ATA GAT GGT
 D   L   Y   C   Y   E   Q   L   N   D           S   S   E   E   E   D   E   I   D   G
123/41                                          153/51
CCA GCT GGA CAA GCA GAA CCG GAC AGA GCC         CAT TAC AAT ATT GTA ACC TTT TGT TGC AAG
 P   A   G   Q   A   E   P   D   R   A           H   Y   N   I   V   T   F   C   C   K
183/61                                          213/71
TGT GAC TCT ACG CTT CGG TTG TGC GTA CAA         AGC ACA CAC GTA GAC ATT CGT ACT TTG GAA
 C   D   S   T   L   R   L   C   V   Q           S   T   H   V   D   I   R   T   L   E
243/81                                          273/91
GAC CTG TTA ATG GGC ACA CTA GGA ATT GTG         TGC CCC ATC TGT TCT CAG AAA CCA ACT AGT
 D   L   L   M   G   T   L   G   I   V           C   P   I   C   S   Q   K   P   T   S
303/101                                         333/111
GGT GCC GGT GGC GGC GGA TCC CAC ATG GCC         AAG ACA ATT GCG TAC GAC GAA GAG GCC CGT
 G   G   G   G   G   G   S   H   M   A           K   T   I   A   Y   D   E   E   A   R
363/121                                         393/131
CGC GGC CTC GAG CGG GGC TTG AAC GCC CTC         GCC GAT GCG GTA AAG GTG ACA TTG GGC CCC
 R   G   L   E   R   G   L   N   A   L           A   D   A   V   K   V   T   L   G   P
423/141                                         453/151
AAG GGC CGC AAC GTC GTC CTG GAA AAG AAG         TGG GGT GCC CCC ACG ATC ACC AAC GAT GGT
 K   G   R   N   V   V   L   E   K   K           W   G   A   P   T   I   T   N   D   G
483/161                                         513/171
GTG TCC ATC GCC AAG GAG ATC GAG CTG GAG         GAT CCG TAC GAG AAG ATC GGC GCC GAG CTG
 V   S   I   A   K   E   I   E   L   E           D   P   Y   E   K   I   G   A   E   L
543/181                                         573/191
GTC AAA GAG GTA GCC AAG AAG ACC GAT GAC         GTC GCC GGT GAC GGC ACC ACG ACG GCC ACC
 V   K   E   V   A   K   K   T   D   D           V   A   G   D   G   T   T   T   A   T
603/201                                         633/211
GTG CTG GCC CAG GCG TTG GTT CGC GAG GGC         CTG CGC AAC GTC GCG GCC GGC GCC AAC CCG
 V   L   A   Q   A   L   V   R   E   G           L   R   N   V   A   A   G   A   N   P
663/221                                         693/231
CTC GGT CTC AAA CGC GGC ATC GAA AAG GCC         GTG GAG AAG GTC ACC GAG ACC CTG CTC AAG
 L   G   L   K   R   G   I   E   K   A           V   E   K   V   T   E   T   L   L   K
723/241                                         753/251
GGC GCC AAG GAG GTC GAG ACC AAG GAG CAG         ATT GCG GCC ACC GCA GCG ATT TCG GCG GGT
 G   A   K   E   V   E   T   K   E   Q           I   A   A   T   A   A   I   S   A   G
783/261                                         813/271
GAC CAG TCC ATC GGT GAC CTG ATC GCC GAG         GCG ATG GAC AAG GTG GGC AAC GAG GGC GTC
 D   Q   S   I   G   D   L   I   A   E           A   M   D   K   V   G   N   E   G   V
843/281                                         873/291
ATC ACC GTC GAG GAG TCC AAC ACC TTT GGG         CTG CAG CTC GAG CTC ACC GAG GGT ATG CGG
 I   T   V   E   E   S   N   T   F   G           L   Q   L   E   L   T   E   G   M   R
903/301                                         933/311
TTC GAC AAG GGC TAC ATC TCG GGG TAC TTC         GTG ACC GAC CCG GAG CGT CAG GAG GCG GTC
 F   D   K   G   Y   I   S   G   Y   F           V   T   D   P   E   R   Q   E   A   V
963/321                                         993/331
CTG GAG GAC CCC TAC ATC CTG CTG GTC AGC         TCC AAG GTG TCC ACT GTC AAG GAT CTG CTG
 L   E   D   P   Y   I   L   L   V   S           S   K   V   S   T   V   K   D   L   L
1023/341                                        1053/351
CCG CTG CTC GAG AAG GTC ATC GGA GCC GGT         AAG CCG CTG CTG ATC ATC GCC GAG GAC GTC
 P   L   L   E   K   V   I   G   A   G           K   P   L   L   I   I   A   E   D   V
1083/361                                        1113/371
GAG GGC GAG GCG CTG TCC ACC CTG GTC GTC         AAC AAG ATC CGC GGC ACC TTC AAG TCG GTG
 E   G   E   A   L   S   T   L   V   V           N   K   I   R   G   T   F   K   S   V
1143/381                                        1173/391
GCG GTC AAG GCT CCC GGC TTC GGC GAC CGC         CGC AAG GCG ATG CTG CAG GAT ATG GCC ATT
 A   V   K   A   P   G   F   G   D   R           R   K   A   M   L   Q   D   M   A   I
1203/401                                        1233/411
CTC ACC GGT GGT CAG GTG ATC AGC GAA GAG         GTC GGC CTG ACG CTG GAG AAC GCC GAC CTG
 L   T   G   G   Q   V   I   S   E   E           V   G   L   T   L   E   N   A   D   L
```

FIG. 10A

```
1263/421                                    1293/431
TCG CTG CTA GGC AAG GCC CGC AAG GTC GTG GTC ACC AAG GAC GAG ACC ACC ATC GTC GAG
 S   L   L   G   K   A   R   K   V   V   V   T   K   D   E   T   T   I   V   E
1323/441                                    1353/451
GGC GCC GGT GAC ACC GAC GCC ATC GCC GGA CGA GTG GCC CAG ATC CGC CAG GAG ATC GAG
 G   A   G   D   T   D   A   I   A   G   R   V   A   Q   I   R   Q   E   I   E
1383/461                                    1413/471
AAC AGC GAC TCC GAC TAC GAC CGT GAG AAG CTG CAG GAG CGG CTG GCC AAG CTG GCC GGT
 N   S   D   S   D   Y   D   R   E   K   L   Q   E   R   L   A   K   L   A   G
1443/481                                    1473/491
GGT GTC GCG GTG ATC AAG GCC GGT GCC GCC ACC GAG GTC GAA CTC AAG GAG CGC AAG CAC
 G   V   A   V   I   K   A   G   A   A   T   E   V   E   L   K   E   R   K   H
1503/501                                    1533/511
CGC ATC GAG GAT GCG GTT CGC AAT GCC AAG GCC GCC GTC GAG GAG GGC ATC GTC GCC GGT
 R   I   E   D   A   V   R   N   A   K   A   A   V   E   E   G   I   V   A   G
1563/521                                    1593/531
GGG GGT GTG ACG CTG TTG CAA GCG GCC CCG ACC CTG GAC GAG CTG AAG CTC GAA GGC GAC
 G   G   V   T   L   L   Q   A   A   P   T   L   D   E   L   K   L   E   G   D
1623/541                                    1653/551
GAG GCG ACC GGC GCC AAC ATC GTG AAG GTG GCG CTG GAG GCC CCG CTG AAG CAG ATC GCC
 E   A   T   G   A   N   I   V   K   V   A   L   E   A   P   L   K   Q   I   A
1683/561                                    1713/571
TTC AAC TCC GGG CTG GAG CCG GGC GTG GTG GCC GAG AAG GTG CGC AAC CTG CCG GCT GGC
 F   N   S   G   L   E   P   G   V   V   A   E   K   V   R   N   L   P   A   G
1743/581                                    1773/591
CAC GGA CTG AAC GCT CAG ACC GGT GTC TAC GAG GAT CTG CTC GCT GCC GGC GTT GCT GAC
 H   G   L   N   A   Q   T   G   V   Y   E   D   L   L   A   A   G   V   A   D
1803/601                                    1833/611
CCG GTC AAG GTG ACC CGT TCG GCG CTG CAG AAT GCG GCG TCC ATC GCG GGG CTG TTC CTG
 P   V   K   V   T   R   S   A   L   Q   N   A   A   S   I   A   G   L   F   L
1863/621                                    1893/631
ACC ACC GAG GCC GTC GTT GCC GAC AAG CCG GAA AAG GAG AAG GCT TCC GTT CCC GGT GGC
 T   T   E   A   V   V   A   D   K   P   E   K   E   K   A   S   V   P   G   G
1923/641
GGC GAC ATG GGT GGC ATG GAT TTC TGA
 G   D   M   G   G   M   D   F   *
```

FIG. 10B

```
3/1                                            33/11
ATG GCC AAG ACA ATT GCG TAC GAC GAA GAG  GCC CGT CGC GGC CTC GAG CGG GGC TTG AAC
 M   A   K   T   I   A   Y   D   E   E    A   R   R   G   L   E   R   G   L   N
63/21                                          93/31
GCC CTC GCC GAT GCG GTA AAG GTG ACA TTG  GGC CCC AAG GGC CGC AAC GTC GTC CTG GAA
 A   L   A   D   A   V   K   V   T   L    G   P   K   G   R   N   V   V   L   E
123/41                                         153/51
AAG AAG TGG GGT GCC CCC ACG ATC ACC AAC  GAT GGT GTG TCC ATC GCC AAG GAG ATC GAG
 K   K   W   G   A   P   T   I   T   N    D   G   V   S   I   A   K   E   I   E
183/61                                         213/71
CTG GAG GAT CCG TAC GAG AAG ATC GGC GCC  GAG CTG GTC AAA GAG GTA GCC AAG AAG ACC
 L   E   D   P   Y   E   K   I   G   A    E   L   V   K   E   V   A   K   K   T
243/81                                         273/91
GAT GAC GTC GCC GGT GAC GGC ACC ACG ACG  GCC ACC GTG CTG GCC CAG GCG TTG GTT CGC
 D   D   V   A   G   D   G   T   T   T    A   T   V   L   A   Q   A   L   V   R
303/101                                        333/111
GAG GGC CTG CGC AAC GTC GCG GCC GGC GCC  AAC CCG CTC GGT CTC AAA CGC GGC ATC GAA
 E   G   L   R   N   V   A   A   G   A    N   P   L   G   L   K   R   G   I   E
363/121                                        393/131
AAG GCC GTG GAG AAG GTC ACC GAG ACC CTG  CTC AAG GGC GCC AAG GAC GTC GAG ACC AAG
 K   A   V   E   K   V   T   E   T   L    L   K   G   A   K   E   V   E   T   K
423/141                                        453/151
GAG CAG ATT GCG GCC ACC GCA GCG ATT TCG  GCG GGT GAC CAG TCC ATC GGT GAC CTG ATC
 E   Q   I   A   A   T   A   A   I   S    A   G   D   Q   S   I   G   D   L   I
483/161                                        513/171
GCC GAG GCG ATG GAC AAG GTG GGC AAC GAG  GGC GTC ATC ACC GTC GAG GAG TCC AAC ACC
 A   E   A   M   D   K   V   G   N   E    G   V   I   T   V   E   E   S   N   T
543/181                                        573/191
TTT GGG CTG CAG CTC GAG CTC ACC GAG GGT  ATG CGG TTC GAC AAG GGC CAT ATG CAT GGA
 F   G   L   Q   L   E   L   T   E   G    M   R   F   D   K   G   H   M   H   G
603/201                                        633/211
GAT ACA CCT ACA TTG CAT GAA TAT ATG TTA  GAT TTG CAA CCA GAG ACA ACT GAT CTC TAC
 D   T   P   T   L   H   E   Y   M   L    D   L   Q   P   E   T   T   D   L   Y
663/221                                        693/231
TGT TAT GAG CAA TTA AAT GAC AGC TCA GAG  GAG GAG GAT GAA ATA GAT GGT CCA GCT GGA
 C   Y   E   Q   L   N   D   S   S   E    E   E   D   E   I   D   G   P   A   G
723/241                                        753/251
CAA GCA GAA CCG GAC AGA GCC CAT TAC AAT  ATT GTA ACC TTT TGT TGC AAG TGT GAC TCT
 Q   A   E   P   D   R   A   H   Y   N    I   V   T   F   C   C   K   C   D   S
783/261                                        813/271
ACG CTT CGG TTG TGC GTA CAA AGC ACA CAC  GTA GAC ATT CGT ACT TTG GAA GAC CTG TTA
 T   L   R   L   C   V   Q   S   T   H    V   D   I   R   T   L   E   D   L   L
843/281                                        873/291
ATG GGC ACA CTA GGA ATT GTG TGC CCC ATC  TGT TCT CAG AAA CCA TAA
 M   G   T   L   G   I   V   C   P   I    C   S   Q   K   P   *
```

FIG. 11

```
108/1                                    138/11
ATG GCG AAG GTG AAC ATC AAG CCA CTC GAG GAC AAG ATT CTC GTG CAG GCC AAC GAG GCC
 M   A   K   V   N   I   K   P   L   E   D   K   I   L   V   Q   A   N   E   A
168/21                                   198/31
GAG ACC ACG ACC GCG TCC GGT CTG GTC ATT CCT GAC ACC GCC AAG GAG AAG CCG CAG GAG
 E   T   T   T   A   S   G   L   V   I   P   D   T   A   K   E   K   P   Q   E
228/41                                   258/51
GGC ACC GTC GTT GCC GTC GGC CCT GGC CGG TGG GAC GAG GAC GGC GAG AAG CGG ATC CCG
 G   T   V   V   A   V   G   P   G   R   W   D   E   D   G   E   K   R   I   P
288/61                                   318/71
CTG GAC GTT GCG GAG GGT GAC ACC GTC ATC TAC AGC AAG TAC GGC GGC ACC GAG ATC AAG
 L   D   V   A   E   G   D   T   V   I   Y   S   K   Y   G   G   T   E   I   K
348/81                                   378/91
TAC AAC GGC GAG GAA TAC CTG ATC CTG TCG GCA CGC GAC GTG CTG GCC GTC GTT TCC AAG
 Y   N   G   E   E   Y   L   I   L   S   A   R   D   V   L   A   V   V   S   K
408/101                                  438/111
ATG CAT GGA GAT ACA CCT ACA TTG CAT GAA TAT ATG TTA GAT TTG CAA CCA GAG ACA ACT
 M   H   G   D   T   P   T   L   H   E   Y   M   L   D   L   Q   P   E   T   T
468/121                                  498/131
GAT CTC TAC TGT TAT GAG CAA TTA AAT GAC AGC TCA GAG GAG GAG GAT GAA ATA GAT GGT
 D   L   Y   C   Y   E   Q   L   N   D   S   S   E   E   E   D   E   I   D   G
528/141                                  558/151
CCA GCT GGA CAA GCA GAA CCG GAC AGA GCC CAT TAC AAT ATT GTA ACC TTT TGT TGC AAG
 P   A   G   Q   A   E   P   D   R   A   H   Y   N   I   V   T   F   C   C   K
588/161                                  618/171
TGT GAC TCT ACG CTT CGG TTG TGC GTA CAA AGC ACA CAC GTA GAC ATT CGT ACT TTG GAA
 C   D   S   T   L   R   L   C   V   Q   S   T   H   V   D   I   R   T   L   E
648/181                                  678/191
GAC CTG TTA ATG GGC ACA CTA GGA ATT GTG TGC CCC ATC TGT TCT CAG AAA CCA TAG
 D   L   L   M   G   T   L   G   I   V   C   P   I   C   S   Q   K   P   *
```

FIG. 12

```
3/1                                                  33/11
atg gat gga gat aca cct aca ttg cat gaa             tat atg tta gat ttg caa cca gag aca act
 M   D   G   D   T   P   T   L   H   E               Y   M   L   D   L   Q   P   E   T   T
63/21                                                93/31
gat ctc tac tgt tat gag caa tta aat gac             agc tca gag gag gag gat gaa ata gat ggc
 D   L   Y   C   Y   E   Q   L   N   D               S   S   E   E   E   D   E   I   D   G
123/41                                               153/51
cca gct gga caa gca gaa ccg gac aga gcc             cat tac aat att gta acc ttt tgt tgc aag
 P   A   G   Q   A   E   P   D   R   A               H   Y   N   I   V   T   F   C   C   K
183/61                                               213/71
tgt gac tct acg ctt cgg ttg tgc gta caa             agc aca cac gta gac att cgt act ttg gaa
 C   D   S   T   L   R   L   C   V   Q               S   T   H   V   D   I   R   T   L   E
243/81                                               273/91
gac ctg tta atg ggc aca cta gga att gtg             tgc ccc atc tgt tct cag aaa cca gcc atg
 D   L   L   M   G   T   L   G   I   V               C   P   I   C   S   Q   K   P   A   M
303/101                                              333/111
gCT CGT GCG GTC GGG ATC GAC CTC GGG ACC             ACC AAC TCC GTC GTC TCG GTT CTG GAA GGT
 A   R   A   V   G   I   D   L   G   T               T   N   S   V   V   S   V   L   E   G
363/121                                              393/131
GGC GAC CCG GTC GTC GTC GCC AAC TCC GAG             GGC TCC AGG ACC ACC CCG TCA ATT GTC GCG
 G   D   P   V   V   V   A   N   S   E               G   S   R   T   T   P   S   I   V   A
423/141                                              453/151
TTC GCC CGC AAC GGT GAG GTG CTG GTC GGC             CAG CCC GCC AAG AAC CAG GCG GTG ACC AAC
 F   A   R   N   G   E   V   L   V   G               Q   P   A   K   N   Q   A   V   T   N
483/161                                              513/171
GTC GAT CGC ACC GTG CGC TCG GTC AAG CGA             CAC ATG GGC AGC GAC TGG TCC ATA GAG ATT
 V   D   R   T   V   R   S   V   K   R               H   M   G   S   D   W   S   I   E   I
543/181                                              573/191
GAC GGC AAG AAA TAC ACC GCG CCG GAG ATC             AGC GCC CGC ATT CTG ATG AAG CTG AAG CGC
 D   G   K   K   Y   T   A   P   E   I               S   A   R   I   L   M   K   L   K   R
603/201                                              633/211
GAC GCC GAG GCC TAC CTC GGT GAG GAC ATT             ACC GAC GCG GTT ATC ACG ACG CCC GCC TAC
 D   A   E   A   Y   L   G   E   D   I               T   D   A   V   I   T   T   P   A   Y
663/221                                              693/231
TTC AAT GAC GCC CAG CGT CAG GCC ACC AAG             GAC GCC GGC CAG ATC GCC GGC CTC AAC GTG
 F   N   D   A   Q   R   Q   A   T   K               D   A   G   Q   I   A   G   L   N   V
723/241                                              753/251
CTG CGG ATC GTC AAC GAG CCG ACC GCG GCC             GCG ctg gcc TAC GGC CTC GAC AAG GGC GAG
 L   R   I   V   N   E   P   T   A   A               A   L   A   Y   G   L   D   K   G   E
783/261                                              813/271
AAG GAG CAG CGA ATC CTG GTC TTC GAC TTG             GGT GGT GGC ACT TTC GAC GTT TCC CTG CTG
 K   E   Q   R   I   L   V   F   D   L               G   G   G   T   F   D   V   S   L   L
843/281                                              873/291
GAG ATC GGC GAG GGT GTG GTT CAG GTC CGT             GCC ACT TCG GGT GAC AAC CAC CTC GGC GGC
 E   I   G   E   G   V   V   Q   V   R               A   T   S   G   D   N   H   L   G   G
903/301                                              933/311
GAC GAC TGG GAC CAG CGG GTC GTC GAT TGG             CTG GTG GAC AAG TTC AAG GGC ACC AGC GGC
 D   D   W   D   Q   R   V   V   D   W               L   V   D   K   F   K   G   T   S   G
963/321                                              993/331
ATC GAT CTG ACC AAG GAC AAG ATG GCG ATG             CAG CGG CTG CGG GAA GCC GCC GAG AAG GCA
 I   D   L   T   K   D   K   M   A   M               Q   R   L   R   E   A   A   E   K   A
1023/341                                             1053/351
AAG ATC GAG CTG AGT TCG AGT CAG TCC ACC             TCG ATC AAC CTG CCC TAC ATC ACC GTC GAC
 K   I   E   L   S   S   S   Q   S   T               S   I   N   L   P   Y   I   T   V   D
1083/361                                             1113/371
GCC GAC AAG AAC CCG TTG TTC TTA GAC GAG             CAG CTG ACC CGC GCG GAG TTC CAA CGG ATC
 A   D   K   N   P   L   F   L   D   E               Q   L   T   R   A   E   F   Q   R   I
1143/381                                             1173/391
ACT CAG GAC CTG CTG GAC CGC ACT CGC AAG             CCG TTC CAG TCG GTG ATC GCT GAC ACC GGC
 T   Q   D   L   L   D   R   T   R   K               P   F   Q   S   V   I   A   D   T   G
1203/401                                             1233/411
ATT TCG GTG TCG GAG ATC GAT CAC GTT GTG             CTC GTG GGT GGT TCG ACC CGG ATG CCC GCG
 I   S   V   S   E   I   D   H   V   V               L   V   G   G   S   T   R   M   P   A
```

FIG. 13A

```
1263/421                                    1293/431
GTG ACC GAT CTG GTC AAG GAA CTC ACC GGC     GGC AAG GAA CCC AAC AAG GGC GTC AAC CCC
 V   T   D   L   V   K   E   L   T   G      G   K   E   P   N   K   G   V   N   P
1323/441                                    1353/451
GAT GAG GTT GTC GCG GTG GGA GCC GCT CTG     CAG GCC GGC GTC CTC AAG GGC GAG GTG AAA
 D   E   V   V   A   V   G   A   A   L      Q   A   G   V   L   K   G   E   V   K
1383/461                                    1413/471
GAC GTT CTG CTG CTT GAT GTT ACC CCG CTG     AGC CTG GGT ATC GAG ACC AAG GGC GGG GTG
 D   V   L   L   L   D   V   T   P   L      S   L   G   I   E   T   K   G   G   V
1443/481                                    1473/491
ATG ACC AGG CTC ATC GAG CGC AAC ACC ACG     ATC CCC ACC AAG CGG TCG GAG ACT TTC ACC
 M   T   R   L   I   E   R   N   T   T      I   P   T   K   R   S   E   T   F   T
1503/501                                    1533/511
ACC GCC GAC GAC AAC CAA CCG TCG GTG CAG     ATC CAG GTC TAT CAG GGG GAG CGT GAG ATC
 T   A   D   D   N   Q   P   S   V   Q      I   Q   V   Y   Q   G   E   R   E   I
1563/521                                    1593/531
GCC GCG CAC AAC AAG TTG CTC GGG TCC TTC     GAG CTG ACC GGC ATC CCG CCG GCG CCG CGG
 A   A   H   N   K   L   L   G   S   F      E   L   T   G   I   P   P   A   P   R
1623/541                                    1653/551
GGG ATT CCG CAG ATC GAG GTC ACT TTC GAC     ATC GAC GCC AAC GGC ATT GTG CAC GTC ACC
 G   I   P   Q   I   E   V   T   F   D      I   D   A   N   G   I   V   H   V   T
1683/561                                    1713/571
GCC AAG GAC AAG GGC ACC GGC AAG GAG AAC     ACG ATC CGA ATC CAG GAA GGC TCG GGC CTG
 A   K   D   K   G   T   G   K   E   N      T   I   R   I   Q   E   G   S   G   L
1743/581                                    1773/591
TCC AAG GAA GAC ATT GAC CGC ATG ATC AAG     GAC GCC GAA GCG CAC GCC GAG GAG GAT CGC
 S   K   E   D   I   D   R   M   I   K      D   A   E   A   H   A   E   E   D   R
1803/601                                    1833/611
AAG CGT CGC GAG GAG GCC GAT GTT CGT AAT     CAA GCC GAG ACA TTG GTC TAC CAG ACG GAG
 K   R   R   E   E   A   D   V   R   N      Q   A   E   T   L   V   Y   Q   T   E
1863/621                                    1893/631
AAG TTC GTC AAA GAA CAG CGT GAG GCC GAG     GGT GGT TCG AAG GTA CCT GAA GAC ACG CTG
 K   F   V   K   E   Q   R   E   A   E      G   G   S   K   V   P   E   D   T   L
1923/641                                    1953/651
AAC AAG GTT GAT GCC GCG GTG GCG GAA GCg     AAG GCG GCA CTT GGC GGA TCG GAT ATT TCG
 N   K   V   D   A   A   V   A   E   A      K   A   A   L   G   G   S   D   I   S
1983/661                                    2013/671
GCC ATC AAG TCG GCG ATG GAG AAG CTG GGC     CAG GAG TCG CAG GCT CTG GGG CAA GCG ATC
 A   I   K   S   A   M   E   K   L   G      Q   E   S   Q   A   L   G   Q   A   I
2043/681                                    2073/691
TAC GAA GCA GCT CAG GCT GCG TCA CAG GCC     ACT GGC GCT GCC CAC CCC GGC GGC GAG CCG
 Y   E   A   A   Q   A   A   S   Q   A      T   G   A   A   H   P   G   G   E   P
2103/701                                    2133/711
GGC GGT GCC CAC CCC GGC TCG GCT GAG CTA GCA TGA
 G   G   A   H   P   G   S   A   E   L   A   *
```

FIG. 13B

```
  3/1                                           33/11
  atg gat gga gat aca cct aca ttg cat gaa tat atg tta gat ttg caa cca gag aca act
   M   D   G   D   T   P   T   L   H   E   Y   M   L   D   L   Q   P   E   T   T
 63/21                                          93/31
  gat ctc tac tgt tat gag caa tta aat gac agc tca gag gag gag gat gaa ata gat ggt
   D   L   Y   C   Y   E   Q   L   N   D   S   S   E   E   E   D   E   I   D   G
123/41                                         153/51
  cca gct gga caa gca gaa ccg gac aga gcc cat tac aat att gta acc ttt tgt tgc aag
   P   A   G   Q   A   E   P   D   R   A   H   Y   N   I   V   T   F   C   C   K
183/61                                         213/71
  tgt gac tct acg ctt cgg ttg tgc gta caa agc aca cac gta gac att cgt act ttg gaa
   C   D   S   T   L   R   L   C   V   Q   S   T   H   V   D   I   R   T   L   E
243/81                                         273/91
  gac ctg tta atg ggc aca cta gga att gtg tgc ccc atc tgt tct cag aaa cca gcc atg
   D   L   L   M   G   T   L   G   I   V   C   P   I   C   S   Q   K   P   A   M
303/101                                        333/111
  gCT CGT GCG GTC GGG ATC GAC CTC GGG ACC ACC AAC TCC GTC GTC TCG GTT CTG GAA GGT
   A   R   A   V   G   I   D   L   G   T   T   N   S   V   V   S   V   L   E   G
363/121                                        393/131
  GGC GAC CCG GTC GTC GTC GCC AAC TCC GAG GGC TCC AGG ACC ACC CCG TCA ATT GTC GCG
   G   D   P   V   V   V   A   N   S   E   G   S   R   T   T   P   S   I   V   A
423/141                                        453/151
  TTC GCC CGC AAC GGT GAG GTG CTG GTC GGC CAG CCC GCC AAG AAC CAG GCG GTG ACC AAC
   F   A   R   N   G   E   V   L   V   G   Q   P   A   K   N   Q   A   V   T   N
483/161                                        513/171
  GTC GAT CGC ACC GTG CGC TCG GTC AAG CGA CAC ATG GGC AGC GAC TGG TCC ATA GAG ATT
   V   D   R   T   V   R   S   V   K   R   H   M   G   S   D   W   S   I   E   I
543/181                                        573/191
  GAC GGC AAG AAA TAC ACC GCG CCG GAG ATC AGC GCC CGC ATT CTG ATG AAG CTG AAG CGC
   D   G   K   K   Y   T   A   P   E   I   S   A   R   I   L   M   K   L   K   R
603/201                                        633/211
  GAC GCC GAG GCC TAC CTC GGT GAG GAC ATT ACC GAC GCG GTT ATC ACG ACG CCC GCC TAC
   D   A   E   A   Y   L   G   E   D   I   T   D   A   V   I   T   T   P   A   Y
663/221                                        693/231
  TTC AAT GAC GCC CAG CGT CAG GCC ACC AAG GAC GCC GGC CAG ATC GCC GGC CTC AAC GTG
   F   N   D   A   Q   R   Q   A   T   K   D   A   G   Q   I   A   G   L   N   V
723/241                                        753/251
  CTG CGG ATC GTC AAC GAG CCG ACC GCG GCC GCG ctg gcc TAC GGC CTC GAC AAG GGC GAG
   L   R   I   V   N   E   P   T   A   A   A   L   A   Y   G   L   D   K   G   E
783/261                                        813/271
  AAG GAG CAG CGA ATC CTG GTC TTC GAC TTG GGT GGT GGC ACT TTC GAC GTT TCC CTG CTG
   K   E   Q   R   I   L   V   F   D   L   G   G   G   T   F   D   V   S   L   L
843/281                                        873/291
  GAG ATC GGC GAG GGT GTG GTT GAG GTC CGT GCC ACT TCG GGT GAC AAC CAC CTC GGC GGC
   E   I   G   E   G   V   V   E   V   R   A   T   S   G   D   N   H   L   G   G
903/301                                        933/311
  GAC GAC TGG GAC CAG CGG GTC GTC GAT TGG CTG GTG GAC AAG TTC AAG GGC ACC AGC GGC
   D   D   W   D   Q   R   V   V   D   W   L   V   D   K   F   K   G   T   S   G
963/321                                        993/331
  ATC GAT CTG ACC AAG GAC AAG ATG GCG ATG CAG CGG CTG CGG GAA GCC GCC GAG AAG GCA
   I   D   L   T   K   D   K   M   A   M   Q   R   L   R   E   A   A   E   K   A
1023/341                                       1053/351
  AAG ATC GAG CTG AGT TCG AGT CAG TCC ACC TCG ATC AAC CTG CCC TAC ATC ACC GTC GAC
   K   I   E   L   S   S   S   Q   S   T   S   I   N   L   P   Y   I   T   V   D
1083/361                                       1113/371
  GCC GAC AAG AAC CCG TTG TTC TTA GAC GAG CAG CTG ACC CGC GCG GAG TTC CAA CGG ATC
   A   D   K   N   P   L   F   L   D   E   Q   L   T   R   A   E   F   Q   R   I
1143/381                                       1173/391
  ACT CAG GAC CTG CTG GAC CGC ACT CGC AAG CCG TTC CAG TCG GTG ATC GCT GAC ACC GGC
   T   Q   D   L   L   D   R   T   R   K   P   F   Q   S   V   I   A   D   T   G
1203/401                                       1233/411
  ATT TCG GTG TCG GAG ATC GAT CAC GTT GTG CTC GTG GGT GGT TCG ACC CGG ATG CCC GCG
   I   S   V   S   E   I   D   H   V   V   L   V   G   G   S   T   R   M   P   A
```

FIG. 14A

```
1263/421                                              1293/431
GTG ACC GAT CTG GTC AAG GAA CTC ACC GGC  GGC AAG GAA CCC AAC AAG GGC GTC AAC CCC
 V   T   D   L   V   K   E   L   T   G    G   K   E   P   N   K   G   V   N   P
1323/441                                              1353/451
GAT GAG GTT GTC GCG GTG GGA GCC GCT CTG  CAG GCC GGC GTC CTC AAG GGC GAG GTG AAA
 D   E   V   V   A   V   G   A   A   L    Q   A   G   V   L   K   G   E   V   K
1383/461                                              1413/471
GAC GTT CTG CTG CTT GAT GTT ACC CCG CTG  AGC CTG GGT ATC GAG ACC AAG GGC GGG GTG
 D   V   L   L   L   D   V   T   P   L    S   L   G   I   E   T   K   G   G   V
1443/481                                              1473/491
ATG ACC AGG CTC ATC GAG CGC AAC ACC ACG  ATC CCC ACC AAG CGG TCG GAG ACT TTC ACC
 M   T   R   L   I   E   R   N   T   T    I   P   T   K   R   S   E   T   F   T
1503/501                                              1533/511
ACC GCC GAC GAC AAC CAA CCG TCG GTG CAG  ATC CAG GTC TAT CAG GGG GAG CGT GAG ATC
 T   A   D   D   N   Q   P   S   V   Q    I   Q   V   Y   Q   G   E   R   E   I
1563/521                                              1593/531
GCC GCG CAC AAC AAG TTG CTC GGG TCC TTC  GAG CTG ACC GGC ATC CCG CCG GCG CCG CGG
 A   A   H   N   K   L   L   G   S   F    E   L   T   G   I   P   P   A   P   R
1623/541                                              1653/551
GGG ATT CCG CAG ATC GAG GTC ACT TTC GAC  ATC GAC GCC AAC GGC ATT GTG CAC GTC ACC
 G   I   P   Q   I   E   V   T   F   D    I   D   A   N   G   I   V   H   V   T
1683/561                                              1713/571
GCC AAG GAC AAG GGC ACC GGC AAG GAG AAC  ACG ATC CGA ATC CAG GAA GGC TCG GGC CTG
 A   K   D   K   G   T   G   K   E   N    T   I   R   I   Q   E   G   S   G   L
1743/581                                              1773/591
TCC AAG GAA GAC ATT GAC CGC ATG ATC AAG  GAC GCC GAA GCG CAC GCC GAG GAG GAT CGC
 S   K   E   D   I   D   R   M   I   K    D   A   E   A   H   A   E   E   D   R
1803/601                                              1833/611
AAG CGT CGC GAG GAG GCC GAT GTT CGT AAT  CAA GCC GAG ACA TTG GTC TAC CAG ACG GAG
 K   R   R   E   E   A   D   V   R   N    Q   A   E   T   L   V   Y   Q   T   E
1863/621                                              1893/631
AAG TTC GTC AAA GAA CAG CGT GAG GCC GAG  GGT GGT TCG AAg gta ccT GAA GAC ACG CTG
 K   F   V   K   E   Q   R   E   A   E    G   G   S   K   V   P   E   D   T   L
1923/641                                              1953/651
AAC AAG GTT GAT GCC GCG GTG GCG GAA GCg  AAG GCG GCA CTT GGC GGA TCG GAT ATT TCG
 N   K   V   D   A   A   V   A   E   A    K   A   A   L   G   G   S   D   I   S
1983/661                                              2013/671
GCC ATC AAG TCG GCG ATG GAG AAG CTG GGC  CAG GAG TCG CAG GCT CTG GGG CAA GCG ATC
 A   I   K   S   A   M   E   K   L   G    Q   E   S   Q   A   L   G   Q   A   I
2043/681                                              2073/691
TAC GAA GCA GCT CAG GCT GCG TCA CAG GCC  ACT GGC GCT GCC CAC CCC GGC GGC GAG CCG
 Y   E   A   A   Q   A   A   S   Q   A    T   G   A   A   H   P   G   G   E   P
2103/701                                              2133/711
GGC GGT GCC CAC CCC GGC TCG GCT GAT GAC  GTT GTG GAC GCG GAG GTG GTC GAC GAC GGC
 G   G   A   H   P   G   S   A   D   D    V   V   D   A   E   V   V   D   D   G
2163/721
CGG GAG GCC AAG TGA
 R   E   A   K   *
```

FIG. 14B

```
3/1                                             33/11
atg gCA AAA GAA ATT AAA TTT TCA TCA GAT         GCC CGT TCA GCT ATG GTC CGT GGT GTC GAT
M   A   K   E   I   K   F   S   S   D           A   R   S   A   M   V   R   G   V   D
63/21                                           93/31
ATC CTT GCA GAT ACT GTT AAA GTA ACT TTG         GGA CCA AAA GGT CGC AAT GTC GTT CTT GAA
I   L   A   D   T   V   K   V   T   L           G   P   K   G   R   N   V   V   L   E
123/41                                          153/51
AAG TCA TTC GGT TCA CCC TTG ATT ACC AAT         GAC GGT GTG ACT ATT GCC AAA GAA ATT GAA
K   S   F   G   S   P   L   I   T   N           D   G   V   T   I   A   K   E   I   E
183/61                                          213/71
TTA GAA GAC CAT TTT GAA AAT ATG GGT GCC         AAA TTG GTA TCA GAA GTA GCT TCA AAA ACC
L   E   D   H   F   E   N   M   G   A           K   L   V   S   E   V   A   S   K   T
243/81                                          273/91
AAT GAT ATC GCA GGT GAT GGA ACT ACA ACT         GCA ACT GTT TTG ACC CAA GCA ATC GTC CGT
N   D   I   A   G   D   G   T   T   T           A   T   V   L   T   Q   A   I   V   R
303/101                                         333/111
GAA GGA ATC AAA AAC GTC ACA GCA GGT GCA         AAT CCA ATC GGT ATT CGT CGT GGG ATT GAA
E   G   I   K   N   V   T   A   G   A           N   P   I   G   I   R   R   G   I   E
363/121                                         393/131
ACA GCA GTT GCC GCA GCA GTT GAA GCT TTG         AAA AAC AAC GTC ATC CCT GTT GCC AAT AAA
T   A   V   A   A   A   V   E   A   L           K   N   N   V   I   P   V   A   N   K
423/141                                         453/151
GAA GCT ATC GCT CAA GTT GCA GCC GTA TCT         TCT CGT TCT GAA AAA GTT GGT GAG TAC ATC
E   A   I   A   Q   V   A   A   V   S           S   R   S   E   K   V   G   E   Y   I
483/161                                         513/171
TCT GAA GCA ATG GAA AAA GTT GGC AAA GAC         GGT GTC ATC ACC ATC GAA GAG TCA CGT GGT
S   E   A   M   E   K   V   G   K   D           G   V   I   T   I   E   E   S   R   G
543/181                                         573/191
ATG GAA ACA GAG CTT GAA GTC GTA GAA GGA         ATG CAG TTT GAC CGT GGT TAC CTT TCA CAG
M   E   T   E   L   E   V   V   E   G           M   Q   F   D   R   G   Y   L   S   Q
603/201                                         633/211
TAC ATG GTG ACA GAT AGC GAA AAA ATG GTG         GCT GAC CTT GAA AAT CCG TAC ATT TTG ATT
Y   M   V   T   D   S   E   K   M   V           A   D   L   E   N   P   Y   I   L   I
663/221                                         693/231
ACA GAC AAG AAA ATT TCC AAT ATC CAA GAA         ATC TTG CCA CTT TTG GAA AGC ATT CTC CAA
T   D   K   K   I   S   N   I   Q   E           I   L   P   L   L   E   S   I   L   Q
723/241                                         753/251
AGC AAT CGT CCA CTC TTG ATT ATT GCG GAT         GAT GTG GAT GGT GAG GCT CTT CCA ACT CTT
S   N   R   P   L   L   I   I   A   D           D   V   D   G   E   A   L   P   T   L
783/261                                         813/271
GTT TTG AAC AAG ATT CGT GGA ACC TTC AAC         GTA GTA GCA GTC AAG GCA CCT GGT TTT GGT
V   L   N   K   I   R   G   T   F   N           V   V   A   V   K   A   P   G   F   G
843/281                                         873/291
GAC CGT CGC AAA GCC ATG CTT GAA GAT ATC         GCC ATC TTA ACA GGC GGA ACA GTT ATC ACA
D   R   R   K   A   M   L   E   D   I           A   I   L   T   G   G   T   V   I   T
903/301                                         933/311
GAA GAC CTT GGT CTT GAG TTG AAA GAT GCG         ACA ATT GAA GCT CTT GGT CAA GCA GCG AGA
E   D   L   G   L   E   L   K   D   A           T   I   E   A   L   G   Q   A   A   R
963/321                                         993/331
GTG ACC GTG GAC AAA GAT AGC ACG GTT ATT         GTA GAA GGT GCA GGA AAT CCT GAA GCG ATT
V   T   V   D   K   D   S   T   V   I           V   E   G   A   G   N   P   E   A   I
1023/341                                        1053/351
TCT CAC CGT GTT GCG GTT ATC AAG TCT CAA         ATC GAA ACT ACA ACT TCT GAA TTT GAC CGT
S   H   R   V   A   V   I   K   S   Q           I   E   T   T   T   S   E   F   D   R
1083/361                                        1113/371
GAA AAA TTG CAA GAA CGC TTG GCC AAA TTG         TCA GGT GGT GTA GCG GTT ATT AAG GTC GGA
E   K   L   Q   E   R   L   A   K   L           S   G   G   V   A   V   I   K   V   G
1143/381                                        1173/391
GCC GCA ACT GAA ACT GAG TTG AAA GAA ATG         AAA CTC CGC ATT GAA GAT GCC CTC AAC GCT
A   A   T   E   T   E   L   K   E   M           K   L   R   I   E   D   A   L   N   A
1203/401                                        1233/411
ACT CGT GCA GCT GTT GAA GAA GGT ATT GTT         GCA GGT GGT GGA ACA GCT CTT GCC AAT GTG
T   R   A   A   V   E   E   G   I   V           A   G   G   G   T   A   L   A   N   V
```

FIG. 15A

```
1263/421                                    1293/431
ATT CCA GCT GTT GCT ACC TTG GAA TTG ACA    GGA GAT GAA GCA ACA GGA CGT AAT ATT GTT
 I   P   A   V   A   T   L   E   L   T      G   D   E   A   T   G   R   N   I   V
1323/441                                    1353/451
CTC CGT GCT TTG GAA GAA CCT GTT CGT CAA    ATT GCT CAC AAT GCA GGA TTT GAA GGA TCT
 L   R   A   L   E   E   P   V   R   Q      I   A   H   N   A   G   F   E   G   S
1383/461                                    1413/471
ATC GTT ATC GAT CGT TTG AAA AAT GCT GAG    CTT GGT ATA GGA TTC AAC GCA GCA ACT GGC
 I   V   I   D   R   L   K   N   A   E      L   G   I   G   F   N   A   A   T   G
1443/481                                    1473/491
GAG TGG GTT AAC ATG ATT GAT CAA GGT ATC    ATT GAT CCA GTT AAA GTG AGT CGT TCA GCC
 E   W   V   N   M   I   D   Q   G   I      I   D   P   V   K   V   S   R   S   A
1503/501                                    1533/511
CTA CAA AAT GCA GCA TCT GTA GCC AGC TTG    ATT TTG ACA ACA GAA GCA GTC GTA GCC AAT
 L   Q   N   A   A   S   V   A   S   L      I   L   T   T   E   A   V   V   A   N
1563/521                                    1593/531
AAA CCA GAA CCA GTA GCC CCA GCT CCA GCA    ATG GAT CCA AGT ATG ATG GGT GGA ATG GGC
 K   P   E   P   V   A   P   A   P   A      M   D   P   S   M   M   G   G   M   G
1623/541                                    1653/551
GGA GCT AGC atg cat gga gat aca cct aca    ttg cat gaa tat atg tta gat ttg caa cca
 G   A   S   M   H   G   D   T   P   T      L   H   E   Y   M   L   D   L   Q   P
1683/561                                    1713/571
gag aca act gat ctc tac tgt tat gag caa    tta aat gac agc tca gag gag gag gat gaa
 E   T   T   D   L   Y   C   Y   E   Q      L   N   D   S   S   E   E   E   D   E
1743/581                                    1773/591
ata gat ggt cca gct gga caa gca gaa ccg    gac aga gcc cat tac aat att gta acc ttt
 I   D   G   P   A   G   Q   A   E   P      D   R   A   H   Y   N   I   V   T   F
1803/601                                    1833/611
tgt tgc aag tgt gac tct acg ctt cgg ttg    tgc gta caa agc aca cac gta gac att cgt
 C   C   K   C   D   S   T   L   R   L      C   V   Q   S   T   H   V   D   I   R
1863/621                                    1893/631
act ttg gaa gac ctg tta atg ggc aca cta    gga att gtg tgc ccc atc tgt tct cag aaa
 T   L   E   D   L   L   M   G   T   L      G   I   V   C   P   I   C   S   Q   K
1923/641
cca TAA
 P   *
```

FIG. 15B

```
4/1                                             34/11
ATG AAA GAG CTC AAG TTC GGT GTC GAA GCC CGT GCT CAG CTC CTC AAG GGT GTT GAC ACT
 M   K   E   L   K   F   G   V   E   A   R   A   Q   L   L   K   G   V   D   T
64/21                                           94/31
CTG GCC AAG GCC GTG ACT TCG ACT CTT GGT CCT AAG GGT CGT AAC GTC CTT ATC GAG TCT
 L   A   K   A   V   T   S   T   L   G   P   K   G   R   N   V   L   I   E   S
124/41                                          154/51
CCC TAT GGC TCC CCT AAG ATC ACC AAG GAT GGT GTC TCT GTT GCC AAG GCC ATC ACT CTC
 P   Y   G   S   P   K   I   T   K   D   G   V   S   V   A   K   A   I   T   L
184/61                                          214/71
CAA GAC AAG TTC GAG AAC CTC GGT GCT CGC CTC CTC CAG GAT GTC GCT TCT AAG ACC AAC
 Q   D   K   F   E   N   L   G   A   R   L   L   Q   D   V   A   S   K   T   N
244/81                                          274/91
GAG ATT GCT GGT GAC GGT ACC ACC ACC GCT ACC GTC CTT GCC CGT GCC ATC TTC TCT GAG
 E   I   A   G   D   G   T   T   T   A   T   V   L   A   R   A   I   F   S   E
304/101                                         334/111
ACC GTG AAG AAT GTT GCT GCT GGC TGC AAC CCC ATG GAT CTG CGC CGC GGT ATC CAG GCT
 T   V   K   N   V   A   A   G   C   N   P   M   D   L   R   R   G   I   Q   A
364/121                                         394/131
GCT GTT GAT GCT GTC GTC GAC TAC CTC CAG AAG AAC AAG CGT GAC ATC ACC ACC GGT GAG
 A   V   D   A   V   V   D   Y   L   Q   K   N   K   R   D   I   T   T   G   E
424/141                                         454/151
GAG ATC GCT CAG GTT GCT ACT ATC TCC GCT AAC GGT GAC ACC CAC ATT GGT AAG CTG ATC
 E   I   A   Q   V   A   T   I   S   A   N   G   D   T   H   I   G   K   L   I
484/161                                         514/171
TCC ACC GCC ATG GAG CGT GTT GGC AAG GAG GGT GTC ATC ACT GTC AAG GAG GGC AAG ACC
 S   T   A   M   E   R   V   G   K   E   G   V   I   T   V   K   E   G   K   T
544/181                                         574/191
ATT GAG GAT GAG CTC GAG GTC ACT GAG GGT ATG CGC TTC GAC CGT GGA TAC ACC TCC CCC
 I   E   D   E   L   E   V   T   E   G   M   R   F   D   R   G   Y   T   S   P
604/201                                         634/211
TAC TTC ATC ACC GAT ACC AAG TCC CAG AAG GTT GAG TTC GAG AAG CCT CTG ATT CTG CTG
 Y   F   I   T   D   T   K   S   Q   K   V   E   F   E   K   P   L   I   L   L
664/221                                         694/231
TCT GAG AAG AAG ATC TCT GCC GTT CAG GAC ATC ATC CCC GCC CTT GAG GCC TCC ACC ACC
 S   E   K   K   I   S   A   V   Q   D   I   I   P   A   L   E   A   S   T   T
724/241                                         754/251
CTC CGC CGC CCC CTG GTT ATT ATC GCA GAG GAC ATT GAG GGT GAG GCT CTC GCC GTC TGC
 L   R   R   P   L   V   I   I   A   E   D   I   E   G   E   A   L   A   V   C
784/261                                         814/271
ATT CTG AAC AAG CTT CGT GGC CAG CTG CAG GTC GCT GCT GTC AAG GCT CCT GGA TTC GGT
 I   L   N   K   L   R   G   Q   L   Q   V   A   A   V   K   A   P   G   F   G
844/281                                         874/291
GAC AAC CGC AAG AGC ATC CTG GGC GAT CTT GCC GTC CTT ACC AAC GGT ACC GTC TTC ACT
 D   N   R   K   S   I   L   G   D   L   A   V   L   T   N   G   T   V   F   T
904/301                                         934/311
GAT GAG CTC GAC ATC AAA CTC GAG AAG CTT ACC CCC GAT ATG CTT GGT TCC ACC GGC GCC
 D   E   L   D   I   K   L   E   K   L   T   P   D   M   L   G   S   T   G   A
964/321                                         994/331
ATC ACC ATC ACC AAG GAG GAC ACC ATC ATC CTG AAC GGG GAG GGC AGC AAG GAC GCC ATT
 I   T   I   T   K   E   D   T   I   I   L   N   G   E   G   S   K   D   A   I
1024/341                                        1054/351
GCC CAG CGC TGC GAG CAG ATT CGC GGT GTC ATG GCG GAC CCC AGC ACC TCC GAA TAC GAG
 A   Q   R   C   E   Q   I   R   G   V   M   A   D   P   S   T   S   E   Y   E
1084/361                                        1114/371
AAG GAG AAG CTC CAG GAG CGT CTA GCT AAG CTC TCT GGC GGT GTT GCC GTC ATC AAG GTC
 K   E   K   L   Q   E   R   L   A   K   L   S   G   G   V   A   V   I   K   V
1144/381                                        1174/391
GGT GGT GCC TCC GAG GTT GAG GTC GGT GAG AAG AAG GAC CGT GTT GTC GAT GCT CTC AAT
 G   G   A   S   E   V   E   V   G   E   K   K   D   R   V   V   D   A   L   N
1204/401                                        1234/411
GCT ACC CGT GCT GCT GTT GAG GAG GGT ATC CTC CCC GGT GGT GGT ACC GCC CTT CTC AAG
 A   T   R   A   A   V   E   E   G   I   L   P   G   G   G   T   A   L   L   K
```

FIG. 16A

```
1264/421                              1294/431
GCC GCC GCC AAC GGC CTT GAC AAT GTC AAG CCC GAG AAC TTC GAC CAG CAA CTC GGT GTG
 A   A   A   N   G   L   D   N   V   K   P   E   N   F   D   Q   Q   L   G   V
1324/441                              1354/451
AGC ATC ATC AAG AAT GCC ATC ACC CGC CCC GCT CGC ACC ATT GTT GAG AAC GCC GGC CTC
 S   I   I   K   N   A   I   T   R   P   A   R   T   I   V   E   N   A   G   L
1384/461                              1414/471
GAG GGC AGC GTC ATT GTC GGC AAG CTG ACC GAC GAG TTC GCC AAG GAC TTC AAC CGC GGT
 E   G   S   V   I   V   G   K   L   T   D   E   F   A   K   D   F   N   R   G
1444/481                              1474/491
TTC GAC AGC TCC AAG GGC GAG TAC GTC GAC ATG ATC TCC AGC GGT ATC CTC GAT CCC CTC
 F   D   S   S   K   G   E   Y   V   D   M   I   S   S   G   I   L   D   P   L
1504/501                              1534/511
AAG GTT GTT CGC ACC GCT CTG CTC GAC GCC AGC GGT GTC GCC TCC CTG CTC GGT ACC ACT
 K   V   V   R   T   A   L   L   D   A   S   G   V   A   S   L   L   G   T   T
1564/521                              1594/531
GAG GTC GCT ATT GTT GAG GCC CCT GAG GAG AAG GGC CCC GCT GCT CCT GGC ATG GGT GGT
 E   V   A   I   V   E   A   P   E   E   K   G   P   A   A   P   G   M   G   G
1624/541                              1654/551
ATG GGT GGT ATG GGC GGC ATG GGC GGC ATG CAT GGA GAT ACA CCT ACA TTG CAT GAA TAT
 M   G   G   M   G   G   M   G   G   M   H   G   D   T   P   T   L   H   E   Y
1684/561                              1714/571
ATG TTA GAT TTG CAA CCA GAG ACA ACT GAT CTC TAC TGT TAT GAG CAA TTA AAT GAC AGC
 M   L   D   L   Q   P   E   T   T   D   L   Y   C   Y   E   Q   L   N   D   S
1744/581                              1774/591
TCA GAG GAG GAG GAT GAA ATA GAT GGT CCA GCT GGA CAA GCA GAA CCG GAC AGA GCC CAT
 S   E   E   E   D   E   I   D   G   P   A   G   Q   A   E   P   D   R   A   H
1804/601                              1834/611
TAC AAT ATT GTA ACC TTT TGT TGC AAG TGT GAC TCT ACG CTT CGG TTG TGC GTA CAA AGC
 Y   N   I   V   T   F   C   C   K   C   D   S   T   L   R   L   C   V   Q   S
1864/621                              1894/631
ACA CAC GTA GAC ATT CGT ACT TTG GAA GAC CTG TTA ATG GGC ACA CTA GGA ATT GTG TGC
 T   H   V   D   I   R   T   L   E   D   L   L   M   G   T   L   G   I   V   C
1924/641
CCC ATC TGT TCT CAG AAA CCA TAG
 P   I   C   S   Q   K   P   *
```

FIG. 16B

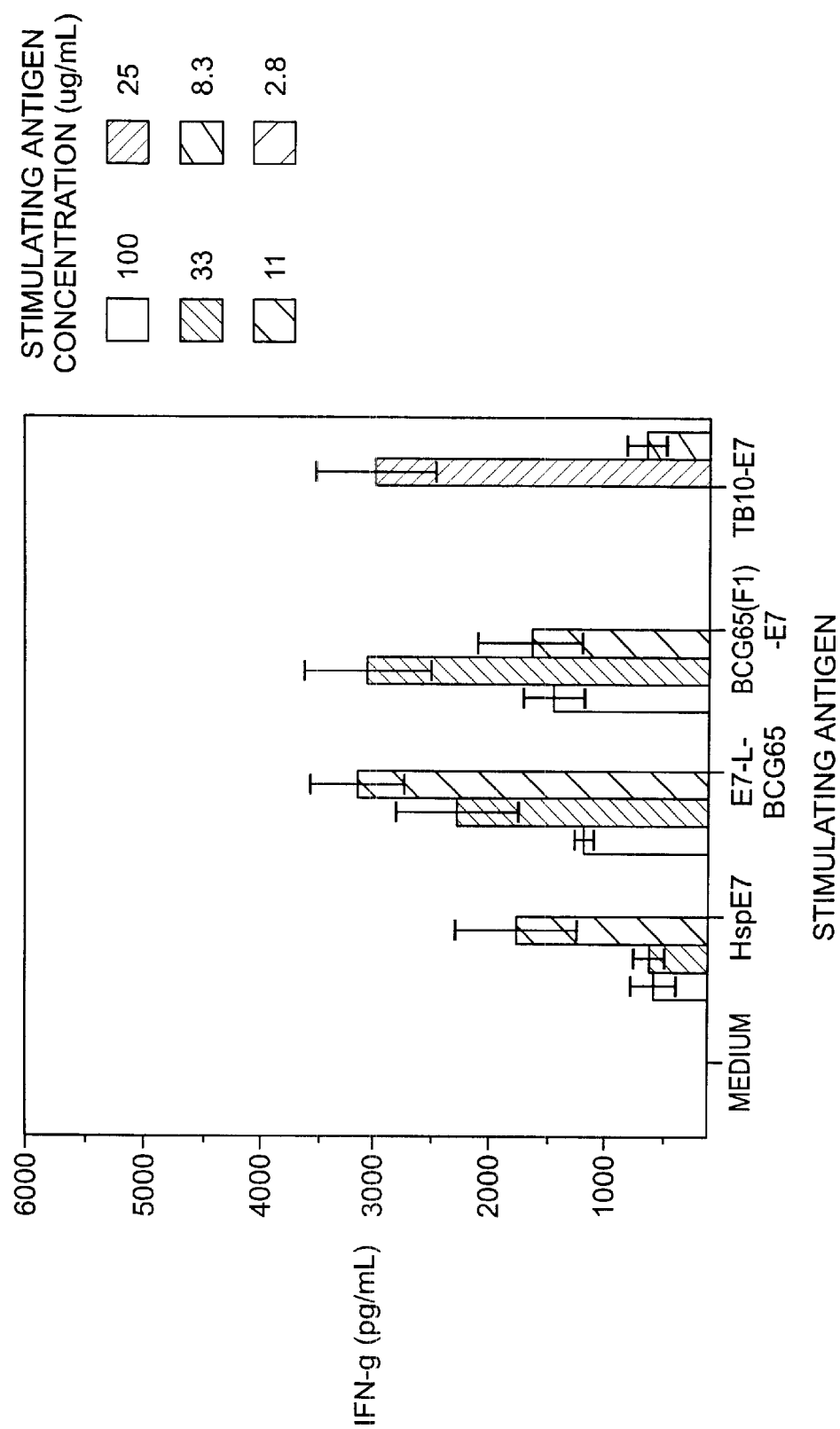

SEQUENCE LISTING

<160> NUMBER OF SEQ ID NOS: 55

<210> SEQ ID NO 1
<211> LENGTH: 24
<212> TYPE: DNA
<213> ORGANISM: Artificial Sequence
<220> FEATURE:
<223> OTHER INFORMATION: fusion sequence

<400> SEQUENCE: 1
ttcgccatgg ccaagacaat tgcg                                        24

<210> SEQ ID NO 2
<211> LENGTH: 27
<212> TYPE: DNA
<213> ORGANISM: Artificial Sequence
<220> FEATURE:
<223> OTHER INFORMATION: fusion sequence

<400> SEQUENCE: 2
ttctcggcta gctcagaaat ccatgcc                                               27

<210> SEQ ID NO 3
<211> LENGTH: 1623
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1620)

<400> SEQUENCE: 3

| atg | gcc | aag | aca | att | gcg | tac | gac | gaa | gag | gcc | cgt | cgc | ggc | ctc | gag | 48 |
|---|---|---|---|---|---|---|---|---|---|---|---|---|---|---|---|---|
| Met | Ala | Lys | Thr | Ile | Ala | Tyr | Asp | Glu | Glu | Ala | Arg | Arg | Gly | Leu | Glu | |
| 1 | | | | 5 | | | | | 10 | | | | | 15 | | |

| cgg | ggc | ttg | aac | gcc | ctc | gcc | gat | gcg | gta | aag | gtg | aca | ttg | ggc | ccc | 96 |
|---|---|---|---|---|---|---|---|---|---|---|---|---|---|---|---|---|
| Arg | Gly | Leu | Asn | Ala | Leu | Ala | Asp | Ala | Val | Lys | Val | Thr | Leu | Gly | Pro | |
| | | | | 20 | | | | | 25 | | | | | 30 | | |

| aag | ggc | cgc | aac | gtc | gtc | ctg | gaa | aag | aag | tgg | ggt | gcc | ccc | acg | atc | 144 |
|---|---|---|---|---|---|---|---|---|---|---|---|---|---|---|---|---|
| Lys | Gly | Arg | Asn | Val | Val | Leu | Glu | Lys | Lys | Trp | Gly | Ala | Pro | Thr | Ile | |
| | | | 35 | | | | | 40 | | | | | 45 | | | |

| acc | aac | gat | ggt | gtg | tcc | atc | gcc | aag | gag | atc | gag | ctg | gag | gat | ccg | 192 |
|---|---|---|---|---|---|---|---|---|---|---|---|---|---|---|---|---|
| Thr | Asn | Asp | Gly | Val | Ser | Ile | Ala | Lys | Glu | Ile | Glu | Leu | Glu | Asp | Pro | |
| | 50 | | | | | 55 | | | | | 60 | | | | | |

| tac | gag | aag | atc | ggc | gcc | gag | ctg | gtc | aaa | gag | gta | gcc | aag | aag | acc | 240 |
|---|---|---|---|---|---|---|---|---|---|---|---|---|---|---|---|---|
| Tyr | Glu | Lys | Ile | Gly | Ala | Glu | Leu | Val | Lys | Glu | Val | Ala | Lys | Lys | Thr | |
| 65 | | | | | 70 | | | | | 75 | | | | | 80 | |

| gat | gac | gtc | gcc | ggt | gac | ggc | acc | acg | acg | gcc | acc | gtg | ctg | gcc | cag | 288 |
|---|---|---|---|---|---|---|---|---|---|---|---|---|---|---|---|---|
| Asp | Asp | Val | Ala | Gly | Asp | Gly | Thr | Thr | Thr | Ala | Thr | Val | Leu | Ala | Gln | |
| | | | | 85 | | | | | 90 | | | | | 95 | | |

| gcg | ttg | gtt | cgc | gag | ggc | ctg | cgc | aac | gtc | gcg | gcc | ggc | gcc | aac | ccg | 336 |
|---|---|---|---|---|---|---|---|---|---|---|---|---|---|---|---|---|
| Ala | Leu | Val | Arg | Glu | Gly | Leu | Arg | Asn | Val | Ala | Ala | Gly | Ala | Asn | Pro | |
| | | | 100 | | | | | 105 | | | | | 110 | | | |

| ctc | ggt | ctc | aaa | cgc | ggc | atc | gaa | aag | gcc | gtg | gag | aag | gtc | acc | gag | 384 |
|---|---|---|---|---|---|---|---|---|---|---|---|---|---|---|---|---|
| Leu | Gly | Leu | Lys | Arg | Gly | Ile | Glu | Lys | Ala | Val | Glu | Lys | Val | Thr | Glu | |
| | | 115 | | | | | 120 | | | | | 125 | | | | |

| acc | ctg | ctc | aag | ggc | gcc | aag | gag | gtc | gag | acc | aag | gag | cag | att | gcg | 432 |
|---|---|---|---|---|---|---|---|---|---|---|---|---|---|---|---|---|
| Thr | Leu | Leu | Lys | Gly | Ala | Lys | Glu | Val | Glu | Thr | Lys | Glu | Gln | Ile | Ala | |
| | 130 | | | | | 135 | | | | | 140 | | | | | |

| gcc | acc | gca | gcg | att | tcg | gcg | ggt | gac | cag | tcc | atc | ggt | gac | ctg | atc | 480 |
|---|---|---|---|---|---|---|---|---|---|---|---|---|---|---|---|---|
| Ala | Thr | Ala | Ala | Ile | Ser | Ala | Gly | Asp | Gln | Ser | Ile | Gly | Asp | Leu | Ile | |
| 145 | | | | | 150 | | | | | 155 | | | | | 160 | |

| gcc | gag | gcg | atg | gac | aag | gtg | ggc | aac | gag | ggc | gtc | atc | acc | gtc | gag | 528 |
|---|---|---|---|---|---|---|---|---|---|---|---|---|---|---|---|---|
| Ala | Glu | Ala | Met | Asp | Lys | Val | Gly | Asn | Glu | Gly | Val | Ile | Thr | Val | Glu | |
| | | | | 165 | | | | | 170 | | | | | 175 | | |

| gag | tcc | aac | acc | ttt | ggg | ctg | cag | ctc | gag | ctc | acc | gag | ggt | atg | cgg | 576 |
|---|---|---|---|---|---|---|---|---|---|---|---|---|---|---|---|---|
| Glu | Ser | Asn | Thr | Phe | Gly | Leu | Gln | Leu | Glu | Leu | Thr | Glu | Gly | Met | Arg | |
| | | | 180 | | | | | 185 | | | | | 190 | | | |

| ttc | gac | aag | ggc | tac | atc | tcg | ggg | tac | ttc | gtg | acc | gac | ccg | gag | cgt | 624 |
|---|---|---|---|---|---|---|---|---|---|---|---|---|---|---|---|---|
| Phe | Asp | Lys | Gly | Tyr | Ile | Ser | Gly | Tyr | Phe | Val | Thr | Asp | Pro | Glu | Arg | |
| | | 195 | | | | | 200 | | | | | 205 | | | | |

| cag | gag | gcg | gtc | ctg | gag | gac | ccc | tac | atc | ctg | ctg | gtc | agc | tcc | aag | 672 |
|---|---|---|---|---|---|---|---|---|---|---|---|---|---|---|---|---|
| Gln | Glu | Ala | Val | Leu | Glu | Asp | Pro | Tyr | Ile | Leu | Leu | Val | Ser | Ser | Lys | |
| | 210 | | | | | 215 | | | | | 220 | | | | | |

| gtg | tcc | act | gtc | aag | gat | ctg | ctg | ccg | ctg | ctc | gag | aag | gtc | atc | gga | 720 |
|---|---|---|---|---|---|---|---|---|---|---|---|---|---|---|---|---|
| Val | Ser | Thr | Val | Lys | Asp | Leu | Leu | Pro | Leu | Leu | Glu | Lys | Val | Ile | Gly | |
| 225 | | | | | 230 | | | | | 235 | | | | | 240 | |

| gcc | ggt | aag | ccg | ctg | ctg | atc | atc | gcc | gag | gac | gtc | gag | ggc | gag | gcg | 768 |
|---|---|---|---|---|---|---|---|---|---|---|---|---|---|---|---|---|
| Ala | Gly | Lys | Pro | Leu | Leu | Ile | Ile | Ala | Glu | Asp | Val | Glu | Gly | Glu | Ala | |
| | | | | 245 | | | | | 250 | | | | | 255 | | |

| ctg | tcc | acc | ctg | gtc | gtc | aac | aag | atc | cgc | ggc | acc | ttc | aag | tcg | gtg | 816 |

-continued

```
Leu Ser Thr Leu Val Val Asn Lys Ile Arg Gly Thr Phe Lys Ser Val
            260                 265                 270 gcg gtc aag gct ccc ggc ttc ggc gac cgc cgc aag gcg atg ctg cag      864
Ala Val Lys Ala Pro Gly Phe Gly Asp Arg Arg Lys Ala Met Leu Gln
        275                 280                 285 gat atg gcc att ctc acc ggt ggt cag gtg atc agc gaa gag gtc ggc      912
Asp Met Ala Ile Leu Thr Gly Gly Gln Val Ile Ser Glu Glu Val Gly
    290                 295                 300 ctg acg ctg gag aac gcc gac ctg tcg ctg cta ggc aag gcc cgc aag      960
Leu Thr Leu Glu Asn Ala Asp Leu Ser Leu Leu Gly Lys Ala Arg Lys
305                 310                 315                 320 gtc gtg gtc acc aag gac gag acc acc atc gtc gag ggc gcc ggt gac     1008
Val Val Val Thr Lys Asp Glu Thr Thr Ile Val Glu Gly Ala Gly Asp
                325                 330                 335 acc gac gcc atc gcc gga cga gtg gcc cag atc cgc cag gag atc gag     1056
Thr Asp Ala Ile Ala Gly Arg Val Ala Gln Ile Arg Gln Glu Ile Glu
            340                 345                 350 aac agc gac tcc gac tac gac cgt gag aag ctg cag gag cgg ctg gcc     1104
Asn Ser Asp Ser Asp Tyr Asp Arg Glu Lys Leu Gln Glu Arg Leu Ala
        355                 360                 365 aag ctg gcc ggt ggt gtc gcg gtg atc aag gcc ggt gcc gcc acc gag     1152
Lys Leu Ala Gly Gly Val Ala Val Ile Lys Ala Gly Ala Ala Thr Glu
    370                 375                 380 gtc gaa ctc aag gag cgc aag cac cgc atc gag gat gcg gtt cgc aat     1200
Val Glu Leu Lys Glu Arg Lys His Arg Ile Glu Asp Ala Val Arg Asn
385                 390                 395                 400 gcc aag gcc gcc gtc gag gag ggc atc gtc gcc ggt ggg ggt gtg acg     1248
Ala Lys Ala Ala Val Glu Glu Gly Ile Val Ala Gly Gly Gly Val Thr
                405                 410                 415 ctg ttg caa gcg gcc ccg acc ctg gac gag ctg aag ctc gaa ggc gac     1296
Leu Leu Gln Ala Ala Pro Thr Leu Asp Glu Leu Lys Leu Glu Gly Asp
            420                 425                 430 gag gcg acc ggc gcc aac atc gtg aag gtg gcg ctg gag gcc ccg ctg     1344
Glu Ala Thr Gly Ala Asn Ile Val Lys Val Ala Leu Glu Ala Pro Leu
        435                 440                 445 aag cag atc gcc ttc aac tcc ggg ctg gag ccg ggc gtg gtg gcc gag     1392
Lys Gln Ile Ala Phe Asn Ser Gly Leu Glu Pro Gly Val Val Ala Glu
    450                 455                 460 aag gtg cgc aac ctg ccg gct ggc cac gga ctg aac gct cag acc ggt     1440
Lys Val Arg Asn Leu Pro Ala Gly His Gly Leu Asn Ala Gln Thr Gly
465                 470                 475                 480 gtc tac gag gat ctg ctc gct gcc ggc gtt gct gac ccg gtc aag gtg     1488
Val Tyr Glu Asp Leu Leu Ala Ala Gly Val Ala Asp Pro Val Lys Val
                485                 490                 495 acc cgt tcg gcg ctg cag aat gcg gcg tcc atc gcg ggg ctg ttc ctg     1536
Thr Arg Ser Ala Leu Gln Asn Ala Ala Ser Ile Ala Gly Leu Phe Leu
            500                 505                 510 acc acc gag gcc gtc gtt gcc gac aag ccg gaa aag gag aag gct tcc     1584
Thr Thr Glu Ala Val Val Ala Asp Lys Pro Glu Lys Glu Lys Ala Ser
        515                 520                 525 gtt ccc ggt ggc ggc gac atg ggt ggc atg gat ttc tga                 1623
Val Pro Gly Gly Gly Asp Met Gly Gly Met Asp Phe
    530                 535                 540

<210> SEQ ID NO 4
<211> LENGTH: 540
<212> TYPE: PRT
<213> ORGANISM: Artificial Sequence
<220> FEATURE:
<223> OTHER INFORMATION: fusion sequence
```

-continued

<400> SEQUENCE: 4

```
Met Ala Lys Thr Ile Ala Tyr Asp Glu Glu Ala Arg Arg Gly Leu Glu
 1               5                  10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Thr
                405                 410                 415
```

```
Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540

<210> SEQ ID NO 5
<211> LENGTH: 24
<212> TYPE: DNA
<213> ORGANISM: Artificial Sequence
<220> FEATURE:
<223> OTHER INFORMATION: fusion sequence

<400> SEQUENCE: 5
ccagctgtaa ccatggatgg agat                                           24

<210> SEQ ID NO 6
<211> LENGTH: 24
<212> TYPE: DNA
<213> ORGANISM: Artificial Sequence
<220> FEATURE:
<223> OTHER INFORMATION: fusion sequence

<400> SEQUENCE: 6
agccatgaat tcttatggtt tctg                                           24

<210> SEQ ID NO 7
<211> LENGTH: 297
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(294)

<400> SEQUENCE: 7 atg gat gga gat aca cct aca ttg cat gaa tat atg tta gat ttg caa     48
Met Asp Gly Asp Thr Pro Thr Leu His Glu Tyr Met Leu Asp Leu Gln
 1               5                  10                  15 cca gag aca act gat ctc tac tgt tat gag caa tta aat gac agc tca     96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac    144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg    192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa    240
Leu Arg Leu Cys Val Gln Ser Thr His Val Asp Ile Arg Thr Leu Glu
```

```
                65                  70                  75                  80
gac ctg tta atg ggc aca cta gga att gtg tgc ccc atc tgt tct cag    288
Asp Leu Leu Met Gly Thr Leu Gly Ile Val Cys Pro Ile Cys Ser Gln
                85                  90                  95 aaa cca taa                                                        297
Lys Pro

<210> SEQ ID NO 8
<211> LENGTH: 98
<212> TYPE: PRT
<213> ORGANISM: Artificial Sequence
<220> FEATURE:
<223> OTHER INFORMATION: fusion sequence

<400> SEQUENCE: 8

Met Asp Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 9
<211> LENGTH: 27
<212> TYPE: DNA
<213> ORGANISM: Artificial Sequence
<220> FEATURE:
<223> OTHER INFORMATION: fusion sequence

<400> SEQUENCE: 9
aacccagctg ctagcatgca tggagat                                      27

<210> SEQ ID NO 10
<211> LENGTH: 24
<212> TYPE: DNA
<213> ORGANISM: Artificial Sequence
<220> FEATURE:
<223> OTHER INFORMATION: fusion sequence

<400> SEQUENCE: 10
agccatgaat tcttatggtt tctg                                         24

<210> SEQ ID NO 11
<211> LENGTH: 366
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(363)

<400> SEQUENCE: 11 atg ggc agc agc cat cat cat cat cat cac agc agc ggc ctg gtg ccg    48
Met Gly Ser Ser His His His His His His Ser Ser Gly Leu Val Pro
  1               5                  10                  15
```

```
cgc ggc agc cat atg gct agc atg cat gga gat aca cct aca ttg cat        96
Arg Gly Ser His Met Ala Ser Met His Gly Asp Thr Pro Thr Leu His
         20                  25                  30 gaa tat atg tta gat ttg caa cca gag aca act gat ctc tac tgt tat       144
Glu Tyr Met Leu Asp Leu Gln Pro Glu Thr Thr Asp Leu Tyr Cys Tyr
 35                  40                  45 gag caa tta aat gac agc tca gag gag gag gat gaa ata gat ggt cca       192
Glu Gln Leu Asn Asp Ser Ser Glu Glu Glu Asp Glu Ile Asp Gly Pro
 50                  55                  60 gct gga caa gca gaa ccg gac aga gcc cat tac aat att gta acc ttt       240
Ala Gly Gln Ala Glu Pro Asp Arg Ala His Tyr Asn Ile Val Thr Phe
 65                  70                  75                  80 tgt tgc aag tgt gac tct acg ctt cgg ttg tgc gta caa agc aca cac       288
Cys Cys Lys Cys Asp Ser Thr Leu Arg Leu Cys Val Gln Ser Thr His
             85                  90                  95 gta gac att cgt act ttg gaa gac ctg tta atg ggc aca cta gga att       336
Val Asp Ile Arg Thr Leu Glu Asp Leu Leu Met Gly Thr Leu Gly Ile
            100                 105                 110 gtg tgc ccc atc tgt tct cag aaa cca taa                               366
Val Cys Pro Ile Cys Ser Gln Lys Pro
            115                 120
```

<210> SEQ ID NO 12
<211> LENGTH: 121
<212> TYPE: PRT
<213> ORGANISM: Artificial Sequence
<220> FEATURE:
<223> OTHER INFORMATION: fusion sequence

<400> SEQUENCE: 12

```
Met Gly Ser Ser His His His His His His Ser Ser Gly Leu Val Pro
 1               5                   10                  15

Arg Gly Ser His Met Ala Ser Met His Gly Asp Thr Pro Thr Leu His
             20                  25                  30

Glu Tyr Met Leu Asp Leu Gln Pro Glu Thr Thr Asp Leu Tyr Cys Tyr
 35                  40                  45

Glu Gln Leu Asn Asp Ser Ser Glu Glu Glu Asp Glu Ile Asp Gly Pro
 50                  55                  60

Ala Gly Gln Ala Glu Pro Asp Arg Ala His Tyr Asn Ile Val Thr Phe
 65                  70                  75                  80

Cys Cys Lys Cys Asp Ser Thr Leu Arg Leu Cys Val Gln Ser Thr His
             85                  90                  95

Val Asp Ile Arg Thr Leu Glu Asp Leu Leu Met Gly Thr Leu Gly Ile
            100                 105                 110

Val Cys Pro Ile Cys Ser Gln Lys Pro
            115                 120
```

<210> SEQ ID NO 13
<211> LENGTH: 36
<212> TYPE: DNA
<213> ORGANISM: Artificial Sequence
<220> FEATURE:
<223> OTHER INFORMATION: fusion sequence

<400> SEQUENCE: 13
cgctcggacg ctagctcaca tatggaaatc catgcc        36

<210> SEQ ID NO 14
<211> LENGTH: 24
<212> TYPE: DNA
<213> ORGANISM: Artificial Sequence
<220> FEATURE:
<223> OTHER INFORMATION: fusion sequence

<400> SEQUENCE: 14
ccagctgtac atatgcatgg agat                                          24

<210> SEQ ID NO 15
<211> LENGTH: 24
<212> TYPE: DNA
<213> ORGANISM: Artificial Sequence
<220> FEATURE:
<223> OTHER INFORMATION: fusion sequence

<400> SEQUENCE: 15
agccatgaat tcttatggtt tctg                                          24

<210> SEQ ID NO 16
<211> LENGTH: 1920
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1917)

<400> SEQUENCE: 16

| atg | gcc | aag | aca | att | gcg | tac | gac | gaa | gag | gcc | cgt | cgc | ggc | ctc | gag | 48 |
|---|---|---|---|---|---|---|---|---|---|---|---|---|---|---|---|---|
| Met | Ala | Lys | Thr | Ile | Ala | Tyr | Asp | Glu | Glu | Ala | Arg | Arg | Gly | Leu | Glu | |
| 1 | | | | 5 | | | | | 10 | | | | | 15 | | |

| cgg | ggc | ttg | aac | gcc | ctc | gcc | gat | gcg | gta | aag | gtg | aca | ttg | ggc | ccc | 96 |
|---|---|---|---|---|---|---|---|---|---|---|---|---|---|---|---|---|
| Arg | Gly | Leu | Asn | Ala | Leu | Ala | Asp | Ala | Val | Lys | Val | Thr | Leu | Gly | Pro | |
| | | | 20 | | | | | 25 | | | | | 30 | | | |

| aag | ggc | cgc | aac | gtc | gtc | ctg | gaa | aag | aag | tgg | ggt | gcc | ccc | acg | atc | 144 |
|---|---|---|---|---|---|---|---|---|---|---|---|---|---|---|---|---|
| Lys | Gly | Arg | Asn | Val | Val | Leu | Glu | Lys | Lys | Trp | Gly | Ala | Pro | Thr | Ile | |
| | 35 | | | | | 40 | | | | | 45 | | | | | |

| acc | aac | gat | ggt | gtg | tcc | atc | gcc | aag | gag | atc | gag | ctg | gag | gat | ccg | 192 |
|---|---|---|---|---|---|---|---|---|---|---|---|---|---|---|---|---|
| Thr | Asn | Asp | Gly | Val | Ser | Ile | Ala | Lys | Glu | Ile | Glu | Leu | Glu | Asp | Pro | |
| 50 | | | | | 55 | | | | | 60 | | | | | | |

| tac | gag | aag | atc | ggc | gcc | gag | ctg | gtc | aaa | gag | gta | gcc | aag | aag | acc | 240 |
|---|---|---|---|---|---|---|---|---|---|---|---|---|---|---|---|---|
| Tyr | Glu | Lys | Ile | Gly | Ala | Glu | Leu | Val | Lys | Glu | Val | Ala | Lys | Lys | Thr | |
| 65 | | | | | 70 | | | | | 75 | | | | | 80 | |

| gat | gac | gtc | gcc | ggt | gac | ggc | acc | acg | gcc | acc | gtg | ctg | gcc | cag | | 288 |
|---|---|---|---|---|---|---|---|---|---|---|---|---|---|---|---|---|
| Asp | Asp | Val | Ala | Gly | Asp | Gly | Thr | Thr | Thr | Ala | Thr | Val | Leu | Ala | Gln | |
| | | | | 85 | | | | | 90 | | | | | 95 | | |

| gcg | ttg | gtt | cgc | gag | ggc | ctg | cgc | aac | gtc | gcg | gcc | ggc | gcc | aac | ccg | 336 |
|---|---|---|---|---|---|---|---|---|---|---|---|---|---|---|---|---|
| Ala | Leu | Val | Arg | Glu | Gly | Leu | Arg | Asn | Val | Ala | Ala | Gly | Ala | Asn | Pro | |
| | | 100 | | | | | 105 | | | | | 110 | | | | |

| ctc | ggt | ctc | aaa | cgc | ggc | atc | gaa | aag | gcc | gtg | gag | aag | gtc | acc | gag | 384 |
|---|---|---|---|---|---|---|---|---|---|---|---|---|---|---|---|---|
| Leu | Gly | Leu | Lys | Arg | Gly | Ile | Glu | Lys | Ala | Val | Glu | Lys | Val | Thr | Glu | |
| | | | 115 | | | | | 120 | | | | | 125 | | | |

| acc | ctg | ctc | aag | ggc | gcc | aag | gag | gtc | gag | acc | aag | gag | cag | att | gcg | 432 |
|---|---|---|---|---|---|---|---|---|---|---|---|---|---|---|---|---|
| Thr | Leu | Leu | Lys | Gly | Ala | Lys | Glu | Val | Glu | Thr | Lys | Glu | Gln | Ile | Ala | |
| | 130 | | | | | 135 | | | | | 140 | | | | | |

| gcc | acc | gca | gcg | att | tcg | gcg | ggt | gac | cag | tcc | atc | ggt | gac | ctg | atc | 480 |
|---|---|---|---|---|---|---|---|---|---|---|---|---|---|---|---|---|
| Ala | Thr | Ala | Ala | Ile | Ser | Ala | Gly | Asp | Gln | Ser | Ile | Gly | Asp | Leu | Ile | |
| 145 | | | | | 150 | | | | | 155 | | | | | 160 | |

| gcc | gag | gcg | atg | gac | aag | gtg | ggc | aac | gag | ggc | gtc | atc | acc | gtc | gag | 528 |
|---|---|---|---|---|---|---|---|---|---|---|---|---|---|---|---|---|
| Ala | Glu | Ala | Met | Asp | Lys | Val | Gly | Asn | Glu | Gly | Val | Ile | Thr | Val | Glu | |
| | | | | 165 | | | | | 170 | | | | | 175 | | |

| gag | tcc | aac | acc | ttt | ggg | ctg | cag | ctc | gag | ctc | acc | gag | ggt | atg | cgg | 576 |
|---|---|---|---|---|---|---|---|---|---|---|---|---|---|---|---|---|
| Glu | Ser | Asn | Thr | Phe | Gly | Leu | Gln | Leu | Glu | Leu | Thr | Glu | Gly | Met | Arg | |
| | | | 180 | | | | | 185 | | | | | 190 | | | |

```
ttc gac aag ggc tac atc tcg ggg tac ttc gtg acc gac ccg gag cgt      624
Phe Asp Lys Gly Tyr Ile Ser Gly Tyr Phe Val Thr Asp Pro Glu Arg
            195                 200                 205 cag gag gcg gtc ctg gag gac ccc tac atc ctg ctg gtc agc tcc aag      672
Gln Glu Ala Val Leu Glu Asp Pro Tyr Ile Leu Leu Val Ser Ser Lys
    210                 215                 220 gtg tcc act gtc aag gat ctg ctg ccg ctg ctc gag aag gtc atc gga      720
Val Ser Thr Val Lys Asp Leu Leu Pro Leu Leu Glu Lys Val Ile Gly
225                 230                 235                 240 gcc ggt aag ccg ctg ctg atc atc gcc gag gac gtc gag ggc gag gcg      768
Ala Gly Lys Pro Leu Leu Ile Ile Ala Glu Asp Val Glu Gly Glu Ala
                245                 250                 255 ctg tcc acc ctg gtc gtc aac aag atc cgc ggc acc ttc aag tcg gtg      816
Leu Ser Thr Leu Val Val Asn Lys Ile Arg Gly Thr Phe Lys Ser Val
            260                 265                 270 gcg gtc aag gct ccc ggc ttc ggc gac cgc cgc aag gcg atg ctg cag      864
Ala Val Lys Ala Pro Gly Phe Gly Asp Arg Arg Lys Ala Met Leu Gln
    275                 280                 285 gat atg gcc att ctc acc ggt ggt cag gtg atc agc gaa gag gtc ggc      912
Asp Met Ala Ile Leu Thr Gly Gly Gln Val Ile Ser Glu Glu Val Gly
290                 295                 300 ctg acg ctg gag aac gcc gac ctg tcg ctg cta ggc aag gcc cgc aag      960
Leu Thr Leu Glu Asn Ala Asp Leu Ser Leu Leu Gly Lys Ala Arg Lys
305                 310                 315                 320 gtc gtg gtc acc aag gac gag acc acc atc gtc gag ggc gcc ggt gac     1008
Val Val Val Thr Lys Asp Glu Thr Thr Ile Val Glu Gly Ala Gly Asp
                325                 330                 335 acc gac gcc atc gcc gga cga gtg gcc cag atc cgc cag gag atc gag     1056
Thr Asp Ala Ile Ala Gly Arg Val Ala Gln Ile Arg Gln Glu Ile Glu
            340                 345                 350 aac agc gac tcc gac tac gac cgt gag aag ctg cag gag cgg ctg gcc     1104
Asn Ser Asp Ser Asp Tyr Asp Arg Glu Lys Leu Gln Glu Arg Leu Ala
    355                 360                 365 aag ctg gcc ggt ggt gtc gcg gtg atc aag gcc ggt gcc gcc acc gag     1152
Lys Leu Ala Gly Gly Val Ala Val Ile Lys Ala Gly Ala Ala Thr Glu
370                 375                 380 gtc gaa ctc aag gag cgc aag cac cgc atc gag gat gcg gtt cgc aat     1200
Val Glu Leu Lys Glu Arg Lys His Arg Ile Glu Asp Ala Val Arg Asn
385                 390                 395                 400 gcc aag gcc gcc gtc gag gag ggc atc gtc gcc ggt ggg ggt gtg acg     1248
Ala Lys Ala Ala Val Glu Glu Gly Ile Val Ala Gly Gly Gly Val Thr
                405                 410                 415 ctg ttg caa gcg gcc ccg acc ctg gac gag ctg aag ctc gaa ggc gac     1296
Leu Leu Gln Ala Ala Pro Thr Leu Asp Glu Leu Lys Leu Glu Gly Asp
            420                 425                 430 gag gcg acc ggc gcc aac atc gtg aag gtg gcg ctg gag gcc ccg ctg     1344
Glu Ala Thr Gly Ala Asn Ile Val Lys Val Ala Leu Glu Ala Pro Leu
    435                 440                 445 aag cag atc gcc ttc aac tcc ggg ctg gag ccg ggc gtg gtg gcc gag     1392
Lys Gln Ile Ala Phe Asn Ser Gly Leu Glu Pro Gly Val Val Ala Glu
450                 455                 460 aag gtg cgc aac ctg ccg gct ggc cac gga ctg aac gct cag acc ggt     1440
Lys Val Arg Asn Leu Pro Ala Gly His Gly Leu Asn Ala Gln Thr Gly
465                 470                 475                 480 gtc tac gag gat ctg ctc gct gcc ggc gtt gct gac ccg gtc aag gtg     1488
Val Tyr Glu Asp Leu Leu Ala Ala Gly Val Ala Asp Pro Val Lys Val
                485                 490                 495 acc cgt tcg gcg ctg cag aat gcg gcg tcc atc gcg ggg ctg ttc ctg     1536
Thr Arg Ser Ala Leu Gln Asn Ala Ala Ser Ile Ala Gly Leu Phe Leu
            500                 505                 510
```

```
acc acc gag gcc gtc gtt gcc gac aag ccg gaa aag gag aag gct tcc   1584
Thr Thr Glu Ala Val Val Ala Asp Lys Pro Glu Lys Glu Lys Ala Ser
        515                 520                 525 gtt ccc ggt ggc ggc gac atg ggt ggc atg gat ttc cat atg cat gga   1632
Val Pro Gly Gly Gly Asp Met Gly Gly Met Asp Phe His Met His Gly
    530                 535                 540 gat aca cct aca ttg cat gaa tat atg tta gat ttg caa cca gag aca   1680
Asp Thr Pro Thr Leu His Glu Tyr Met Leu Asp Leu Gln Pro Glu Thr
545                 550                 555                 560 act gat ctc tac tgt tat gag caa tta aat gac agc tca gag gag gag   1728
Thr Asp Leu Tyr Cys Tyr Glu Gln Leu Asn Asp Ser Ser Glu Glu Glu
            565                 570                 575 gat gaa ata gat ggt cca gct gga caa gca gaa ccg gac aga gcc cat   1776
Asp Glu Ile Asp Gly Pro Ala Gly Gln Ala Glu Pro Asp Arg Ala His
        580                 585                 590 tac aat att gta acc ttt tgt tgc aag tgt gac tct acg ctt cgg ttg   1824
Tyr Asn Ile Val Thr Phe Cys Cys Lys Cys Asp Ser Thr Leu Arg Leu
    595                 600                 605 tgc gta caa agc aca cac gta gac att cgt act ttg gaa gac ctg tta   1872
Cys Val Gln Ser Thr His Val Asp Ile Arg Thr Leu Glu Asp Leu Leu
610                 615                 620 atg ggc aca cta gga att gtg tgc ccc atc tgt tct cag aaa cca       1917
Met Gly Thr Leu Gly Ile Val Cys Pro Ile Cys Ser Gln Lys Pro
625                 630                 635 taa                                                                1920
```

<210> SEQ ID NO 17
<211> LENGTH: 639
<212> TYPE: PRT
<213> ORGANISM: Artificial Sequence
<220> FEATURE:
<223> OTHER INFORMATION: fusion sequence

<400> SEQUENCE: 17

```
Met Ala Lys Thr Ile Ala Tyr Asp Glu Glu Ala Arg Arg Gly Leu Glu
  1               5                  10                  15

Arg Gly Leu Asn Ala Leu Ala Asp Ala Val Lys Val Thr Leu Gly Pro
                 20                  25                  30

Lys Gly Arg Asn Val Val Leu Glu Lys Lys Trp Gly Ala Pro Thr Ile
             35                  40                  45

Thr Asn Asp Gly Val Ser Ile Ala Lys Glu Ile Glu Leu Glu Asp Pro
         50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                 85                  90                  95

Ala Leu Val Arg Glu Gly Leu Arg Asn Val Ala Ala Gly Ala Asn Pro
                100                 105                 110

Leu Gly Leu Lys Arg Gly Ile Glu Lys Ala Val Glu Lys Val Thr Glu
            115                 120                 125

Thr Leu Leu Lys Gly Ala Lys Glu Val Glu Thr Lys Glu Gln Ile Ala
        130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
```

-continued

```
                180                 185                 190
Phe Asp Lys Gly Tyr Ile Ser Gly Tyr Phe Val Thr Asp Pro Glu Arg
            195                 200                 205
Gln Glu Ala Val Leu Glu Asp Pro Tyr Ile Leu Val Ser Ser Lys
210                 215                 220
Val Ser Thr Val Lys Asp Leu Leu Pro Leu Leu Glu Lys Val Ile Gly
225                 230                 235                 240
Ala Gly Lys Pro Leu Leu Ile Ile Ala Glu Asp Val Glu Gly Glu Ala
                245                 250                 255
Leu Ser Thr Leu Val Val Asn Lys Ile Arg Gly Thr Phe Lys Ser Val
                260                 265                 270
Ala Val Lys Ala Pro Gly Phe Gly Asp Arg Arg Lys Ala Met Leu Gln
                275                 280                 285
Asp Met Ala Ile Leu Thr Gly Gly Gln Val Ile Ser Glu Glu Val Gly
            290                 295                 300
Leu Thr Leu Glu Asn Ala Asp Leu Ser Leu Leu Gly Lys Ala Arg Lys
305                 310                 315                 320
Val Val Val Thr Lys Asp Glu Thr Thr Ile Val Glu Gly Ala Gly Asp
                325                 330                 335
Thr Asp Ala Ile Ala Gly Arg Val Ala Gln Ile Arg Gln Glu Ile Glu
            340                 345                 350
Asn Ser Asp Ser Asp Tyr Asp Arg Glu Lys Leu Gln Glu Arg Leu Ala
                355                 360                 365
Lys Leu Ala Gly Gly Val Ala Val Ile Lys Ala Gly Ala Ala Thr Glu
            370                 375                 380
Val Glu Leu Lys Glu Arg Lys His Arg Ile Glu Asp Ala Val Arg Asn
385                 390                 395                 400
Ala Lys Ala Ala Val Glu Glu Gly Ile Val Ala Gly Gly Val Thr
                405                 410                 415
Leu Leu Gln Ala Ala Pro Thr Leu Asp Glu Leu Lys Leu Glu Gly Asp
                420                 425                 430
Glu Ala Thr Gly Ala Asn Ile Val Lys Val Ala Leu Glu Ala Pro Leu
            435                 440                 445
Lys Gln Ile Ala Phe Asn Ser Gly Leu Glu Pro Gly Val Val Ala Glu
            450                 455                 460
Lys Val Arg Asn Leu Pro Ala Gly His Gly Leu Asn Ala Gln Thr Gly
465                 470                 475                 480
Val Tyr Glu Asp Leu Leu Ala Ala Gly Val Ala Asp Pro Val Lys Val
                485                 490                 495
Thr Arg Ser Ala Leu Gln Asn Ala Ala Ser Ile Ala Gly Leu Phe Leu
            500                 505                 510
Thr Thr Glu Ala Val Val Ala Asp Lys Pro Glu Lys Glu Lys Ala Ser
            515                 520                 525
Val Pro Gly Gly Gly Asp Met Gly Gly Met Asp Phe His Met His Gly
530                 535                 540
Asp Thr Pro Thr Leu His Glu Tyr Met Leu Asp Leu Gln Pro Glu Thr
545                 550                 555                 560
Thr Asp Leu Tyr Cys Tyr Glu Gln Leu Asn Asp Ser Ser Glu Glu Glu
                565                 570                 575
Asp Glu Ile Asp Gly Pro Ala Gly Gln Ala Glu Pro Asp Arg Ala His
            580                 585                 590
Tyr Asn Ile Val Thr Phe Cys Cys Lys Cys Asp Ser Thr Leu Arg Leu
            595                 600                 605
```

```
Cys Val Gln Ser Thr His Val Asp Ile Arg Thr Leu Glu Asp Leu Leu
    610                 615                 620

Met Gly Thr Leu Gly Ile Val Cys Pro Ile Cys Ser Gln Lys Pro
625                 630                 635

<210> SEQ ID NO 18
<211> LENGTH: 1482
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1479)

<400> SEQUENCE: 18 atg gcc caa agg gaa tgg gtc gaa aaa gac ttc tac cag gag ctg ggc        48
Met Ala Gln Arg Glu Trp Val Glu Lys Asp Phe Tyr Gln Glu Leu Gly
  1               5                  10                  15 gtc tcc tct gat gcc agt cct gaa gag atc aaa cgt gcc tat cgg aag        96
Val Ser Ser Asp Ala Ser Pro Glu Glu Ile Lys Arg Ala Tyr Arg Lys
                 20                  25                  30 ttg gcg cgc gac ctg cat ccg gac gcg aac ccg ggc aac ccg gcc gcc       144
Leu Ala Arg Asp Leu His Pro Asp Ala Asn Pro Gly Asn Pro Ala Ala
             35                  40                  45 ggc gaa cgg ttc aag gcg gtt tcg gag gcg cat aac gtg ctg tcg gat       192
Gly Glu Arg Phe Lys Ala Val Ser Glu Ala His Asn Val Leu Ser Asp
         50                  55                  60 ccg gcc aag cgc aag gag tac gac gaa acc cgc cgc ctg ttc gcc ggc       240
Pro Ala Lys Arg Lys Glu Tyr Asp Glu Thr Arg Arg Leu Phe Ala Gly
 65                  70                  75                  80 ggc ggg ttc ggc ggc cgt cgg ttc gac agc ggc ttt ggg ggc ggg ttc       288
Gly Gly Phe Gly Gly Arg Arg Phe Asp Ser Gly Phe Gly Gly Gly Phe
                 85                  90                  95 ggc ggt ttc ggg gtc ggt gga gac ggc gcc gag ttc aac ctc aac gac       336
Gly Gly Phe Gly Val Gly Gly Asp Gly Ala Glu Phe Asn Leu Asn Asp
            100                 105                 110 ttg ttc gac gcc gcc agc cga acc ggc ggt acc acc atc ggt gac ttg       384
Leu Phe Asp Ala Ala Ser Arg Thr Gly Gly Thr Thr Ile Gly Asp Leu
        115                 120                 125 ttc ggt ggc ttg ttc gga cgc ggt ggc agc gcc cgt ccc agc cgc ccg       432
Phe Gly Gly Leu Phe Gly Arg Gly Gly Ser Ala Arg Pro Ser Arg Pro
    130                 135                 140 cga cgc ggc aac gac ctg gag acc gag acc gag ttg gat ttc gtg gag       480
Arg Arg Gly Asn Asp Leu Glu Thr Glu Thr Glu Leu Asp Phe Val Glu
145                 150                 155                 160 gcc gcc aag ggc gtg gcg atg ccg ctg cga tta acc agc ccg gcg ccg       528
Ala Ala Lys Gly Val Ala Met Pro Leu Arg Leu Thr Ser Pro Ala Pro
                165                 170                 175 tgc acc aac tgc cat ggc agc ggg gcc cgg cca ggc acc agc cca aag       576
Cys Thr Asn Cys His Gly Ser Gly Ala Arg Pro Gly Thr Ser Pro Lys
            180                 185                 190 gtg tgt ccc act tgc aac ggg tcg ggc gtg atc aac cgc aat cag ggc       624
Val Cys Pro Thr Cys Asn Gly Ser Gly Val Ile Asn Arg Asn Gln Gly
        195                 200                 205 gcg ttc ggc ttc tcc gag ccg tgc acc gac tgc cga ggt agc ggc tcg       672
Ala Phe Gly Phe Ser Glu Pro Cys Thr Asp Cys Arg Gly Ser Gly Ser
    210                 215                 220 atc atc gag cac ccc tgc gag gag tgc aaa ggc acc ggc gtg acc acc       720
Ile Ile Glu His Pro Cys Glu Glu Cys Lys Gly Thr Gly Val Thr Thr
225                 230                 235                 240
```

```
cgc acc cga acc atc aac gtg cgg atc ccg ccc ggt gtc gag gat ggg    768
Arg Thr Arg Thr Ile Asn Val Arg Ile Pro Pro Gly Val Glu Asp Gly
                245                 250                 255 cag cgc atc cgg cta gcc ggt cag ggc gag gcc ggg ttg cgc ggc gct    816
Gln Arg Ile Arg Leu Ala Gly Gln Gly Glu Ala Gly Leu Arg Gly Ala
            260                 265                 270 ccc tcg ggg gat ctc tac gtg acg gtg cat gtg cgg ccc gac aag atc    864
Pro Ser Gly Asp Leu Tyr Val Thr Val His Val Arg Pro Asp Lys Ile
        275                 280                 285 ttc ggc cgc gac ggc gac gac ctc acc gtc acc gtt ccg gtc agc ttc    912
Phe Gly Arg Asp Gly Asp Asp Leu Thr Val Thr Val Pro Val Ser Phe
    290                 295                 300 acc gaa ttg gct ttg ggc tcg acg ctg tcg gtg cct acc ctg gac ggc    960
Thr Glu Leu Ala Leu Gly Ser Thr Leu Ser Val Pro Thr Leu Asp Gly
305                 310                 315                 320 acg gtc ggg gtc cgg gtg ccc aaa ggc acc gct gac ggc cgc att ctg   1008
Thr Val Gly Val Arg Val Pro Lys Gly Thr Ala Asp Gly Arg Ile Leu
                325                 330                 335 cgt gtg cgc gga cgc ggt gtg ccc aag cgc agt ggg ggt agc ggc gac   1056
Arg Val Arg Gly Arg Gly Val Pro Lys Arg Ser Gly Gly Ser Gly Asp
            340                 345                 350 cta ctt gtc acc gtg aag gtg gcc gtg ccg ccc aat ttg gca ggc gcc   1104
Leu Leu Val Thr Val Lys Val Ala Val Pro Pro Asn Leu Ala Gly Ala
        355                 360                 365 gct cag gaa gct ctg gaa gcc tat gcg gcg gcg gag cgg tcc agt ggt   1152
Ala Gln Glu Ala Leu Glu Ala Tyr Ala Ala Ala Glu Arg Ser Ser Gly
    370                 375                 380 ttc aac ccg cgg gcc gga tgg gca ggt aat cgc atg cat gga gat aca   1200
Phe Asn Pro Arg Ala Gly Trp Ala Gly Asn Arg Met His Gly Asp Thr
385                 390                 395                 400 cct aca ttg cat gaa tat atg tta gat ttg caa cca gag aca act gat   1248
Pro Thr Leu His Glu Tyr Met Leu Asp Leu Gln Pro Glu Thr Thr Asp
                405                 410                 415 ctc tac tgt tat gag caa tta aat gac agc tca gag gag gag gat gaa   1296
Leu Tyr Cys Tyr Glu Gln Leu Asn Asp Ser Ser Glu Glu Glu Asp Glu
            420                 425                 430 ata gat ggt cca gct gga caa gca gaa ccg gac aga gcc cat tac aat   1344
Ile Asp Gly Pro Ala Gly Gln Ala Glu Pro Asp Arg Ala His Tyr Asn
        435                 440                 445 att gta acc ttt tgt tgc aag tgt gac tct acg ctt cgg ttg tgc gta   1392
Ile Val Thr Phe Cys Cys Lys Cys Asp Ser Thr Leu Arg Leu Cys Val
    450                 455                 460 caa agc aca cac gta gac att cgt act ttg gaa gac ctg tta atg ggc   1440
Gln Ser Thr His Val Asp Ile Arg Thr Leu Glu Asp Leu Leu Met Gly
465                 470                 475                 480 aca cta gga att gtg tgc ccc atc tgt tct cag aaa cca tag            1482
Thr Leu Gly Ile Val Cys Pro Ile Cys Ser Gln Lys Pro
                485                 490

<210> SEQ ID NO 19
<211> LENGTH: 493
<212> TYPE: PRT
<213> ORGANISM: Artificial Sequence
<220> FEATURE:
<223> OTHER INFORMATION: fusion sequence

<400> SEQUENCE: 19

Met Ala Gln Arg Glu Trp Val Glu Lys Asp Phe Tyr Gln Glu Leu Gly
 1               5                  10                  15

Val Ser Ser Asp Ala Ser Pro Glu Glu Ile Lys Arg Ala Tyr Arg Lys
                20                  25                  30
```

```
Leu Ala Arg Asp Leu His Pro Asp Ala Asn Pro Gly Asn Pro Ala Ala
        35                  40                  45
Gly Glu Arg Phe Lys Ala Val Ser Glu Ala His Asn Val Leu Ser Asp
 50                  55                  60
Pro Ala Lys Arg Lys Glu Tyr Asp Glu Thr Arg Arg Leu Phe Ala Gly
 65                  70                  75                  80
Gly Gly Phe Gly Gly Arg Phe Asp Ser Gly Phe Gly Gly Phe
                 85                  90                  95
Gly Gly Phe Gly Val Gly Gly Asp Gly Ala Glu Phe Asn Leu Asn Asp
                100                 105                 110
Leu Phe Asp Ala Ala Ser Arg Thr Gly Thr Thr Ile Gly Asp Leu
            115                 120                 125
Phe Gly Gly Leu Phe Gly Arg Gly Gly Ser Ala Arg Pro Ser Arg Pro
130                 135                 140
Arg Arg Gly Asn Asp Leu Glu Thr Glu Thr Glu Leu Asp Phe Val Glu
145                 150                 155                 160
Ala Ala Lys Gly Val Ala Met Pro Leu Arg Leu Thr Ser Pro Ala Pro
                165                 170                 175
Cys Thr Asn Cys His Gly Ser Gly Ala Arg Pro Gly Thr Ser Pro Lys
                180                 185                 190
Val Cys Pro Thr Cys Asn Gly Ser Gly Val Ile Asn Arg Asn Gln Gly
            195                 200                 205
Ala Phe Gly Phe Ser Glu Pro Cys Thr Asp Cys Arg Gly Ser Gly Ser
                210                 215                 220
Ile Ile Glu His Pro Cys Glu Glu Cys Lys Gly Thr Gly Val Thr Thr
225                 230                 235                 240
Arg Thr Arg Thr Ile Asn Val Arg Ile Pro Pro Gly Val Glu Asp Gly
                245                 250                 255
Gln Arg Ile Arg Leu Ala Gly Gln Gly Glu Ala Gly Leu Arg Gly Ala
                260                 265                 270
Pro Ser Gly Asp Leu Tyr Val Thr Val His Val Arg Pro Asp Lys Ile
            275                 280                 285
Phe Gly Arg Asp Gly Asp Asp Leu Thr Val Thr Val Pro Val Ser Phe
290                 295                 300
Thr Glu Leu Ala Leu Gly Ser Thr Leu Ser Val Pro Thr Leu Asp Gly
305                 310                 315                 320
Thr Val Gly Val Arg Val Pro Lys Gly Thr Ala Asp Gly Arg Ile Leu
                325                 330                 335
Arg Val Arg Gly Arg Gly Val Pro Lys Arg Ser Gly Ser Gly Asp
            340                 345                 350
Leu Leu Val Thr Val Lys Val Ala Val Pro Pro Asn Leu Ala Gly Ala
            355                 360                 365
Ala Gln Glu Ala Leu Glu Ala Tyr Ala Ala Ala Glu Arg Ser Ser Gly
    370                 375                 380
Phe Asn Pro Arg Ala Gly Trp Ala Gly Asn Arg Met His Gly Asp Thr
385                 390                 395                 400
Pro Thr Leu His Glu Tyr Met Leu Asp Leu Gln Pro Glu Thr Thr Asp
                405                 410                 415
Leu Tyr Cys Tyr Glu Gln Leu Asn Asp Ser Ser Glu Glu Asp Glu
            420                 425                 430
Ile Asp Gly Pro Ala Gly Gln Ala Glu Pro Asp Arg Ala His Tyr Asn
            435                 440                 445
```

| | | | | | | | | | | |
|---|---|---|---|---|---|---|---|---|---|---|
| Ile | Val | Thr | Phe | Cys | Cys | Lys | Cys | Asp | Ser | Thr | Leu | Arg | Leu | Cys | Val |
| | 450 | | | | 455 | | | | 460 | |

Gln Ser Thr His Val Asp Ile Arg Thr Leu Glu Asp Leu Leu Met Gly
465 470 475 480

Thr Leu Gly Ile Val Cys Pro Ile Cys Ser Gln Lys Pro
485 490

<210> SEQ ID NO 20
<211> LENGTH: 2847
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(2844)

<400> SEQUENCE: 20

```
atg ggc agc agc cat cat cat cat cat cac agc agc ggc ctg gtg ccg       48
Met Gly Ser Ser His His His His His His Ser Ser Gly Leu Val Pro
 1               5                  10                  15 cgc ggc agc cat atg gcc aag aca att gcg tac gac gaa gag gcc cgt       96
Arg Gly Ser His Met Ala Lys Thr Ile Ala Tyr Asp Glu Glu Ala Arg
            20                  25                  30 cgc ggc ctc gag cgg ggc ttg aac gcc ctc gcc gat gcg gta aag gtg      144
Arg Gly Leu Glu Arg Gly Leu Asn Ala Leu Ala Asp Ala Val Lys Val
        35                  40                  45 aca ttg ggc ccc aag ggc cgc aac gtc gtc ctg gaa aag aag tgg ggt      192
Thr Leu Gly Pro Lys Gly Arg Asn Val Val Leu Glu Lys Lys Trp Gly
    50                  55                  60 gcc ccc acg atc acc aac gat ggt gtg tcc atc gcc aag gag atc gag      240
Ala Pro Thr Ile Thr Asn Asp Gly Val Ser Ile Ala Lys Glu Ile Glu
 65                  70                  75                  80 ctg gag gat ccg tac gag aag atc ggc gcc gag ctg gtc aaa gag gta      288
Leu Glu Asp Pro Tyr Glu Lys Ile Gly Ala Glu Leu Val Lys Glu Val
                85                  90                  95 gcc aag aag acc gat gac gtc gcc ggt gac ggc acc acg acg gcc acc      336
Ala Lys Lys Thr Asp Asp Val Ala Gly Asp Gly Thr Thr Thr Ala Thr
            100                 105                 110 gtg ctg gcc cag gcg ttg gtt cgc gag ggc ctg cgc aac gtc gcg gcc      384
Val Leu Ala Gln Ala Leu Val Arg Glu Gly Leu Arg Asn Val Ala Ala
        115                 120                 125 ggc gcc aac ccg ctc ggt ctc aaa cgc ggc atc gaa aag gcc gtg gag      432
Gly Ala Asn Pro Leu Gly Leu Lys Arg Gly Ile Glu Lys Ala Val Glu
    130                 135                 140 aag gtc acc gag acc ctg ctc aag ggc gcc aag gag gtc gag acc aag      480
Lys Val Thr Glu Thr Leu Leu Lys Gly Ala Lys Glu Val Glu Thr Lys
145                 150                 155                 160 gag cag att gcg gcc acc gca gcg att tcg gcg ggt gac cag tcc atc      528
Glu Gln Ile Ala Ala Thr Ala Ala Ile Ser Ala Gly Asp Gln Ser Ile
                165                 170                 175 ggt gac ctg atc gcc gag gcg atg gac aag gtg ggc aac gag ggc gtc      576
Gly Asp Leu Ile Ala Glu Ala Met Asp Lys Val Gly Asn Glu Gly Val
            180                 185                 190 atc acc gtc gag gag tcc aac acc ttt ggg ctg cag ctc gag ctc acc      624
Ile Thr Val Glu Glu Ser Asn Thr Phe Gly Leu Gln Leu Glu Leu Thr
        195                 200                 205 gag ggt atg cgg ttc gac aag ggc tac atc tcg ggg tac ttc gtg acc      672
Glu Gly Met Arg Phe Asp Lys Gly Tyr Ile Ser Gly Tyr Phe Val Thr
    210                 215                 220 gac ccg gag cgt cag gag gcg gtc ctg gag gac ccc tac atc ctg ctg      720
Asp Pro Glu Arg Gln Glu Ala Val Leu Glu Asp Pro Tyr Ile Leu Leu
```

-continued

| | | |
|---|---|---|
| 225 | 230 | 235 | 240 |

| | |
|---|---|
| gtc agc tcc aag gtg tcc act gtc aag gat ctg ctg ccg ctg ctc gag<br>Val Ser Ser Lys Val Ser Thr Val Lys Asp Leu Leu Pro Leu Leu Glu<br>245          250          255 | 768 |
| aag gtc atc gga gcc ggt aag ccg ctg ctg atc atc gcc gag gac gtc<br>Lys Val Ile Gly Ala Gly Lys Pro Leu Leu Ile Ile Ala Glu Asp Val<br>260          265          270 | 816 |
| gag ggc gag gcg ctg tcc acc ctg gtc gtc aac aag atc cgc ggc acc<br>Glu Gly Glu Ala Leu Ser Thr Leu Val Val Asn Lys Ile Arg Gly Thr<br>275          280          285 | 864 |
| ttc aag tcg gtg gcg gtc aag gct ccc ggc ttc ggc gac cgc cgc aag<br>Phe Lys Ser Val Ala Val Lys Ala Pro Gly Phe Gly Asp Arg Arg Lys<br>290          295          300 | 912 |
| gcg atg ctg cag gat atg gcc att ctc acc ggt ggt cag gtg atc agc<br>Ala Met Leu Gln Asp Met Ala Ile Leu Thr Gly Gly Gln Val Ile Ser<br>305          310          315          320 | 960 |
| gaa gag gtc ggc ctg acg ctg gag aac gcc gac ctg tcg ctg cta ggc<br>Glu Glu Val Gly Leu Thr Leu Glu Asn Ala Asp Leu Ser Leu Leu Gly<br>325          330          335 | 1008 |
| aag gcc cgc aag gtc gtg gtc acc aag gac gag acc acc atc gtc gag<br>Lys Ala Arg Lys Val Val Val Thr Lys Asp Glu Thr Thr Ile Val Glu<br>340          345          350 | 1056 |
| ggc gcc ggt gac acc gac gcc atc gcc gga cga gtg gcc cag atc cgc<br>Gly Ala Gly Asp Thr Asp Ala Ile Ala Gly Arg Val Ala Gln Ile Arg<br>355          360          365 | 1104 |
| cag gag atc gag aac agc gac tcc gac tac gac cgt gag aag ctg cag<br>Gln Glu Ile Glu Asn Ser Asp Ser Asp Tyr Asp Arg Glu Lys Leu Gln<br>370          375          380 | 1152 |
| gag cgg ctg gcc aag ctg gcc ggt ggt gtc gcg gtg atc aag gcc ggt<br>Glu Arg Leu Ala Lys Leu Ala Gly Gly Val Ala Val Ile Lys Ala Gly<br>385          390          395          400 | 1200 |
| gcc gcc acc gag gtc gaa ctc aag gag cgc aag cac cgc atc gag gat<br>Ala Ala Thr Glu Val Glu Leu Lys Glu Arg Lys His Arg Ile Glu Asp<br>405          410          415 | 1248 |
| gcg gtt cgc aat gcc aag gcc gcc gtc gag gag ggc atc gtc gcc ggt<br>Ala Val Arg Asn Ala Lys Ala Ala Val Glu Glu Gly Ile Val Ala Gly<br>420          425          430 | 1296 |
| ggg ggt gtg acg ctg ttg caa gcg gcc ccg acc ctg gac gag ctg aag<br>Gly Gly Val Thr Leu Leu Gln Ala Ala Pro Thr Leu Asp Glu Leu Lys<br>435          440          445 | 1344 |
| ctc gaa ggc gac gag gcg acc ggc gcc aac atc gtg aag gtg gcg ctg<br>Leu Glu Gly Asp Glu Ala Thr Gly Ala Asn Ile Val Lys Val Ala Leu<br>450          455          460 | 1392 |
| gag gcc ccg ctg aag cag atc gcc ttc aac tcc ggg ctg gag ccg ggc<br>Glu Ala Pro Leu Lys Gln Ile Ala Phe Asn Ser Gly Leu Glu Pro Gly<br>465          470          475          480 | 1440 |
| gtg gtg gcc gag aag gtg cgc aac ctg ccg gct ggc cac gga ctg aac<br>Val Val Ala Glu Lys Val Arg Asn Leu Pro Ala Gly His Gly Leu Asn<br>485          490          495 | 1488 |
| gct cag acc ggt gtc tac gag gat ctg ctc gct gcc ggc gtt gct gac<br>Ala Gln Thr Gly Val Tyr Glu Asp Leu Leu Ala Ala Gly Val Ala Asp<br>500          505          510 | 1536 |
| ccg gtc aag gtg acc cgt tcg gcg ctg cag aat gcg gcg tcc atc gcg<br>Pro Val Lys Val Thr Arg Ser Ala Leu Gln Asn Ala Ala Ser Ile Ala<br>515          520          525 | 1584 |
| ggg ctg ttc ctg acc acc gag gcc gtc gtt gcc gac aag ccg gaa aag<br>Gly Leu Phe Leu Thr Thr Glu Ala Val Val Ala Asp Lys Pro Glu Lys<br>530          535          540 | 1632 |
| gag aag gct tcc gtt ccc ggt ggc ggc gac atg ggt ggc atg gat ttc | 1680 |

-continued

```
Glu Lys Ala Ser Val Pro Gly Gly Gly Asp Met Gly Gly Met Asp Phe
545                 550                 555                 560 gct agc atg ggc tcc atc ggc gca gca agc atg gaa ttt tgt ttt gat    1728
Ala Ser Met Gly Ser Ile Gly Ala Ala Ser Met Glu Phe Cys Phe Asp
                565                 570                 575 gta ttc aag gag ctc aaa gtc cac cat gcc aat gag aac atc ttc tac    1776
Val Phe Lys Glu Leu Lys Val His His Ala Asn Glu Asn Ile Phe Tyr
            580                 585                 590 tgc ccc att gcc atc atg tca gct cta gcc atg gta tac ctg ggt gca    1824
Cys Pro Ile Ala Ile Met Ser Ala Leu Ala Met Val Tyr Leu Gly Ala
        595                 600                 605 aaa gac agc acc agg aca cag ata aat aag gtt gtt cgc ttt gat aaa    1872
Lys Asp Ser Thr Arg Thr Gln Ile Asn Lys Val Val Arg Phe Asp Lys
    610                 615                 620 ctt cca gga ttc gga gac agt att gaa gct cag tgt ggc aca tct gta    1920
Leu Pro Gly Phe Gly Asp Ser Ile Glu Ala Gln Cys Gly Thr Ser Val
625                 630                 635                 640 aac gtt cac tct tca ctt aga gac atc ctc aac caa atc acc aaa cca    1968
Asn Val His Ser Ser Leu Arg Asp Ile Leu Asn Gln Ile Thr Lys Pro
                645                 650                 655 aat gat gtt tat tcg ttc agc ctt gcc agt aga ctt tat gct gaa gag    2016
Asn Asp Val Tyr Ser Phe Ser Leu Ala Ser Arg Leu Tyr Ala Glu Glu
            660                 665                 670 aga tac cca atc ctg cca gaa tac ttg cag tgt gtg aag gaa ctg tat    2064
Arg Tyr Pro Ile Leu Pro Glu Tyr Leu Gln Cys Val Lys Glu Leu Tyr
        675                 680                 685 aga gga ggc ttg gaa cct atc aac ttt caa aca gct gca gat caa gcc    2112
Arg Gly Gly Leu Glu Pro Ile Asn Phe Gln Thr Ala Ala Asp Gln Ala
    690                 695                 700 aga gag ctc atc aat tcc tgg gta gaa agt cag aca aat gga att atc    2160
Arg Glu Leu Ile Asn Ser Trp Val Glu Ser Gln Thr Asn Gly Ile Ile
705                 710                 715                 720 aga aat gtc ctt cag cca agc tcc gtg gat tct caa act gca atg gtt    2208
Arg Asn Val Leu Gln Pro Ser Ser Val Asp Ser Gln Thr Ala Met Val
                725                 730                 735 ctg gtt aat gcc att gtc ttc aaa gga ctg tgg gag aaa aca ttt aag    2256
Leu Val Asn Ala Ile Val Phe Lys Gly Leu Trp Glu Lys Thr Phe Lys
            740                 745                 750 gat gaa gac aca caa gca atg cct ttc aga gtg act gag caa gaa agc    2304
Asp Glu Asp Thr Gln Ala Met Pro Phe Arg Val Thr Glu Gln Glu Ser
        755                 760                 765 aaa cct gtg cag atg atg tac cag att ggt tta ttt aga gtg gca tca    2352
Lys Pro Val Gln Met Met Tyr Gln Ile Gly Leu Phe Arg Val Ala Ser
    770                 775                 780 atg gct tct gag aaa atg aag atc ctg gag ctt cca ttt gcc agt ggg    2400
Met Ala Ser Glu Lys Met Lys Ile Leu Glu Leu Pro Phe Ala Ser Gly
785                 790                 795                 800 aca atg agc atg ttg gtg ctg ttg cct gat gaa gtc tca ggc ctt gag    2448
Thr Met Ser Met Leu Val Leu Leu Pro Asp Glu Val Ser Gly Leu Glu
                805                 810                 815 cag ctt gag agt ata atc aac ttt gaa aaa ctg act gaa tgg acc agt    2496
Gln Leu Glu Ser Ile Ile Asn Phe Glu Lys Leu Thr Glu Trp Thr Ser
            820                 825                 830 tct aat gtt atg gaa gag agg aag atc aaa gtg tac tta cct cgc atg    2544
Ser Asn Val Met Glu Glu Arg Lys Ile Lys Val Tyr Leu Pro Arg Met
        835                 840                 845 aag atg gag gaa aaa tac aac ctc aca tct gtc tta atg gct atg ggc    2592
Lys Met Glu Glu Lys Tyr Asn Leu Thr Ser Val Leu Met Ala Met Gly
    850                 855                 860
```

-continued

```
att act gac gtg ttt agc tct tca gcc aat ctg tct ggc atc tcc tca    2640
Ile Thr Asp Val Phe Ser Ser Ser Ala Asn Leu Ser Gly Ile Ser Ser
865                 870                 875                 880 gca gag agc ctg aag ata tct caa gct gtc cat gca gca cat gca gaa    2688
Ala Glu Ser Leu Lys Ile Ser Gln Ala Val His Ala Ala His Ala Glu
                885                 890                 895 atc aat gaa gca ggc aga gag gtg gta ggg tca gca gag gct gga gtg    2736
Ile Asn Glu Ala Gly Arg Glu Val Val Gly Ser Ala Glu Ala Gly Val
            900                 905                 910 gat gct gca agc gtc tct gaa gaa ttt agg gct gac cat cca ttc ctc    2784
Asp Ala Ala Ser Val Ser Glu Glu Phe Arg Ala Asp His Pro Phe Leu
        915                 920                 925 ttc tgt atc aag cac atc gca acc aac gcc gtt ctc ttc ttt ggc aga    2832
Phe Cys Ile Lys His Ile Ala Thr Asn Ala Val Leu Phe Phe Gly Arg
    930                 935                 940 tgt gtt gga tcc taa                                                 2847
Cys Val Gly Ser
945
```

<210> SEQ ID NO 21
<211> LENGTH: 948
<212> TYPE: PRT
<213> ORGANISM: Artificial Sequence
<220> FEATURE:
<223> OTHER INFORMATION: fusion sequence

<400> SEQUENCE: 21

```
Met Gly Ser Ser His His His His His His Ser Ser Gly Leu Val Pro
1               5                   10                  15

Arg Gly Ser His Met Ala Lys Thr Ile Ala Tyr Asp Glu Glu Ala Arg
            20                  25                  30

Arg Gly Leu Glu Arg Gly Leu Asn Ala Leu Ala Asp Ala Val Lys Val
        35                  40                  45

Thr Leu Gly Pro Lys Gly Arg Asn Val Val Leu Glu Lys Lys Trp Gly
    50                  55                  60

Ala Pro Thr Ile Thr Asn Asp Gly Val Ser Ile Ala Lys Glu Ile Glu
65                  70                  75                  80

Leu Glu Asp Pro Tyr Glu Lys Ile Gly Ala Glu Leu Val Lys Glu Val
                85                  90                  95

Ala Lys Lys Thr Asp Asp Val Ala Gly Asp Gly Thr Thr Thr Ala Thr
            100                 105                 110

Val Leu Ala Gln Ala Leu Val Arg Glu Gly Leu Arg Asn Val Ala Ala
        115                 120                 125

Gly Ala Asn Pro Leu Gly Leu Lys Arg Gly Ile Glu Lys Ala Val Glu
    130                 135                 140

Lys Val Thr Glu Thr Leu Leu Lys Gly Ala Lys Glu Val Glu Thr Lys
145                 150                 155                 160

Glu Gln Ile Ala Ala Thr Ala Ala Ile Ser Ala Gly Asp Gln Ser Ile
                165                 170                 175

Gly Asp Leu Ile Ala Glu Ala Met Asp Lys Val Gly Asn Glu Gly Val
            180                 185                 190

Ile Thr Val Glu Glu Ser Asn Thr Phe Gly Leu Gln Leu Glu Leu Thr
        195                 200                 205

Glu Gly Met Arg Phe Asp Lys Gly Tyr Ile Ser Gly Tyr Phe Val Thr
    210                 215                 220

Asp Pro Glu Arg Gln Glu Ala Val Leu Glu Asp Pro Tyr Ile Leu Leu
225                 230                 235                 240
```

-continued

```
Val Ser Ser Lys Val Ser Thr Val Lys Asp Leu Leu Pro Leu Leu Glu
            245                 250                 255

Lys Val Ile Gly Ala Gly Lys Pro Leu Leu Ile Ile Ala Glu Asp Val
            260                 265                 270

Glu Gly Glu Ala Leu Ser Thr Leu Val Val Asn Lys Ile Arg Gly Thr
            275                 280                 285

Phe Lys Ser Val Ala Val Lys Ala Pro Gly Phe Gly Asp Arg Arg Lys
            290                 295                 300

Ala Met Leu Gln Asp Met Ala Ile Leu Thr Gly Gly Gln Val Ile Ser
305                 310                 315                 320

Glu Glu Val Gly Leu Thr Leu Glu Asn Ala Asp Leu Ser Leu Leu Gly
                325                 330                 335

Lys Ala Arg Lys Val Val Thr Lys Asp Glu Thr Thr Ile Val Glu
            340                 345                 350

Gly Ala Gly Asp Thr Asp Ala Ile Ala Gly Arg Val Ala Gln Ile Arg
            355                 360                 365

Gln Glu Ile Glu Asn Ser Asp Ser Asp Tyr Asp Arg Glu Lys Leu Gln
    370                 375                 380

Glu Arg Leu Ala Lys Leu Ala Gly Gly Val Ala Val Ile Lys Ala Gly
385                 390                 395                 400

Ala Ala Thr Glu Val Glu Leu Lys Glu Arg Lys His Arg Ile Glu Asp
            405                 410                 415

Ala Val Arg Asn Ala Lys Ala Ala Val Glu Glu Gly Ile Val Ala Gly
            420                 425                 430

Gly Gly Val Thr Leu Leu Gln Ala Ala Pro Thr Leu Asp Glu Leu Lys
            435                 440                 445

Leu Glu Gly Asp Glu Ala Thr Gly Ala Asn Ile Val Lys Val Ala Leu
    450                 455                 460

Glu Ala Pro Leu Lys Gln Ile Ala Phe Asn Ser Gly Leu Glu Pro Gly
465                 470                 475                 480

Val Val Ala Glu Lys Val Arg Asn Leu Pro Ala Gly His Gly Leu Asn
            485                 490                 495

Ala Gln Thr Gly Val Tyr Glu Asp Leu Leu Ala Ala Gly Val Ala Asp
            500                 505                 510

Pro Val Lys Val Thr Arg Ser Ala Leu Gln Asn Ala Ala Ser Ile Ala
            515                 520                 525

Gly Leu Phe Leu Thr Thr Glu Ala Val Val Ala Asp Lys Pro Glu Lys
            530                 535                 540

Glu Lys Ala Ser Val Pro Gly Gly Gly Asp Met Gly Gly Met Asp Phe
545                 550                 555                 560

Ala Ser Met Gly Ser Ile Gly Ala Ala Ser Met Glu Phe Cys Phe Asp
            565                 570                 575

Val Phe Lys Glu Leu Lys Val His His Ala Asn Glu Asn Ile Phe Tyr
            580                 585                 590

Cys Pro Ile Ala Ile Met Ser Ala Leu Ala Met Val Tyr Leu Gly Ala
            595                 600                 605

Lys Asp Ser Thr Arg Thr Gln Ile Asn Lys Val Val Arg Phe Asp Lys
            610                 615                 620

Leu Pro Gly Phe Gly Asp Ser Ile Glu Ala Gln Cys Gly Thr Ser Val
625                 630                 635                 640

Asn Val His Ser Ser Leu Arg Asp Ile Leu Asn Gln Ile Thr Lys Pro
            645                 650                 655

Asn Asp Val Tyr Ser Phe Ser Leu Ala Ser Arg Leu Tyr Ala Glu Glu
```

```
                    660               665               670
Arg Tyr Pro Ile Leu Pro Glu Tyr Leu Gln Cys Val Lys Glu Leu Tyr
                675               680               685

Arg Gly Gly Leu Glu Pro Ile Asn Phe Gln Thr Ala Ala Asp Gln Ala
            690               695               700

Arg Glu Leu Ile Asn Ser Trp Val Glu Ser Gln Thr Asn Gly Ile Ile
705               710               715               720

Arg Asn Val Leu Gln Pro Ser Ser Val Asp Ser Gln Thr Ala Met Val
                725               730               735

Leu Val Asn Ala Ile Val Phe Lys Gly Leu Trp Glu Lys Thr Phe Lys
            740               745               750

Asp Glu Asp Thr Gln Ala Met Pro Phe Arg Val Thr Glu Gln Glu Ser
            755               760               765

Lys Pro Val Gln Met Met Tyr Gln Ile Gly Leu Phe Arg Val Ala Ser
        770               775               780

Met Ala Ser Glu Lys Met Lys Ile Leu Glu Leu Pro Phe Ala Ser Gly
785               790               795               800

Thr Met Ser Met Leu Val Leu Leu Pro Asp Glu Val Ser Gly Leu Glu
                805               810               815

Gln Leu Glu Ser Ile Ile Asn Phe Glu Lys Leu Thr Glu Trp Thr Ser
            820               825               830

Ser Asn Val Met Glu Glu Arg Lys Ile Lys Val Tyr Leu Pro Arg Met
            835               840               845

Lys Met Glu Glu Lys Tyr Asn Leu Thr Ser Val Leu Met Ala Met Gly
        850               855               860

Ile Thr Asp Val Phe Ser Ser Ser Ala Asn Leu Ser Gly Ile Ser Ser
865               870               875               880

Ala Glu Ser Leu Lys Ile Ser Gln Ala Val His Ala Ala His Ala Glu
                885               890               895

Ile Asn Glu Ala Gly Arg Glu Val Val Gly Ser Ala Glu Ala Gly Val
            900               905               910

Asp Ala Ala Ser Val Ser Glu Glu Phe Arg Ala Asp His Pro Phe Leu
            915               920               925

Phe Cys Ile Lys His Ile Ala Thr Asn Ala Val Leu Phe Phe Gly Arg
        930               935               940

Cys Val Gly Ser
945

<210> SEQ ID NO 22
<211> LENGTH: 738
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(735)

<400> SEQUENCE: 22 atg tcc cct ata cta ggt tat tgg aaa att aag ggc ctt gtg caa ccc    48
Met Ser Pro Ile Leu Gly Tyr Trp Lys Ile Lys Gly Leu Val Gln Pro
  1               5                  10                  15 act cga ctt ctt ttg gaa tat ctt gaa gaa aaa tat gaa gag cat ttg    96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg   144
Tyr Glu Arg Asp Glu Gly Asp Lys Trp Arg Asn Lys Lys Phe Glu Leu
            35                  40                  45
```

```
ggt ttg gag ttt ccc aat ctt cct tat tat att gat ggt gat gtt aaa      192
Gly Leu Glu Phe Pro Asn Leu Pro Tyr Tyr Ile Asp Gly Asp Val Lys
     50                  55                  60 tta aca cag tct atg gcc atc ata cgt tat ata gct gac aag cac aac      240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa      288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt      336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa      384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat      432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat      480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta      528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac      576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc      624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt      672
Thr Phe Gly Gly Gly Asp His Pro Pro Lys Ser Asp Leu Val Pro Arg
    210                 215                 220 gga tcc cca gga att ccc ggg tcg act cga gca cca cca cca cca cca      720
Gly Ser Pro Gly Ile Pro Gly Ser Thr Arg Ala Pro Pro Pro Pro Pro
225                 230                 235                 240 ctg aga tcc ggc tgc taa                                              738
Leu Arg Ser Gly Cys
                245

<210> SEQ ID NO 23
<211> LENGTH: 245
<212> TYPE: PRT
<213> ORGANISM: Artificial Sequence
<220> FEATURE:
<223> OTHER INFORMATION: fusion sequence

<400> SEQUENCE: 23

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
```

```
                       85                      90                      95
Gly Ala Val Leu Asp Ile Arg Tyr Gly Val Ser Arg Ile Ala Tyr Ser
                100                     105                     110

Lys Asp Phe Glu Thr Leu Lys Val Asp Phe Leu Ser Lys Leu Pro Glu
                115                     120                     125

Met Leu Lys Met Phe Glu Asp Arg Leu Cys His Lys Thr Tyr Leu Asn
                130                     135                     140

Gly Asp His Val Thr His Pro Asp Phe Met Leu Tyr Asp Ala Leu Asp
145                     150                     155                     160

Val Val Leu Tyr Met Asp Pro Met Cys Leu Asp Ala Phe Pro Lys Leu
                        165                     170                     175

Val Cys Phe Lys Lys Arg Ile Glu Ala Ile Pro Gln Ile Asp Lys Tyr
                180                     185                     190

Leu Lys Ser Ser Lys Tyr Ile Ala Trp Pro Leu Gln Gly Trp Gln Ala
                195                     200                     205

Thr Phe Gly Gly Gly Asp His Pro Pro Lys Ser Asp Leu Val Pro Arg
                210                     215                     220

Gly Ser Pro Gly Ile Pro Gly Ser Thr Arg Ala Pro Pro Pro Pro Pro
225                     230                     235                     240

Leu Arg Ser Gly Cys
                245

<210> SEQ ID NO 24
<211> LENGTH: 975
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(972)

<400> SEQUENCE: 24 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
  1               5                  10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
                 20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
             35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
         50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140
```

```
ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                    165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
                180                 185                 190 ttg aaa tcc agc aag tat ata gca tgg cct ttg cag ggc tgg caa gcc     624
Leu Lys Ser Ser Lys Tyr Ile Ala Trp Pro Leu Gln Gly Trp Gln Ala
            195                 200                 205 acg ttt ggt ggt ggc gac cat cct cca aaa tcg gat ctg gtt ccg cgt     672
Thr Phe Gly Gly Gly Asp His Pro Pro Lys Ser Asp Leu Val Pro Arg
210                 215                 220 gga tcc atg cat gga gat aca cct aca ttg cat gaa tat atg tta gat     720
Gly Ser Met His Gly Asp Thr Pro Thr Leu His Glu Tyr Met Leu Asp
225                 230                 235                 240 ttg caa cca gag aca act gat ctc tac tgt tat gag caa tta aat gac     768
Leu Gln Pro Glu Thr Thr Asp Leu Tyr Cys Tyr Glu Gln Leu Asn Asp
                245                 250                 255 agc tca gag gag gag gat gaa ata gat ggt cca gct gga caa gca gaa     816
Ser Ser Glu Glu Glu Asp Glu Ile Asp Gly Pro Ala Gly Gln Ala Glu
                260                 265                 270 ccg gac aga gcc cat tac aat att gta acc ttt tgt tgc aag tgt gac     864
Pro Asp Arg Ala His Tyr Asn Ile Val Thr Phe Cys Cys Lys Cys Asp
            275                 280                 285 tct acg ctt cgg ttg tgc gta caa agc aca cac gta gac att cgt act     912
Ser Thr Leu Arg Leu Cys Val Gln Ser Thr His Val Asp Ile Arg Thr
        290                 295                 300 ttg gaa gac ctg tta atg ggc aca cta gga att gtg tgc ccc atc tgt     960
Leu Glu Asp Leu Leu Met Gly Thr Leu Gly Ile Val Cys Pro Ile Cys
305                 310                 315                 320 tct cag aaa cca taa                                                 975
Ser Gln Lys Pro
```

<210> SEQ ID NO 25
<211> LENGTH: 324
<212> TYPE: PRT
<213> ORGANISM: Artificial Sequence
<220> FEATURE:
<223> OTHER INFORMATION: fusion sequence

<400> SEQUENCE: 25

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110
```

```
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Met His Gly Asp Thr Pro Thr Leu His Glu Tyr Met Leu Asp
225                 230                 235                 240
Leu Gln Pro Glu Thr Thr Asp Leu Tyr Cys Tyr Glu Gln Leu Asn Asp
                245                 250                 255
Ser Ser Glu Glu Glu Asp Glu Ile Asp Gly Pro Ala Gly Gln Ala Glu
            260                 265                 270
Pro Asp Arg Ala His Tyr Asn Ile Val Thr Phe Cys Cys Lys Cys Asp
        275                 280                 285
Ser Thr Leu Arg Leu Cys Val Gln Ser Thr His Val Asp Ile Arg Thr
    290                 295                 300
Leu Glu Asp Leu Leu Met Gly Thr Leu Gly Ile Val Cys Pro Ile Cys
305                 310                 315                 320
Ser Gln Lys Pro

<210> SEQ ID NO 26
<211> LENGTH: 24
<212> TYPE: DNA
<213> ORGANISM: Artificial Sequence
<220> FEATURE:
<223> OTHER INFORMATION: fusion sequence

<400> SEQUENCE: 26
ccagctgtaa ccatggatgg agat                                          24

<210> SEQ ID NO 27
<211> LENGTH: 27
<212> TYPE: DNA
<213> ORGANISM: Artificial Sequence
<220> FEATURE:
<223> OTHER INFORMATION: fusion sequence

<400> SEQUENCE: 27
gccatggtac tagttggttt ctgagaa                                       27

<210> SEQ ID NO 28
<211> LENGTH: 1947
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1944)

<400> SEQUENCE: 28 atg gat gga gat aca cct aca ttg cat gaa tat atg tta gat ttg caa    48
Met Asp Gly Asp Thr Pro Thr Leu His Glu Tyr Met Leu Asp Leu Gln
```

```
       1                 5                  10                 15
cca gag aca act gat ctc tac tgt tat gag caa tta aat gac agc tca       96
Pro Glu Thr Thr Asp Leu Tyr Cys Tyr Glu Gln Leu Asn Asp Ser Ser
                    20                  25                  30 gag gag gag gat gaa ata gat ggt cca gct gga caa gca gaa ccg gac      144
Glu Glu Glu Asp Glu Ile Asp Gly Pro Ala Gly Gln Ala Glu Pro Asp
             35                  40                  45 aga gcc cat tac aat att gta acc ttt tgt tgc aag tgt gac tct acg      192
Arg Ala His Tyr Asn Ile Val Thr Phe Cys Cys Lys Cys Asp Ser Thr
         50                  55                  60 ctt cgg ttg tgc gta caa agc aca cac gta gac att cgt act ttg gaa      240
Leu Arg Leu Cys Val Gln Ser Thr His Val Asp Ile Arg Thr Leu Glu
 65                  70                  75                  80 gac ctg tta atg ggc aca cta gga att gtg tgc ccc atc tgt tct cag      288
Asp Leu Leu Met Gly Thr Leu Gly Ile Val Cys Pro Ile Cys Ser Gln
                 85                  90                  95 aaa cca act agt ggt ggc ggt ggc gga tcc cac atg gcc aag aca          336
Lys Pro Thr Ser Gly Gly Gly Gly Gly Ser His Met Ala Lys Thr
             100                 105                 110 att gcg tac gac gaa gag gcc cgt cgc ggc ctc gag cgg ggc ttg aac      384
Ile Ala Tyr Asp Glu Glu Ala Arg Arg Gly Leu Glu Arg Gly Leu Asn
         115                 120                 125 gcc ctc gcc gat gcg gta aag gtg aca ttg ggc ccc aag ggc cgc aac      432
Ala Leu Ala Asp Ala Val Lys Val Thr Leu Gly Pro Lys Gly Arg Asn
130                 135                 140 gtc gtc ctg gaa aag aag tgg ggt gcc ccc acg atc acc aac gat ggt      480
Val Val Leu Glu Lys Lys Trp Gly Ala Pro Thr Ile Thr Asn Asp Gly
145                 150                 155                 160 gtg tcc atc gcc aag gag atc gag ctg gag gat ccg tac gag aag atc      528
Val Ser Ile Ala Lys Glu Ile Glu Leu Glu Asp Pro Tyr Glu Lys Ile
                 165                 170                 175 ggc gcc gag ctg gtc aaa gag gta gcc aag aag acc gat gac gtc gcc      576
Gly Ala Glu Leu Val Lys Glu Val Ala Lys Lys Thr Asp Asp Val Ala
             180                 185                 190 ggt gac ggc acc acg acg gcc acc gtg ctg gcc cag gcg ttg gtt cgc      624
Gly Asp Gly Thr Thr Thr Ala Thr Val Leu Ala Gln Ala Leu Val Arg
         195                 200                 205 gag ggc ctg cgc aac gtc gcg gcc ggc gcc aac ccg ctc ggt ctc aaa      672
Glu Gly Leu Arg Asn Val Ala Ala Gly Ala Asn Pro Leu Gly Leu Lys
     210                 215                 220 cgc ggc atc gaa aag gcc gtg gag aag gtc acc gag acc ctg ctc aag      720
Arg Gly Ile Glu Lys Ala Val Glu Lys Val Thr Glu Thr Leu Leu Lys
225                 230                 235                 240 ggc gcc aag gag gtc gag acc aag gag cag att gcg gcc acc gca gcg      768
Gly Ala Lys Glu Val Glu Thr Lys Glu Gln Ile Ala Ala Thr Ala Ala
                 245                 250                 255 att tcg gcg ggt gac cag tcc atc ggt gac ctg atc gcc gag gcg atg      816
Ile Ser Ala Gly Asp Gln Ser Ile Gly Asp Leu Ile Ala Glu Ala Met
             260                 265                 270 gac aag gtg ggc aac gag ggc gtc atc acc gtc gag gag tcc aac acc      864
Asp Lys Val Gly Asn Glu Gly Val Ile Thr Val Glu Glu Ser Asn Thr
         275                 280                 285 ttt ggg ctg cag ctc gag ctc acc gag ggt atg cgg ttc gac aag ggc      912
Phe Gly Leu Gln Leu Glu Leu Thr Glu Gly Met Arg Phe Asp Lys Gly
     290                 295                 300 tac atc tcg ggg tac ttc gtg acc gac ccg gag cgt cag gag gcg gtc      960
Tyr Ile Ser Gly Tyr Phe Val Thr Asp Pro Glu Arg Gln Glu Ala Val
305                 310                 315                 320 ctg gag gac ccc tac atc ctg ctg gtc agc tcc aag gtg tcc act gtc     1008
```

```
                                                            -continued

Leu Glu Asp Pro Tyr Ile Leu Leu Val Ser Ser Lys Val Ser Thr Val
            325                 330                 335 aag gat ctg ctg ccg ctg ctc gag aag gtc atc gga gcc ggt aag ccg        1056
Lys Asp Leu Leu Pro Leu Leu Glu Lys Val Ile Gly Ala Gly Lys Pro
                340                 345                 350 ctg ctg atc atc gcc gag gac gtc gag ggc gag gcg ctg tcc acc ctg        1104
Leu Leu Ile Ile Ala Glu Asp Val Glu Gly Glu Ala Leu Ser Thr Leu
                355                 360                 365 gtc gtc aac aag atc cgc ggc acc ttc aag tcg gtg gcg gtc aag gct        1152
Val Val Asn Lys Ile Arg Gly Thr Phe Lys Ser Val Ala Val Lys Ala
    370                 375                 380 ccc ggc ttc ggc gac cgc cgc aag gcg atg ctg cag gat atg gcc att        1200
Pro Gly Phe Gly Asp Arg Arg Lys Ala Met Leu Gln Asp Met Ala Ile
385                 390                 395                 400 ctc acc ggt ggt cag gtg atc agc gaa gag gtc ggc ctg acg ctg gag        1248
Leu Thr Gly Gly Gln Val Ile Ser Glu Glu Val Gly Leu Thr Leu Glu
                405                 410                 415 aac gcc gac ctg tcg ctg cta ggc aag gcc cgc aag gtc gtg gtc acc        1296
Asn Ala Asp Leu Ser Leu Leu Gly Lys Ala Arg Lys Val Val Val Thr
                420                 425                 430 aag gac gag acc acc atc gtc gag ggc gcc ggt gac acc gac gcc atc        1344
Lys Asp Glu Thr Thr Ile Val Glu Gly Ala Gly Asp Thr Asp Ala Ile
                435                 440                 445 gcc gga cga gtg gcc cag atc cgc cag gag atc gag aac agc gac tcc        1392
Ala Gly Arg Val Ala Gln Ile Arg Gln Glu Ile Glu Asn Ser Asp Ser
    450                 455                 460 gac tac gac cgt gag aag ctg cag gag cgg ctg gcc aag ctg gcc ggt        1440
Asp Tyr Asp Arg Glu Lys Leu Gln Glu Arg Leu Ala Lys Leu Ala Gly
465                 470                 475                 480 ggt gtc gcg gtg atc aag gcc ggt gcc gcc acc gag gtc gaa ctc aag        1488
Gly Val Ala Val Ile Lys Ala Gly Ala Ala Thr Glu Val Glu Leu Lys
                485                 490                 495 gag cgc aag cac cgc atc gag gat gcg gtt cgc aat gcc aag gcc gcc        1536
Glu Arg Lys His Arg Ile Glu Asp Ala Val Arg Asn Ala Lys Ala Ala
                500                 505                 510 gtc gag gag ggc atc gtc gcc ggt ggg ggt gtg acg ctg ttg caa gcg        1584
Val Glu Glu Gly Ile Val Ala Gly Gly Gly Val Thr Leu Leu Gln Ala
                515                 520                 525 gcc ccg acc ctg gac gag ctg aag ctc gaa ggc gac gag gcg acc ggc        1632
Ala Pro Thr Leu Asp Glu Leu Lys Leu Glu Gly Asp Glu Ala Thr Gly
    530                 535                 540 gcc aac atc gtg aag gtg gcg ctg gag gcc ccg ctg aag cag atc gcc        1680
Ala Asn Ile Val Lys Val Ala Leu Glu Ala Pro Leu Lys Gln Ile Ala
545                 550                 555                 560 ttc aac tcc ggg ctg gag ccg ggc gtg gtg gcc gag aag gtg cgc aac        1728
Phe Asn Ser Gly Leu Glu Pro Gly Val Val Ala Glu Lys Val Arg Asn
                565                 570                 575 ctg ccg gct ggc cac gga ctg aac gct cag acc ggt gtc tac gag gat        1776
Leu Pro Ala Gly His Gly Leu Asn Ala Gln Thr Gly Val Tyr Glu Asp
                580                 585                 590 ctc ctc gct gcc ggc gtt gct gac ccg gtc aag gtg acc cgt tcg gcg        1824
Leu Leu Ala Ala Gly Val Ala Asp Pro Val Lys Val Thr Arg Ser Ala
    595                 600                 605 ctg cag aat gcg gcg tcc atc gcg ggg ctg ttc ctg acc acc gag gcc        1872
Leu Gln Asn Ala Ala Ser Ile Ala Gly Leu Phe Leu Thr Thr Glu Ala
                610                 615                 620 gtc gtt gcc gac aag ccg gaa aag gag aag gct tcc gtt ccc ggt ggc        1920
Val Val Ala Asp Lys Pro Glu Lys Glu Lys Ala Ser Val Pro Gly Gly
625                 630                 635                 640
```

```
ggc gac atg ggt ggc atg gat ttc tga                                    1947
Gly Asp Met Gly Gly Met Asp Phe
            645
```

<210> SEQ ID NO 29
<211> LENGTH: 648
<212> TYPE: PRT
<213> ORGANISM: Artificial Sequence
<220> FEATURE:
<223> OTHER INFORMATION: fusion sequence

<400> SEQUENCE: 29

```
Met Asp Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Thr Ser Gly Gly Gly Gly Gly Ser His Met Ala Lys Thr
                100                 105                 110

Ile Ala Tyr Asp Glu Glu Ala Arg Arg Gly Leu Glu Arg Gly Leu Asn
            115                 120                 125

Ala Leu Ala Asp Ala Val Lys Val Thr Leu Gly Pro Lys Gly Arg Asn
130                 135                 140

Val Val Leu Glu Lys Lys Trp Gly Ala Pro Thr Ile Thr Asn Asp Gly
145                 150                 155                 160

Val Ser Ile Ala Lys Glu Ile Glu Leu Glu Asp Pro Tyr Glu Lys Ile
                165                 170                 175

Gly Ala Glu Leu Val Lys Glu Val Ala Lys Lys Thr Asp Asp Val Ala
            180                 185                 190

Gly Asp Gly Thr Thr Thr Ala Thr Val Leu Ala Gln Ala Leu Val Arg
        195                 200                 205

Glu Gly Leu Arg Asn Val Ala Ala Gly Ala Asn Pro Leu Gly Leu Lys
    210                 215                 220

Arg Gly Ile Glu Lys Ala Val Glu Lys Val Thr Glu Thr Leu Leu Lys
225                 230                 235                 240

Gly Ala Lys Glu Val Glu Thr Lys Glu Gln Ile Ala Ala Thr Ala Ala
                245                 250                 255

Ile Ser Ala Gly Asp Gln Ser Ile Gly Asp Leu Ile Ala Glu Ala Met
            260                 265                 270

Asp Lys Val Gly Asn Glu Gly Val Ile Thr Val Glu Glu Ser Asn Thr
        275                 280                 285

Phe Gly Leu Gln Leu Glu Leu Thr Glu Gly Met Arg Phe Asp Lys Gly
    290                 295                 300

Tyr Ile Ser Gly Tyr Phe Val Thr Asp Pro Glu Arg Gln Glu Ala Val
305                 310                 315                 320

Leu Glu Asp Pro Tyr Ile Leu Leu Val Ser Ser Lys Val Ser Thr Val
                325                 330                 335

Lys Asp Leu Leu Pro Leu Leu Glu Lys Val Ile Gly Ala Gly Lys Pro
            340                 345                 350
```

```
Leu Leu Ile Ile Ala Glu Asp Val Glu Gly Ala Leu Ser Thr Leu
        355                 360                 365

Val Val Asn Lys Ile Arg Gly Thr Phe Lys Ser Val Ala Val Lys Ala
        370                 375                 380

Pro Gly Phe Gly Asp Arg Arg Lys Ala Met Leu Gln Asp Met Ala Ile
385                 390                 395                 400

Leu Thr Gly Gly Gln Val Ile Ser Glu Glu Val Gly Leu Thr Leu Glu
                405                 410                 415

Asn Ala Asp Leu Ser Leu Leu Gly Lys Ala Arg Lys Val Val Val Thr
                420                 425                 430

Lys Asp Glu Thr Thr Ile Val Glu Gly Ala Gly Asp Thr Asp Ala Ile
            435                 440                 445

Ala Gly Arg Val Ala Gln Ile Arg Gln Glu Ile Glu Asn Ser Asp Ser
            450                 455                 460

Asp Tyr Asp Arg Glu Lys Leu Gln Glu Arg Leu Ala Lys Leu Ala Gly
465                 470                 475                 480

Gly Val Ala Val Ile Lys Ala Gly Ala Ala Thr Glu Val Glu Leu Lys
                485                 490                 495

Glu Arg Lys His Arg Ile Glu Asp Ala Val Arg Asn Ala Lys Ala Ala
                500                 505                 510

Val Glu Glu Gly Ile Val Ala Gly Gly Gly Val Thr Leu Leu Gln Ala
            515                 520                 525

Ala Pro Thr Leu Asp Glu Leu Lys Leu Glu Gly Asp Glu Ala Thr Gly
            530                 535                 540

Ala Asn Ile Val Lys Val Ala Leu Glu Ala Pro Leu Lys Gln Ile Ala
545                 550                 555                 560

Phe Asn Ser Gly Leu Glu Pro Gly Val Val Ala Glu Lys Val Arg Asn
                565                 570                 575

Leu Pro Ala Gly His Gly Leu Asn Ala Gln Thr Gly Val Tyr Glu Asp
                580                 585                 590

Leu Leu Ala Ala Gly Val Ala Asp Pro Val Lys Val Thr Arg Ser Ala
            595                 600                 605

Leu Gln Asn Ala Ala Ser Ile Ala Gly Leu Phe Leu Thr Thr Glu Ala
            610                 615                 620

Val Val Ala Asp Lys Pro Glu Lys Glu Lys Ala Ser Val Pro Gly Gly
625                 630                 635                 640

Gly Asp Met Gly Gly Met Asp Phe
                645

<210> SEQ ID NO 30
<211> LENGTH: 24
<212> TYPE: DNA
<213> ORGANISM: Artificial Sequence
<220> FEATURE:
<223> OTHER INFORMATION: fusion sequence

<400> SEQUENCE: 30
ttcgccatgg ccaagacaat tgcg                                          24

<210> SEQ ID NO 31
<211> LENGTH: 35
<212> TYPE: DNA
<213> ORGANISM: Artificial Sequence
<220> FEATURE:
<223> OTHER INFORMATION: fusion sequence

<400> SEQUENCE: 31
```

```
gtacccgac atatggccct tgtcgaaccg catac                                      35
```

<210> SEQ ID NO 32
<211> LENGTH: 888
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(885)

<400> SEQUENCE: 32

```
atg gcc aag aca att gcg tac gac gaa gag gcc cgt cgc ggc ctc gag           48
Met Ala Lys Thr Ile Ala Tyr Asp Glu Glu Ala Arg Arg Gly Leu Glu
 1               5                  10                  15 cgg ggc ttg aac gcc ctc gcc gat gcg gta aag gtg aca ttg ggc ccc           96
Arg Gly Leu Asn Ala Leu Ala Asp Ala Val Lys Val Thr Leu Gly Pro
             20                  25                  30 aag ggc cgc aac gtc gtc ctg gaa aag aag tgg ggt gcc ccc acg atc          144
Lys Gly Arg Asn Val Val Leu Glu Lys Lys Trp Gly Ala Pro Thr Ile
         35                  40                  45 acc aac gat ggt gtg tcc atc gcc aag gag atc gag ctg gag gat ccg          192
Thr Asn Asp Gly Val Ser Ile Ala Lys Glu Ile Glu Leu Glu Asp Pro
 50                  55                  60 tac gag aag atc ggc gcc gag ctg gtc aaa gag gta gcc aag aag acc          240
Tyr Glu Lys Ile Gly Ala Glu Leu Val Lys Glu Val Ala Lys Lys Thr
 65                  70                  75                  80 gat gac gtc gcc ggt gac ggc acc acg acg gcc acc gtg ctg gcc cag          288
Asp Asp Val Ala Gly Asp Gly Thr Thr Thr Ala Thr Val Leu Ala Gln
                 85                  90                  95 gcg ttg gtt cgc gag ggc ctg cgc aac gtc gcg gcc ggc gcc aac ccg          336
Ala Leu Val Arg Glu Gly Leu Arg Asn Val Ala Ala Gly Ala Asn Pro
            100                 105                 110 ctc ggt ctc aaa cgc ggc atc gaa aag gcc gtg gag aag gtc acc gag          384
Leu Gly Leu Lys Arg Gly Ile Glu Lys Ala Val Glu Lys Val Thr Glu
        115                 120                 125 acc ctg ctc aag ggc gcc aag gag gtc gag acc aag gag cag att gcg          432
Thr Leu Leu Lys Gly Ala Lys Glu Val Glu Thr Lys Glu Gln Ile Ala
    130                 135                 140 gcc acc gca gcg att tcg gcg ggt gac cag tcc atc ggt gac ctg atc          480
Ala Thr Ala Ala Ile Ser Ala Gly Asp Gln Ser Ile Gly Asp Leu Ile
145                 150                 155                 160 gcc gag gcg atg gac aag gtg ggc aac gag ggc gtc atc acc gtc gag          528
Ala Glu Ala Met Asp Lys Val Gly Asn Glu Gly Val Ile Thr Val Glu
                165                 170                 175 gag tcc aac acc ttt ggg ctg cag ctc gag ctc acc gag ggt atg cgg          576
Glu Ser Asn Thr Phe Gly Leu Gln Leu Glu Leu Thr Glu Gly Met Arg
            180                 185                 190 ttc gac aag ggc cat atg cat gga gat aca cct aca ttg cat gaa tat          624
Phe Asp Lys Gly His Met His Gly Asp Thr Pro Thr Leu His Glu Tyr
        195                 200                 205 atg tta gat ttg caa cca gag aca act gat ctc tac tgt tat gag caa          672
Met Leu Asp Leu Gln Pro Glu Thr Thr Asp Leu Tyr Cys Tyr Glu Gln
    210                 215                 220 tta aat gac agc tca gag gag gag gat gaa ata gat ggt cca gct gga          720
Leu Asn Asp Ser Ser Glu Glu Glu Asp Glu Ile Asp Gly Pro Ala Gly
225                 230                 235                 240 caa gca gaa ccg gac aga gcc cat tac aat att gta acc ttt tgt tgc          768
Gln Ala Glu Pro Asp Arg Ala His Tyr Asn Ile Val Thr Phe Cys Cys
                245                 250                 255
```

```
aag tgt gac tct acg ctt cgg ttg tgc gta caa agc aca cac gta gac      816
Lys Cys Asp Ser Thr Leu Arg Leu Cys Val Gln Ser Thr His Val Asp
        260                 265                 270 att cgt act ttg gaa gac ctg tta atg ggc aca cta gga att gtg tgc      864
Ile Arg Thr Leu Glu Asp Leu Leu Met Gly Thr Leu Gly Ile Val Cys
        275                 280                 285 ccc atc tgt tct cag aaa cca taa                                      888
Pro Ile Cys Ser Gln Lys Pro
        290                 295
```

<210> SEQ ID NO 33
<211> LENGTH: 295
<212> TYPE: PRT
<213> ORGANISM: Artificial Sequence
<220> FEATURE:
<223> OTHER INFORMATION: fusion sequence

<400> SEQUENCE: 33

```
Met Ala Lys Thr Ile Ala Tyr Asp Glu Glu Ala Arg Arg Gly Leu Glu
  1               5                  10                  15

Arg Gly Leu Asn Ala Leu Ala Asp Ala Val Lys Val Thr Leu Gly Pro
             20                  25                  30

Lys Gly Arg Asn Val Val Leu Glu Lys Lys Trp Gly Ala Pro Thr Ile
         35                  40                  45

Thr Asn Asp Gly Val Ser Ile Ala Lys Glu Ile Glu Leu Glu Asp Pro
     50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                 85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly His Met His Gly Asp Thr Pro Thr Leu His Glu Tyr
        195                 200                 205

Met Leu Asp Leu Gln Pro Glu Thr Thr Asp Leu Tyr Cys Tyr Glu Gln
    210                 215                 220

Leu Asn Asp Ser Ser Glu Glu Asp Glu Ile Asp Gly Pro Ala Gly
225                 230                 235                 240

Gln Ala Glu Pro Asp Arg Ala His Tyr Asn Ile Val Thr Phe Cys Cys
                245                 250                 255

Lys Cys Asp Ser Thr Leu Arg Leu Cys Val Gln Ser Thr His Val Asp
            260                 265                 270

Ile Arg Thr Leu Glu Asp Leu Leu Met Gly Thr Leu Gly Ile Val Cys
        275                 280                 285

Pro Ile Cys Ser Gln Lys Pro
    290                 295
```

<210> SEQ ID NO 34
<211> LENGTH: 597
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(594)

<400> SEQUENCE: 34

```
atg gcg aag gtg aac atc aag cca ctc gag gac aag att ctc gtg cag      48
Met Ala Lys Val Asn Ile Lys Pro Leu Glu Asp Lys Ile Leu Val Gln
 1               5                  10                  15 gcc aac gag gcc gag acc acg acc gcg tcc ggt ctg gtc att cct gac      96
Ala Asn Glu Ala Glu Thr Thr Thr Ala Ser Gly Leu Val Ile Pro Asp
            20                  25                  30 acc gcc aag gag aag ccg cag gag ggc acc gtc gtt gcc gtc ggc cct     144
Thr Ala Lys Glu Lys Pro Gln Glu Gly Thr Val Val Ala Val Gly Pro
        35                  40                  45 ggc cgg tgg gac gag gac ggc gag aag cgg atc ccg ctg gac gtt gcg     192
Gly Arg Trp Asp Glu Asp Gly Glu Lys Arg Ile Pro Leu Asp Val Ala
    50                  55                  60 gag ggt gac acc gtc atc tac agc aag tac ggc ggc acc gag atc aag     240
Glu Gly Asp Thr Val Ile Tyr Ser Lys Tyr Gly Gly Thr Glu Ile Lys
65                  70                  75                  80 tac aac ggc gag gaa tac ctg atc ctg tcg gca cgc gac gtg ctg gcc     288
Tyr Asn Gly Glu Glu Tyr Leu Ile Leu Ser Ala Arg Asp Val Leu Ala
                85                  90                  95 gtc gtt tcc aag atg cat gga gat aca cct aca ttg cat gaa tat atg     336
Val Val Ser Lys Met His Gly Asp Thr Pro Thr Leu His Glu Tyr Met
            100                 105                 110 tta gat ttg caa cca gag aca act gat ctc tac tgt tat gag caa tta     384
Leu Asp Leu Gln Pro Glu Thr Thr Asp Leu Tyr Cys Tyr Glu Gln Leu
        115                 120                 125 aat gac agc tca gag gag gag gat gaa ata gat ggt cca gct gga caa     432
Asn Asp Ser Ser Glu Glu Glu Asp Glu Ile Asp Gly Pro Ala Gly Gln
    130                 135                 140 gca gaa ccg gac aga gcc cat tac aat att gta acc ttt tgt tgc aag     480
Ala Glu Pro Asp Arg Ala His Tyr Asn Ile Val Thr Phe Cys Cys Lys
145                 150                 155                 160 tgt gac tct acg ctt cgg ttg tgc gta caa agc aca cac gta gac att     528
Cys Asp Ser Thr Leu Arg Leu Cys Val Gln Ser Thr His Val Asp Ile
                165                 170                 175 cgt act ttg gaa gac ctg tta atg ggc aca cta gga att gtg tgc ccc     576
Arg Thr Leu Glu Asp Leu Leu Met Gly Thr Leu Gly Ile Val Cys Pro
            180                 185                 190 atc tgt tct cag aaa cca tag                                         597
Ile Cys Ser Gln Lys Pro
        195
```

<210> SEQ ID NO 35
<211> LENGTH: 198
<212> TYPE: PRT
<213> ORGANISM: Artificial Sequence
<220> FEATURE:
<223> OTHER INFORMATION: fusion sequence

<400> SEQUENCE: 35

```
Met Ala Lys Val Asn Ile Lys Pro Leu Glu Asp Lys Ile Leu Val Gln
 1               5                  10                  15

Ala Asn Glu Ala Glu Thr Thr Thr Ala Ser Gly Leu Val Ile Pro Asp
            20                  25                  30
```

```
Thr Ala Lys Glu Lys Pro Gln Glu Gly Thr Val Val Ala Val Gly Pro
        35                  40                  45

Gly Arg Trp Asp Glu Asp Gly Glu Lys Arg Ile Pro Leu Asp Val Ala
    50                  55                  60

Glu Gly Asp Thr Val Ile Tyr Ser Lys Tyr Gly Gly Thr Glu Ile Lys
65                  70                  75                  80

Tyr Asn Gly Glu Glu Tyr Leu Ile Leu Ser Ala Arg Asp Val Leu Ala
                85                  90                  95

Val Val Ser Lys Met His Gly Asp Thr Pro Thr Leu His Glu Tyr Met
            100                 105                 110

Leu Asp Leu Gln Pro Glu Thr Thr Asp Leu Tyr Cys Tyr Glu Gln Leu
        115                 120                 125

Asn Asp Ser Ser Glu Glu Asp Glu Ile Asp Gly Pro Ala Gly Gln
130                 135                 140

Ala Glu Pro Asp Arg Ala His Tyr Asn Ile Val Thr Phe Cys Cys Lys
145                 150                 155                 160

Cys Asp Ser Thr Leu Arg Leu Cys Val Gln Ser Thr His Val Asp Ile
            165                 170                 175

Arg Thr Leu Glu Asp Leu Leu Met Gly Thr Leu Gly Ile Val Cys Pro
        180                 185                 190

Ile Cys Ser Gln Lys Pro
        195
```

<210> SEQ ID NO 36
<211> LENGTH: 24
<212> TYPE: DNA
<213> ORGANISM: Artificial Sequence
<220> FEATURE:
<223> OTHER INFORMATION: fusion sequence

<400> SEQUENCE: 36
ttcaccatgg ctcgtgcggt cggg                                    24

<210> SEQ ID NO 37
<211> LENGTH: 27
<212> TYPE: DNA
<213> ORGANISM: Artificial Sequence
<220> FEATURE:
<223> OTHER INFORMATION: fusion sequence

<400> SEQUENCE: 37
acctccgcgt ccacagctag ctcagcc                                 27

<210> SEQ ID NO 38
<211> LENGTH: 24
<212> TYPE: DNA
<213> ORGANISM: Artificial Sequence
<220> FEATURE:
<223> OTHER INFORMATION: fusion sequence

<400> SEQUENCE: 38
ccagctgtaa ccatggatgg agat                                    24

<210> SEQ ID NO 39
<211> LENGTH: 29
<212> TYPE: DNA
<213> ORGANISM: Artificial Sequence
<220> FEATURE:
<223> OTHER INFORMATION: fusion sequence

<400> SEQUENCE: 39

-continued

```
ggatcagaca tggccatggc tggtttctg                                29
```

<210> SEQ ID NO 40
<211> LENGTH: 2136
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(2133)

<400> SEQUENCE: 40

| | | | | | | | | | | | | | | | | |
|---|---|---|---|---|---|---|---|---|---|---|---|---|---|---|---|---|
| atg | gat | gga | gat | aca | cct | aca | ttg | cat | gaa | tat | atg | tta | gat | ttg | caa | 48 |
| Met | Asp | Gly | Asp | Thr | Pro | Thr | Leu | His | Glu | Tyr | Met | Leu | Asp | Leu | Gln | |
| 1 | | | | 5 | | | | | 10 | | | | | 15 | | |
| cca | gag | aca | act | gat | ctc | tac | tgt | tat | gag | caa | tta | aat | gac | agc | tca | 96 |
| Pro | Glu | Thr | Thr | Asp | Leu | Tyr | Cys | Tyr | Glu | Gln | Leu | Asn | Asp | Ser | Ser | |
| | | 20 | | | | | 25 | | | | | 30 | | | | |
| gag | gag | gag | gat | gaa | ata | gat | ggt | cca | gct | gga | caa | gca | gaa | ccg | gac | 144 |
| Glu | Glu | Glu | Asp | Glu | Ile | Asp | Gly | Pro | Ala | Gly | Gln | Ala | Glu | Pro | Asp | |
| | 35 | | | | | 40 | | | | | 45 | | | | | |
| aga | gcc | cat | tac | aat | att | gta | acc | ttt | tgt | tgc | aag | tgt | gac | tct | acg | 192 |
| Arg | Ala | His | Tyr | Asn | Ile | Val | Thr | Phe | Cys | Cys | Lys | Cys | Asp | Ser | Thr | |
| | 50 | | | | | 55 | | | | | 60 | | | | | |
| ctt | cgg | ttg | tgc | gta | caa | agc | aca | cac | gta | gac | att | cgt | act | ttg | gaa | 240 |
| Leu | Arg | Leu | Cys | Val | Gln | Ser | Thr | His | Val | Asp | Ile | Arg | Thr | Leu | Glu | |
| 65 | | | | | 70 | | | | | 75 | | | | | 80 | |
| gac | ctg | tta | atg | ggc | aca | cta | gga | att | gtg | tgc | ccc | atc | tgt | tct | cag | 288 |
| Asp | Leu | Leu | Met | Gly | Thr | Leu | Gly | Ile | Val | Cys | Pro | Ile | Cys | Ser | Gln | |
| | | | | 85 | | | | | 90 | | | | | 95 | | |
| aaa | cca | gcc | atg | gct | cgt | gcg | gtc | ggg | atc | gac | ctc | ggg | acc | acc | aac | 336 |
| Lys | Pro | Ala | Met | Ala | Arg | Ala | Val | Gly | Ile | Asp | Leu | Gly | Thr | Thr | Asn | |
| | | | 100 | | | | | 105 | | | | | 110 | | | |
| tcc | gtc | gtc | tcg | gtt | ctg | gaa | ggt | ggc | gac | ccg | gtc | gtc | gtc | gcc | aac | 384 |
| Ser | Val | Val | Ser | Val | Leu | Glu | Gly | Gly | Asp | Pro | Val | Val | Val | Ala | Asn | |
| | | 115 | | | | | 120 | | | | | 125 | | | | |
| tcc | gag | ggc | tcc | agg | acc | acc | ccg | tca | att | gtc | gcg | ttc | gcc | cgc | aac | 432 |
| Ser | Glu | Gly | Ser | Arg | Thr | Thr | Pro | Ser | Ile | Val | Ala | Phe | Ala | Arg | Asn | |
| | 130 | | | | | 135 | | | | | 140 | | | | | |
| ggt | gag | gtg | ctg | gtc | ggc | cag | ccc | gcc | aag | aac | cag | gcg | gtg | acc | aac | 480 |
| Gly | Glu | Val | Leu | Val | Gly | Gln | Pro | Ala | Lys | Asn | Gln | Ala | Val | Thr | Asn | |
| 145 | | | | | 150 | | | | | 155 | | | | | 160 | |
| gtc | gat | cgc | acc | gtg | cgc | tcg | gtc | aag | cga | cac | atg | ggc | agc | gac | tgg | 528 |
| Val | Asp | Arg | Thr | Val | Arg | Ser | Val | Lys | Arg | His | Met | Gly | Ser | Asp | Trp | |
| | | | | 165 | | | | | 170 | | | | | 175 | | |
| tcc | ata | gag | att | gac | ggc | aag | aaa | tac | acc | gcg | ccg | gag | atc | agc | gcc | 576 |
| Ser | Ile | Glu | Ile | Asp | Gly | Lys | Lys | Tyr | Thr | Ala | Pro | Glu | Ile | Ser | Ala | |
| | | | 180 | | | | | 185 | | | | | 190 | | | |
| cgc | att | ctg | atg | aag | ctg | aag | cgc | gac | gcc | gag | gcc | tac | ctc | ggt | gag | 624 |
| Arg | Ile | Leu | Met | Lys | Leu | Lys | Arg | Asp | Ala | Glu | Ala | Tyr | Leu | Gly | Glu | |
| | | 195 | | | | | 200 | | | | | 205 | | | | |
| gac | att | acc | gac | gcg | gtt | atc | acg | acg | ccc | gcc | tac | ttc | aat | gac | gcc | 672 |
| Asp | Ile | Thr | Asp | Ala | Val | Ile | Thr | Thr | Pro | Ala | Tyr | Phe | Asn | Asp | Ala | |
| | 210 | | | | | 215 | | | | | 220 | | | | | |
| cag | cgt | cag | gcc | acc | aag | gac | gcc | ggc | cag | atc | gcc | ggc | ctc | aac | gtg | 720 |
| Gln | Arg | Gln | Ala | Thr | Lys | Asp | Ala | Gly | Gln | Ile | Ala | Gly | Leu | Asn | Val | |
| 225 | | | | | 230 | | | | | 235 | | | | | 240 | |
| ctg | cgg | atc | gtc | aac | gag | ccg | acc | gcg | gcc | gcg | ctg | gcc | tac | ggc | ctc | 768 |
| Leu | Arg | Ile | Val | Asn | Glu | Pro | Thr | Ala | Ala | Ala | Leu | Ala | Tyr | Gly | Leu | |
| | | | | 245 | | | | | 250 | | | | | 255 | | |

| | | |
|---|---|---|
| gac aag ggc gag aag gag cag cga atc ctg gtc ttc gac ttg ggt ggt<br>Asp Lys Gly Glu Lys Glu Gln Arg Ile Leu Val Phe Asp Leu Gly Gly<br>260 265 270 | | 816 |
| ggc act ttc gac gtt tcc ctg ctg gag atc ggc gag ggt gtg gtt gag<br>Gly Thr Phe Asp Val Ser Leu Leu Glu Ile Gly Glu Gly Val Val Glu<br>275 280 285 | | 864 |
| gtc cgt gcc act tcg ggt gac aac cac ctc ggc ggc gac gac tgg gac<br>Val Arg Ala Thr Ser Gly Asp Asn His Leu Gly Gly Asp Asp Trp Asp<br>290 295 300 | | 912 |
| cag cgg gtc gtc gat tgg ctg gtg gac aag ttc aag ggc acc agc ggc<br>Gln Arg Val Val Asp Trp Leu Val Asp Lys Phe Lys Gly Thr Ser Gly<br>305 310 315 320 | | 960 |
| atc gat ctg acc aag gac aag atg gcg atg cag cgg ctg cgg gaa gcc<br>Ile Asp Leu Thr Lys Asp Lys Met Ala Met Gln Arg Leu Arg Glu Ala<br>325 330 335 | | 1008 |
| gcc gag aag gca aag atc gag ctg agt tcg agt cag tcc acc tcg atc<br>Ala Glu Lys Ala Lys Ile Glu Leu Ser Ser Ser Gln Ser Thr Ser Ile<br>340 345 350 | | 1056 |
| aac ctg ccc tac atc acc gtc gac gcc gac aag aac ccg ttg ttc tta<br>Asn Leu Pro Tyr Ile Thr Val Asp Ala Asp Lys Asn Pro Leu Phe Leu<br>355 360 365 | | 1104 |
| gac gag cag ctg acc cgc gcg gag ttc caa cgg atc act cag gac ctg<br>Asp Glu Gln Leu Thr Arg Ala Glu Phe Gln Arg Ile Thr Gln Asp Leu<br>370 375 380 | | 1152 |
| ctg gac cgc act cgc aag ccg ttc cag tcg gtg atc gct gac acc ggc<br>Leu Asp Arg Thr Arg Lys Pro Phe Gln Ser Val Ile Ala Asp Thr Gly<br>385 390 395 400 | | 1200 |
| att tcg gtg tcg gag atc gat cac gtt gtg ctc gtg ggt ggt tcg acc<br>Ile Ser Val Ser Glu Ile Asp His Val Val Leu Val Gly Gly Ser Thr<br>405 410 415 | | 1248 |
| cgg atg ccc gcg gtg acc gat ctg gtc aag gaa ctc acc ggc ggc aag<br>Arg Met Pro Ala Val Thr Asp Leu Val Lys Glu Leu Thr Gly Gly Lys<br>420 425 430 | | 1296 |
| gaa ccc aac aag ggc gtc aac ccc gat gag gtt gtc gcg gtg gga gcc<br>Glu Pro Asn Lys Gly Val Asn Pro Asp Glu Val Val Ala Val Gly Ala<br>435 440 445 | | 1344 |
| gct ctg cag gcc ggc gtc ctc aag ggc gag gtg aaa gac gtt ctg ctg<br>Ala Leu Gln Ala Gly Val Leu Lys Gly Glu Val Lys Asp Val Leu Leu<br>450 455 460 | | 1392 |
| ctt gat gtt acc ccg ctg agc ctg ggt atc gag acc aag ggc ggg gtg<br>Leu Asp Val Thr Pro Leu Ser Leu Gly Ile Glu Thr Lys Gly Gly Val<br>465 470 475 480 | | 1440 |
| atg acc agg ctc atc gag cgc aac acc acg atc ccc acc aag cgg tcg<br>Met Thr Arg Leu Ile Glu Arg Asn Thr Thr Ile Pro Thr Lys Arg Ser<br>485 490 495 | | 1488 |
| gag act ttc acc acc gcc gac gac aac caa ccg tcg gtg cag atc cag<br>Glu Thr Phe Thr Thr Ala Asp Asp Asn Gln Pro Ser Val Gln Ile Gln<br>500 505 510 | | 1536 |
| gtc tat cag ggg gag cgt gag atc gcc gcg cac aac aag ttg ctc ggg<br>Val Tyr Gln Gly Glu Arg Glu Ile Ala Ala His Asn Lys Leu Leu Gly<br>515 520 525 | | 1584 |
| tcc ttc gag ctg acc ggc atc ccg ccg gcg ccg cgg ggg att ccg cag<br>Ser Phe Glu Leu Thr Gly Ile Pro Pro Ala Pro Arg Gly Ile Pro Gln<br>530 535 540 | | 1632 |
| atc gag gtc act ttc gac atc gac gcc aac ggc att gtg cac gtc acc<br>Ile Glu Val Thr Phe Asp Ile Asp Ala Asn Gly Ile Val His Val Thr<br>545 550 555 560 | | 1680 |
| gcc aag gac aag ggc acc ggc aag gag aac acg atc cga atc cag gaa<br>Ala Lys Asp Lys Gly Thr Gly Lys Glu Asn Thr Ile Arg Ile Gln Glu<br>565 570 575 | | 1728 |

```
ggc tcg ggc ctg tcc aag gaa gac att gac cgc atg atc aag gac gcc    1776
Gly Ser Gly Leu Ser Lys Glu Asp Ile Asp Arg Met Ile Lys Asp Ala
            580                 585                 590 gaa gcg cac gcc gag gag gat cgc aag cgt cgc gag gag gcc gat gtt    1824
Glu Ala His Ala Glu Glu Asp Arg Lys Arg Arg Glu Glu Ala Asp Val
        595                 600                 605 cgt aat caa gcc gag aca ttg gtc tac cag acg gag aag ttc gtc aaa    1872
Arg Asn Gln Ala Glu Thr Leu Val Tyr Gln Thr Glu Lys Phe Val Lys
    610                 615                 620 gaa cag cgt gag gcc gag ggt ggt tcg aag gta cct gaa gac acg ctg    1920
Glu Gln Arg Glu Ala Glu Gly Gly Ser Lys Val Pro Glu Asp Thr Leu
625                 630                 635                 640 aac aag gtt gat gcc gcg gtg gcg gaa gcg aag gcg gca ctt ggc gga    1968
Asn Lys Val Asp Ala Ala Val Ala Glu Ala Lys Ala Ala Leu Gly Gly
                645                 650                 655 tcg gat att tcg gcc atc aag tcg gcg atg gag aag ctg ggc cag gag    2016
Ser Asp Ile Ser Ala Ile Lys Ser Ala Met Glu Lys Leu Gly Gln Glu
            660                 665                 670 tcg cag gct ctg ggg caa gcg atc tac gaa gca gct cag gct gcg tca    2064
Ser Gln Ala Leu Gly Gln Ala Ile Tyr Glu Ala Ala Gln Ala Ala Ser
        675                 680                 685 cag gcc act ggc gct gcc cac ccc ggc ggc gag ccg ggc ggt gcc cac    2112
Gln Ala Thr Gly Ala Ala His Pro Gly Gly Glu Pro Gly Gly Ala His
    690                 695                 700 ccc ggc tcg gct gag cta gca tga                                    2136
Pro Gly Ser Ala Glu Leu Ala
705                 710
```

<210> SEQ ID NO 41
<211> LENGTH: 711
<212> TYPE: PRT
<213> ORGANISM: Artificial Sequence
<220> FEATURE:
<223> OTHER INFORMATION: fusion sequence

<400> SEQUENCE: 41

```
Met Asp Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
    65                  70                  75                  80

Asp Leu Leu Met Gly Thr Leu Gly Ile Val Cys Pro Ile Cys Ser Gln
                85                  90                  95

Lys Pro Ala Met Ala Arg Ala Val Gly Ile Asp Leu Gly Thr Thr Asn
                100                 105                 110

Ser Val Val Ser Val Leu Glu Gly Gly Asp Pro Val Val Val Ala Asn
            115                 120                 125

Ser Glu Gly Ser Arg Thr Thr Pro Ser Ile Val Ala Phe Ala Arg Asn
        130                 135                 140

Gly Glu Val Leu Val Gly Gln Pro Ala Lys Asn Gln Ala Val Thr Asn
145                 150                 155                 160

Val Asp Arg Thr Val Arg Ser Val Lys Arg His Met Gly Ser Asp Trp
                165                 170                 175
```

```
Ser Ile Glu Ile Asp Gly Lys Lys Tyr Thr Ala Pro Glu Ile Ser Ala
            180                 185                 190

Arg Ile Leu Met Lys Leu Lys Arg Asp Ala Glu Ala Tyr Leu Gly Glu
            195                 200                 205

Asp Ile Thr Asp Ala Val Ile Thr Thr Pro Ala Tyr Phe Asn Asp Ala
            210                 215                 220

Gln Arg Gln Ala Thr Lys Asp Ala Gly Gln Ile Ala Gly Leu Asn Val
225                 230                 235                 240

Leu Arg Ile Val Asn Glu Pro Thr Ala Ala Leu Ala Tyr Gly Leu
            245                 250                 255

Asp Lys Gly Glu Lys Glu Gln Arg Ile Leu Val Phe Asp Leu Gly Gly
            260                 265                 270

Gly Thr Phe Asp Val Ser Leu Leu Glu Ile Gly Glu Gly Val Val Glu
            275                 280                 285

Val Arg Ala Thr Ser Gly Asp Asn His Leu Gly Gly Asp Asp Trp Asp
            290                 295                 300

Gln Arg Val Val Asp Trp Leu Val Asp Lys Phe Lys Gly Thr Ser Gly
305                 310                 315                 320

Ile Asp Leu Thr Lys Asp Lys Met Ala Met Gln Arg Leu Arg Glu Ala
            325                 330                 335

Ala Glu Lys Ala Lys Ile Glu Leu Ser Ser Gln Ser Thr Ser Ile
            340                 345                 350

Asn Leu Pro Tyr Ile Thr Val Asp Ala Asp Lys Asn Pro Leu Phe Leu
            355                 360                 365

Asp Glu Gln Leu Thr Arg Ala Glu Phe Gln Arg Ile Thr Gln Asp Leu
            370                 375                 380

Leu Asp Arg Thr Arg Lys Pro Phe Gln Ser Val Ile Ala Asp Thr Gly
385                 390                 395                 400

Ile Ser Val Ser Glu Ile Asp His Val Val Leu Val Gly Gly Ser Thr
            405                 410                 415

Arg Met Pro Ala Val Thr Asp Leu Val Lys Glu Leu Thr Gly Gly Lys
            420                 425                 430

Glu Pro Asn Lys Gly Val Asn Pro Asp Glu Val Val Ala Val Gly Ala
            435                 440                 445

Ala Leu Gln Ala Gly Val Leu Lys Gly Glu Val Lys Asp Val Leu Leu
450                 455                 460

Leu Asp Val Thr Pro Leu Ser Leu Gly Ile Glu Thr Lys Gly Gly Val
465                 470                 475                 480

Met Thr Arg Leu Ile Glu Arg Asn Thr Thr Ile Pro Thr Lys Arg Ser
            485                 490                 495

Glu Thr Phe Thr Thr Ala Asp Asp Asn Gln Pro Ser Val Gln Ile Gln
            500                 505                 510

Val Tyr Gln Gly Glu Arg Glu Ile Ala Ala His Asn Lys Leu Leu Gly
            515                 520                 525

Ser Phe Glu Leu Thr Gly Ile Pro Pro Ala Pro Arg Gly Ile Pro Gln
            530                 535                 540

Ile Glu Val Thr Phe Asp Ile Asp Ala Asn Gly Ile Val His Val Thr
545                 550                 555                 560

Ala Lys Asp Lys Gly Thr Gly Lys Glu Asn Thr Ile Arg Ile Gln Glu
            565                 570                 575

Gly Ser Gly Leu Ser Lys Glu Asp Ile Asp Arg Met Ile Lys Asp Ala
            580                 585                 590
```

```
Glu Ala His Ala Glu Glu Asp Arg Lys Arg Glu Glu Ala Asp Val
        595                 600                 605

Arg Asn Gln Ala Glu Thr Leu Val Tyr Gln Thr Glu Lys Phe Val Lys
    610                 615                 620

Glu Gln Arg Glu Ala Glu Gly Gly Ser Lys Val Pro Glu Asp Thr Leu
625                 630                 635                 640

Asn Lys Val Asp Ala Val Ala Glu Ala Lys Ala Ala Leu Gly Gly
                645                 650                 655

Ser Asp Ile Ser Ala Ile Lys Ser Ala Met Glu Lys Leu Gly Gln Glu
                660                 665                 670

Ser Gln Ala Leu Gly Gln Ala Ile Tyr Glu Ala Ala Gln Ala Ala Ser
    675                 680                 685

Gln Ala Thr Gly Ala Ala His Pro Gly Gly Glu Pro Gly Gly Ala His
    690                 695                 700

Pro Gly Ser Ala Glu Leu Ala
705                 710

<210> SEQ ID NO 42
<211> LENGTH: 20
<212> TYPE: DNA
<213> ORGANISM: Artificial Sequence
<220> FEATURE:
<223> OTHER INFORMATION: fusion sequence

<400> SEQUENCE: 42
gagggtggtt cgaaggtacc                                                  20

<210> SEQ ID NO 43
<211> LENGTH: 27
<212> TYPE: DNA
<213> ORGANISM: Artificial Sequence
<220> FEATURE:
<223> OTHER INFORMATION: fusion sequence

<400> SEQUENCE: 43
tttgatttcg ctagctcact tggcctc                                          27

<210> SEQ ID NO 44
<211> LENGTH: 2175
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(2172)

<400> SEQUENCE: 44 atg gat gga gat aca cct aca ttg cat gaa tat atg tta gat ttg caa      48
Met Asp Gly Asp Thr Pro Thr Leu His Glu Tyr Met Leu Asp Leu Gln
  1               5                  10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
                 20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
             35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
         50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
 65                  70                  75                  80
```

```
gac ctg tta atg ggc aca cta gga att gtg tgc ccc atc tgt tct cag      288
Asp Leu Leu Met Gly Thr Leu Gly Ile Val Cys Pro Ile Cys Ser Gln
                85                  90                  95 aaa cca gcc atg gct cgt gcg gtc ggg atc gac ctc ggg acc acc aac      336
Lys Pro Ala Met Ala Arg Ala Val Gly Ile Asp Leu Gly Thr Thr Asn
                100                 105                 110 tcc gtc gtc tcg gtt ctg gaa ggt ggc gac ccg gtc gtc gtc gcc aac      384
Ser Val Val Ser Val Leu Glu Gly Gly Asp Pro Val Val Val Ala Asn
            115                 120                 125 tcc gag ggc tcc agg acc acc ccg tca att gtc gcg ttc gcc cgc aac      432
Ser Glu Gly Ser Arg Thr Thr Pro Ser Ile Val Ala Phe Ala Arg Asn
    130                 135                 140 ggt gag gtg ctg gtc ggc cag ccc gcc aag aac cag gcg gtg acc aac      480
Gly Glu Val Leu Val Gly Gln Pro Ala Lys Asn Gln Ala Val Thr Asn
145                 150                 155                 160 gtc gat cgc acc gtg cgc tcg gtc aag cga cac atg ggc agc gac tgg      528
Val Asp Arg Thr Val Arg Ser Val Lys Arg His Met Gly Ser Asp Trp
                165                 170                 175 tcc ata gag att gac ggc aag aaa tac acc gcg ccg gag atc agc gcc      576
Ser Ile Glu Ile Asp Gly Lys Lys Tyr Thr Ala Pro Glu Ile Ser Ala
                180                 185                 190 cgc att ctg atg aag ctg aag cgc gac gcc gag gcc tac ctc ggt gag      624
Arg Ile Leu Met Lys Leu Lys Arg Asp Ala Glu Ala Tyr Leu Gly Glu
            195                 200                 205 gac att acc gac gcg gtt atc acg acg ccc gcc tac ttc aat gac gcc      672
Asp Ile Thr Asp Ala Val Ile Thr Thr Pro Ala Tyr Phe Asn Asp Ala
    210                 215                 220 cag cgt cag gcc acc aag gac gcc ggc cag atc gcc ggc ctc aac gtg      720
Gln Arg Gln Ala Thr Lys Asp Ala Gly Gln Ile Ala Gly Leu Asn Val
225                 230                 235                 240 ctg cgg atc gtc aac gag ccg acc gcg gcc gcg ctg gcc tac ggc ctc      768
Leu Arg Ile Val Asn Glu Pro Thr Ala Ala Ala Leu Ala Tyr Gly Leu
                245                 250                 255 gac aag ggc gag aag gag cag cga atc ctg gtc ttc gac ttg ggt ggt      816
Asp Lys Gly Glu Lys Glu Gln Arg Ile Leu Val Phe Asp Leu Gly Gly
                260                 265                 270 ggc act ttc gac gtt tcc ctg ctg gag atc ggc gag ggt gtg gtt gag      864
Gly Thr Phe Asp Val Ser Leu Leu Glu Ile Gly Glu Gly Val Val Glu
            275                 280                 285 gtc cgt gcc act tcg ggt gac aac cac ctc ggc ggc gac gac tgg gac      912
Val Arg Ala Thr Ser Gly Asp Asn His Leu Gly Gly Asp Asp Trp Asp
    290                 295                 300 cag cgg gtc gtc gat tgg ctg gtg gac aag ttc aag ggc acc agc ggc      960
Gln Arg Val Val Asp Trp Leu Val Asp Lys Phe Lys Gly Thr Ser Gly
305                 310                 315                 320 atc gat ctg acc aag gac aag atg gcg atg cag cgg ctg cgg gaa gcc     1008
Ile Asp Leu Thr Lys Asp Lys Met Ala Met Gln Arg Leu Arg Glu Ala
                325                 330                 335 gcc gag aag gca aag atc gag ctg agt tcg agt cag tcc acc tcg atc     1056
Ala Glu Lys Ala Lys Ile Glu Leu Ser Ser Ser Gln Ser Thr Ser Ile
                340                 345                 350 aac ctg ccc tac atc acc gtc gac gcc gac aag aac ccg ttg ttc tta     1104
Asn Leu Pro Tyr Ile Thr Val Asp Ala Asp Lys Asn Pro Leu Phe Leu
            355                 360                 365 gac gag cag ctg acc cgc gcg gag ttc caa cgg atc act cag gac ctg     1152
Asp Glu Gln Leu Thr Arg Ala Glu Phe Gln Arg Ile Thr Gln Asp Leu
    370                 375                 380 ctg gac cgc act cgc aag ccg ttc cag tcg gtg atc gct gac acc ggc     1200
Leu Asp Arg Thr Arg Lys Pro Phe Gln Ser Val Ile Ala Asp Thr Gly
```

```
                                                              -continued
385                     390                     395                     400
att tcg gtg tcg gag atc gat cac gtt gtg ctc gtg ggt ggt tcg acc    1248
Ile Ser Val Ser Glu Ile Asp His Val Val Leu Val Gly Gly Ser Thr
                405                     410                     415 cgg atg ccc gcg gtg acc gat ctg gtc aag gaa ctc acc ggc ggc aag    1296
Arg Met Pro Ala Val Thr Asp Leu Val Lys Glu Leu Thr Gly Gly Lys
                420                     425                     430 gaa ccc aac aag ggc gtc aac ccc gat gag gtt gtc gcg gtg gga gcc    1344
Glu Pro Asn Lys Gly Val Asn Pro Asp Glu Val Val Ala Val Gly Ala
                435                     440                     445 gct ctg cag gcc ggc gtc ctc aag ggc gag gtg aaa gac gtt ctg ctg    1392
Ala Leu Gln Ala Gly Val Leu Lys Gly Glu Val Lys Asp Val Leu Leu
        450                     455                     460 ctt gat gtt acc ccg ctg agc ctg ggt atc gag acc aag ggc ggg gtg    1440
Leu Asp Val Thr Pro Leu Ser Leu Gly Ile Glu Thr Lys Gly Gly Val
465                     470                     475                     480 atg acc agg ctc atc gag cgc aac acc acg atc ccc acc aag cgg tcg    1488
Met Thr Arg Leu Ile Glu Arg Asn Thr Thr Ile Pro Thr Lys Arg Ser
                485                     490                     495 gag act ttc acc acc gcc gac gac aac caa ccg tcg gtg cag atc cag    1536
Glu Thr Phe Thr Thr Ala Asp Asp Asn Gln Pro Ser Val Gln Ile Gln
                500                     505                     510 gtc tat cag ggg gag cgt gag atc gcc gcg cac aac aag ttg ctc ggg    1584
Val Tyr Gln Gly Glu Arg Glu Ile Ala Ala His Asn Lys Leu Leu Gly
        515                     520                     525 tcc ttc gag ctg acc ggc atc ccg ccg gcg ccg cgg ggg att ccg cag    1632
Ser Phe Glu Leu Thr Gly Ile Pro Pro Ala Pro Arg Gly Ile Pro Gln
        530                     535                     540 atc gag gtc act ttc gac atc gac gcc aac ggc att gtg cac gtc acc    1680
Ile Glu Val Thr Phe Asp Ile Asp Ala Asn Gly Ile Val His Val Thr
545                     550                     555                     560 gcc aag gac aag ggc acc ggc aag gag aac acg atc cga atc cag gaa    1728
Ala Lys Asp Lys Gly Thr Gly Lys Glu Asn Thr Ile Arg Ile Gln Glu
                565                     570                     575 ggc tcg ggc ctg tcc aag gaa gac att gac cgc atg atc aag gac gcc    1776
Gly Ser Gly Leu Ser Lys Glu Asp Ile Asp Arg Met Ile Lys Asp Ala
                580                     585                     590 gaa gcg cac gcc gag gag gat cgc aag cgt cgc gag gag gcc gat gtt    1824
Glu Ala His Ala Glu Glu Asp Arg Lys Arg Arg Glu Glu Ala Asp Val
        595                     600                     605 cgt aat caa gcc gag aca ttg gtc tac cag acg gag aag ttc gtc aaa    1872
Arg Asn Gln Ala Glu Thr Leu Val Tyr Gln Thr Glu Lys Phe Val Lys
        610                     615                     620 gaa cag cgt gag gcc gag ggt ggt tcg aag gta cct gaa gac acg ctg    1920
Glu Gln Arg Glu Ala Glu Gly Gly Ser Lys Val Pro Glu Asp Thr Leu
625                     630                     635                     640 aac aag gtt gat gcc gcg gtg gcg gaa gcg aag gcg gca ctt ggc gga    1968
Asn Lys Val Asp Ala Ala Val Ala Glu Ala Lys Ala Ala Leu Gly Gly
                645                     650                     655 tcg gat att tcg gcc atc aag tcg gcg atg gag aag ctg ggc cag gag    2016
Ser Asp Ile Ser Ala Ile Lys Ser Ala Met Glu Lys Leu Gly Gln Glu
                660                     665                     670 tcg cag gct ctg ggg caa gcg atc tac gaa gca gct cag gct gcg tca    2064
Ser Gln Ala Leu Gly Gln Ala Ile Tyr Glu Ala Ala Gln Ala Ala Ser
        675                     680                     685 cag gcc act ggc gct gcc cac ccc ggc ggc gag ccg ggc ggt gcc cac    2112
Gln Ala Thr Gly Ala Ala His Pro Gly Gly Glu Pro Gly Gly Ala His
        690                     695                     700 ccc ggc tcg gct gat gac gtt gtg gac gcg gag gtg gtc gac gac ggc    2160
```

```
Pro Gly Ser Ala Asp Asp Val Val Asp Ala Glu Val Val Asp Asp Gly
705                 710                 715                 720 cgg gag gcc aag tga                                                      2175
Arg Glu Ala Lys
```

<210> SEQ ID NO 45
<211> LENGTH: 724
<212> TYPE: PRT
<213> ORGANISM: Artificial Sequence
<220> FEATURE:
<223> OTHER INFORMATION: fusion sequence

<400> SEQUENCE: 45

```
Met Asp Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Ala Met Ala Arg Ala Val Gly Ile Asp Leu Thr Thr Asn
            100                 105                 110

Ser Val Val Ser Val Leu Glu Gly Gly Asp Pro Val Val Val Ala Asn
        115                 120                 125

Ser Glu Gly Ser Arg Thr Thr Pro Ser Ile Val Ala Phe Ala Arg Asn
130                 135                 140

Gly Glu Val Leu Val Gly Gln Pro Ala Lys Asn Gln Ala Val Thr Asn
145                 150                 155                 160

Val Asp Arg Thr Val Arg Ser Val Lys Arg His Met Gly Ser Asp Trp
                165                 170                 175

Ser Ile Glu Ile Asp Gly Lys Lys Tyr Thr Ala Pro Glu Ile Ser Ala
            180                 185                 190

Arg Ile Leu Met Lys Leu Lys Arg Asp Ala Glu Ala Tyr Leu Gly Glu
        195                 200                 205

Asp Ile Thr Asp Ala Val Ile Thr Thr Pro Ala Tyr Phe Asn Asp Ala
    210                 215                 220

Gln Arg Gln Ala Thr Lys Asp Ala Gly Gln Ile Ala Gly Leu Asn Val
225                 230                 235                 240

Leu Arg Ile Val Asn Glu Pro Thr Ala Ala Ala Leu Ala Tyr Gly Leu
                245                 250                 255

Asp Lys Gly Glu Lys Glu Gln Arg Ile Leu Val Phe Asp Leu Gly Gly
            260                 265                 270

Gly Thr Phe Asp Val Ser Leu Leu Glu Ile Gly Glu Gly Val Val Glu
        275                 280                 285

Val Arg Ala Thr Ser Gly Asp Asn His Leu Gly Gly Asp Asp Trp Asp
    290                 295                 300

Gln Arg Val Val Asp Trp Leu Val Asp Lys Phe Lys Gly Thr Ser Gly
305                 310                 315                 320

Ile Asp Leu Thr Lys Asp Lys Met Ala Met Gln Arg Leu Arg Glu Ala
                325                 330                 335
```

```
Ala Glu Lys Ala Lys Ile Glu Leu Ser Ser Gln Ser Thr Ser Ile
            340                 345                 350

Asn Leu Pro Tyr Ile Thr Val Asp Ala Asp Lys Asn Pro Leu Phe Leu
            355                 360                 365

Asp Glu Gln Leu Thr Arg Ala Glu Phe Gln Arg Ile Thr Gln Asp Leu
        370                 375                 380

Leu Asp Arg Thr Arg Lys Pro Phe Gln Ser Val Ile Ala Asp Thr Gly
385                 390                 395                 400

Ile Ser Val Ser Glu Ile Asp His Val Val Leu Val Gly Gly Ser Thr
                405                 410                 415

Arg Met Pro Ala Val Thr Asp Leu Val Lys Glu Leu Thr Gly Gly Lys
                420                 425                 430

Glu Pro Asn Lys Gly Val Asn Pro Asp Glu Val Val Ala Val Gly Ala
            435                 440                 445

Ala Leu Gln Ala Gly Val Leu Lys Gly Glu Val Lys Asp Val Leu Leu
        450                 455                 460

Leu Asp Val Thr Pro Leu Ser Leu Gly Ile Glu Thr Lys Gly Gly Val
465                 470                 475                 480

Met Thr Arg Leu Ile Glu Arg Asn Thr Thr Ile Pro Thr Lys Arg Ser
                485                 490                 495

Glu Thr Phe Thr Thr Ala Asp Asp Asn Gln Pro Ser Val Gln Ile Gln
            500                 505                 510

Val Tyr Gln Gly Glu Arg Glu Ile Ala Ala His Asn Lys Leu Leu Gly
        515                 520                 525

Ser Phe Glu Leu Thr Gly Ile Pro Pro Ala Pro Arg Gly Ile Pro Gln
        530                 535                 540

Ile Glu Val Thr Phe Asp Ile Asp Ala Asn Gly Ile Val His Val Thr
545                 550                 555                 560

Ala Lys Asp Lys Gly Thr Gly Lys Glu Asn Thr Ile Arg Ile Gln Glu
                565                 570                 575

Gly Ser Gly Leu Ser Lys Glu Asp Ile Asp Arg Met Ile Lys Asp Ala
            580                 585                 590

Glu Ala His Ala Glu Glu Asp Arg Lys Arg Arg Glu Glu Ala Asp Val
            595                 600                 605

Arg Asn Gln Ala Glu Thr Leu Val Tyr Gln Thr Glu Lys Phe Val Lys
        610                 615                 620

Glu Gln Arg Glu Ala Glu Gly Gly Ser Lys Val Pro Glu Asp Thr Leu
625                 630                 635                 640

Asn Lys Val Asp Ala Ala Val Ala Glu Ala Lys Ala Ala Leu Gly Gly
                645                 650                 655

Ser Asp Ile Ser Ala Ile Lys Ser Ala Met Glu Lys Leu Gly Gln Glu
                660                 665                 670

Ser Gln Ala Leu Gly Gln Ala Ile Tyr Glu Ala Ala Gln Ala Ala Ser
        675                 680                 685

Gln Ala Thr Gly Ala Ala His Pro Gly Gly Glu Pro Gly Gly Ala His
        690                 695                 700

Pro Gly Ser Ala Asp Asp Val Val Asp Ala Glu Val Val Asp Asp Gly
705                 710                 715                 720

Arg Glu Ala Lys

<210> SEQ ID NO 46
<211> LENGTH: 21
<212> TYPE: DNA
<213> ORGANISM: Artificial Sequence
```

```
<220> FEATURE:
<223> OTHER INFORMATION: fusion sequence

<400> SEQUENCE: 46
gcagccccat ggcaaaagaa a                                              21

<210> SEQ ID NO 47
<211> LENGTH: 30
<212> TYPE: DNA
<213> ORGANISM: Artificial Sequence
<220> FEATURE:
<223> OTHER INFORMATION: fusion sequence

<400> SEQUENCE: 47
gctcgaattc ggtcagctag ctccgcccat                                     30

<210> SEQ ID NO 48
<211> LENGTH: 27
<212> TYPE: DNA
<213> ORGANISM: Artificial Sequence
<220> FEATURE:
<223> OTHER INFORMATION: fusion sequence

<400> SEQUENCE: 48
aacccagctg ctagcatgca tggagat                                        27

<210> SEQ ID NO 49
<211> LENGTH: 24
<212> TYPE: DNA
<213> ORGANISM: Artificial Sequence
<220> FEATURE:
<223> OTHER INFORMATION: fusion sequence

<400> SEQUENCE: 49
agccatgaat tcttatggtt tctg                                           24

<210> SEQ ID NO 50
<211> LENGTH: 1926
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1923)

<400> SEQUENCE: 50 atg gca aaa gaa att aaa ttt tca tca gat gcc cgt tca gct atg gtc     48
Met Ala Lys Glu Ile Lys Phe Ser Ser Asp Ala Arg Ser Ala Met Val
 1               5                  10                  15 cgt ggt gtc gat atc ctt gca gat act gtt aaa gta act ttg gga cca     96
Arg Gly Val Asp Ile Leu Ala Asp Thr Val Lys Val Thr Leu Gly Pro
             20                  25                  30 aaa ggt cgc aat gtc gtt ctt gaa aag tca ttc ggt tca ccc ttg att    144
Lys Gly Arg Asn Val Val Leu Glu Lys Ser Phe Gly Ser Pro Leu Ile
         35                  40                  45 acc aat gac ggt gtg act att gcc aaa gaa att gaa tta gaa gac cat    192
Thr Asn Asp Gly Val Thr Ile Ala Lys Glu Ile Glu Leu Glu Asp His
     50                  55                  60 ttt gaa aat atg ggt gcc aaa ttg gta tca gaa gta gct tca aaa acc    240
Phe Glu Asn Met Gly Ala Lys Leu Val Ser Glu Val Ala Ser Lys Thr
 65                  70                  75                  80 aat gat atc gca ggt gat gga act aca act gca act gtt ttg acc caa    288
Asn Asp Ile Ala Gly Asp Gly Thr Thr Thr Ala Thr Val Leu Thr Gln
                 85                  90                  95
```

```
gca atc gtc cgt gaa gga atc aaa aac gtc aca gca ggt gca aat cca      336
Ala Ile Val Arg Glu Gly Ile Lys Asn Val Thr Ala Gly Ala Asn Pro
            100                 105                 110 atc ggt att cgt cgt ggg att gaa aca gca gtt gcc gca gca gtt gaa      384
Ile Gly Ile Arg Arg Gly Ile Glu Thr Ala Val Ala Ala Ala Val Glu
                115                 120                 125 gct ttg aaa aac aac gtc atc cct gtt gcc aat aaa gaa gct atc gct      432
Ala Leu Lys Asn Asn Val Ile Pro Val Ala Asn Lys Glu Ala Ile Ala
130                 135                 140 caa gtt gca gcc gta tct tct cgt tct gaa aaa gtt ggt gag tac atc      480
Gln Val Ala Ala Val Ser Ser Arg Ser Glu Lys Val Gly Glu Tyr Ile
145                 150                 155                 160 tct gaa gca atg gaa aaa gtt ggc aaa gac ggt gtc atc acc atc gaa      528
Ser Glu Ala Met Glu Lys Val Gly Lys Asp Gly Val Ile Thr Ile Glu
                165                 170                 175 gag tca cgt ggt atg gaa aca gag ctt gaa gtc gta gaa gga atg cag      576
Glu Ser Arg Gly Met Glu Thr Glu Leu Glu Val Val Glu Gly Met Gln
                180                 185                 190 ttt gac cgt ggt tac ctt tca cag tac atg gtg aca gat agc gaa aaa      624
Phe Asp Arg Gly Tyr Leu Ser Gln Tyr Met Val Thr Asp Ser Glu Lys
                195                 200                 205 atg gtg gct gac ctt gaa aat ccg tac att ttg att aca gac aag aaa      672
Met Val Ala Asp Leu Glu Asn Pro Tyr Ile Leu Ile Thr Asp Lys Lys
210                 215                 220 att tcc aat atc caa gaa atc ttg cca ctt ttg gaa agc att ctc caa      720
Ile Ser Asn Ile Gln Glu Ile Leu Pro Leu Leu Glu Ser Ile Leu Gln
225                 230                 235                 240 agc aat cgt cca ctc ttg att att gcg gat gat gtg gat ggt gag gct      768
Ser Asn Arg Pro Leu Leu Ile Ile Ala Asp Asp Val Asp Gly Glu Ala
                245                 250                 255 ctt cca act ctt gtt ttg aac aag att cgt gga acc ttc aac gta gta      816
Leu Pro Thr Leu Val Leu Asn Lys Ile Arg Gly Thr Phe Asn Val Val
                260                 265                 270 gca gtc aag gca cct ggt ttt ggt gac cgt cgc aaa gcc atg ctt gaa      864
Ala Val Lys Ala Pro Gly Phe Gly Asp Arg Arg Lys Ala Met Leu Glu
                275                 280                 285 gat atc gcc atc tta aca ggc gga aca gtt atc aca gaa gac ctt ggt      912
Asp Ile Ala Ile Leu Thr Gly Gly Thr Val Ile Thr Glu Asp Leu Gly
290                 295                 300 ctt gag ttg aaa gat gcg aca att gaa gct ctt ggt caa gca gcg aga      960
Leu Glu Leu Lys Asp Ala Thr Ile Glu Ala Leu Gly Gln Ala Ala Arg
305                 310                 315                 320 gtg acc gtg gac aaa gat agc acg gtt att gta gaa ggt gca gga aat     1008
Val Thr Val Asp Lys Asp Ser Thr Val Ile Val Glu Gly Ala Gly Asn
                325                 330                 335 cct gaa gcg att tct cac cgt gtt gcg gtt atc aag tct caa atc gaa     1056
Pro Glu Ala Ile Ser His Arg Val Ala Val Ile Lys Ser Gln Ile Glu
                340                 345                 350 act aca act tct gaa ttt gac cgt gaa aaa ttg caa gaa cgc ttg gcc     1104
Thr Thr Thr Ser Glu Phe Asp Arg Glu Lys Leu Gln Glu Arg Leu Ala
                355                 360                 365 aaa ttg tca ggt ggt gta gcg gtt att aag gtc gga gcc gca act gaa     1152
Lys Leu Ser Gly Gly Val Ala Val Ile Lys Val Gly Ala Ala Thr Glu
370                 375                 380 act gag ttg aaa gaa atg aaa ctc cgc att gaa gat gcc ctc aac gct     1200
Thr Glu Leu Lys Glu Met Lys Leu Arg Ile Glu Asp Ala Leu Asn Ala
385                 390                 395                 400 act cgt gca gct gtt gaa gaa ggt att gtt gca ggt ggt gga aca gct     1248
Thr Arg Ala Ala Val Glu Glu Gly Ile Val Ala Gly Gly Gly Thr Ala
                405                 410                 415
```

```
ctt gcc aat gtg att cca gct gtt gct acc ttg gaa ttg aca gga gat    1296
Leu Ala Asn Val Ile Pro Ala Val Ala Thr Leu Glu Leu Thr Gly Asp
            420                 425                 430 gaa gca aca gga cgt aat att gtt ctc cgt gct ttg gaa gaa cct gtt    1344
Glu Ala Thr Gly Arg Asn Ile Val Leu Arg Ala Leu Glu Glu Pro Val
        435                 440                 445 cgt caa att gct cac aat gca gga ttt gaa gga tct atc gtt atc gat    1392
Arg Gln Ile Ala His Asn Ala Gly Phe Glu Gly Ser Ile Val Ile Asp
    450                 455                 460 cgt ttg aaa aat gct gag ctt ggt ata gga ttc aac gca gca act ggc    1440
Arg Leu Lys Asn Ala Glu Leu Gly Ile Gly Phe Asn Ala Ala Thr Gly
465                 470                 475                 480 gag tgg gtt aac atg att gat caa ggt atc att gat cca gtt aaa gtg    1488
Glu Trp Val Asn Met Ile Asp Gln Gly Ile Ile Asp Pro Val Lys Val
                485                 490                 495 agt cgt tca gcc cta caa aat gca gca tct gta gcc agc ttg att ttg    1536
Ser Arg Ser Ala Leu Gln Asn Ala Ala Ser Val Ala Ser Leu Ile Leu
            500                 505                 510 aca aca gaa gca gtc gta gcc aat aaa cca gaa cca gta gcc cca gct    1584
Thr Thr Glu Ala Val Val Ala Asn Lys Pro Glu Pro Val Ala Pro Ala
        515                 520                 525 cca gca atg gat cca agt atg atg ggt gga atg ggc gga gct agc atg    1632
Pro Ala Met Asp Pro Ser Met Met Gly Gly Met Gly Gly Ala Ser Met
    530                 535                 540 cat gga gat aca cct aca ttg cat gaa tat atg tta gat ttg caa cca    1680
His Gly Asp Thr Pro Thr Leu His Glu Tyr Met Leu Asp Leu Gln Pro
545                 550                 555                 560 gag aca act gat ctc tac tgt tat gag caa tta aat gac agc tca gag    1728
Glu Thr Thr Asp Leu Tyr Cys Tyr Glu Gln Leu Asn Asp Ser Ser Glu
                565                 570                 575 gag gag gat gaa ata gat ggt cca gct gga caa gca gaa ccg gac aga    1776
Glu Glu Asp Glu Ile Asp Gly Pro Ala Gly Gln Ala Glu Pro Asp Arg
            580                 585                 590 gcc cat tac aat att gta acc ttt tgt tgc aag tgt gac tct acg ctt    1824
Ala His Tyr Asn Ile Val Thr Phe Cys Cys Lys Cys Asp Ser Thr Leu
        595                 600                 605 cgg ttg tgc gta caa agc aca cac gta gac att cgt act ttg gaa gac    1872
Arg Leu Cys Val Gln Ser Thr His Val Asp Ile Arg Thr Leu Glu Asp
    610                 615                 620 ctg tta atg ggc aca cta gga att gtg tgc ccc atc tgt tct cag aaa    1920
Leu Leu Met Gly Thr Leu Gly Ile Val Cys Pro Ile Cys Ser Gln Lys
625                 630                 635                 640 cca taa                                                            1926
Pro

<210> SEQ ID NO 51
<211> LENGTH: 641
<212> TYPE: PRT
<213> ORGANISM: Artificial Sequence
<220> FEATURE:
<223> OTHER INFORMATION: fusion sequence

<400> SEQUENCE: 51

Met Ala Lys Glu Ile Lys Phe Ser Ser Asp Ala Arg Ser Ala Met Val
 1               5                  10                  15

Arg Gly Val Asp Ile Leu Ala Asp Thr Val Lys Val Thr Leu Gly Pro
                20                  25                  30

Lys Gly Arg Asn Val Val Leu Glu Lys Ser Phe Gly Ser Pro Leu Ile
            35                  40                  45
```

```
Thr Asn Asp Gly Val Thr Ile Ala Lys Glu Ile Glu Leu Glu Asp His
     50                  55                  60

Phe Glu Asn Met Gly Ala Lys Leu Val Ser Glu Val Ala Ser Lys Thr
 65                  70                  75                  80

Asn Asp Ile Ala Gly Asp Gly Thr Thr Thr Ala Thr Val Leu Thr Gln
                 85                  90                  95

Ala Ile Val Arg Glu Gly Ile Lys Asn Val Thr Ala Gly Ala Asn Pro
                100                 105                 110

Ile Gly Ile Arg Arg Gly Ile Glu Thr Ala Val Ala Ala Val Glu
                115                 120                 125

Ala Leu Lys Asn Asn Val Ile Pro Val Ala Asn Lys Glu Ala Ile Ala
    130                 135                 140

Gln Val Ala Ala Val Ser Ser Arg Ser Glu Lys Val Gly Glu Tyr Ile
145                 150                 155                 160

Ser Glu Ala Met Glu Lys Val Gly Lys Asp Gly Val Ile Thr Ile Glu
                165                 170                 175

Glu Ser Arg Gly Met Glu Thr Glu Leu Glu Val Val Glu Gly Met Gln
                180                 185                 190

Phe Asp Arg Gly Tyr Leu Ser Gln Tyr Met Val Thr Asp Ser Glu Lys
            195                 200                 205

Met Val Ala Asp Leu Glu Asn Pro Tyr Ile Leu Ile Thr Asp Lys Lys
    210                 215                 220

Ile Ser Asn Ile Gln Glu Ile Leu Pro Leu Leu Glu Ser Ile Leu Gln
225                 230                 235                 240

Ser Asn Arg Pro Leu Leu Ile Ala Asp Asp Val Asp Gly Glu Ala
                245                 250                 255

Leu Pro Thr Leu Val Leu Asn Lys Ile Arg Gly Thr Phe Asn Val Val
            260                 265                 270

Ala Val Lys Ala Pro Gly Phe Gly Asp Arg Arg Lys Ala Met Leu Glu
    275                 280                 285

Asp Ile Ala Ile Leu Thr Gly Gly Thr Val Ile Thr Glu Asp Leu Gly
    290                 295                 300

Leu Glu Leu Lys Asp Ala Thr Ile Glu Ala Leu Gly Gln Ala Ala Arg
305                 310                 315                 320

Val Thr Val Asp Lys Asp Ser Thr Val Ile Val Glu Gly Ala Gly Asn
                325                 330                 335

Pro Glu Ala Ile Ser His Arg Val Ala Val Ile Lys Ser Gln Ile Glu
                340                 345                 350

Thr Thr Thr Ser Glu Phe Asp Arg Glu Lys Leu Gln Glu Arg Leu Ala
            355                 360                 365

Lys Leu Ser Gly Gly Val Ala Val Ile Lys Val Gly Ala Ala Thr Glu
    370                 375                 380

Thr Glu Leu Lys Glu Met Lys Leu Arg Ile Glu Asp Ala Leu Asn Ala
385                 390                 395                 400

Thr Arg Ala Ala Val Glu Glu Gly Ile Val Ala Gly Gly Thr Ala
                405                 410                 415

Leu Ala Asn Val Ile Pro Ala Val Ala Thr Leu Glu Leu Thr Gly Asp
                420                 425                 430

Glu Ala Thr Gly Arg Asn Ile Val Leu Arg Ala Leu Glu Pro Val
            435                 440                 445

Arg Gln Ile Ala His Asn Ala Gly Phe Glu Gly Ser Ile Val Ile Asp
    450                 455                 460

Arg Leu Lys Asn Ala Glu Leu Gly Ile Gly Phe Asn Ala Ala Thr Gly
```

```
465                 470                 475                 480
Glu Trp Val Asn Met Ile Asp Gln Gly Ile Ile Asp Pro Val Lys Val
                        485                 490                 495
Ser Arg Ser Ala Leu Gln Asn Ala Ala Ser Val Ala Ser Leu Ile Leu
                500                 505                 510
Thr Thr Glu Ala Val Val Ala Asn Lys Pro Glu Pro Val Ala Pro Ala
            515                 520                 525
Pro Ala Met Asp Pro Ser Met Met Gly Gly Met Gly Gly Ala Ser Met
        530                 535                 540
His Gly Asp Thr Pro Thr Leu His Glu Tyr Met Leu Asp Leu Gln Pro
545                 550                 555                 560
Glu Thr Thr Asp Leu Tyr Cys Tyr Glu Gln Leu Asn Asp Ser Ser Glu
                565                 570                 575
Glu Glu Asp Glu Ile Asp Gly Pro Ala Gly Gln Ala Glu Pro Asp Arg
                580                 585                 590
Ala His Tyr Asn Ile Val Thr Phe Cys Cys Lys Cys Asp Ser Thr Leu
            595                 600                 605
Arg Leu Cys Val Gln Ser Thr His Val Asp Ile Arg Thr Leu Glu Asp
        610                 615                 620
Leu Leu Met Gly Thr Leu Gly Ile Val Cys Pro Ile Cys Ser Gln Lys
625                 630                 635                 640
Pro

<210> SEQ ID NO 52
<211> LENGTH: 1944
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1941)

<400> SEQUENCE: 52 atg aaa gag ctc aag ttc ggt gtc gaa gcc cgt gct cag ctc ctc aag     48
Met Lys Glu Leu Lys Phe Gly Val Glu Ala Arg Ala Gln Leu Leu Lys
 1               5                  10                  15 ggt gtt gac act ctg gcc aag gcc gtg act tcg act ctt ggt cct aag     96
Gly Val Asp Thr Leu Ala Lys Ala Val Thr Ser Thr Leu Gly Pro Lys
                20                  25                  30 ggt cgt aac gtc ctt atc gag tct ccc tat ggc tcc cct aag atc acc    144
Gly Arg Asn Val Leu Ile Glu Ser Pro Tyr Gly Ser Pro Lys Ile Thr
            35                  40                  45 aag gat ggt gtc tct gtt gcc aag gcc atc act ctc caa gac aag ttc    192
Lys Asp Gly Val Ser Val Ala Lys Ala Ile Thr Leu Gln Asp Lys Phe
        50                  55                  60 gag aac ctc ggt gct cgc ctc ctc cag gat gtc gct tct aag acc aac    240
Glu Asn Leu Gly Ala Arg Leu Leu Gln Asp Val Ala Ser Lys Thr Asn
 65                  70                  75                  80 gag att gct ggt gac ggt acc acc acc gct acc gtc ctt gcc cgt gcc    288
Glu Ile Ala Gly Asp Gly Thr Thr Thr Ala Thr Val Leu Ala Arg Ala
                 85                  90                  95 atc ttc tct gag acc gtg aag aat gtt gct gct ggc tgc aac ccc atg    336
Ile Phe Ser Glu Thr Val Lys Asn Val Ala Ala Gly Cys Asn Pro Met
                100                 105                 110 gat ctg cgc cgc ggt atc cag gct gct gtt gat gct gtc gtc gac tac    384
Asp Leu Arg Arg Gly Ile Gln Ala Ala Val Asp Ala Val Val Asp Tyr
            115                 120                 125 ctc cag aag aac aag cgt gac atc acc acc ggt gag gag atc gct cag    432
```

```
                                                           -continued

Leu Gln Lys Asn Lys Arg Asp Ile Thr Thr Gly Glu Ile Ala Gln
    130                 135                 140 gtt gct act atc tcc gct aac ggt gac acc cac att ggt aag ctg atc        480
Val Ala Thr Ile Ser Ala Asn Gly Asp Thr His Ile Gly Lys Leu Ile
145                 150                 155                 160 tcc acc gcc atg gag cgt gtt ggc aag gag ggt gtc atc act gtc aag        528
Ser Thr Ala Met Glu Arg Val Gly Lys Glu Gly Val Ile Thr Val Lys
                165                 170                 175 gag ggc aag acc att gag gat gag ctc gag gtc act gag ggt atg cgc        576
Glu Gly Lys Thr Ile Glu Asp Glu Leu Glu Val Thr Glu Gly Met Arg
                180                 185                 190 ttc gac cgt gga tac acc tcc ccc tac ttc atc acc gat acc aag tcc        624
Phe Asp Arg Gly Tyr Thr Ser Pro Tyr Phe Ile Thr Asp Thr Lys Ser
            195                 200                 205 cag aag gtt gag ttc gag aag cct ctg att ctg ctg tct gag aag aag        672
Gln Lys Val Glu Phe Glu Lys Pro Leu Ile Leu Leu Ser Glu Lys Lys
        210                 215                 220 atc tct gcc gtt cag gac atc atc ccc gcc ctt gag gcc tcc acc acc        720
Ile Ser Ala Val Gln Asp Ile Ile Pro Ala Leu Glu Ala Ser Thr Thr
225                 230                 235                 240 ctc cgc cgc ccc ctg gtt att atc gca gag gac att gag ggt gag gct        768
Leu Arg Arg Pro Leu Val Ile Ile Ala Glu Asp Ile Glu Gly Glu Ala
                245                 250                 255 ctc gcc gtc tgc att ctg aac aag ctt cgt ggc cag ctg cag gtc gct        816
Leu Ala Val Cys Ile Leu Asn Lys Leu Arg Gly Gln Leu Gln Val Ala
                260                 265                 270 gct gtc aag gct cct gga ttc ggt gac aac cgc aag agc atc ctg ggc        864
Ala Val Lys Ala Pro Gly Phe Gly Asp Asn Arg Lys Ser Ile Leu Gly
            275                 280                 285 gat ctt gcc gtc ctt acc aac ggt acc gtc ttc act gat gag ctc gac        912
Asp Leu Ala Val Leu Thr Asn Gly Thr Val Phe Thr Asp Glu Leu Asp
        290                 295                 300 atc aaa ctc gag aag ctt acc ccc gat atg ctt ggt tcc acc ggc gcc        960
Ile Lys Leu Glu Lys Leu Thr Pro Asp Met Leu Gly Ser Thr Gly Ala
305                 310                 315                 320 atc acc atc acc aag gag gac acc atc atc ctg aac ggg gag ggc agc       1008
Ile Thr Ile Thr Lys Glu Asp Thr Ile Ile Leu Asn Gly Glu Gly Ser
                325                 330                 335 aag gac gcc att gcc cag cgc tgc gag cag att cgc ggt gtc atg gcg       1056
Lys Asp Ala Ile Ala Gln Arg Cys Glu Gln Ile Arg Gly Val Met Ala
                340                 345                 350 gac ccc agc acc tcc gaa tac gag aag gag aag ctc cag gag cgt cta       1104
Asp Pro Ser Thr Ser Glu Tyr Glu Lys Glu Lys Leu Gln Glu Arg Leu
            355                 360                 365 gct aag ctc tct ggc ggt gtt gcc gtc atc aag gtc ggt ggt gcc tcc       1152
Ala Lys Leu Ser Gly Gly Val Ala Val Ile Lys Val Gly Gly Ala Ser
370                 375                 380 gag gtt gag gtc ggt gag aag aag gac cgt gtt gtc gat gct ctc aat       1200
Glu Val Glu Val Gly Glu Lys Lys Asp Arg Val Val Asp Ala Leu Asn
385                 390                 395                 400 gct acc cgt gct gct gtt gag gag ggt atc ctc ccc ggt ggt ggt acc       1248
Ala Thr Arg Ala Ala Val Glu Glu Gly Ile Leu Pro Gly Gly Gly Thr
                405                 410                 415 gcc ctt ctc aag gcc gcc gcc aac ggc ctt gac aat gtc aag ccc gag       1296
Ala Leu Leu Lys Ala Ala Ala Asn Gly Leu Asp Asn Val Lys Pro Glu
                420                 425                 430 aac ttc gac cag caa ctc ggt gtg agc atc atc aag aat gcc atc acc       1344
Asn Phe Asp Gln Gln Leu Gly Val Ser Ile Ile Lys Asn Ala Ile Thr
            435                 440                 445
```

```
cgc ccc gct cgc acc att gtt gag aac gcc ggc ctc gag ggc agc gtc      1392
Arg Pro Ala Arg Thr Ile Val Glu Asn Ala Gly Leu Glu Gly Ser Val
    450                 455                 460 att gtc ggc aag ctg acc gac gag ttc gcc aag gac ttc aac cgc ggt      1440
Ile Val Gly Lys Leu Thr Asp Glu Phe Ala Lys Asp Phe Asn Arg Gly
465                 470                 475                 480 ttc gac agc tcc aag ggc gag tac gtc gac atg atc tcc agc ggt atc      1488
Phe Asp Ser Ser Lys Gly Glu Tyr Val Asp Met Ile Ser Ser Gly Ile
                485                 490                 495 ctc gat ccc ctc aag gtt gtt cgc acc gct ctg ctc gac gcc agc ggt      1536
Leu Asp Pro Leu Lys Val Val Arg Thr Ala Leu Leu Asp Ala Ser Gly
            500                 505                 510 gtc gcc tcc ctg ctc ggt acc act gag gtc gct att gtt gag gcc cct      1584
Val Ala Ser Leu Leu Gly Thr Thr Glu Val Ala Ile Val Glu Ala Pro
        515                 520                 525 gag gag aag ggc ccc gct gct cct ggc atg ggt ggt atg ggt ggt atg      1632
Glu Glu Lys Gly Pro Ala Ala Pro Gly Met Gly Gly Met Gly Gly Met
    530                 535                 540 ggc ggc atg ggc ggc atg cat gga gat aca cct aca ttg cat gaa tat      1680
Gly Gly Met Gly Gly Met His Gly Asp Thr Pro Thr Leu His Glu Tyr
545                 550                 555                 560 atg tta gat ttg caa cca gag aca act gat ctc tac tgt tat gag caa      1728
Met Leu Asp Leu Gln Pro Glu Thr Thr Asp Leu Tyr Cys Tyr Glu Gln
                565                 570                 575 tta aat gac agc tca gag gag gag gat gaa ata gat ggt cca gct gga      1776
Leu Asn Asp Ser Ser Glu Glu Glu Asp Glu Ile Asp Gly Pro Ala Gly
            580                 585                 590 caa gca gaa ccg gac aga gcc cat tac aat att gta acc ttt tgt tgc      1824
Gln Ala Glu Pro Asp Arg Ala His Tyr Asn Ile Val Thr Phe Cys Cys
        595                 600                 605 aag tgt gac tct acg ctt cgg ttg tgc gta caa agc aca cac gta gac      1872
Lys Cys Asp Ser Thr Leu Arg Leu Cys Val Gln Ser Thr His Val Asp
    610                 615                 620 att cgt act ttg gaa gac ctg tta atg ggc aca cta gga att gtg tgc      1920
Ile Arg Thr Leu Glu Asp Leu Leu Met Gly Thr Leu Gly Ile Val Cys
625                 630                 635                 640 ccc atc tgt tct cag aaa cca tag                                      1944
Pro Ile Cys Ser Gln Lys Pro
                645

<210> SEQ ID NO 53
<211> LENGTH: 647
<212> TYPE: PRT
<213> ORGANISM: Artificial Sequence
<220> FEATURE:
<223> OTHER INFORMATION: fusion sequence

<400> SEQUENCE: 53

Met Lys Glu Leu Lys Phe Gly Val Glu Ala Arg Ala Gln Leu Leu Lys
1               5                   10                  15

Gly Val Asp Thr Leu Ala Lys Ala Val Thr Ser Thr Leu Gly Pro Lys
            20                  25                  30

Gly Arg Asn Val Leu Ile Glu Ser Pro Tyr Gly Ser Pro Lys Ile Thr
        35                  40                  45

Lys Asp Gly Val Ser Val Ala Lys Ala Ile Thr Leu Gln Asp Lys Phe
    50                  55                  60

Glu Asn Leu Gly Ala Arg Leu Leu Gln Asp Val Ala Ser Lys Thr Asn
65                  70                  75                  80

Glu Ile Ala Gly Asp Gly Thr Thr Thr Ala Thr Val Leu Ala Arg Ala
                85                  90                  95
```

-continued

```
Ile Phe Ser Glu Thr Val Lys Asn Val Ala Ala Gly Cys Asn Pro Met
            100                 105                 110
Asp Leu Arg Arg Gly Ile Gln Ala Ala Asp Ala Val Val Asp Tyr
        115                 120                 125
Leu Gln Lys Asn Lys Arg Asp Ile Thr Thr Gly Glu Glu Ile Ala Gln
    130                 135                 140
Val Ala Thr Ile Ser Ala Asn Gly Asp Thr His Ile Gly Lys Leu Ile
145                 150                 155                 160
Ser Thr Ala Met Glu Arg Val Gly Lys Glu Gly Val Ile Thr Val Lys
                165                 170                 175
Glu Gly Lys Thr Ile Glu Asp Glu Leu Glu Val Thr Glu Gly Met Arg
            180                 185                 190
Phe Asp Arg Gly Tyr Thr Ser Pro Tyr Phe Ile Thr Asp Thr Lys Ser
        195                 200                 205
Gln Lys Val Glu Phe Glu Lys Pro Leu Ile Leu Leu Ser Glu Lys Lys
    210                 215                 220
Ile Ser Ala Val Gln Asp Ile Ile Pro Ala Leu Glu Ala Ser Thr Thr
225                 230                 235                 240
Leu Arg Arg Pro Leu Val Ile Ile Ala Glu Asp Ile Glu Gly Glu Ala
                245                 250                 255
Leu Ala Val Cys Ile Leu Asn Lys Leu Arg Gly Gln Leu Gln Val Ala
            260                 265                 270
Ala Val Lys Ala Pro Gly Phe Gly Asp Asn Arg Lys Ser Ile Leu Gly
        275                 280                 285
Asp Leu Ala Val Leu Thr Asn Gly Thr Val Phe Thr Asp Glu Leu Asp
    290                 295                 300
Ile Lys Leu Glu Lys Leu Thr Pro Asp Met Leu Gly Ser Thr Gly Ala
305                 310                 315                 320
Ile Thr Ile Thr Lys Glu Asp Thr Ile Ile Leu Asn Gly Glu Gly Ser
                325                 330                 335
Lys Asp Ala Ile Ala Gln Arg Cys Glu Gln Ile Arg Gly Val Met Ala
            340                 345                 350
Asp Pro Ser Thr Ser Glu Tyr Glu Lys Glu Lys Leu Gln Glu Arg Leu
        355                 360                 365
Ala Lys Leu Ser Gly Gly Val Ala Val Ile Lys Val Gly Gly Ala Ser
    370                 375                 380
Glu Val Glu Val Gly Glu Lys Lys Asp Arg Val Val Asp Ala Leu Asn
385                 390                 395                 400
Ala Thr Arg Ala Ala Val Glu Glu Gly Ile Leu Pro Gly Gly Gly Thr
                405                 410                 415
Ala Leu Leu Lys Ala Ala Ala Asn Gly Leu Asp Asn Val Lys Pro Glu
            420                 425                 430
Asn Phe Asp Gln Gln Leu Gly Val Ser Ile Ile Lys Asn Ala Ile Thr
        435                 440                 445
Arg Pro Ala Arg Thr Ile Val Glu Asn Ala Gly Leu Glu Gly Ser Val
    450                 455                 460
Ile Val Gly Lys Leu Thr Asp Glu Phe Ala Lys Asp Phe Asn Arg Gly
465                 470                 475                 480
Phe Asp Ser Ser Lys Gly Glu Tyr Val Asp Met Ile Ser Ser Gly Ile
                485                 490                 495
Leu Asp Pro Leu Lys Val Val Arg Thr Ala Leu Leu Asp Ala Ser Gly
            500                 505                 510
```

```
Val Ala Ser Leu Leu Gly Thr Thr Glu Val Ala Ile Val Glu Ala Pro
            515                 520                 525

Glu Glu Lys Gly Pro Ala Ala Pro Gly Met Gly Met Gly Gly Met
        530                 535             540

Gly Gly Met Gly Gly Met His Gly Asp Thr Pro Thr Leu His Glu Tyr
545                 550                 555                 560

Met Leu Asp Leu Gln Pro Glu Thr Thr Asp Leu Tyr Cys Tyr Glu Gln
                565                 570                 575

Leu Asn Asp Ser Ser Glu Glu Asp Glu Ile Asp Gly Pro Ala Gly
            580                 585                 590

Gln Ala Glu Pro Asp Arg Ala His Tyr Asn Ile Val Thr Phe Cys Cys
        595                 600                 605

Lys Cys Asp Ser Thr Leu Arg Leu Cys Val Gln Ser Thr His Val Asp
        610                 615                 620

Ile Arg Thr Leu Glu Asp Leu Leu Met Gly Thr Leu Gly Ile Val Cys
625                 630                 635                 640

Pro Ile Cys Ser Gln Lys Pro
                645
```

<210> SEQ ID NO 54
<211> LENGTH: 1230
<212> TYPE: DNA
<213> ORGANISM: Artificial Sequence
<220> FEATURE:
<223> OTHER INFORMATION: fusion sequence
<221> NAME/KEY: CDS
<222> LOCATION: (1)...(1227)

<400> SEQUENCE: 54

```
atg ggc agc agc cat cat cat cat cat cac agc agc ggc ctg gtg ccg    48
Met Gly Ser Ser His His His His His His Ser Ser Gly Leu Val Pro
  1               5                  10                  15 cgc ggc agc cat atg gct agc atg ggc tcc atc ggc gca gca agc atg    96
Arg Gly Ser His Met Ala Ser Met Gly Ser Ile Gly Ala Ala Ser Met
             20                  25                  30 gaa ttt tgt ttt gat gta ttc aag gag ctc aaa gtc cac cat gcc aat   144
Glu Phe Cys Phe Asp Val Phe Lys Glu Leu Lys Val His His Ala Asn
         35                  40                  45 gag aac atc ttc tac tgc ccc att gcc atc atg tca gct cta gcc atg   192
Glu Asn Ile Phe Tyr Cys Pro Ile Ala Ile Met Ser Ala Leu Ala Met
     50                  55                  60 gta tac ctg ggt gca aaa gac agc acc agg aca cag ata aat aag gtt   240
Val Tyr Leu Gly Ala Lys Asp Ser Thr Arg Thr Gln Ile Asn Lys Val
 65                  70                  75                  80 gtt cgc ttt gat aaa ctt cca gga ttc gga gac agt att gaa gct cag   288
Val Arg Phe Asp Lys Leu Pro Gly Phe Gly Asp Ser Ile Glu Ala Gln
                 85                  90                  95 tgt ggc aca tct gta aac gtt cac tct tca ctt aga gac atc ctc aac   336
Cys Gly Thr Ser Val Asn Val His Ser Ser Leu Arg Asp Ile Leu Asn
            100                 105                 110 caa atc acc aaa cca aat gat gtt tat tcg ttc agc ctt gcc agt aga   384
Gln Ile Thr Lys Pro Asn Asp Val Tyr Ser Phe Ser Leu Ala Ser Arg
        115                 120                 125 ctt tat gct gaa gag aga tac cca atc ctg cca gaa tac ttg cag tgt   432
Leu Tyr Ala Glu Glu Arg Tyr Pro Ile Leu Pro Glu Tyr Leu Gln Cys
    130                 135                 140 gtg aag gaa ctg tat aga gga ggc ttg gaa cct atc aac ttt caa aca   480
Val Lys Glu Leu Tyr Arg Gly Gly Leu Glu Pro Ile Asn Phe Gln Thr
145                 150                 155                 160
```

```
gct gca gat caa gcc aga gag ctc atc aat tcc tgg gta gaa agt cag      528
Ala Ala Asp Gln Ala Arg Glu Leu Ile Asn Ser Trp Val Glu Ser Gln
                165                 170                 175 aca aat gga att atc aga aat gtc ctt cag cca agc tcc gtg gat tct      576
Thr Asn Gly Ile Ile Arg Asn Val Leu Gln Pro Ser Ser Val Asp Ser
            180                 185                 190 caa act gca atg gtt ctg gtt aat gcc att gtc ttc aaa gga ctg tgg      624
Gln Thr Ala Met Val Leu Val Asn Ala Ile Val Phe Lys Gly Leu Trp
        195                 200                 205 gag aaa aca ttt aag gat gaa gac aca caa gca atg cct ttc aga gtg      672
Glu Lys Thr Phe Lys Asp Glu Asp Thr Gln Ala Met Pro Phe Arg Val
    210                 215                 220 act gag caa gaa agc aaa cct gtg cag atg atg tac cag att ggt tta      720
Thr Glu Gln Glu Ser Lys Pro Val Gln Met Met Tyr Gln Ile Gly Leu
225                 230                 235                 240 ttt aga gtg gca tca atg gct tct gag aaa atg aag atc ctg gag ctt      768
Phe Arg Val Ala Ser Met Ala Ser Glu Lys Met Lys Ile Leu Glu Leu
                245                 250                 255 cca ttt gcc agt ggg aca atg agc atg ttg gtg ctg ttg cct gat gaa      816
Pro Phe Ala Ser Gly Thr Met Ser Met Leu Val Leu Leu Pro Asp Glu
            260                 265                 270 gtc tca ggc ctt gag cag ctt gag agt ata atc aac ttt gaa aaa ctg      864
Val Ser Gly Leu Glu Gln Leu Glu Ser Ile Ile Asn Phe Glu Lys Leu
        275                 280                 285 act gaa tgg acc agt tct aat gtt atg gaa gag agg aag atc aaa gtg      912
Thr Glu Trp Thr Ser Ser Asn Val Met Glu Glu Arg Lys Ile Lys Val
    290                 295                 300 tac tta cct cgc atg aag atg gag gaa aaa tac aac ctc aca tct gtc      960
Tyr Leu Pro Arg Met Lys Met Glu Glu Lys Tyr Asn Leu Thr Ser Val
305                 310                 315                 320 tta atg gct atg ggc att act gac gtg ttt agc tct tca gcc aat ctg     1008
Leu Met Ala Met Gly Ile Thr Asp Val Phe Ser Ser Ser Ala Asn Leu
                325                 330                 335 tct ggc atc tcc tca gca gag agc ctg aag ata tct caa gct gtc cat     1056
Ser Gly Ile Ser Ser Ala Glu Ser Leu Lys Ile Ser Gln Ala Val His
            340                 345                 350 gca gca cat gca gaa atc aat gaa gca ggc aga gag gtg gta ggg tca     1104
Ala Ala His Ala Glu Ile Asn Glu Ala Gly Arg Glu Val Val Gly Ser
        355                 360                 365 gca gag gct gga gtg gat gct gca agc gtc tct gaa gaa ttt agg gct     1152
Ala Glu Ala Gly Val Asp Ala Ala Ser Val Ser Glu Glu Phe Arg Ala
    370                 375                 380 gac cat cca ttc ctc ttc tgt atc aag cac atc gca acc aac gcc gtt     1200
Asp His Pro Phe Leu Phe Cys Ile Lys His Ile Ala Thr Asn Ala Val
385                 390                 395                 400 ctc ttc ttt ggc aga tgt gtt gga tcc taa                             1230
Leu Phe Phe Gly Arg Cys Val Gly Ser
                405

<210> SEQ ID NO 55
<211> LENGTH: 409
<212> TYPE: PRT
<213> ORGANISM: Artificial Sequence
<220> FEATURE:
<223> OTHER INFORMATION: fusion sequence

<400> SEQUENCE: 55

Met Gly Ser Ser His His His His His His Ser Ser Gly Leu Val Pro
  1               5                  10                  15

Arg Gly Ser His Met Ala Ser Met Gly Ser Ile Gly Ala Ala Ser Met
             20                  25                  30
```

-continued

```
Glu Phe Cys Phe Asp Val Phe Lys Glu Leu Lys Val His His Ala Asn
         35                  40                  45
Glu Asn Ile Phe Tyr Cys Pro Ile Ala Ile Met Ser Ala Leu Ala Met
 50                  55                  60
Val Tyr Leu Gly Ala Lys Asp Ser Thr Arg Thr Gln Ile Asn Lys Val
 65                  70                  75                  80
Val Arg Phe Asp Lys Leu Pro Gly Phe Gly Asp Ser Ile Glu Ala Gln
                 85                  90                  95
Cys Gly Thr Ser Val Asn Val His Ser Ser Leu Arg Asp Ile Leu Asn
             100                 105                 110
Gln Ile Thr Lys Pro Asn Asp Val Tyr Ser Phe Ser Leu Ala Ser Arg
             115                 120                 125
Leu Tyr Ala Glu Glu Arg Tyr Pro Ile Leu Pro Glu Tyr Leu Gln Cys
130                 135                 140
Val Lys Glu Leu Tyr Arg Gly Leu Glu Pro Ile Asn Phe Gln Thr
145                 150                 155                 160
Ala Ala Asp Gln Ala Arg Glu Leu Ile Asn Ser Trp Val Glu Ser Gln
                 165                 170                 175
Thr Asn Gly Ile Ile Arg Asn Val Leu Gln Pro Ser Ser Val Asp Ser
             180                 185                 190
Gln Thr Ala Met Val Leu Val Asn Ala Ile Val Phe Lys Gly Leu Trp
             195                 200                 205
Glu Lys Thr Phe Lys Asp Glu Asp Thr Gln Ala Met Pro Phe Arg Val
             210                 215                 220
Thr Glu Gln Glu Ser Lys Pro Val Gln Met Met Tyr Gln Ile Gly Leu
225                 230                 235                 240
Phe Arg Val Ala Ser Met Ala Ser Glu Lys Met Lys Ile Leu Glu Leu
                 245                 250                 255
Pro Phe Ala Ser Gly Thr Met Ser Met Leu Val Leu Leu Pro Asp Glu
             260                 265                 270
Val Ser Gly Leu Glu Gln Leu Glu Ser Ile Ile Asn Phe Glu Lys Leu
             275                 280                 285
Thr Glu Trp Thr Ser Ser Asn Val Met Glu Glu Arg Lys Ile Lys Val
             290                 295                 300
Tyr Leu Pro Arg Met Lys Met Glu Glu Lys Tyr Asn Leu Thr Ser Val
305                 310                 315                 320
Leu Met Ala Met Gly Ile Thr Asp Val Phe Ser Ser Ala Asn Leu
                 325                 330                 335
Ser Gly Ile Ser Ser Ala Glu Ser Leu Lys Ile Ser Gln Ala Val His
             340                 345                 350
Ala Ala His Ala Glu Ile Asn Glu Ala Gly Arg Glu Val Val Gly Ser
             355                 360                 365
Ala Glu Ala Gly Val Asp Ala Ala Ser Val Ser Glu Glu Phe Arg Ala
370                 375                 380
Asp His Pro Phe Leu Phe Cys Ile Lys His Ile Ala Thr Asn Ala Val
385                 390                 395                 400
Leu Phe Phe Gly Arg Cys Val Gly Ser
                 405
```

INDUCTION OF A TH1-LIKE RESPONSE IN VITRO

CROSS REFERENCE TO RELATED APPLICATIONS

This application claims priority from U.S. Provisional Application No. 60/143,757, filed Jul. 8, 1999. The content of this application is incorporated herein by reference in its entirety.

FIELD OF THE INVENTION

The invention relates to fusion proteins and methods of stimulating a Th1-like response in vitro.

BACKGROUND

T lymphocytes can generally be divided into two classes based upon expression of the CD4 and CD8 antigens. The immune response mediated by CD4+ T cells is restricted by class II major histocompatibility complex (MHC) molecules. CD4+ T cells, also known as helper T lymphocytes, carry out their helper functions via the secretion of lymphokines. The immune response mediated by CD8+ T cells is restricted by class I MHC molecules. CD8+ T cells, also known as cytolytic T lymphocytes (CTLs), carry out cell mediated cytotoxicity and also secrete some lymphokines upon activation.

CD4+ T cells can be further divided into Th1 and Th2 subsets. Th1 cells participate in cell mediated immunity by producing lymphokines, such as interferon (IFN)-gamma and tumor necrosis factor (TNF)-beta, that activate cell mediated immunity. Th2 cells provide help for humoral immunity by secreting lymphokines that stimulate B cells, such as IL-4 and IL-5. Antigenic stimuli that activate either the Th1 or Th2 pathway can inhibit the development of the other. For example, IFN-gamma produced by a stimulated Th1 cell can inhibit the formation of Th2 cells, and IL-4 produced by a stimulated Th2 cell can inhibit the formation of Th1 cells.

Certain disease conditions, such as cancer, allergy, and parasitic infections, are characterized by a predominantly Th2 response. Under certain circumstances, the induction of the Th1 response, typified by the production of IFN-gamma, may ameliorate these conditions.

SUMMARY OF THE INVENTION

The invention is based on the discovery that a cell sample containing naive lymphocytes can be stimulated in vitro to exhibit a Th1-like response.

Accordingly, the invention features a method of determining whether a fusion protein stimulates a Th1-like response by: (a) providing a cell sample containing naive lymphocytes in vitro; (b) providing a fusion protein containing (i) a heat shock protein (Hsp) or a fragment thereof at least eight amino acid residues in length, fused to (ii) a heterologous polypeptide at least eight amino acid residues in length; (c) contacting the cell sample with the fusion protein; and (d) determining whether the fusion protein stimulates a Th1-like response in the cell sample.

"Naive lymphocytes" are lymphocytes that have not been exposed to the fusion protein (in vivo or in vitro) prior to their use in a method the invention. An "Hsp" is a polypeptide consisting of a sequence that is at least 40% identical to that of a protein whose expression is induced or enhanced in a cell exposed to stress, e.g., heat shock. A "fusion protein" is a non-naturally occurring polypeptide containing amino acid sequences derived from at least two different proteins.

The Hsp used in the method can be selected from the group consisting of Hsp65, Hsp40, Hsp10, Hsp60, and Hsp71. Additionally, the fusion protein can contain the full amino acid sequence of any of Hsp65, Hsp40, Hsp10, Hsp60, or Hsp71. In some embodiments, the fusion protein contains a fragment of an Hsp, e.g., amino acids 1–200 of Hsp65 of *Mycobacterium bovis*.

The heterologous polypeptide can contain a sequence identical to at least eight consecutive amino acids of (i) a protein of a human pathogen, e.g., a virus, or (ii) a tumor associated antigen. Examples of viruses include human papilloma virus (HPV), herpes simplex virus (HSV), hepatitis B virus (HBV), hepatitis C virus (HCV), cytomegalovirus (CMV), Epstein-Barr virus (EBV), influenza virus, measles virus, and human immunodeficiency virus (HIV). The heterologous polypeptide can contain an HPV E6 antigen, e.g., HPV16 E6, an HPV E7 antigen, e.g., HPV16 E7, or a fragment of any of these antigens that is at least eight amino acid residues in length.

In one example, the fusion protein contains *Mycobacterium bovis* BCG Hsp65 and HPV16 E7.

The cell sample used in the methods of the invention can contain cells derived from a spleen, lymph node, peripheral blood, bone marrow, thymus, lung, respiratory tract, or anogenital mucosa. In preferred embodiments, the cells are splenocytes or lymph node cells.

The stimulation of a Th1-like response can be determined by detecting the presence of a lymphokine produced by the cell sample, e.g. IFN-gamma or TNF-beta.

In one embodiment, the method also includes the steps of: (e) providing a second cell sample containing naive lymphocytes; (f) contacting the second cell sample with a second fusion protein; and (g) determining whether the second fusion protein stimulates a Th1-like response in the second cell sample. In this example, the first fusion protein contains the sequence of a full-length, naturally occurring Hsp, and the second fusion protein contains at least eight amino acids but less than all of the sequence of a naturally occurring Hsp.

In another aspect, the invention features a method of screening a compound by: (a) providing a cell sample containing naive lymphocytes in vitro; (b) providing a fusion protein containing (i) a Hsp or a fragment thereof at least eight amino acid residues in length, fused to (ii) a heterologous polypeptide at least eight amino acid residues in length; (c) contacting the cell sample with the compound and the fusion protein; and (d) determining whether the cell sample exhibits a Th1-like response following the contacting step. In this method, a decrease in the Th1-like response in the presence of the compound compared to in the absence of the compound indicates that the compound inhibits a Th1-like response by the cell sample.

The invention also includes a method of screening a compound by: (a) providing a cell sample containing naive lymphocytes in vitro; (b) providing a fusion protein containing (i) a Hsp or a fragment thereof at least eight amino acid residues in length, fused to (ii) a heterologous polypeptide at least eight amino acid residues in length; (c) contacting the cell sample with the compound and the fusion protein; and (d) determining whether the cell sample exhibits a Th1-like response following the contacting step. In this method, an increase in the Th1-like response in the presence of the compound compared to in the absence of the compound indicates that the compound promotes a Th1-like response by the cell sample.

In another aspect, the invention features a method of determining whether a hybrid compound stimulates a Th1- like response by: (a) providing a cell sample containing naive lymphocytes in vitro; (b) providing a hybrid compound that is non-naturally occurring and contains (i) a non-peptide compound having a molecular weight of less than 1,500, covalently linked to (ii) a polypeptide of at least eight amino acids in length, wherein the hybrid compound is made by covalently linking the non-peptide compound to the polypeptide; (c) contacting the cell sample with the hybrid compound; and (d) determining whether the hybrid compound stimulates a Th1-like response in the cell sample. In one embodiment, the non-peptide compound has a molecular weight of at least 100.

In another aspect, the invention features a method of determining whether a hybrid compound stimulates a Th1-like response by: (a) producing a hybrid compound by covalently linking a non-peptide compound to a polypeptide of at least eight amino acids in length; (b) providing a cell sample containing naive lymphocytes in vitro; (c) contacting the cell sample with the hybrid compound; and (d) determining whether the hybrid compound stimulates a Th1-like response in the cell sample. In one embodiment, the non-peptide compound has a molecular weight between 100 and 1,500.

In another aspect, the invention features a method of determining whether a fusion protein stimulates a Th1-like response by: (a) providing a cell sample containing naive lymphocytes in vitro; (b) providing a fusion protein comprising (i) a first polypeptide at least eight amino acids in length, fused to (ii) a second polypeptide at least eight amino acids in length; (c) contacting the cell sample with the fusion protein; and (d) detecting a Th1-like response exhibited by the cell sample following the contacting step. In one embodiment, the detected Th1-like response is greater than a Th1-like response exhibited by a second cell sample containing naive lymphocytes when the second cell sample is contacted with either the first polypeptide, the second polypeptide, or a mixture of the first polypeptide and the second polypeptide. In one example, the detected Th1-like response is at least two times greater than the Th1-like response exhibited by the second cell sample. In another example, the detected Th1-like response is at least five times greater than the Th1-like response exhibited by the second cell sample.

In another aspect, the invention provides a fusion protein containing (i) a Hsp10 protein or a fragment thereof at least eight amino acid residues in length, and (ii) a heterologous polypeptide at least eight amino acids in length. The Hsp 10 protein of the fusion protein can be a mycobacterial protein, e.g., *Mycobacterium tuberculosis* Hsp 10 protein. The heterologous polypeptide can contain a sequence identical to at least eight consecutive amino acids of a protein of a human virus, e.g., HPV. In one example, the heterologous polypeptide contains HPV16 E7.

In another aspect, the invention provides a fusion protein containing (i) a Hsp40 protein or a fragment thereof at least eight amino acid residues in length, and (ii) a heterologous polypeptide at least eight amino acids in length. The Hsp40 protein of the fusion protein can be a mycobacterial protein, e.g., *Mycobacterium tuberculosis* Hsp40 protein. The heterologous polypeptide can contain a sequence identical to at least eight consecutive amino acids of a protein of a human virus, e.g., HPV. In one example, the heterologous polypeptide contains HPV16 E7.

In another aspect, the invention provides a fusion protein containing (i) a Hsp71 protein or a fragment thereof at least eight amino acid residues in length, and (ii) a heterologous polypeptide at least eight amino acids in length. The Hsp71 protein of the fusion protein can be a mycobacterial protein, e.g., *Mycobacterium tuberculosis* Hsp71 protein. The heterologous polypeptide can contain a sequence identical to at least eight consecutive amino acids of a protein of a human virus, e.g., HPV. In one example, the heterologous polypeptide contains HPV16 E7.

In another aspect, the invention features a method of determining whether a compound stimulates a Th1-like response by: (a) providing a cell sample containing naive lymphocytes in vitro; (b) providing a compound; (c) contacting the cell sample with the compound; and (d) detecting a Th1-like response exhibited by the cell sample following the contacting step.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A–1B show the sequence of plasmid pET65 coding for expression of Hsp65.

FIG. 2 shows the sequence of plasmid pET/E7 (NH) coding for expression of E7.

FIG. 3 shows the sequence of plasmid pET/H/E7 coding for expression of (h)E7.

FIGS. 4A–4B show the sequence of plasmid pET65C/E7-1N coding for expression of HspE7.

FIGS. 5A–5B show the sequence of plasmid pETMT40E7 coding for expression of MT40-E7.

FIG. 6 shows the sequence of plasmid pET/OVA coding for expression of ovalbumin (OVA).

FIGS. 7A–7C show the sequence of plasmid pET65H/OVA coding for expression of HspOVA.

FIG. 8 shows the sequence of plasmid pGEX/K coding for expression of GST.

FIG. 9 shows the sequence of plasmid pGEX/K/E7 coding for expression of GST-E7.

FIGS. 10A–10B show the sequence of plasmid pET/E7/5'65 coding for expression of E7-L-BCG65.

FIG. 11 shows the sequence of plasmid pET65F/1/E7 coding for expression of BCG65(F1)-E7.

FIG. 12 shows the sequence of plasmid pETESE7 coding for expression of TB 10-E7.

FIGS. 13A–13B show the sequence of plasmid pET/E7/71 coding for expression of E7-TB71.

FIGS. 14A–14B show the sequence of plasmid pET/E7/71' coding for expression of a fusion protein.

FIGS. 15A–15B show the sequence of plasmid pET/SP65c-E7 coding for expression of SP65(2)-E7.

FIGS. 16A–16B show the sequence of plasmid pETAF60E7 coding for expression of AF60-E7.

FIGS. 20A–20B show enhanced IFN-gamma release by splenocytes upon exposure to fusion proteins containing stress proteins of different types, stress proteins from different organisms, or a fragment of a stress protein.

DETAILED DESCRIPTION

Figure 17A:
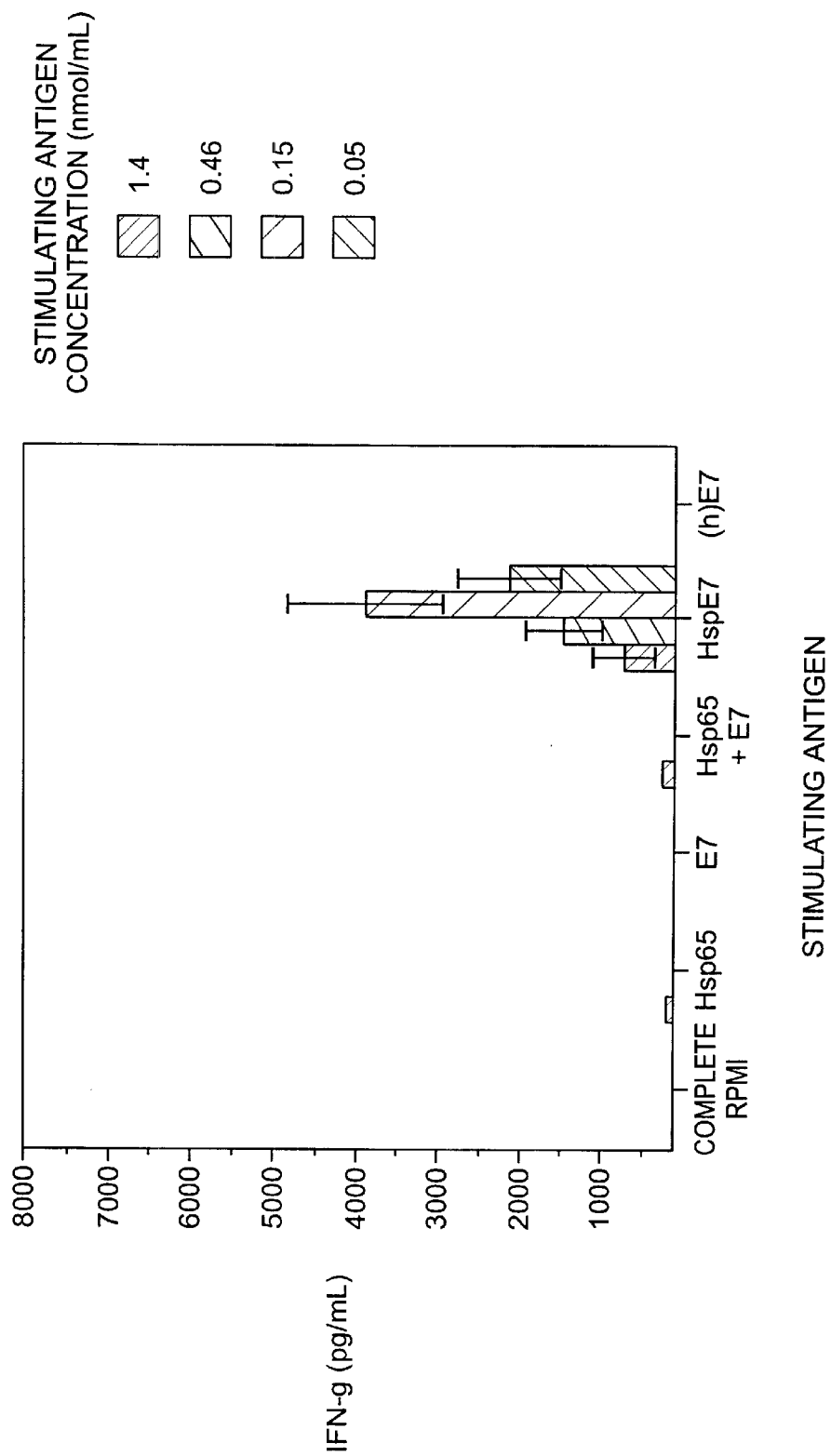
FIGS. 17A–17B show enhanced IFN-gamma release by splenocytes from C57BL/6 mice obtained from the Charles River Laboratory (FIG. 17A) and the Jackson Laboratory (FIG. 17B) upon exposure to HspE7.

The invention relates to methods of stimulating in vitro a Th1-like response in a cell sample containing naive lymphocytes. These methods are useful for assessing the ability of a protein, e.g., a fusion protein containing an Hsp linked to a heterologous polypeptide, to function as a stimulator of a Th1-like response. Additionally, the method can be used to identify compounds that can regulate a Th1-like response. Various materials and procedures suitable for use in the methods of the invention are discussed below.

The terms stress protein and heat shock protein (Hsp) are used synonymously herein. An Hsp is a polypeptide consisting of a sequence that is at least 40% identical to that of a protein whose expression is induced or enhanced in a cell exposed to stress. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells. As used herein, a "stress protein," also known as a "heat shock protein" or "Hsp," is a protein that is encoded by a stress gene, and is therefore typically produced in significantly greater amounts upon the contact or exposure of the stressor to the organism. A "stress gene," also known as "heat shock gene" is used herein as a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., *Heat Shock Response*, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

An antigen can be any compound, peptide or protein to which an immune response is desired. Antigens of particular interest are tumor-associated antigens, allergens of any origin, and proteins from viruses, mycoplasma, bacteria, fungi, protozoa and other parasites.

Fusion Proteins

The invention provides Hsp fusion proteins. As used herein, a "fusion protein" is a non-naturally occurring polypeptide containing at least two amino acid sequences which generally are from two different proteins. The amino acid sequence of the full length fusion protein is not identical to the amino acid sequence of a naturally occurring protein or a fragment thereof. An Hsp fusion protein contains an Hsp or a fragment thereof at least eight amino acids in length linked to a heterologous polypeptide. An "Hsp polypeptide" refers to a polypeptide consisting of a sequence that is at least 40% identical to that of a protein whose expression is induced or enhanced in a cell exposed to stress, e.g., heat shock. A "heterologous polypeptide" refers to a polypeptide that is fused to the Hsp protein or fragment thereof. The heterologous polypeptide is preferably at least eight amino acids in length. In some embodiments, the heterologous polypeptide is at least 10, 20, 50, 100, 150, 180, 200, or 300 amino acids in length. The heterologous polypeptide generally is not part or all of a naturally occurring Hsp. However, the fusion protein can also be a fusion between a first Hsp and a second, different, Hsp, or between all or portion of an Hsp fused to all or a portion of the same Hsp (as long as the resultant fusion is not identical to a naturally occurring protein). The Hsp polypeptide can be attached to the N-terminus or C-terminus of the heterologous polypeptide. Preferably the fusion protein is a purified protein.

The preferred Hsp fusion protein has one Hsp polypeptide linked to one heterologous polypeptide, but other conformations are within the invention. In one embodiment, the fusion protein comprises at least two copies of the heterologous polypeptide, e.g., HPV16 E7. In another embodiment, the fusion protein contains at least two copies of the Hsp polypeptide, e.g., Hsp65. Additionally, the fusion protein can contain at least two different heterologous polypeptides, e.g., two or more fragments of a single antigenic protein representing different epitopes or fragments of two or more different antigenic proteins derived from the same or different tumors or pathogens, and/or at least two different Hsp polypeptides.

The Hsp and heterologous polypeptide can be directly fused without a linker sequence. In preferred embodiments, the C-terminus of the Hsp can be directly fused to the N-terminus of the heterologous polypeptide or the C-terminus of the heterologous polypeptide can be directly fused to the N-terminus of the Hsp.

Alternatively, Hsp and heterologous polypeptides can be linked to each other via a peptide linker sequence. Preferred linker sequences (1) should adopt a flexible extended conformation, (2) should not exhibit a propensity for developing an ordered secondary structure which could interact with the functional Hsp and heterologous polypeptide domains, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other neutral or near-neutral amino acids, such as Thr and Ala, can also be used in the linker sequence. Any other amino acid can also be used in the linker. A linker sequence length of fewer than 20 amino acids can be used to provide a suitable separation of functional protein domains, although longer linker sequences may also be used.

The Hsp fusion protein may be further fused to another amino acid sequence that facilitates the purification of the fusion protein. One useful fusion protein is a GST fusion protein in which the Hsp-heterologous polypeptide sequences are fused to the C-terminus or N-terminus of the GST sequence. Another useful fusion protein is a poly-histidine (His) fusion protein in which the Hsp-heterologous polypeptide sequences are fused to either the C-terminus or N-terminus of the poly-histidine sequence, e.g. His x 6. In another embodiment, the fusion protein contains the chitin-binding region of intein, thereby permitting the purification of the fusion protein by chitin beads (Hoang et al. (1999) Gene 1999 237:361–71). In another embodiment, the fusion protein contains a signal sequence from another protein. In certain host cells (e.g., mammalian host cells), expression and/or secretion of the Hsp fusion protein can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic signal sequences include the secretory sequences of melittin and human placental alkaline phosphatase (Stratagene; La Jolla, Calif.). Prokaryotic signal sequences useful for increasing secretion by a prokaryotic host cell include the phoA secretory signal (Molecular Cloning, Sambrook et al., second edition, Cold Spring Harbor Laboratory Press, 1989) and the protein A secretory signal (Pharmacia Biotech; Piscataway, N.J.).

Fusion proteins of the invention, e.g., a fusion protein of Hsp65 and HPV16 E7, can be produced by standard recombinant techniques. For example, DNA fragments coding for the different polypeptide sequences are ligated together, in any order, in-frame in accordance with conventional techniques. Such techniques can include employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Correct linkage of the two nucleic acids requires that the product of the linkage encode a chimeric protein consisting of a Hsp moiety and a heterologous polypeptide moiety. In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments, which are subsequently annealed and reamplified to generate a chimeric gene sequence (see, e.g., Current Protocols in Molecular Biology, Ausubel et al. eds., John Wiley & Sons: 1992).

Expression vectors encoding fusion proteins containing a heterologous polypeptide and either an Hsp or a protein other than an Hsp can be prepared by the above procedures. Examples of Hsp fusion proteins can be found in international patent application WO 99/07860, incorporated herein by reference, that describes vector construction, expression and purification of Mycobacterium bovis BCG Hsp65—HPV16 E7 (HspE7) fusion protein as well as of HPV16 E7 (E7), histidine tagged HPV16 E7 (hE7), and M. bovis BCG Hsp65 (Hsp65). Additional examples of nucleic acids encoding an Hsp optionally linked to a heterologous polypeptide, e.g., an HPV antigen, are described in WO 89/12455, WO 94/29459, WO 98/23735, and references cited therein, the contents of which are herein incorporated by reference.

A variety of heat shock proteins have been isolated, cloned, and characterized from a diverse array of organisms (Mizzen, Biotherapy 10:173–189, 1998). Any Hsp or fragment thereof may be suitable for use in the fusion polypeptides and conjugates of the invention. For example, Hsp70, Hsp60, Hsp20–30, and Hsp10 are among the major determinants recognized by host immune responses to infection by Mycobacterium tuberculosis and Mycobacterium leprae. In addition, Hsp65 of Bacille Calmette Guerin (BCG), a strain of Mycobacterium bovis, was found to be an effective stimulatory agent, as described in the examples below.

Families of stress genes and proteins for use in the present invention are well known in the art and include, for example, Hsp100–200, Hsp100, Hsp90, Lon, Hsp70, Hsp60, TF55, Hsp40, FKBPs, cyclophilins, Hsp20–30, ClpP, GrpE, Hsp10, ubiquitin, calnexin, and protein disulfide isomerases. See, e.g., Macario, Cold Spring Harbor Laboratory Res. 25:59–70, 1995; Parsell et al., Rev. Genet. 27:437–496, 1993; and U.S. Pat. No. 5,232,833. Preferred Hsps include Hsp65, Hsp40, Hsp10, Hsp60, and Hsp71.

The Hsp portion of the fusion protein can include either a full length Hsp or a fragment of an Hsp at least eight amino acids in length. In some embodiments, the Hsp fragment is greater than 10 amino acids in length, and preferably is at least 20, 50, 100, 150, 180, 200, or 300 amino acids in length. In one embodiment, the Hsp portion of the fusion protein consists of amino acids 1–200 of Hsp65 of Mycobacterium bovis. Other portions of Hsp65 and other Hsps can be used in a fusion protein to elicit a Th1-like response in vitro. Other preferred Hsps include Hsp40 of M. tuberculosis, Hsp10 of M. tuberculosis, Hsp65 of Streptococcus pneumoniae, and Hsp60 of Aspergillus fumigatus. Heterologous polypeptides can contain any amino acid sequence useful for stimulating an immune response, in vitro and/or in vivo. Preferably, the heterologous polypeptide contains an MHC-binding epitope, e.g., an MHC class I or MHC class II binding epitope. The heterologous polypeptide can contain sequences found in a protein produced by a human pathogen, e.g., viruses, bacteria, mycoplasma, fungi, protozoa, and other parasites, or sequences found in the protein of a tumor associated antigen (TAA). Examples of viruses include human papilloma virus (HPV), herpes simplex virus (HSV), hepatitis B virus (HBV), hepatitis C virus (HCV), cytomegalovirus (CMV), Epstein-Barr virus (EBV), influenza virus, measles virus, and human immunodeficiency virus (HIV). Examples of tumor associated antigens include MAGE1, MAGE2, MAGE3, BAGE, GAGE, PRAME, SSX-2, Tyrosinase, MART-1, NY-ESO-1, gp100, TRP-1, TRP-2, A2 melanotope, BCR/ABL, Proeinase-3/Myeloblastin, HER2/neu, CEA, P1A, HK2, PAPA, PSA, PSCA, PSMA, pg75, MUM-1, MUC-1, E6, E7, GnT-V, Beta-catenin, CDK4 and P15.

HPV antigens from any strain of HPV are suitable for use in the fusion polypeptide. HPV expresses six or seven non-structural and two structural proteins. Viral capsid proteins L1 and L2 are the late structural proteins. L1 is the major capsid protein, the amino acid sequence of which is highly conserved among different HPV types. There are seven early non-structural proteins. Proteins E1, E2, and E4 play an important role in virus replication. Protein E4 also plays a role in virus maturation. The role of E5 is less well known. Proteins E6 and E7 are oncoproteins critical for viral replication, as well as for host cell immortalization and transformation. Fusion proteins of the invention can contain either the entire sequence of an HPV protein or a fragment thereof, e.g., a fragment of at least 8 amino acids. In one embodiment, the HPV antigenic sequence is derived from a "high risk" HPV, such as HPV16 or HPV18 E7 protein. The HPV antigenic sequence can include an MHC-binding epitope, e.g., an MHC class I and/or an MHC class II binding epitope.

In addition to Hsp fusion proteins, other fusion proteins can be used in the in vitro assay described herein. These non-Hsp fusion proteins contain a first polypeptide at least eight amino acids in length, fused to a second polypeptide at least eight amino acids in length, wherein the first and second polypeptides are derived from different proteins (preferably naturally occurring proteins). The fusion protein itself does not have the sequence of a naturally occurring protein.

In the fusion protein of the invention, neither the first nor second polypeptide is an amino acid sequence that is commonly used for protein purification or detection, e.g., GST or poly-histidine.

In order to produce the fusion protein, a nucleic acid encoding the fusion protein can be introduced into a host cell, e.g., a bacterium, a primary cell, or an immortalized cell line using an expression vector. The recombinant cells are then used to produce the fusion protein. The transfection can be transient or stable, the later sometimes accomplished by homologous recombination.

The nucleotide sequence encoding a fusion protein will usually be operably linked to one or more regulatory sequences, selected on the basis of the host cells to be used for expression. The term "regulatory sequence" refers to promoters, enhancers and other expression control elements (e.g., polyadenylation signals). Such regulatory sequences are described, for example, in Goeddel (1990) *Gene Expression Technology: Methods in Enzymology* 185, Academic Press, San Diego, Calif., the content of which is incorporated herein by reference. Regulatory sequences include those that direct constitutive expression of a nucleotide sequence in many types of host cells, those that direct expression of the nucleotide sequence only in certain host cells (e.g., tissue-specific regulatory sequences), and those that direct expression in a regulatable manner (e.g., only in the presence of an inducing agent). It will be appreciated by those skilled in the art that the design of the expression vector may depend on such factors as the choice of the host cell to be transformed, the level of expression of fusion protein desired, and the like.

Recombinant expression vectors can be designed for expression of fusion proteins in prokaryotic or eukaryotic cells. For example, fusion proteins can be expressed in bacterial cells such as *E. coli*, insect cells (e.g., in the baculovirus expression system), yeast cells or mammalian cells. Some suitable host cells are discussed further in Goeddel (1990) *Gene Expression Technology: Methods in Enzymology* 185, Academic Press, San Diego, Calif. Examples of vectors for expression in yeast *S. cerevisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), and pYES2 (Invitrogen Corporation, San Diego, Calif.). Baculovirus vectors available for expression of fusion proteins in cultured insect cells (e.g., Sf 9 cells) include the pAc series (Smith et al. (1983) *Mol. Cell. Biol.* 3:2156–2165) and the pVL series (Lucklow and Summers (1989) *Virology* 170:31–39).

Examples of mammalian expression vectors include pCDM8 (Seed (1987) *Nature* 329:840) and pMT2PC (Kaufman et al. (1987), *EMBO J.* 6:187–195). When intended for use in mammalian cells, the expression vector's control functions are often provided by viral regulatory elements. For example, commonly used promoters are derived from polyoma, Adenovirus 2, cytomegalovirus and Simian Virus 40.

In addition to the regulatory control sequences discussed above, the recombinant expression vector can contain additional nucleotide sequences. For example, the recombinant expression vector may encode a selectable marker gene to identify host cells that have incorporated the vector. Moreover, to facilitate secretion of the fusion protein from a host cell, in particular mammalian host cells, the recombinant expression vector can encode a signal sequence linked to the amino-terminus of the fusion protein, such that upon expression, the fusion protein is synthesized with the signal sequence fused to its amino terminus. This signal sequence directs the fusion protein into the secretory pathway of the cell and is then usually cleaved, allowing for release of the mature fusion protein (i.e., the fusion protein without the signal sequence) from the host cell. Use of a signal sequence to facilitate secretion of proteins or peptides from mammalian host cells is known in the art.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, microinjection and viral-mediated transfection. Suitable methods for transforming or transfecting host cells can be found in Sambrook et al. (*Molecular Cloning: A Laboratory Manual*, 2nd Edition, Cold Spring Harbor Laboratory Press (1989)), and other laboratory manuals.

Often only a small fraction of mammalian cells integrate the foreign DNA into their genome. In order to identify and select these integrants, a gene that encodes a selectable marker (e.g., resistance to antibiotics) can be introduced into the host cells along with the gene encoding the fusion protein. Preferred selectable markers include those that confer resistance to drugs such as G418, hygromycin and methotrexate. Nucleic acid encoding a selectable marker can be introduced into a host cell on the same vector as that encoding the fusion protein or can be introduced on a separate vector. Cells stably transfected with the introduced nucleic acid can be identified by drug selection (e.g., cells that have incorporated the selectable marker gene will survive, while the other cells die).

Alternatively, a recombinant expression vector can be transcribed and translated in vitro, for example using T7 promoter regulatory sequences and T7 polymerase.

In addition to the recombinant techniques described above, a fusion protein of the invention can be formed by linking two polypeptides, e.g., a Hsp and a heterologous polypeptide, to form a conjugate. Methods of forming Hsp conjugates are described in WO 89/12455, WO 94/29459, WO 98/23735, and WO 99/07860, the contents of which are herein incorporated by reference. As used herein, an Hsp "conjugate" comprises an Hsp that has been covalently linked to a heterologous polypeptide via the action of a coupling agent. A conjugate thus comprises two separate molecules that have been coupled one to the other. The term "coupling agent," as used herein, refers to a reagent capable of coupling one polypeptide to another polypeptide, e.g., a Hsp to a heterologous polypeptide. Any bond which is capable of linking the components such that the linkage is stable under physiological conditions for the time needed for the assay (e.g., at least 12 hours, preferably at least 72 hours) is suitable. The link between two components may be direct, e.g., where a Hsp is linked directly to a heterologous polypeptide, or indirect, e.g., where a Hsp is linked to an intermediate, e.g., a backbone, and that intermediate is also linked to the heterologous polypeptide. A coupling agent should function under conditions of temperature, pH, salt, solvent system, and other reactants that substantially retain the chemical stability of the Hsp, the backbone (if present), and the heterologous polypeptide.

A coupling agent can link components, e.g., a Hsp and a heterologous polypeptide, without the addition of the coupling agent to the resulting fusion protein. Other coupling agents result in the addition of the coupling agent to the resulting fusion protein. For example, coupling agents can be cross-linking agents that are homo- or heterobifunctional, and wherein one or more atomic components of the agent is retained in the composition. A coupling agent that is not a cross-linking agent can be removed entirely following the coupling reaction, so that the molecular product is composed entirely of the Hsp, the heterologous polypeptide, and a backbone moiety (if present).

Many coupling agents react with an amine and a carboxylate, to form an amide, or an alcohol and a carboxylate to form an ester. Coupling agents are known in the art, see, e.g., M. Bodansky, "Principles of Peptide Synthesis", 2nd ed., referenced herein, and T. Greene and P. Wuts, "Protective Groups in Organic Synthesis,"2nd Ed, 1991, John Wiley, N.Y. Coupling agents should link component moieties stably, but such that there is minimal or no denaturation or deactivation of the Hsp or the heterologous polypeptide.

The conjugates of the invention can be prepared by coupling a Hsp to a heterologous polypeptide using methods known in the art. A variety of coupling agents, including cross-linking agents, can be used for covalent conjugation. Examples of cross-linking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl) cyclohexane-1-carboxylate (sulfo-SMCC). See, e.g., Karpovsky et al. (1984) *J. Exp. Med.* 160:1686 and Liu et al. (1985) *Proc. Natl. Acad. Sci. USA* 82:8648. Other methods include those described by Paulus (1985) *Behring Ins. Mitt.* 78:118–132; Brennan et al. (1985) *Science* 229:81–83; and Glennie et al. (1987) *J. Immunol.* 139: 2367–2375. A large number of coupling agents for peptides and proteins, along with buffers, solvents, and methods of use, are described in the Pierce Chemical Co. catalog, pages T-155—T-200, 1994 (3747 N. Meridian Rd., Rockford Ill., 61105, U.S.A.; Pierce Europe B.V., P.O. Box 1512, 3260 BA Oud Beijerland, The Netherlands), which catalog is hereby incorporated by reference.

DCC is a useful coupling agent (Pierce #20320; Rockford, Ill.). It promotes coupling of the alcohol NHS in DMSO (Pierce #20684), forming an activated ester which can be cross-linked to polylysine. DCC (N,N'-dicyclohexylcarbodiimide) is a carboxyreactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4 and a spacer arm length of 6.8 angstroms, is reactive to NHS-esters and pyridyldithio groups, and produces cleavable cross-linking such that upon further reaction, the agent is eliminated so the Hsp can be linked directly to a backbone or heterologous polypeptide. Other useful conjugating agents are SATA (Pierce #26102) for introduction of blocked SH groups for two-step cross-linking, which are deblocked with hydroxylamine-HCl (Pierce #26103), and sulfo-SMCC (Pierce #22322), reactive towards amines and sulfhydryls. Other cross-linking and coupling agents are also available from Pierce Chemical Co. (Rockford, Ill.). Additional compounds and processes, particularly those involving a Schiff base as an intermediate, for conjugation of proteins to other proteins or to other compositions, for example to reporter groups or to chelators for metal ion labeling of a protein, are disclosed in EP 243,929 A2 (published Nov. 4, 1987).

Polypeptides that contain carboxyl groups can be joined to lysine ε-amino groups in the heterologous polypeptide either by preformed reactive esters (such as N-hydroxy succinimide ester) or esters conjugated in situ by a carbodiimide-mediated reaction. The same applies to Hsps containing sulfonic acid groups, which can be transformed to sulfonyl chlorides that react with amino groups. Hsps that have carboxyl groups can be joined to amino groups on the polypeptide by an in situ carbodiimide method. Hsps can also be attached to hydroxyl groups of serine or threonine residues, or to sulfhydryl groups of cysteine residues.

In addition to conjugates of two polypeptides, e.g., a Hsp and a heterologous polypeptide, hybrid compounds can be constructed containing a non-peptide compound covalently linked to a polypeptide at least eight amino acids in length. The polypeptide component of this hybrid compound can be any of the heterologous polypeptides described herein as a component of a Hsp fusion protein or conjugate. Examples of the non-peptide component of this hybrid compound include polynucleotides, polynucleotide analogs, nucleotides, nucleotide analogs, organic or inorganic compounds having a molecular weight less than about 5,000 grams per mole, preferably between about 1,500 and 100 grams per mole, and salts, esters, and other pharmaceutically acceptable forms of such non-peptide compounds.

In Vitro Assays for Th1-Like Activity

Cell samples containing naive lymphocytes are prepared from any mammal, e.g., a mouse, rat, rabbit, goat, or human, and are plated at an appropriate density in one or more tissue culture plates. A naive lymphocyte is a lymphocyte that has not been exposed (either in vivo or in vitro) to the fusion protein (or to either of the polypeptides that are joined to make the fusion protein) prior to the cell's use in the in vitro assay. The cell sample can be derived from any of various primary or secondary lymphoid organs or tissues of an animal, e.g., spleen, lymph node, peripheral blood, bone marrow, or thymus. The sample may also be derived from any tissue in the body containing lymphoid cells, such as the lung, respiratory tract (including pharynx, larynx, trachea, bronchi, etc), and anogenital mucosa. The cell sample can include naive lymphocytes selected from NK cells, NK T cells, αβT cells and γδT cells. The cell sample can be either unfractionated or enriched for a particular cell type or cell types. In addition to naive lymphocytes, the cell sample can optionally include naive antigen presenting cells such as macrophages, dendtritic cells, and/or B cells. The cell sample can optionally include cell lines, e.g., a transformed T cell line or a T cell clone.

The cell sample is exposed in vitro to a fusion protein or a conjugate described herein. Following a period of incubation between the cell sample and the fusion protein or conjugate, e.g., 6, 12, 24, 36, 48, 60, 72, or 96 hours, a determination is made as to whether a Th1-like response has been elicited in the cell sample. A Th1-like response can be detected, for example, by measuring the production of particular lymphokines, e.g., IFN-gamma or TNF-beta, by the cell sample. Alternatively, a Th1-like response can be detected by assaying for cell surface marker expression, such as SLAM (signaling lymphocytic activation molecule), or for cytokine expression, using a variety of techniques (for example, flow cytometry).

In one example, pooled, unfractionated splenocyte cultures containing naive lymphocytes are prepared from a mouse and are plated in tissue culture plates. Methods of isolating and culturing splenocytes are described in Current Protocols in Immunology, Coligan et al., eds., John Wiley & Sons, 2000. Cultures of splenocytes are then exposed to different concentrations of a test protein, e.g., a recombinant Hsp fusion protein, Hsp, the antigen alone, or another antigen-containing fusion protein, for a time that is sufficient to elicit a measurable IFN-gamma response against a standard antigen-stress protein fusion protein such as, for example, HspE7, described in patent application WO 99/07860 and employed in the Examples below. Following exposure of the cell sample to the test protein, the IFN-gamma level in the extracellular medium is determined using a suitable assay such as an IFN-gamma ELISA.

Results of the assays described below reveal that IFN-gamma release elicited by exposure of splenocytes or lymph node cells to an Hsp fusion protein is much more substantial than that induced by exposure to the antigen itself, the Hsp itself, an admixture of antigen and Hsp, or a fusion between antigen and a protein other than a Hsp.

The assay of the invention can be used to evaluate a preparation of an Hsp fusion protein (e.g., as a quality control assay) or compare different preparations of Hsp fusion proteins. The measurements taken in the assay constitute a method for identifying a particularly active batch or to eliminate substandard batches of fusion protein preparations. The assay may also be used to optimize production procedures, storage regimes, etc. In cases in which a maximal Th1-like response to a particular antigen is desired, the assays can be used to test different fusions between the antigen and different types of Hsps or Hsps of different origins. Furthermore, the assay can be used to test a series of different candidate antigens, to identify the antigen that gives rise to the most pronounced Th1-like response when fused to a Hsp.

The assay can also be used to identify regions in an antigen sequence or an Hsp sequence that are primarily responsible for eliciting a Th1-like response and thus have therapeutic potential. To identify such active regions in an antigen, fusions containing individual subregions of the antigen fused to an Hsp can be prepared and tested in the assay of the invention. To identify active regions in an Hsp, fusions containing individual subregions of the Hsp fused to the antigen can be prepared and tested. These determinations will provide the basis for the construction of shortened fusion proteins comprising subregions of antigen and/or Hsp that are sufficient to elicit a Th1-like response. Fusions containing subregions of a Hsp and/or subregions of an antigen can be tested by comparing the elicited Th1-like response to that induced by a full length fusion protein with known activity, e.g., HspE7.

The fusion proteins described herein are useful in assays for screening compounds for their effectiveness in stimulating a Th1-like response. For example, the Hsp fusion proteins that were found to stimulate IFN-gamma secretion in the in vitro assay can be used as controls to test candidate compounds for their ability to produce the same effect.

The system described herein for stimulating a Th1-like response in vitro can be used to generate activated Th1cells ex vivo for reimplantation into an individual. This may be useful for treating conditions characterized by a dominant Th2 immune response and an insufficient Th1response. The assay can also be used to identify compounds that can regulate a Th1-like response. Compounds can be screened for their ability to inhibit an Hsp-fusion protein-induced Th1-like response, or to promote a Th1-like response in a manner similar to a Hsp fusion protein, or to enhance the Th1-like response induced by a Hsp fusion protein (or any other protein found to act in a manner comparable to a Hsp fusion protein). Inhibitory compounds may be useful to treat conditions characterized by an inappropriate Th1 response, e.g., inflammatory and autoimmune diseases. Potential inhibitors (e.g., of binding of antigen-stress protein fusion proteins to antigen-presenting cells or of stress protein fusion-enhanced antigen processing) can be screened as follows. A cell sample comprising naive lymphocytes is mixed with a fusion protein or conjugate that is known to induce a Th1-like response, e.g., IFN-gamma secretion. Compounds to be screened as potential inhibitors are added to the cell culture either before, after, or simultaneous to the addition of the fusion protein or conjugate. The effect of the compound on the induction of a Th1-like response, e.g., as measured by IFN-gamma release, can be determined by comparing the response to that obtained when the fusion protein or conjugate alone is added to the cell sample.

In a similar manner, compounds can be screened for their ability to promote a Th1-like response. Any compound can be screened for its ability to regulate a Th1-like response, including both peptides and non-peptide chemicals. These compounds include, but are not limited to, peptides, peptidomimetics (e.g., peptoids), amino acids, amino acid analogs, polynucleotides, polynucleotide analogs, nucleotides, nucleotide analogs, organic or inorganic compounds having a molecular weight less than about 5,000 grams per mole, and salts, esters, and other pharmaceutically acceptable forms of such compounds. In this case, a cell sample comprising naive lymphocytes is contacted with a test compound. The effect of the test compound on the induction of a Th1-like response, e.g., as measured by IFN-gamma release, is then measured and compared to a control (no test sample) or compared to an Hsp fusion known to stimulate a Th1-like response. This assay can be used to identify novel compounds that can be used to stimulate a Th1-like response. Preferably the Th1-like response stimulated by the compound is at least 25%, e.g., at least 40%, 50%, 60%, 70%, or 80%, the level of the maximum response induced by an HspE7 fusion protein. In one embodiment, the compound is preferably not a naturally occurring compound. In another embodiment, the compound is a peptide, wherein the peptide does not correspond to the fragment of a naturally occurring protein.

The following are examples of the practice of the invention. They are not to be construed as limiting the scope of the invention in any way.

EXAMPLES

Example 1

Bacterial Growth and Cell Lysis for Production of Recombinant Proteins

*E. coli* strains BL21(DE3) or BLR(DE3) (Novagen) were used as the host for all recombinant protein production, with the exception of pET65, which was transformed into BL21 (DE3) pLysS (Novagen). BL21(DE3) pLysS cells harboring pET65 were grown in 2xYT media (20 g/L tryptone; 10 g/L yeast extract, 20 g/L NaCl; Milli-Q™ quality water) containing 30 μg/ml kanamycin and 34 μg/ml chloramphenicol, while all other transformants were grown in 2xYT media containing 30 μg/ml kanamycin. All bacterial cultures were grown in 2 L shaker flasks at 200–400 rpm to $OD_{600}$=0.5 and then induced with 0.5 mM IPTG for 3 hours at 37° C. Cells were then harvested by centrifugation at 4° C. and 4,000–8,000 g for 5 minutes, then suspended in 300 ml of Lysis Buffer (10 mM TRIS.HCl, 10 mM 2-mercaptoethanol, pH 7.5), lysozyme was added to 200 μg/mL, and the suspension mixed and frozen at −70° C.

To purify the recombinant protein, the cells were thawed using a 37° C. waterbath and proteinase inhibitors were added (2 μg/ml aprotinin, 2 μg/ml leupeptin, 2 μg/ml pepstatin and 2 mM PMSF). The cell suspension was split into 50 mL samples, stored on ice, and sonicated 3–4 times for 30 seconds at Power-Level 5–8 (Sonicator 450, Branson, Corp.). The supernatant was separated from the pellet by centrifugation at 35,000–60,000 g for 10–20 minutes at 4° C. For soluble proteins, the supernatant was kept and processed as the Soluble Fraction. For proteins found in inclusion bodies, the supernatant was discarded and the pellet was washed with Lysis Buffer (optionally containing 1 M urea, 1% (v/v) Triton X-100). The resulting mixture was then centrifugation at 35,000–60,000 g for 10–20 minutes at 4° C. and the supernatant discarded. The pellet was dissolved in Lysis Buffer containing 8 M urea. This mixture was then centrifuged at 4° C. for 10–20 minutes at 35,000–60,000 g and the pellet was discarded and the supernatant stored at −70° C. as the Inclusion Body fraction.

Example 2

**Production of Recombinant *M. bovis* BCG Hsp65 (Hsp65)**

A plasmid encoding Hsp65 was constructed as follows. The *M. bovis* BCG Hsp65 coding sequence was PCR amplified from pRIB1300 (van Eden et al. (1988) Nature 331:171–173) using the following primers. The forward primer (w046: 5' TTC GCC ATG GCC AAG ACA ATT GCG 3'; SEQ ID NO:1) contains an ATG start codon at an NcoI site. The reverse primer (w078: 5' TTC TCG GCT AGC TCA GAA ATC CAT GCC 3'; SEQ ID NO:2) contains an Nhe I site downstream of a TGA stop codon. The PCR product was digested with NcoI and NheI, purified and ligated to pET28a (Novagen) which had been cut with NcoI and NheI. Plasmid pET65 encodes the *M bovis* BCG Hsp65 protein, abbreviated Hsp65. The nucleotide sequence (SEQ ID NO:3) coding for expression of Hsp65 (SEQ ID NO:4) is shown in FIGS. 1A–1B.

The Hsp65 protein was purified as follows. The Soluble Fraction was prepared as described above from *E. coli* BL21(DE3) pLysS cells transformed with plasmid pET65. The *M. bovis* BCG Hsp65 protein (Hsp65) present in the Soluble Fraction was purified by the following chromatographic steps: SP-Sepharose (200 ml column, Amersham Pharmacia), Q-Sepharose (200 ml column, Amersham Pharmacia), Sephacryl S-300 (500 ml column, Amersham Pharmacia) and ceramic hydroxyapatite (HAP; 100 ml column, Biorad). Purified Hsp65 was exchanged into Dulbecco's modified phosphate buffered saline (DPBS)/15% (v/v) glycerol and stored at −70° C.

Example 3

Production of Recombinant HPV16 E7 (E7)

A plasmid encoding HPV16 E7 was constructed as follows. The HPV16 E7 coding sequence was PCR-amplified from pSK/HPV16 (ATCC) using primers w280 and w134 (w280: CCA GCT GTA ACC ATG GAT GGA GAT (SEQ ID NO:5) and w134: AGC CAT GAA TTC TTA TGG TTT CTG (SEQ ID NO:6)). The PCR product was digested with restriction enzyme Nco I and EcoR I and purified from an agarose gel. The purified PCR product was ligated to pET28a that had been previously digested with the same enzymes. The ligation reaction was used to transform *E. coli* DH5alpha and putative clones containing the HPV16 E7 gene insert were selected based on diagnostic restriction digestion. This initial restriction analysis was confirmed by DNA sequence analysis of entire gene, promoter and termination regions. DNA of the confirmed construct, named pET/E7 (NH), was then introduced by electroporation into *E. coli* strain BL21(DE3). The nucleotide sequence (SEQ ID NO:7) coding for expression of E7 (SEQ ID NO:8) is shown in FIG. 2.

The HPV16 E7 protein was purified as follows. The Soluble Fraction was prepared as described above from *E. coli* BL21(DE3) cells transformed with plasmid pET/E7 (NH). The HPV16 E7 protein was purified by the following chromatographic steps: Q-Sepharose (100 ml column, Amersham Pharmacia); Superdex 200 (26/60 column, Amersham Pharmacia); and Ni-chelating Sepharose (100 ml, Amersham Pharmacia) under denaturing conditions with serial washings containing 2% (v/v) Triton X-100 followed by serial washing to remove residual Triton X-100, and the pooled fractions containing HPV E7 protein were then dialyzed overnight against 30 mM TRIS.HCl, 1 M NaCl, 1 mM 2-mercaptoethanol, pH 7.5. The dialyzed protein was further purified by Ni-chelating Sepharose (75 ml, Amersham Pharmacia) under denaturing conditions with serial washings containing 2% (v/v)Triton X-100 followed by serial washing to remove residual Triton X-100. The purity of the protein was checked by SDS-PAGE, the appropriate fractions pooled and dialyzed overnight at 4° C. against DPBS/10% (v/v) glycerol.

Example 4

Production of Recombinant Histidine-tagged HPV16 E7 ((h)E7)

A plasmid encoding (h)E7 was constructed as follows. The HPV16 E7 coding sequence was PCR amplified from HPV16 genomic DNA (pSK/HPV16) using the following primers. The forward primer (w133: 5' AAC CCA GCT GCT AGC ATG CAT GGA GAT 3'; SEQ ID NO:9) contains an NheI site upstream of an ATG start codon. The reverse primer (w134: 5' AGC CAT GAA TTC TTA TGG TTT CTG 3'; SEQ ID NO:10) contains an EcoRI site downstream of a TAA stop codon. The PCR product was digested with NheI and EcoRI, purified and ligated to pET28a which had been cut with NheI and EcoRI. pET/H/E7 which encodes the HPV16 E7 protein containing an N-terminal histidine tag, abbreviated (h)E7, was used to transform *E. coli* BL21(DE3) cells. The nucleotide sequence (SEQ ID NO:11) coding for expression of (h)E7 (SEQ ID NO:12) is shown in FIG. 3.

The (h)E7 protein was purified as follows. The Inclusion Body fraction was prepared as described above from *E. coli* BL21(DE3) cells transformed with plasmid pET/H/E7. The N-terminal histidine-tagged HPV16 E7 protein ((h)E7) present in the Inclusion Body fraction was purified using the following chromatographic steps: Ni-chelating Sepharose (60 ml, Amersham Pharmacia) under denaturing conditions with serial washings containing 2% (v/v) Triton X-100 followed by serial washing to remove residual Triton X-100. Bound (h)E7 was refolded on the resin and eluted by a 50–500 mM imidazole gradient. Purified (h)E7 was dialyzed against DPBS/25% (v/v) glycerol.

Example 5

Production of Recombinant HPV16 E7—*M. bovis* BCG 65 Fusion Protein (HspE7)

A plasmid encoding HspE7 was constructed as follows. The *M. bovis* BCG Hsp65 coding sequence was PCR amplified from pRIB1300 using the same forward primer (w046) as for pET65. The reverse primer (w076: 5' CGC TCG GAC GCT AGC TCA CAT ATG GAA ATC CAT GCC 3'SEQ ID NO:13) contains an NdeI site upstream and an NheI site downstream of a TGA stop codon. The PCR product was digested with NcoI and NheI, purified and ligated to pET28a which had been cut with NcoI and NheI.

The HPV16 E7 coding sequence was PCR amplified from HPV16 genomic DNA (pSK/HPV16) using the following primers. The forward primer (w151: 5' CCA GCT GTA CAT ATG CAT GGA GAT 3'; SEQ ID NO:14) contains an ATG start codon at an NdeI site. The reverse primer (w134: 5' AGC CAT GAA TTC TTA TGG TTT CTG 3'; SEQ ID NO:15) contains an EcoRI site downstream of a TAA stop codon. The PCR product was digested with NdeI and EcoRI, purified and ligated to pET65C which had been cut with NdeI and EcoRI and the resulting plasmid (pET65C/E7-1N) was transformed into *E. coli* BL21(DE3) cells. pET65C/E7-1N encodes a fusion protein consisting of Hsp65 linked via its C-terminus to HPV16 E7, abbreviated HspE7. The nucleotide sequence (SEQ ID NO:16) coding for expression of HspE7 (SEQ ID NO:17) is shown in FIGS. 4A–4B.

The HspE7 protein was purified as follows. The Soluble Fraction was prepared as described above from *E. coli* BL21(DE3) cells transformed with plasmid pET65C/E7-1N. Hsp65-HPV16 E7 fusion protein (HspE7) present in the Soluble Fraction was purified by the following chromatographic steps: 0–15% ammonium sulfate precipitation, Ni-chelating Sepharose (100 ml column, Amersham Pharmacia) and Q-Sepharose (100 ml column, Amersham Pharmacia). Endotoxin was removed by extensive washing with 1% (v/v) Triton X-100 on a Ni-chelating Sepharose column in the presence of 6 M guanidine-HCl (Gu-HCl). Purified HspE7 was exchanged into DPBS/15% (v/v) glycerol and stored at −70° C.

Example 6

Production of Recombinant *M. tuberculosis* Hsp40—HPV16 E7 Fusion Protein (MT40-E7)

pETMT40E7 is a plasmid encoding chimeric recombinant protein MT40E7 composed of *Mycobacterium tuberculosis* (strain H37RV—ATCC 27294) hsp4 o protein with hu HPV16 (ATCC 45113) E7 protein attached at the C-terminus of Hsp40. The plasmid was transformed into *E. coli* BL21(DE3) cells for protein production and purification. The nucleotide sequence (SEQ ID NO:18) coding for expression of MT40-E7 (SEQ ID NO:19) is shown in FIGS. 5A–5B.

The MT40-E7 protein was purified as follows. The Inclusion Body fraction was prepared as described above from *E. coli* BL21(DE3) cells transformed with plasmid pETMT40E7. MT40-E7 protein was purified using the following chromatographic steps: Q-Sepharose (100 ml column, Amersham Pharmacia), Ni-chelating Sepharose (70 ml, Amersham Pharmacia) under native conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS/25% (v/v) glycerol.

Example 7

Ovalbumin (OVA)

Ovalbumin (Lot #37H7010) was purchased from Sigma Chemicals and purified by chromatography using 20 mL of Con A Sepharose (Amersham-Pharmacia). Fractions containing the purified product were pooled and dialyzed overnight against DPBS.

Example 8

Production of Recombinant *M. bovis* BCG Hsp65-Ovalbumin Fusion Protein (HspOva)

A plasmid encoding HspOva was constructed as follows. The full length chicken ovalbumin-coding sequence was excised from pET/OVA with Nhe I and EcoR I digestion and purified from an agarose gel. The sequence coding for expression of OVA is shown in FIG. 6. The purified product was ligated to pET65H previously digested with the same enzymes. The ligation reaction was used to transform *E. coli* DH5alpha and putative clones containing the chicken ovalbumin gene insert were selected based on diagnostic restriction digestion. This initial restriction analysis was confirmed by DNA sequence analysis of the entire fusion gene, promoter and termination regions. DNA of the confirmed construct, named pET65H/OVA, was used to transform *E. coli* BL21(DE3). The nucleotide sequence (SEQ ID NO:20) coding for expression of HspOVA (SEQ ID NO:21) is shown in FIGS. 7A–7C.

The HspOva protein was purified as follows. The Inclusion Body fraction was prepared as described above from *E. coli* BL21(DE3) cells transformed with plasmid pET65H/OVA. The HspOva fusion protein present in the Inclusion Body fraction was purified using the following chromatographic steps: Q-Sepharose (100 ml column, Amersham Pharmacia) and Ni-chelating Sepharose (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS/15% (v/v) glycerol, followed by a dialysis against DPBS/2.5% (w/v) sucrose.

Example 9

Production of Recombinant Glutathione-S-Transferase (GST)

A plasmid encoding Gst was constructed as follows. The kanamycin resistance-coding sequence was excised from pET28a DNA with AlwN I and Xho I digestion and purified from an agarose gel. The purified product was ligated to pGEX-4T-2 that had been previously digested with the same enzymes. The ligation reaction was used to transform *E. coli* DH5alpha and putative clones containing the kanamycin resistance gene insert were selected based on diagnostic restriction digestion. This initial restriction analysis was confirmed by DNA sequence analysis of the entire insert coding sequence, promoter and termination regions. DNA of the confirmed construct, named pGEX/K, was used to transform *E. coli* strain BL21(DE3). The nucleotide sequence (SEQ ID NO:22) coding for expression of GST (SEQ ID NO:23) is shown in FIG. 8.

The GST protein was purified as follows. The Soluble fraction was prepared as described above from *E. coli* BL21(DE3) cells transformed with plasmid pGEX/K. The GST protein present in the Soluble Fraction was purified by Glutathione-Agarose Chromatography as follows. Approximately 20 mL of Glutathione-Agarose (Sigma-Aldrich; Cat. #: G4510) was equilibrated with DPBS, and mixed and incubated overnight with the sample at room temperature on a shaker. The next morning, the resin was packed into a column and serially washed with DPBS. Endotoxin was removed by washing with 2% (v/v) Triton X-100 followed by serial washing to remove residual Triton X-100. Finally, the protein was eluted using 10 mM glutathione (reduced form), 50 mM TRIS.HCl, pH 8.0.

Example 10

Production of Recombinant Glutathione-S-Transferase—HPV16 E7 Fusion Protein (GST-E7)

A plasmid encoding GST-E7 was constructed as follows. The HPV16 E7 coding sequence was excised from pETOVA/E7 with BamH I and EcoR I digestion and purified from an agarose gel. The purified product was ligated to pGEX/K that had been previously digested with the same enzymes. The ligation reaction was used to transform *E. coli* DH5alpha and putative clones containing the HPV16 -E7 gene insert were selected based on diagnostic restriction digestion. This initial restriction analysis was confirmed by DNA sequence analysis of entire fusion gene, promoter and termination regions. DNA of the confirmed construct, named pGEX/K/E7, was used to transform *E. coli* strain BL21 (DE3). The nucleotide sequence (SEQ ID NO:24) coding for expression of GS-TE7 (SEQ ID NO:25) is shown in FIG. 9.

The GST-E7 protein was purified as follows. Bacteria containing the expression vector pGEX/K/E7 were grown and the protein purified using the affinity chromatography procedure essentially as described above for GST.

Exanple 11

Production of Recombinant HPV16 E7—Linker—*M. bovis* BCG Hsp65 Fusion Protein (E7-L-BCG65)

A plasmid encoding E7-L-BCG65 was constructed as follows. The HPV16 E7-coding sequence was PCR-amplified from pSK/HPV16 (ATCC) using primers w280 and w396 (w280: CCA GCT GTA ACC ATG GAT GGA GAT (SEQ ID NO:26) and w396: GCC ATG GTA CTA GTT GGT TTC TGA GAA(SEQ ID NO27:)). The PCR product was digested with restriction enzyme Nco I and Spe I and purified from an agarose gel. The purified PCR product was ligated to pET5'65 (pET5'65 is pET65 with a polyglycine linker sequence inserted at the 5' end of the *M. bovis* BCG hsp65 sequence) that had been previously digested with the same enzymes. The ligation reaction was used to transform *E. coli* DH5alpha and putative clones containing the HPV16 E7 gene insert were selected based on diagnostic restriction digestion. This initial restriction analysis was confirmed by DNA sequence analysis of entire fusion gene, promoter and termination regions. DNA of confirmed construct, named pET/E7/5'65, was used to transform *E. coli* strain BLR (DE3). The nucleotide sequence (SEQ ID NO:28) coding for expression of E7-L-BCG65 (SEQ ID NO:29) is shown in FIGS. 10–10B.

The E7-L-BCG65 protein was purified as follows. The Soluble Fraction was prepared as described above from *E. coli* BLR(DE3) cells transformed with plasmid pET/E7/5'65. The E7-L-BCG65 fusion protein present in the Soluble Fraction was purified using the following chromatographic steps: Butyl Sepharose (100 ml, Amersham-Pharmacia), Q-Sepharose (100 ml column, Amersham Pharmacia), Superdex 200 Gel Filtration (26/60 column, Amersham Pharmacia), and Ni-chelating Sepharose Fast Flow Chromotography (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS. In order to reduce the amount of endotoxin contained in the sample, it was further purified using a pre-packed 1 ml column of DetoxiGel™ (Pierce, Rockford, Ill., USA) according to the manufacturer's instructions.

Example 12

Production of Recombinant HPV16 E7—*M. bovis* BCG Hsp65 Fragment Fusion Protein (BCG65(F1)-E7)

A plasmid encoding BCG65(F1)-E7 was constructed as follows. The first 600 amino terminal base pairs of *M. bovis* BCG hsp65 gene were PCR-amplified from pET65C/E7-1N using primers w046 and w293 (w046: TTC GCC ATG GCC AAG ACA ATT GCG (SEQ ID NO:30) and w293: GTA CCC CGA CAT ATG GCC CTT GTC GAA CCG CAT AC(SEQ ID NO:31)). The PCR product was digested with the restriction enzymes Nco I and Nde I and purified from an agarose gel. The purified PCR product was ligated to pET65C/E7-1N that had been previously digested with the same enzymes. The ligation reaction was used to transform *E. coli* DH5alpha and putative clones containing the truncated BCG65 gene were selected based on diagnostic restriction digestion. This initial restriction analysis was confirmed by DNA sequence analysis of the entire fusion gene, promoter and termination regions. The confirmed plasmid construct, named pET65F1/E7, was used to transform *E. coli* strain BLR(DE3). The nucleotide sequence (SEQ ID NO:32) coding for expression of BCG65(F1)-E7 (SEQ ID NO:33) is shown in FIG. 11.

The BCG65(F1)-E7 protein was purified as follows. The Inclusion Body fraction was prepared as described above from *E. coli* BLR(DE3) cells transformed with plasmid pET65 F1/E7. The BCG65(F1)-E7 fusion protein present in the Inclusion Body fraction was purified using the following chromatographic steps: Source 15Q Sepharose (Amersham-Pharmacia) and Ni-chelating Sepharose (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS.

Example 13

Production of Recombinant *M. tuberculosis* Hsp10—HPV16 E7 Fusion Protein (TB10-E7)

Expression plasmid pETESE7 contains a chimeric gene composed of the *Mycobacterium tuberculosis* strain H37RV (ATCC 27294) groES (hsp 10) coding sequence fused, at its 3' end, to the HPV16 (ATCC 45113) E7 coding. The chimeric gene was cloned into expression vector pET28a and transformed into *E. coli* BL21(DE3) cells for protein production and purification. The nucleotide sequence (SEQ ID NO:34) coding for expression of TB10-E7 (SEQ ID NO:35) is shown in FIG. 12.

The TB10-E7 protein was purified as follows. The Inclusion Body fraction was prepared as described above from *E. coli* BL21(DE3) cells transformed with plasmid pETESE7. The TB10-E7 fusion protein present in the Inclusion Body fraction was purified using the following chromatographic steps: DEAE Sepharose (100 ml column, Amersham Pharmacia), Source 15Q Sepharose (100 ml column, Amersham Pharmacia) and Ni-chelating Sepharose (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS/10% (v/v) glycerol.

Example 14

Production of Recombinant HPV16 E7—*M. tuberculosis* Hsp71 Fusion Protein (E7-TB71)

A plasmid encoding E7-TB71 was constructed as follows. The *M. tuberculosis* hsp71 gene was PCR-amplified from clone pY3111/8 (Mehlert and Young (1989) Mol.Microbiol. 3:125–130) using primers w048 and w079 (w048: 5'-TTC ACC ATG GCT CGT GCG GTC GGG (SEQ ID NO:36) and w079: ACC TCC GCG TCC ACA GCT AGC TCA GCC (SEQ ID NO:37)). The PCR product was digested with Nco I and Nhe I, gel-purified and ligated to pET28a digested with the same enzymes to generate pET/71.

The HPV16 E7-coding sequence was PCR-amplified from pSK/HPV16 (ATCC) using primers w280 and w344 (w280: CCA GCT GTA ACC ATG GAT GGA GAT (SEQ ID NO:38) and w344: GGA TCA GAC ATG GCC ATG GCT GGT TTC TG (SEQ ID NO:39)). The PCR product was digested with restriction enzyme Nco I and purified from an agarose gel. The purified PCR product was ligated to pET/71 DNA that had been previously digested with Nco I and CIAP to remove 5' phosphate. The ligation reaction was used to transform *E. coli* DH5alpha and putative clones containing the HPV16 E7 gene insert were selected based on diagnostic restriction digestion. This initial restriction analysis was confirmed by DNA sequence analysis of entire fusion gene, promoter and termination regions. The confirmed construct, named pET/E7/71, was used to transform *E. coli* strain BL21(DE3). The nucleotide sequence (SEQ ID NO:40) coding for expression of E7-TB71 (SEQ ID NO:41) is shown in FIGS. 13A–13B. The resulting construct, pET/E7/71, was further modified (to complete sequences at the 3'end of the hsp71 gene) by replacement of a Kpn I to Nhe I fragment containing sequences from the 3' end of the hsp71 gene by a Kpn I- and Nhe I-digested PCR fragment amplified from pY3111/8 using primers w391 and w392 (w391: GAG GGT GGT TCG AAG GTA CC (SEQ ID NO:42) and w392: TTT GAT TTC GCT AGC TCA CTT GGC CTC(SEQ ID NO:43)). The resulting final plasmid, pET/E7/71', expresses HPV16 E7 fused to the amino-terminus of full-length Hsp71 protein and was used to transform *E. coli* strain BL21(DE3). The nucleotide sequence (SEQ ID NO:44) coding for expression of the fusion protein (SEQ ID NO:45) of pET/E7/71' is shown in FIGS. 14A–14B.

The E7-TB71 protein was purified as follows. The Inclusion Body fraction was prepared as described above from *E. coli* BL21(DE3) cells transformed with plasmid pET/E7/71'. The E7-TB71 fusion protein present in the Inclusion Body fraction was purified using the following chromatographic steps: Q-Sepharose (100 ml column, Amersham Pharmacia) and Ni-chelating Sepharose (80 ml, Amersham Pharmacia) under native conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS/10% (v/v) glycerol.

Example 15

Production of Recombinant *Streptococcus pneumoniae* HSP65(2)—HPV16 E7 Fusion Protein (SP65(2)-E7)

A plasmid encoding SP65(2)-E7 was constructed as follows. The *Streptococcus pneumoniae* hsp65 gene was PCR-amplified from plasmid pETP60-2(PCT patent application WO 99/35720) using primers w384 and w385 (w384: GCA GCC CCA TGG CAA AAG AAA (SEQ ID NO:46) and w385: GCT CGA ATT CGG TCA GCT AGC TCC GCC CAT (SEQ ID NO:47)). The PCR product was digested with Nco I and EcoR I, gel-purified and ligated to pET28a digested with the same enzymes to generate pET/SP65-2C.

The HPV16 E7-coding sequence was PCR-amplified from pSK/HPV16 (ATCC) using primers w133 and w134 (w133: AAC CCA GCT GCT AGC ATG CAT GGA GAT (SEQ ID NO:48) and w134: AGC CAT GAA TTC TTA TGG TTT CTG (SEQ ID NO:49)). The PCR product was digested with restriction enzymes Nhe I and EcoR I and purified from an agarose gel. The purified PCR product was then ligated to pET/SP65-2C that had been previously digested with Nhe I and EcoR I. The ligation reaction was used to transform *E. coli* DH5alpha and putative clones containing the HPV16 E7 insert were selected based on diagnostic restriction digestion. This initial restriction analysis was confirmed by DNA sequence analysis of entire fusion gene, promoter and termination regions. DNA of the confirmed construct, named pET/SP65c-E7, was used to transform *E. coli* strain BLR(DE3). The nucleotide sequence (SEQ ID NO:50) coding for expression of SP65(2)-E7 (SEQ ID NO:51) is shown in FIGS. 15A–15B.

The SP65(2)-E7 protein was purified as follows. The Inclusion Body fraction was prepared as described above from *E. coli* BLR(DE3) cells transformed with plasmid pET/SP65c-E7. The SP65(2)-E7 fusion protein present in the Inclusion Body fraction was purified using the following chromatographic steps: Q-Sepharose (100 ml column, Amersham Pharmacia) and Ni-chelating (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS.

Example 16

Recombinant Production of *Asperzillus fumigatus* Hsp60- HPV16 E7 Fusion Protein (AF60-E7)

pETAF60E7 is a plasmid encoding a recombinant protein, AF60-E7, composed of the Aspergillus fumigatus (ATCC 26933) Hsp60 protein (without leader) (obtained as described in PCT/CA99/01152) fused at its C-terminus to the HPV16 (ATCC 45113) E7 protein sequence. Plasmid pETAF60E7 was used to transform *E. coli* BL21 (DE3) cells for protein production and purification. The nucleotide sequence (SEQ ID NO:52)coding for expression of AF60-E7 (SEQ ID NO:

The AF60-E7 protein was purified as follows. The Inclusion Body fraction was prepared as described above from *E. coli* BL21(DE3) cells transformed with plasmid pETAF60E7. AF60-E7 protein was purified using the following chromatographic steps: Source 15Q Sepharose (Amersham-Pharmacia) and Ni-chelating Sepharose (60 ml, Amersham Pharmacia) under denaturing conditions with serial washings containing 2% (v/v) Triton X-100 followed by serial washing to remove residual Triton X-100. The purity of the protein was checked by SDS-PAGE, the appropriate fractions pooled and dialyzed overnight at 4° C. against DPBS.

Example 17

Stimulation of IFN-Gamma Release by a Hsp65-HPVE7 (HspE7) Fusion Protein

Pooled, unfractionated splenocytes were prepared from untreated naive C57BL/6 mice obtained from two different sources (Charles River Laboratory and Jackson Laboratory) and were plated in complete medium (complete RPMI) at $6 \times 10^5$ cells/well in flat bottom 96-well tissue culture plates. Replicate cultures (5) were incubated for 72 hours with 0.05 to 1.4 nmol/mL concentrations of recombinant *M. bovis* BCG Hsp65 (Hsp65), HPV16 E7 (E7) or histidine-tagged E7 ((h)E7), an admixture of *M. bovis* BCG Hsp65 and HPV16 E7 (Hsp65+E7), or *M. bovis* BCG Hsp65—HPV16 E7 fusion protein (HspE7). Subsequent to incubation, cells were pelleted, and supernatants were transferred to IFN-gamma capture ELISA plates.

After incubation, the replicate samples were harvested, pooled in eppendorf tubes and pelleted at 1200 rpm for 7 minutes in Beckman GS-6R centrifuge (300×g). The supernatants were removed into cryovials and frozen at −70° C. until time of analysis.

Maxisorp ELISA plates (Nunc cat #442404A) were coated overnight at 4° C. with 1 μg/mL purified rat anti-mouse IFN-gamma (PharMingen cat. no 18181D) in 0.1 M NaHCO$_3$ buffer, pH 8.2. The plates were washed with 0.05% Tween 20 in PBS then blocked with 3% BSA (albumin fraction V: Amersham cat. no 10857) in DPBS (blocking buffer) for 2 hours. After the plates were washed, recombinant mouse IFN-gamma (8000, 4000, 2000, 1000, 500, 250, 125, 62.5 pg/mL in complete RMPI) was placed in triplicate onto each ELISA plate. Sample supernatants were removed from −70° C., thawed quickly at 37° C., and placed undiluted onto the ELISA plates in duplicate. The samples were then serially diluted by seven, 3-fold dilutions in complete RPMI followed by incubation at 4° C. overnight. Background ELISA values were established by measuring eight wells containing all reagents except the target antigen.

Detection of bound murine IFN-gamma was accomplished using 1 μg/mL of a rat anti-mouse IFN-gamma biotin conjugate (PharMingen cat. no 18112D) in blocking buffer. Following washing, bound biotin-conjugated antibody was detected using a 1:1000 dilution of a streptavidin-alkaline phosphatase conjugate (Caltag cat. no SA1008). The plates were washed as before followed by the addition of a chromogenic substrate, p-nitrophenyl phosphate (pNPP; Sigma cat #N-2765) at 1 mg/mL in diethanolamine buffer, pH 9.5. After 30 minutes incubation, the color reaction was stopped using 50 μL of 100 mM EDTA, pH 8.0. The absorbance was measured at 410 nm using a Dynatech MR5000 ELISA plate reader equipped with Biolinx 2.0 software. The levels of IFN-gamma detected in test samples were extrapolated from the standard curves generated on each of the respective ELISA plates. Data is expressed as IFN-gamma released (pg/mL±SD).

Figure 17B:
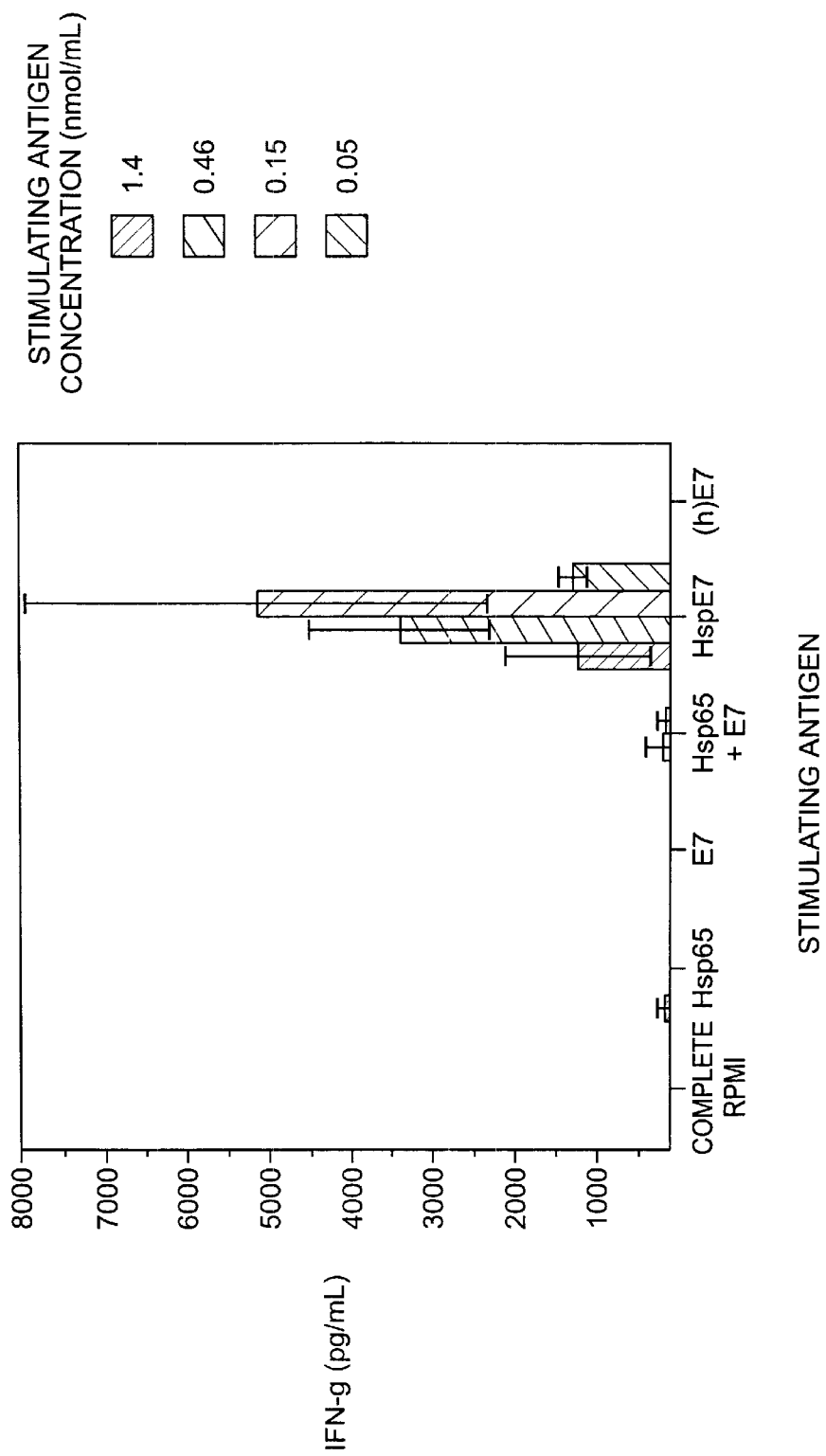

Results of assays are shown in FIGS. 17A–17B. The averages from five replicates are shown along with the standard deviation. Substantial secretion of IFN-gamma was elicited by exposure of splenocytes to 0.05, 0.15, 0.46 and 1.4 nmol/mL HspE7. Hsp65 alone, E7 alone, hE7 alone, and an admixture of Hsp65 and E7 were virtually incapable of stimulating IFN-gamma release. Similar results were obtained with splenocytes prepared from mice obtained from the Charles River Laboratory (FIG. 17A) and from the Jackson Laboratory (FIG. 17B).

Example 18

Figure 18A:
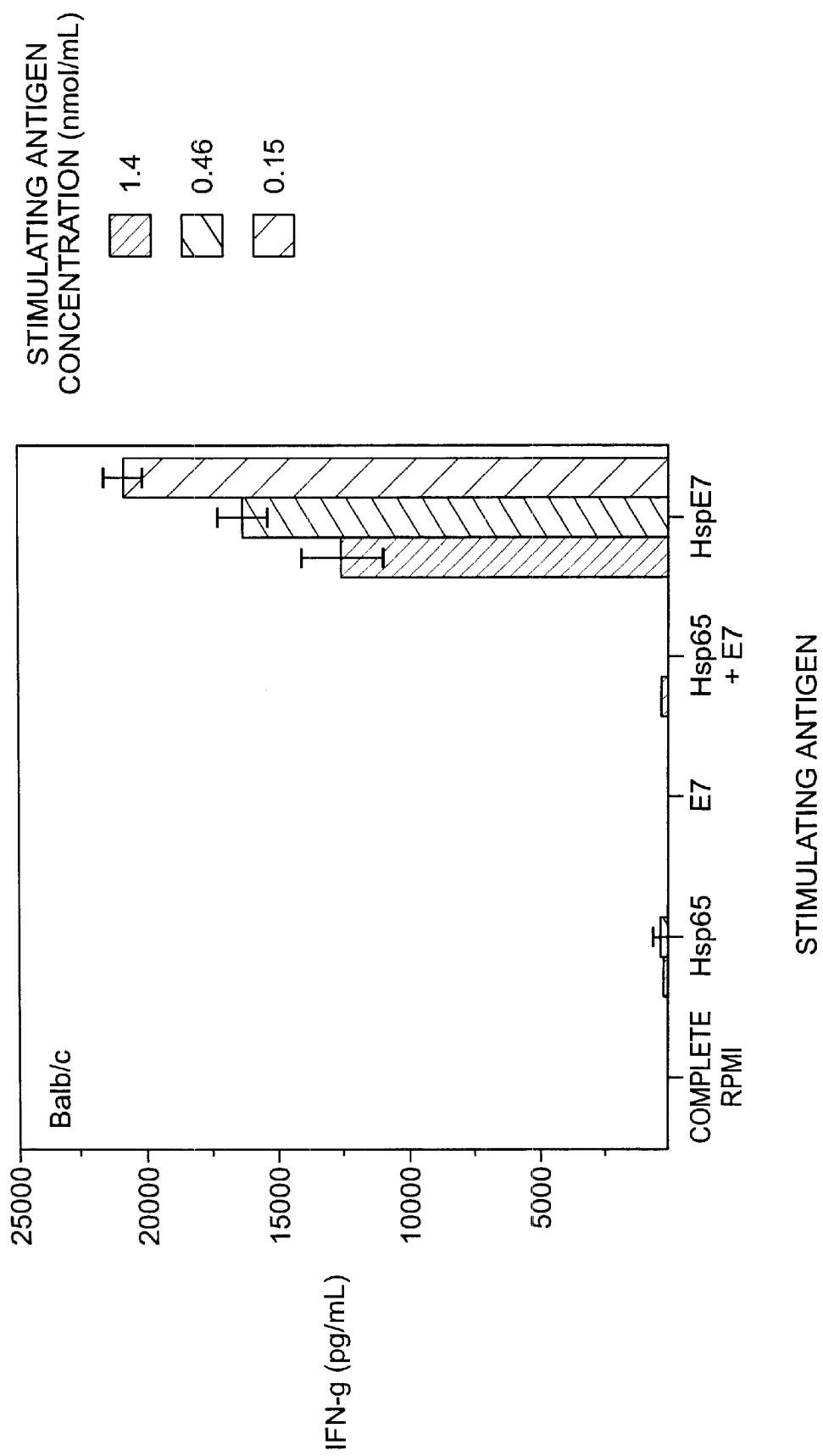
FIGS. 18A–18C show enhanced IFN-gamma release by splenocytes from Balb/c (FIG. 18A), C57BL/6 (FIG. 18B), and C3HeB/FeJ (FIG. 18C) mice upon exposure to HspE7.
Figure 18B:
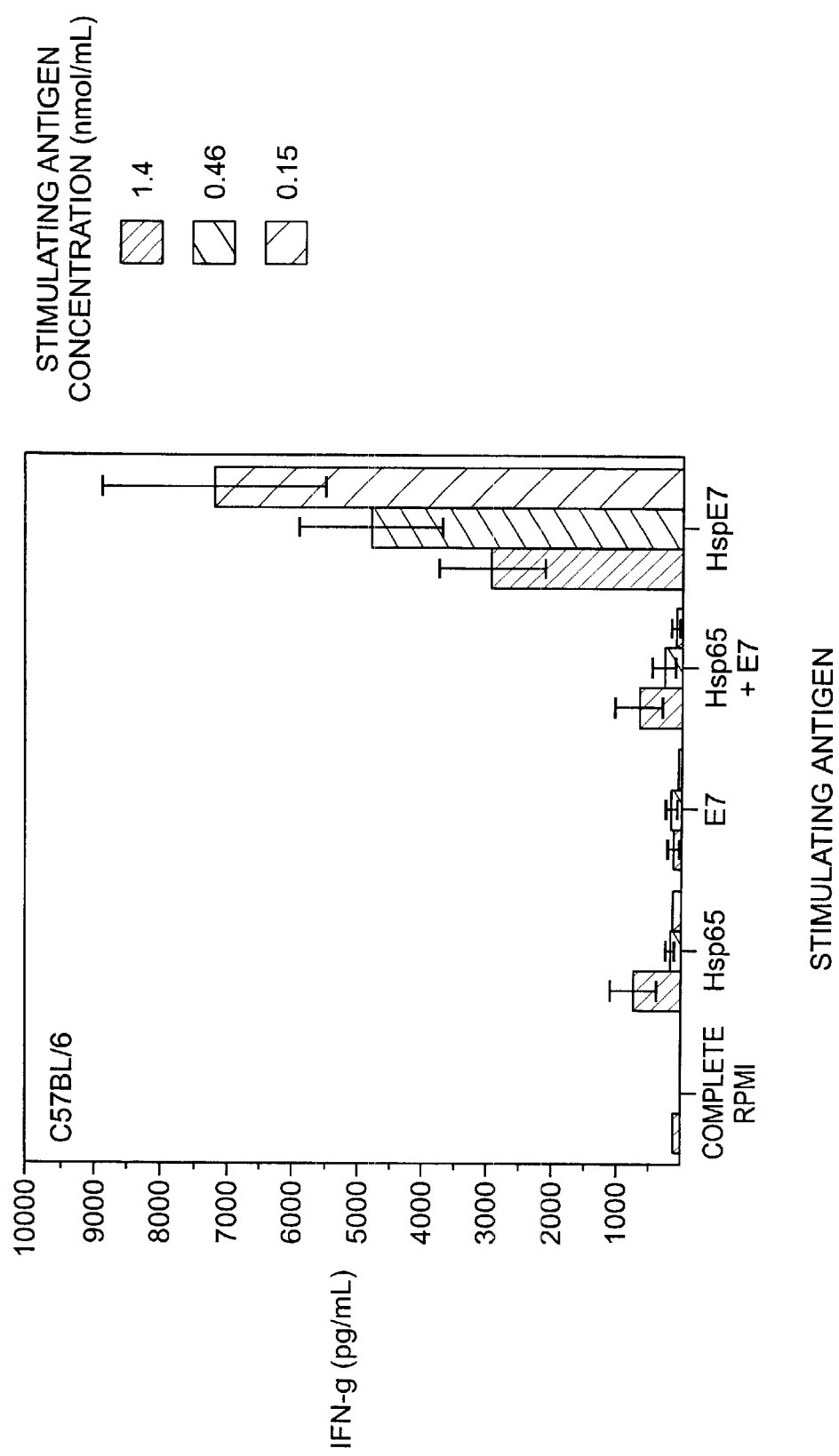
Figure 18C:
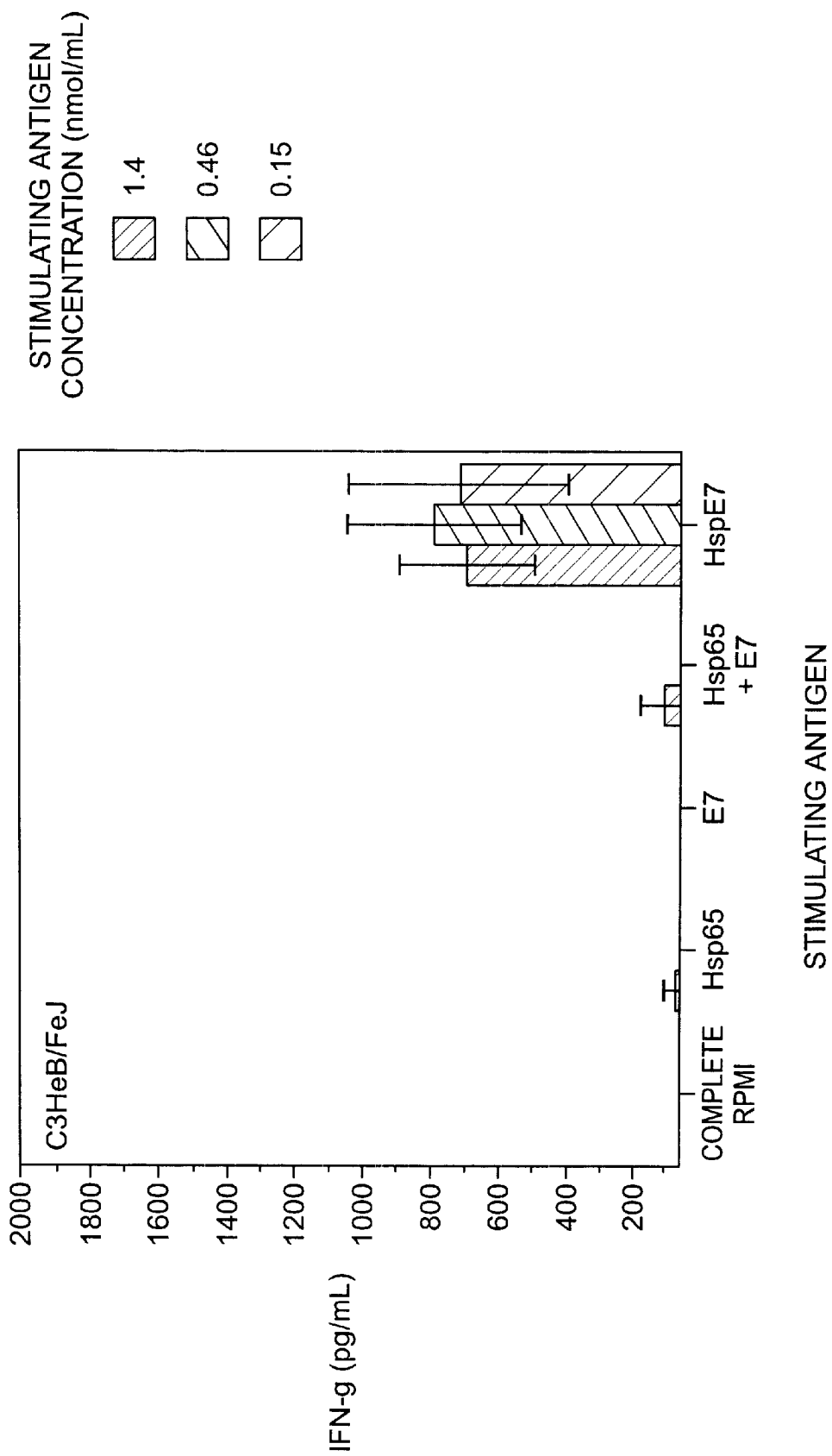

Stimulation of IFN-Gamma Release by a HspE7 Fusion Protein in Splenocyte Cultures from Mice Having Different Genetic Backgrounds Experiments similar to those presented in Example 17 were carried out using splenocytes from mice (from Jackson Laboratory) of three different haplotypes: C57BL/6 (H-2$^b$); Balb/c (H-2$^d$); and C3HeB/FeJ (H-2$^k$). The relative effects of the fusion protein on the different splenocyte preparations were similar, although there were differences in the absolute amounts of IFN-gamma released: the observed order being Balb/c (highest; FIG. 18A), C57BL/6 (intermediate; FIG. 18B), and C3HeB/FeJ (lowest; FIG. 18C). As in Example 17, substantially increased IFN-gamma release was induced by HspE7, but not by E7 alone, Hsp65 alone, or an admixture of E7 and Hsp65.

Example 19

Figure 19:
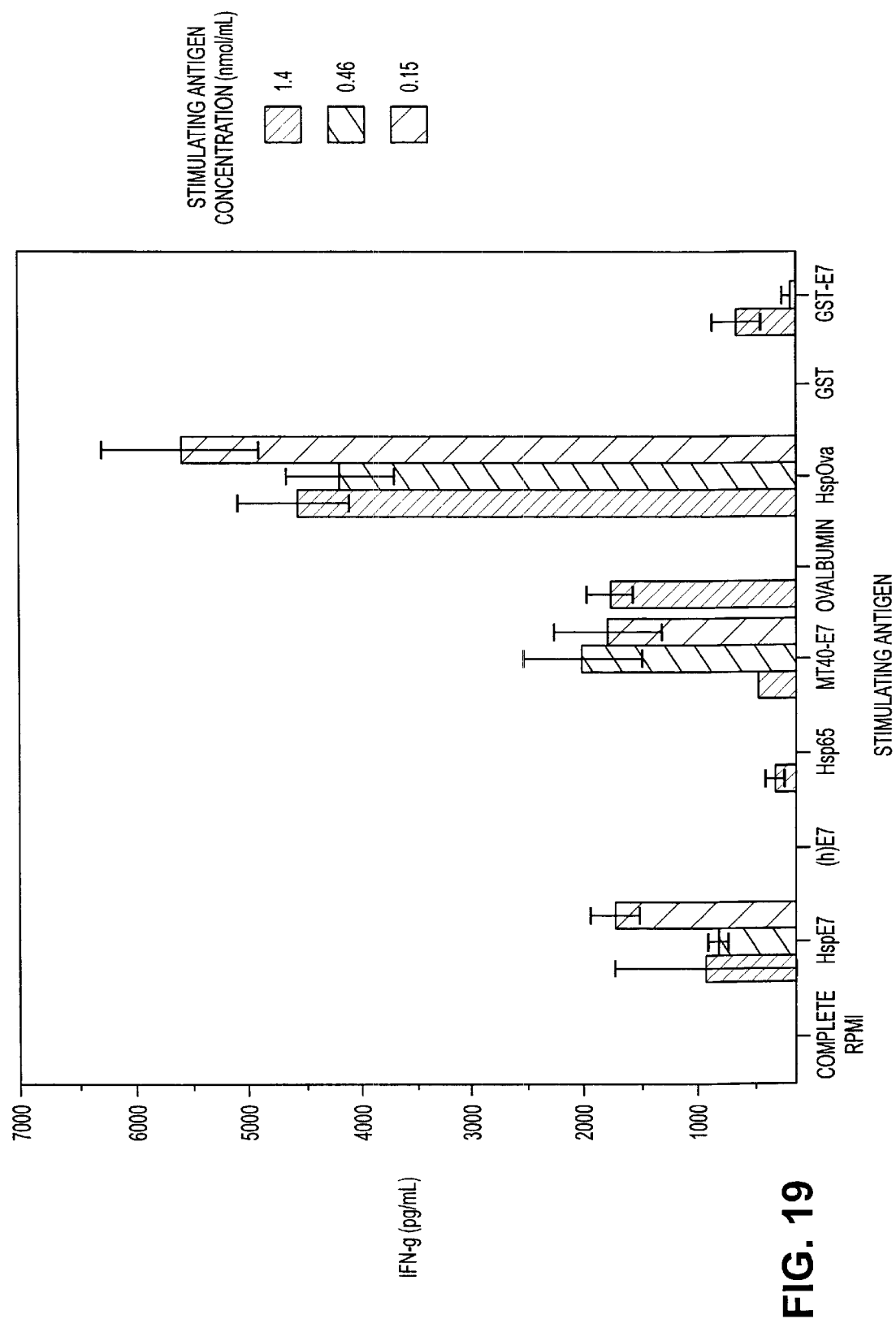
FIG. 19 shows enhanced IFN-gamma release by splenocytes upon exposure to fusion proteins containing an antigen and a stress protein but not upon exposure to a fusion protein containing an antigen and a protein other than a stress protein.

Stimulation of IFN-Gamma Release by Fusion Proteins is Independent of the Nature of the Linked Antigen but Requires a Linked Stress Protein Moiety Experiments were performed as discussed under the previous examples. It was observed that stimulation of naive splenocytes by (h)E7 or Hsp65 (*M. bovis* BCG) produced negligible IFN-gamma release, but that fusion proteins containing E7 and Hsp65 (*M. bovis* BCG) or Hsp40 (*M. tuberculosis*) substantially enhanced IFN-gamma release (FIG. 19). Virtually no induction of IFN-gamma release was mediated by a fusion protein containing E7 and glutathione-S-transferase (GST). When a fusion protein including an ovalbumin fragment and an Hsp (*M. bovis* BCG Hsp65) was tested, high levels of IFN-gamma release were detected. The IFN-gamma release mediated by the HspOVA fusion protein exceeded that resulting from addition of OVA alone to the cell culture. These results demonstrate that the induced release of IFN-gamma is not dependent on the presence of the E7 antigen in the fusion protein, but that other antigens fused to an Hsp can similarly enhance IFN-gamma production.

Example 20

Stimulation of IFN-Gamma Release by E7 Fusion Proteins Having Different Stress Protein Moieties Experiments were performed as discussed under the previous examples. HPV16 E7 was fused to different Hsps, i.e.,

*M. tuberculosis* Hsp10 (TB10-E7), *M. bovis* BCG Hsp65 (HspE7), *Streptococcus pneumoniae* Hsp65 (2) (SP65(2)-E7), and *Aspergillus fumigatus* Hsp60 (AF60-E7). Furthermore, in two cases (E7-L-BCG65 and E7-TB71) the Hsp (*M. bovis* BCG Hsp65 and *M. tuberculosis* Hsp71, respectively) was added to the carboxy terminus of the E7 antigen instead of to the amino terminus as in the other fusions.

Figure 20A:
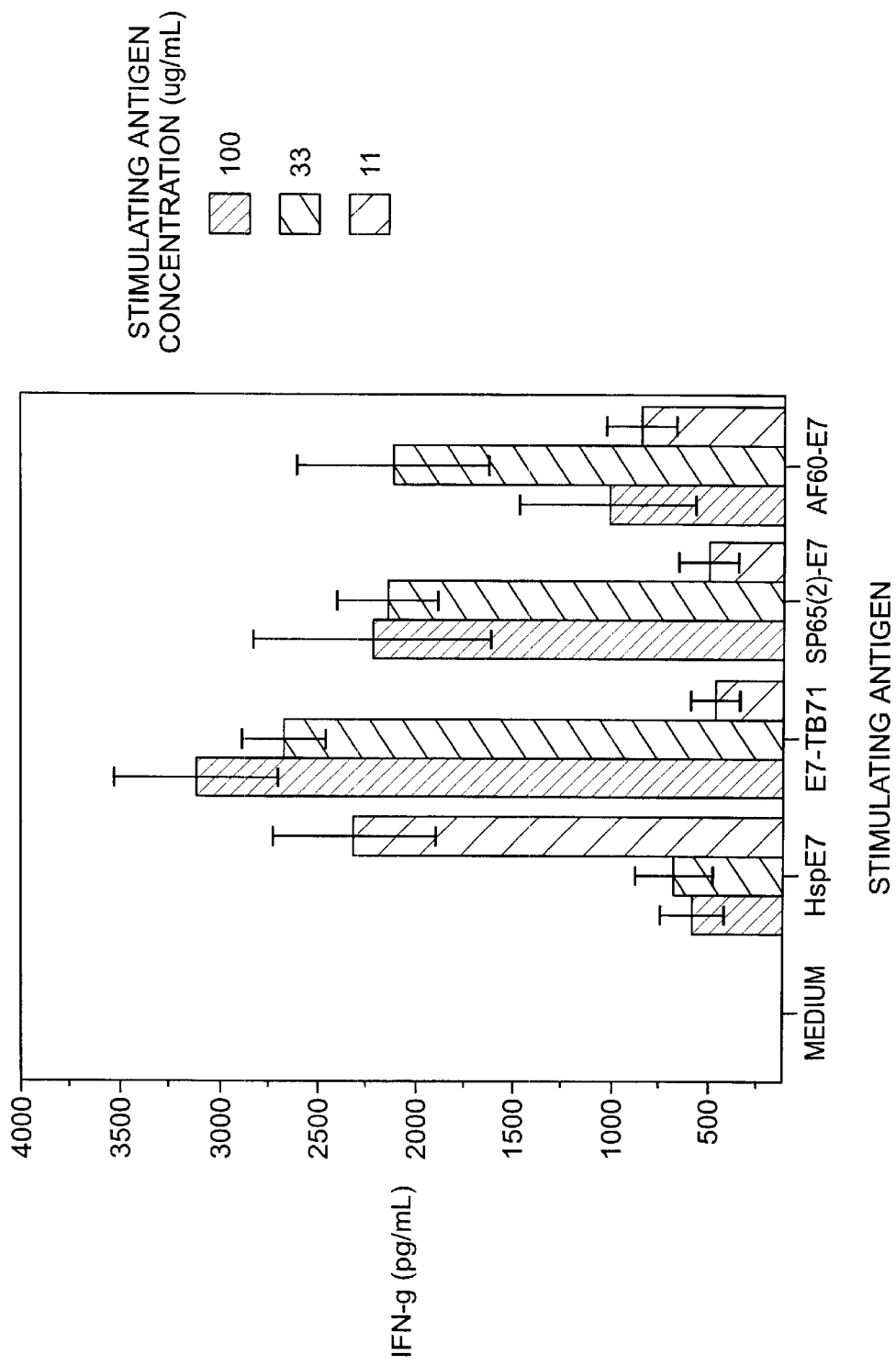

Additionally, one construct was tested, in which the E7 antigen was linked to the amino terminal one third (residues 1–200) of the *M. bovis* BCG Hsp65 sequence (BCG65(F1)-E7), rather than an intact Hsp. It was observed (FIGS. 20A–20B) that stimulation of IFN-gamma release occurred upon exposure of splenocytes to all the different fusion proteins, although differences in the magnitude of the responses were noted. Thus, fusions containing different Hsps, including Hsp65 from different organisms as well as different types of Hsps, were capable of eliciting enhanced IFN-gamma release. Furthermore, fusions containing a stress protein at either the amino terminal end or at the carboxy terminal end of the E7 antigen were active. Finally, BCG65(F1)-E7, containing amino acids 1–200 of *M. bovis* BCG Hsp65, induced IFN-gamma secretion in a manner similar to the full-length Hsp65 sequence (HspE7).

Example 21

Stimulation of IFN-Gamma Release by HspE7 Fusion Protein in Lymph Node Cell Cultures To test for their ability to induce IFN-gamma release, various concentrations of the HspE7 proteins (diluted to the desired starting concentration in complete medium, defined as RPMI 1640 with 10% fetal calf serum) were added as replicate samples (3 to 5 replicates) to flat bottom 96-well tissue culture plates. For the cellular component of the assay, three inguinal lymph nodes were aseptically removed from untreated C57BL/6 mice and placed in 5 ml of Hank's balanced salt solution supplemented with 5% fetal calf serum (medium). Following their transfer to a sterile 0.22 micron nylon mesh, a sterile syringe plunger was used to disperse the cells through the mesh. Medium was used to rinse the cells, yielding a pooled, unfractionated single cell suspension. Cells were washed once, resuspended in complete medium and added to wells at $6 \times 10^5$ cells/well, to a final volume of 0.2 ml. Cultures were exposed to the HspE7 protein in medium or to medium alone for 72 hours at 37° C. in a 5% $CO_2$ atmosphere. Following incubation, replicate cultures were pooled, cells pelleted by centrifugation and supernatants either measured for IFN-gamma content by ELISA according to the procedure described in Example 17, or frozen immediately at −70° C. for later analysis.

Figure 21:
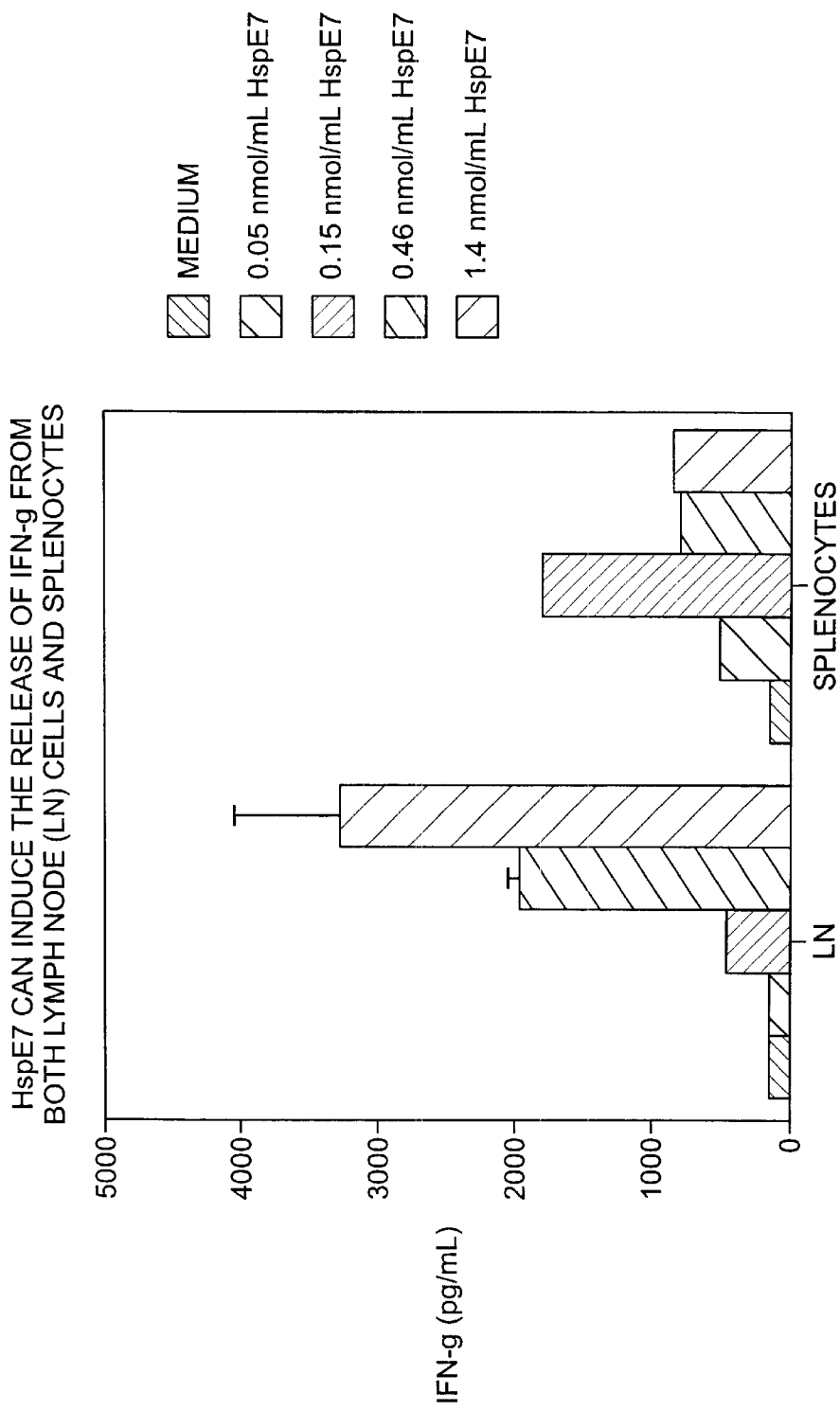
FIG. 21 shows enhanced IFN-gamma release by lymph node cells and splenocytes upon exposure to fusion proteins containing an antigen and a stress protein.

FIG. 21 shows the results of the above experiment, comparing induction of IFN-gamma release by lymph node cells and by splenocytes. The fusion protein was found to elicit a release of IFN-gamma in both cell types. The IFN-gamma release elicited by the fusion protein greatly exceeded that induced by Hsp65 alone.

Example 22

Regression of Pre-Established Tumors in vivo Induced by Administration of Hsp Fusion Proteins Human papilloma virus type 16 (HPV16) is an infectious agent associated with the induction of cervical cancer and its premalignant precursor, cervical intraepithelial neoplasia. The following experiments use Hsp—HPV16 E7 fusion proteins of the invention to target immune recognition as part of a strategy to eliminate HPV16 E7-expressing host cells.

The $H-2^b$ murine epithelial cell-derived tumor line, TC-1 (co-transformed with HPV16 E6 and E7 and activated human Ha-ras), was obtained from T. C. Wu of Johns Hopkins University (Baltimore, Md.). The use of TC-1 cells in assays similar to those used herein is described in PCT patent application WO 99/07860. TC-1 was maintained in complete medium, consisting of: RPMI 1640 (ICN, cat no. 1260354) supplemented with 10% FBS (Hyclone, cat no. SH30071); 2 mM L-Glutamine (ICN, cat no. 16-801-49); 10 mM HEPES (ICN, cat no. 16-884-49); 0.1 mM MEM Non Essential Amino Acid Solution (Gibco BRL, cat no. 11140-050); 1 mM MEM Sodium Pyruvate (Gibco BRL, cat no. 11360-070); 50 $\mu$M 2-Mercaptoethanol (Sigma, cat no. M-7522); and 50 mcg/mL Gentamycin Sulfate (Gibco BRL, cat no. 15750-011). The medium was also supplemented with G418 (0.4 mg/mL active, Gibco BRL, cat no. 11811-023) and Hygromycin B (0.2 mg/mL active, Calbiochem, cat no. 400051).

Since the TC-1 cell line was derived from a C57BL/6 mouse, this mouse strain was used as the host in these experiments. Female C57BL/6 mice of approximately 8 to 10 weeks of age were purchased from Charles River Canada (St-Constant, Quebec, Canada) and housed using filter top cages (four animals per cage).

TC-1 cells were prepared for implantation as follows. TC-1 cells were seeded at a density of $2–5 \times 10^4$ cells /mL and incubated for two to four days until 70 to 90% confluent. Cells were trypsinized using a 30 second exposure to 0.25% Trypsin (10xstock, Gibco cat. no. 1505-065, diluted to 1x with DPBS), then diluted four-fold with supplemented complete medium. Following trypsinization, TC-1 cells were pelleted at 4° C. at 1000 rpm (250xg) for 4 minutes, the supernatant removed by aspiration and 30 mL of cold DPBS added. The cells were then pelleted at 4° C. at 700 rpm (100xg) for 4 minutes, the supernatant removed by aspiration, and a minimal amount (approx. 5 mL) of cold DPBS added. The final cell density for injection was adjusted to $6.5 \times 10^5$ viable cells per mL, as measured by the trypan blue dye exclusion method. At least 90% of the cells used for TC-1 inoculations were viable. The cells were stored on ice for immediate injection into mice.

TC-1 cells were implanted as follows. Between 24 to 72 hours prior to implantation, the hind flank of each mouse was shaved. TC-1 cells were prepared as described above and held on ice until injected. All injections were performed within two hours of cell trypsinization. The cells were swirled gently in the centrifuge tube and drawn into a 1 mL syringe (Becton-Dickinson, cat. no. 309602) without a needle. A 25 gauge needle (Becton-Dickinson, cat. no. 305122) was then attached and any air bubbles were expelled. The shaved skin was raised gently and the needle was inserted bevel side up just beneath the skin surface. Cells ($1.3 \times 10^5$) were injected in a 0.2 mL volume for all studies. A fresh syringe and needle was used for every fifth injection.

Fusion proteins were injected as follows. On treatment days, the fusion proteins HspE7, SP65(2)-E7, AF60-E7, E7-TB71 (shown if FIGS. 23A and 23B as E7-MT71), MT40-E7 and TB10-E7 (prepared as described above) were removed from −70° C. storage and thawed in a 37° C. water bath. Dulbecco's phosphate buffered saline (DPBS) (4° C.) was added to obtain the protein concentration desired for injection. The diluted fusion protein was held on ice until drawn into a 1 mL syringe (Becton-Dickinson, cat no. 309602) with a 30 gauge needle (Becton-Dickinson, cat no. 3095106). The same syringe was used to inject 0.2 mL of fusion protein into each mouse within a dose group; the syringe was refitted with a fresh needle for every fifth injection. Mice were injected subcutaneously in the scruff of the neck, as high on the neck as possible.

Tumor incidence (TI) was measured as follows. TI was generally recorded three times per week, beginning eight days after tumor implantation and continuing for eight weeks. Mice were assessed for the presence or absence of subcutaneous tumor by palpation and visual observation of the tumor injection site.

Tumor volume was measured as follows. Volumes of palpable subcutaneous tumor nodules were measured beginning on approximately Day 8 post implantation. The two longest orthogonal dimensions were measured using a Fowler Sylvac Ultra-Cal Mark III digital caliper with computerized data collection. Data points were tabulated in a Microsoft Excel spreadsheet. Tumor nodule measurements were extrapolated to $mm^3$ using the formula $V = W^2 \times L \times 0.5$ (where V represents volume, W represents width and L represents length) and are presented as average tumor volume ± standard error of the mean. The Student's t test function of Excel (two-tailed, unpaired samples, equal variances) was used to test the significance ($p<0.05$) of the difference of the means of tumor volumes in each group. Seven different HPV16 E7 fusion proteins linked to various hsps were tested for their ability to regress a tumor in vivo.

In the first experiment, C57BL/6 mice (18 per group) were inoculated subcutaneously with $1.3 \times 10^5$ TC-1 cells in the right hind flank (Day 0). After 7 days, groups of mice were treated with 0.2 mL of either DPBS (saline), 115 ug HspE7, 100 ug SP65(2)-E7, or 100 ug AF60-E7. The doses of the two latter proteins were chosen based on the same molar equivalent of E7 contained in HspE7. The mice were monitored for the presence or absence of tumor in addition to tumor volume. The data are represented as percent tumor incidence (TI) per group (FIG. 22A) and tumor volume, expressed as average tumor volume ± standard error of the mean (FIG. 22B).

Figure 22A:
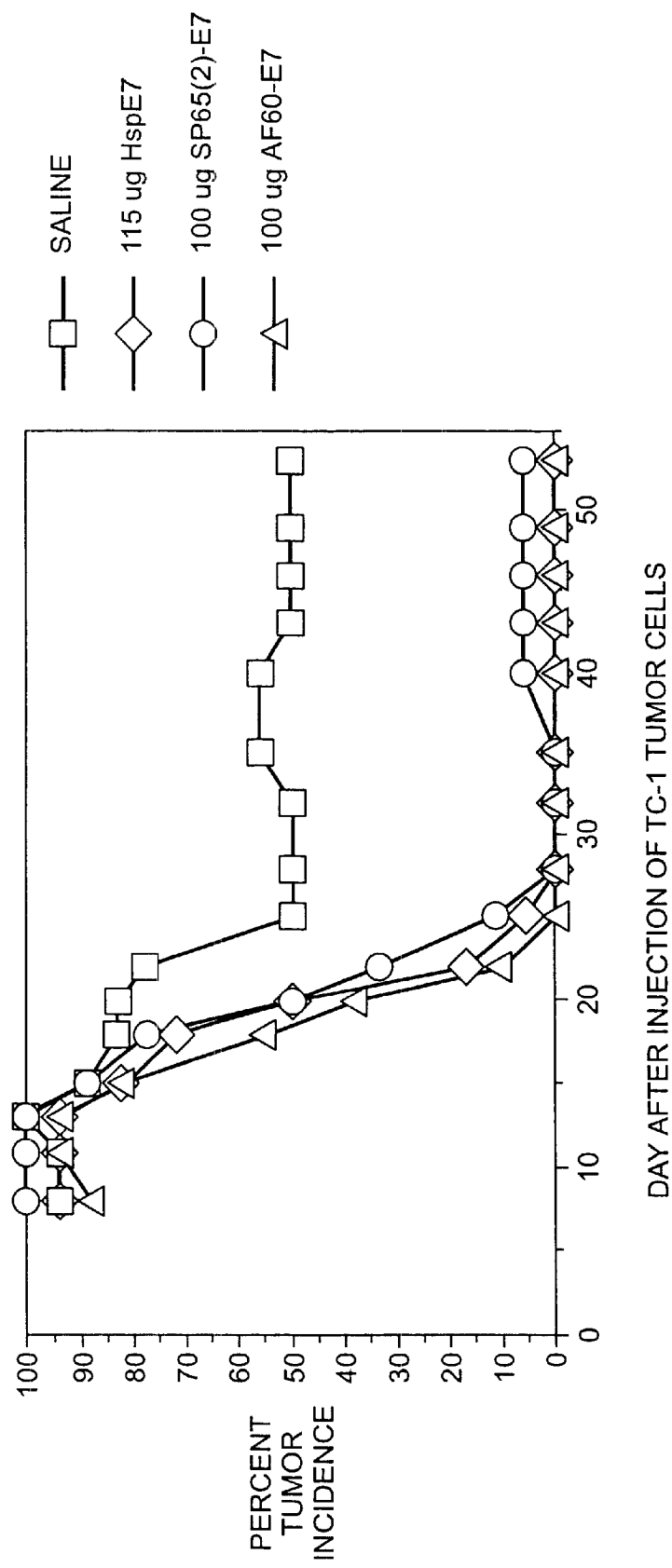
FIGS. 22A–22B show a time course of tumor incidence (FIG. 22A) and tumor volume (FIG. 22B) in mice injected with TC-1 tumor cells followed by an injection with either saline, HspE7, SP65(2)-E7, or AF60-E7.
Figure 22B:
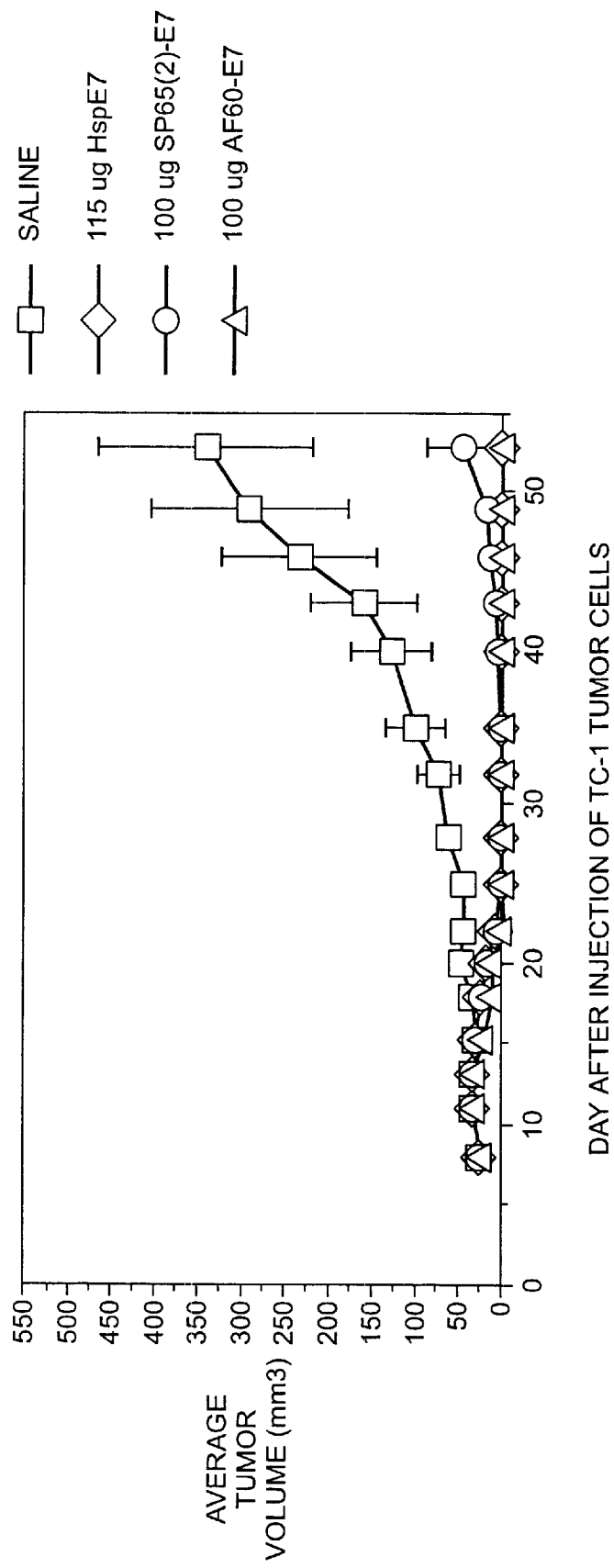

As indicated in FIG. 22A, the majority of animals had detectable tumor by Day 8 post implantation and by Day 13 tumor was evident in 94 to 100% of the mice. After this timepoint, TI in all of the mice declined until day 25 when the incidence for the DPBS-treated animals stabilized to approximately 50% for the remainder of the observation period. In contrast, the animals treated with fusion proteins showed a comparatively sharp decline in TI until day 28, when none of the animals had detectable tumor. This complete absence of tumor was observed for the remainder of the observation period for most of these animals. The complete regression of tumor in the animals treated with the fusion proteins was also clearly seen when measured by tumor volume. FIG. 22B shows that by day 28, the average tumor volume of the animals treated with the fusion proteins was not detectable. By comparison, the average tumor volume of those animals treated with DPBS rose steadily from day 25 onwards.

In the second experiment, C57BL/6 mice (18 per group) were inoculated subcutaneously with $1.3 \times 10^5$ TC-1 cells in the right hind flank (Day 0). After 7 days, groups of mice were treated with 0.2 mL of either DPBS (saline), 100 ug HspE7, 100 ug MT40-E7, 100 ug E7-TB71 (shown if FIGS. 23A and 23B as E7-MT71), or 100 ug TB10-E7. The mice were monitored for the presence or absence of tumor in addition to tumor volume. The data are represented as percent tumor incidence (TI) per group (FIG. 23A) and tumor volume, expressed as average tumor volume ± standard error of the mean (FIG. 23B).

Figure 23A:
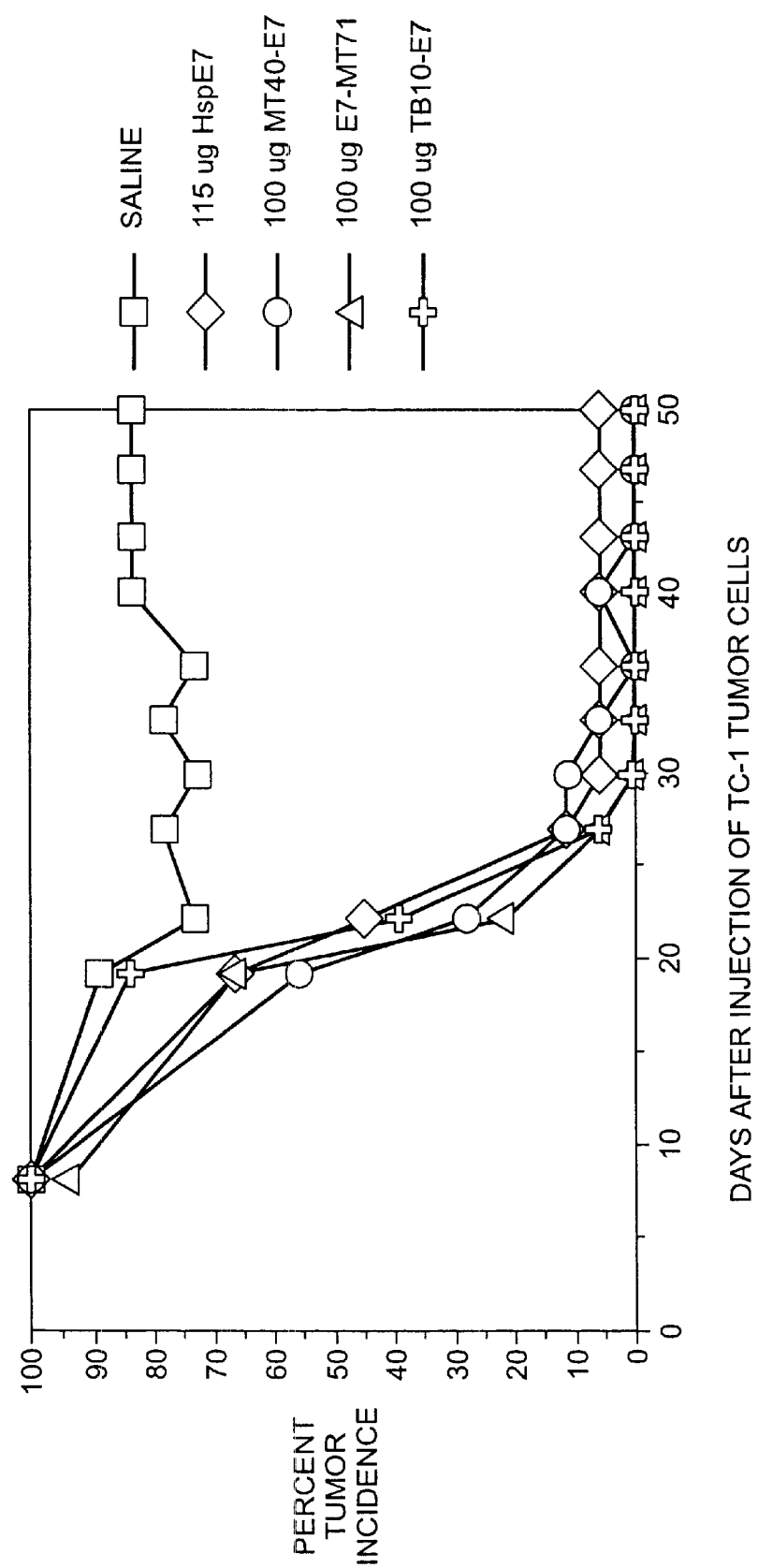
FIGS. 23A–23B show a time course of tumor incidence (FIG. 23A) and tumor volume (FIG. 23B) in mice injected with TC-1 tumor cells followed by an injection with either saline, HspE7, MT40-E7, E7-MT71, or TB10-E7.
Figure 23B:
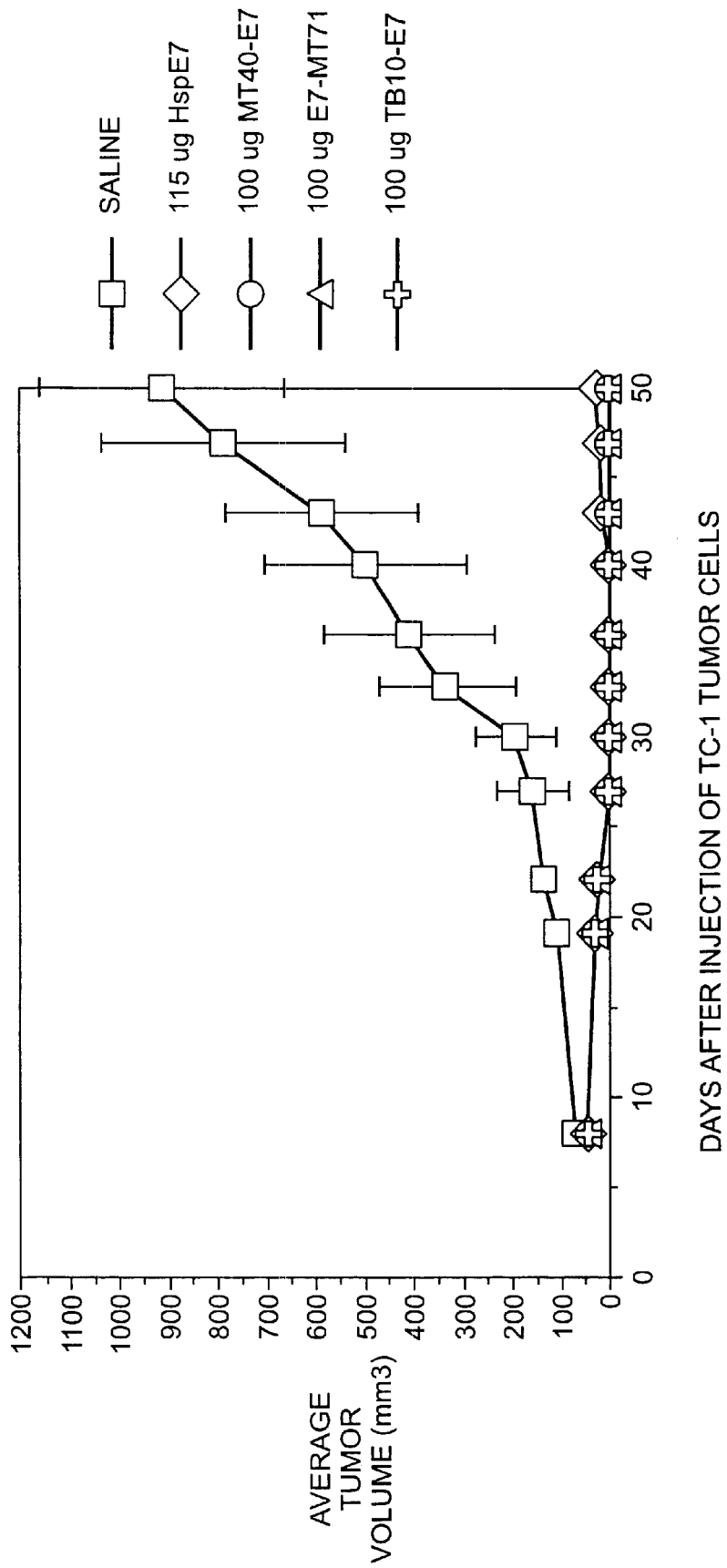

As in FIG. 22A, a majority (approximately 95%) of the animals had visible and palpable tumors on day 8 post tumor implantation (FIG. 23A). By day 19, a decrease in TI was apparent. Following this, a sharp decrease in TI for all of the fusion protein-treated animals was observed such that by day 33, practically all of the animals were tumor-free. In contrast, the TI of the mice treated with DPBS had stabilized to approximately 75%. FIG. 23B shows the average tumor volumes of the mice treated with the respective fusion proteins. The decrease in TI was reflected by the marked decrease in tumor volumes. Average tumor volumes for the animals treated with any of the fusion proteins was essentially not measurable by day 30.

What is claimed is:
1. A method of determining whether a fusion protein stimulates a Th1-like response, the method comprising:
  (a) providing a cell sample comprising naive lymphocytes in vitro;
  (b) providing a fusion protein comprising (i) a heat shock protein (Hsp) or a fragment thereof at least eight amino acid residues in length, fused to (ii) a heterologous polypeptide at least eight amino acid residues in length;
  (c) contacting the cell sample with the fusion protein; and
  (d) determining whether the fusion protein stimulates a Th1-like response in the cell sample.
2. The method of claim 1, wherein the Hsp is selected from the group consisting of Hsp65, Hsp40, Hsp10, Hsp60, and Hsp71.
3. The method of claim 2, wherein the fusion protein comprises a polypeptide selected from the group consisting of Hsp65, Hsp40, Hsp10, Hsp60, and Hsp71.
4. The method of claim 1, wherein the fusion protein comprises amino acids 1–200 of Hsp65 of *Mycobacterium bovis*.
5. The method of claim 1, wherein the heterologous polypeptide comprises a sequence identical to at least eight consecutive amino acids of (i) a protein of a human pathogen or (ii) a tumor associated antigen.
6. The method of claim 1, wherein the heterologous polypeptide comprises a sequence identical to at least eight consecutive amino acids of a protein of a human virus.
7. The method of claim 1, wherein the virus is selected from the group consisting of human papilloma virus (HPV), herpes simplex virus (HSV), hepatitis B virus (HBV), hepatitis C virus (HCV), cytomegalovirus (CMV), Epstein-Barr virus (EBV), influenza virus, measles virus, and human immunodeficiency virus (HIV).
8. The method of claim 7, wherein the heterologous polypeptide comprises HPV E6.
9. The method of claim 7, wherein the heterologous polypeptide comprises HPV E7.
10. The method of claim 1, wherein the heterologous polypeptide comprises HPV16 E7 or a fragment thereof at least eight amino acid residues in length.
11. The method of claim 1, wherein the heterologous polypeptide comprises HPV16 E6 or a fragment thereof at least eight amino acid residues in length.
12. The method of claim 10, wherein the fusion protein comprises *Mycobacterium bovis* Hsp65 and HPV16 E7.
13. The method of claim 1, wherein the cell sample comprises cells derived from a spleen, lymph node, peripheral blood, bone marrow, thymus, lung, respiratory tract, or anogenital mucosa.
14. The method of claim 1, wherein the cell sample comprises splenocytes or lymph node cells.
15. The method of claim 1, wherein the detecting step comprises detecting IFN-gamma produced by the cell sample.
16. The method of claim 1, comprising the further steps of
  (e) providing a second cell sample comprising naive lymphocytes;
  (f) contacting the second cell sample with a second fusion protein; and
  (g) determining whether the second fusion protein stimulates a Th1-like response in the second cell sample,
  wherein the first fusion protein comprises the sequence of a full-length, naturally occurring Hsp, and the second fusion protein comprises at least eight amino acids but less than all of the sequence of a naturally occurring Hsp.

17. A method of screening a compound, the method comprising:
  (a) providing a cell sample comprising naive lymphocytes in vitro;
  (b) providing a fusion protein comprising (i) a Hsp or a fragment thereof at least eight amino acid residues in length, fused to (ii) a heterologous polypeptide at least eight amino acid residues in length;
  (c) contacting the cell sample with the compound and the fusion protein; and
  (d) determining whether the cell sample exhibits a Th1-like response following the contacting step,
  wherein a decrease in the Th1-like response in the presence of the compound compared to in the absence of the compound indicates that the compound inhibits a Th1-like response by the cell sample.
18. The method of claim 17, wherein the determining step comprises detecting IFN-gamma produced by the cell sample.
19. The method of claim 17, wherein the cell sample comprises cells derived from a spleen, lymph node, peripheral blood, bone marrow, thymus, lung, respiratory tract, or anogenital mucosa.
20. The method of claim 17, wherein the cell sample comprises splenocytes or lymph node cells.
21. The method of claim 17, wherein the Hsp is selected from the group consisting of Hsp65, Hsp40, Hsp10, Hsp60, and Hsp71.
22. The method of claim 21, wherein the fusion protein comprises a polypeptide selected from the group consisting of Hsp65, Hsp40, Hsp10, Hsp60, and Hsp71.
23. The method of claim 17, wherein the heterologous polypeptide comprises HPV E6.
24. The method of claim 17, wherein the heterologous polypeptide comprises HPV E7.
25. The method of claim 17, wherein the fusion protein comprises *Mycobacterium bovis* Hsp65 and HPV16 E7.
26. A method of screening a compound, the method comprising:
  (a) providing a cell sample comprising naive lymphocytes in vitro;
  (b) providing a fusion protein comprising (i) a Hsp or a fragment thereof at least eight amino acid residues in length, fused to (ii) a heterologous polypeptide at least eight amino acid residues in length;
  (c) contacting the cell sample with the compound and the fusion protein; and
  (d) determining whether the cell sample exhibits a Th1-like response following the contacting step,
  wherein an increase in the Th1-like response in the presence of the compound compared to in the absence of the compound indicates that the compound promotes a Th1-like response by the cell sample.
27. The method of claim 26, wherein the determining step comprises detecting IFN-gamma produced by the cell sample.
28. The method of claim 26, wherein the cell sample comprises cells derived from a spleen, lymph node, peripheral blood, bone marrow, thymus, lung, respiratory tract, or anogenital mucosa.
29. The method of claim 26, wherein the cell sample comprises splenocytes or lymph node cells.
30. The method of claim 26, wherein the Hsp is selected from the group consisting of Hsp65, Hsp40, Hsp10, Hsp60, and Hsp71.

31. The method of claim 30, wherein the fusion protein comprises a polypeptide selected from the group consisting of Hsp65, Hsp40, Hsp10, Hsp60, and Hsp71.

32. The method of claim 26, wherein the heterologous polypeptide comprises HPV E6.

33. The method of claim 26, wherein the heterologous polypeptide comprises HPV E7.

34. The method of claim 26, wherein the fusion protein comprises *Mycobacterium bovis* BCG Hsp65 and HPV16 E7.

35. A method of determining whether a hybrid compound stimulates a Th1-like response, the method comprising:
   (a) providing a cell sample comprising naive lymphocytes in vitro;
   (b) providing a hybrid compound that is non-naturally occurring and comprises (i) a non-peptide compound having a molecular weight of less than 1,500, covalently linked to (ii) a polypeptide of at least eight amino acids in length, wherein the hybrid compound is made by covalently linking the non-peptide compound to the polypeptide;
   (c) contacting the cell sample with the hybrid compound; and
   (d) determining whether the hybrid compound stimulates a Th1-like response in the cell sample.

36. The method of claim 35, wherein the non-peptide compound has a molecular weight of at least 100.

37. A method of determining whether a hybrid compound stimulates a Th1-like response, the method comprising:
   (a) producing a hybrid compound by covalently linking a non-peptide compound to a polypeptide of at least eight amino acids in length;
   (b) providing a cell sample comprising naive lymphocytes in vitro;
   (c) contacting the cell sample with the hybrid compound; and
   (d) determining whether the hybrid compound stimulates a Th1-like response in the cell sample.

38. The method of claim 37, wherein the non-peptide compound has a molecular weight between 100 and 1,500.

39. A method of determining whether a fusion protein stimulates a Th1-like response, the method comprising:
   (a) providing a cell sample comprising naive lymphocytes in vitro;
   (b) providing a fusion protein comprising (i) a first polypeptide at least eight amino acids in length, fused to (ii) a second polypeptide at least eight amino acids in length;
   (c) contacting the cell sample with the fusion protein; and
   (d) detecting a Th1-like response exhibited by the cell sample following the contacting step.

40. The method of claim 39, wherein the detected Th1-like response is greater than a Th1-like response exhibited by a second cell sample comprising naive lymphocytes when the second cell sample is contacted with either the first polypeptide, the second polypeptide, or a mixture of the first polypeptide and the second polypeptide.

41. The method of claim 40, wherein the detected Th1-like response is at least two times greater than the Th1-like response exhibited by the second cell sample.

42. The method of claim 40, wherein the detected Th1-like response is at least five times greater than the Th1-like response exhibited by the second cell sample.

43. A fusion protein comprising (i) a Hsp10 protein or a fragment thereof at least eight amino acid residues in length, and (ii) a heterologous polypeptide at least eight amino acids in length.

44. The fusion protein of claim 43, comprising a Hsp10 protein.

45. The fusion protein of claim 44, wherein the Hsp10 protein is a mycobacterial protein.

46. The fusion protein of claim 45, comprising the *Mycobacterium tuberculosis* Hsp10 protein.

47. The fusion protein of claim 43, wherein the heterologous polypeptide comprises a sequence identical to at least eight consecutive amino acids of a protein of a human virus.

48. The fusion protein of claim 47, wherein the human virus is HPV.

49. The fusion protein of claim 48, wherein the heterologous polypeptide comprises HPV16 E7.

50. A fusion protein comprising (i) a Hsp40 protein or a fragment thereof at least eight amino acid residues in length, and (ii) a heterologous polypeptide at least eight amino acids in length.

51. The fusion protein of claim 50, comprising a Hsp40 protein.

52. The fusion protein of claim 51, wherein the Hsp40 protein is a mycobacterial protein.

53. The fusion protein of claim 52, comprising the *Mycobacterium tuberculosis* Hsp40 protein.

54. The fusion protein of claim 50, wherein the heterologous polypeptide comprises a sequence identical to at least eight consecutive amino acids of a protein of a human virus.

55. The fusion protein of claim 54, wherein the human virus is HPV.

56. The fusion protein of claim 55, wherein the heterologous polypeptide comprises HPV16 E7.

57. A fusion protein comprising (i) a Hsp71 protein or a fragment thereof at least eight amino acid residues in length, and (ii) a heterologous polypeptide at least eight amino acids in length.

58. The fusion protein of claim 57, comprising a Hsp71 protein.

59. The fusion protein of claim 58, wherein the Hsp71 protein is a mycobacterial protein.

60. The fusion protein of claim 59, comprising the *Mycobacterium tuberculosis* Hsp71 protein.

61. The fusion protein of claim 57, wherein the heterologous polypeptide comprises a sequence identical to at least eight consecutive amino acids of a protein of a human virus.

62. The fusion protein of claim 61, wherein the human virus is HPV.

63. The fusion protein of claim 62, wherein the heterologous polypeptide comprises HPV16 E7.

64. A method of determining whether a compound stimulates a Th1-like response, the method comprising:
   (a) providing a cell sample comprising naive lymphocytes in vitro;
   (b) providing a compound;
   (c) contacting the cell sample with the compound; and
   (d) detecting a Th1-like response exhibited by the cell sample following the contacting step.

* * * * *

UNITED STATES PATENT AND TRADEMARK OFFICE
CERTIFICATE OF CORRECTION

PATENT NO. : 6,495,347 B1
DATED : December 17, 2002
INVENTOR(S) : Marvin Siegel, N. Randall Chu and Lee A. Mizzen It is certified that error appears in the above-identified patent and that said Letters Patent is hereby corrected as shown below:

Column 131,
Line 28, replace "claim 1" with -- claim 6 --

Signed and Sealed this

Thirty-first Day of August, 2004

JON W. DUDAS
*Director of the United States Patent and Trademark Office*